(12) United States Patent
Chen et al.

(10) Patent No.: US 11,136,315 B2
(45) Date of Patent: Oct. 5, 2021

(54) CXCR2 ANTAGONIST

(71) Applicant: MEDSHINE DISCOVERY INC., Jiangsu (CN)

(72) Inventors: Bin Chen, Shanghai (CN); Xiawei Wei, Chengdu (CN); Xuefeng Sun, Shanghai (CN); Lei Zhang, Shanghai (CN); Zhaoying Xu, Shanghai (CN); Wenli Li, Shanghai (CN); Peng Zhang, Shanghai (CN); Feng Gao, Shanghai (CN); Yunfu Luo, Shanghai (CN); Jian Li, Shanghai (CN); Shuhui Chen, Shanghai (CN)

(73) Assignee: MEDSHINE DISCOVERY INC., Jiangsu (CN)

( * ) Notice: Subject to any disclaimer, the term of this patent is extended or adjusted under 35 U.S.C. 154(b) by 0 days.

(21) Appl. No.: 16/960,468

(22) PCT Filed: Jan. 11, 2019

(86) PCT No.: PCT/CN2019/071390
§ 371 (c)(1),
(2) Date: Jul. 7, 2020

(87) PCT Pub. No.: WO2019/137484
PCT Pub. Date: Jul. 18, 2019

(65) Prior Publication Data
US 2020/0339549 A1 Oct. 29, 2020

(30) Foreign Application Priority Data
Jan. 11, 2018 (CN) .......................... 201810027003.2

(51) Int. Cl.
| | |
|---|---|
| C07D 405/12 | (2006.01) |
| A61P 11/00 | (2006.01) |
| C07D 211/54 | (2006.01) |
| C07D 215/38 | (2006.01) |
| C07D 277/64 | (2006.01) |
| C07D 307/81 | (2006.01) |
| C07D 333/52 | (2006.01) |
| C07D 409/12 | (2006.01) |
| C07D 413/12 | (2006.01) |
| C07D 417/12 | (2006.01) |
| C07D 491/048 | (2006.01) |

(52) U.S. Cl.
CPC ............ *C07D 405/12* (2013.01); *A61P 11/00* (2018.01); *C07D 211/54* (2013.01); *C07D 215/38* (2013.01); *C07D 277/64* (2013.01); *C07D 307/81* (2013.01); *C07D 333/52* (2013.01); *C07D 409/12* (2013.01); *C07D 413/12* (2013.01); *C07D 417/12* (2013.01); *C07D 491/048* (2013.01)

(58) Field of Classification Search
CPC .. C07D 405/12; C07D 211/54; C07D 215/38; A61P 11/00
See application file for complete search history.

(56) References Cited

U.S. PATENT DOCUMENTS

| | | |
|---|---|---|
| 7,893,089 B2 | 2/2011 | Busch-Petersen |
| 2003/0055286 A1 | 3/2003 | Widdowson et al. |
| 2007/0249672 A1 | 10/2007 | Busch-Petersen |
| 2009/0093451 A1 | 4/2009 | Busch-Petersen |
| 2009/0298810 A1 | 12/2009 | Busch-Petersen |
| 2011/0059937 A1 | 3/2011 | Busch-Petersen |
| 2011/0105563 A1 | 5/2011 | Busch-Petersen |

FOREIGN PATENT DOCUMENTS

| | | |
|---|---|---|
| CN | 1424910 A | 6/2003 |
| CN | 1635979 A | 7/2005 |
| CN | 101472477 A | 7/2009 |
| CN | 101495113 A | 7/2009 |
| WO | 2004039775 A2 | 5/2004 |
| WO | 2007124424 A2 | 11/2007 |
| WO | 2017156270 A1 | 9/2017 |

*Primary Examiner* — Anna Pagonakis
(74) *Attorney, Agent, or Firm* — Harness, Dickey & Pierce, P.L.C.

(57) ABSTRACT

A compound as a CXCR2 antagonist and an application thereof in preparing a drug as a CXCR2 antagonist. In particular, the present invention relates to a compound represented by formula (II) or an isomer or pharmaceutically acceptable salt thereof.

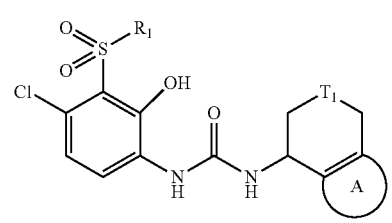

18 Claims, 2 Drawing Sheets

CXCR2 ANTAGONIST

CROSS-REFERENCE TO RELATED APPLICATIONS

This application is a 371 National Phase of International Application No. PCT/CN2019/071390, filed Jan. 11, 2019, which claims the benefit of Chinese Patent Application No. CN 201810027003.2, filed Jan. 11, 2018. The entire disclosures of the above applications are incorporated herein by reference.

TECHNICAL FIELD

The present disclosure relates to a series of compounds as CXCR2 antagonist and a use thereof in the manufacture of a medicament as CXCR2 antagonist. Specifically, the present disclosure relates to a compound represented by formula (I), an isomer thereof or a pharmaceutically acceptable salt thereof.

BACKGROUND ART

Chronic obstructive pulmonary disease (COPD) is a debilitating disease characterized by progressive airflow limitation caused by chronic airway inflammation. COPD is usually caused by inhalation of harmful particles and gases mainly from smoking and air pollution. Its symptoms include excessive mucus secretion, narrowing of the airways, fibrosis, and loss of alveoli. It can cause average weight loss, osteoporosis, cardiovascular disease and psychological damage. Current treatments for moderate to severe chronic obstructive pulmonary disease are relatively ineffective, and there are no drugs available which can significantly reduce disease progression or death. Global Initiative for Chronic Obstructive Pulmonary Disease (GOLD) recommends the use of long-lasting bronchodilators (LABA and LAMA) as the first-line maintenance therapy for patients suffering from moderate to severe COPD. Although these drugs produce effective bronchiectasis, they cannot treat the underlying inflammation in patients suffering from chronic obstructive pulmonary disease. Although inhaled glucocorticoid (ICS) has certain efficacy on asthma patients, it is largely ineffective against chronic obstructive pulmonary disease. Therefore, when bronchodilators are not effective for patients, additional treatments including inhaled glucocorticoids (ICS) can only be used with caution.

COPD is a chronic inflammatory disease, which indicates that effective anti-inflammatory therapy is currently the largest unmet therapeutic need in the field of chronic obstructive pulmonary disease. Roflumilast is an oral phosphodiesterase 4 (PDE4) inhibitor, which is the first approved oral anti-inflammatory drug for the treatment of chronic obstructive pulmonary disease. However, the use of roflumilast is limited by its strong side effects, so it is necessary to develop other new anti-inflammatory targets for the treatment of chronic obstructive pulmonary disease.

Interleukin 8 (IL-8 or CXCL8) is a protein containing 72 amino acid residues, which is a key factor controlling the recruitment and transfer of leukocytes at the site of inflammation. Interleukin 8 works by binding to its receptor. Its receptor is a G-protein coupled receptor that belongs to the CXC chemokine receptor, including CXCR1 and CXCR2. CXCR2 is highly expressed on the surface of human neutrophils. When interleukin 8 binds to CXCR2 on the surface of neutrophils, it will induce a series of intracellular reactions, including changes in calcium flux, degranulation and subsequent chemotaxis. Interleukin 8 is increased in various inflammatory diseases, such as arthritis, asthma, chronic obstructive pulmonary disease and the like, indicating that blocking its interaction with its receptors will be beneficial to the treatment of these diseases.

WO2007124424 discloses the use of CXCR2 antagonist danirixin in the treatment of related diseases.

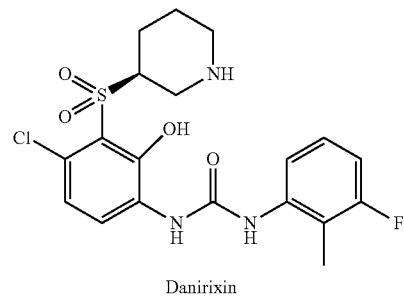

Danirixin

CONTENT OF THE DISCLOSURE

The present disclosure provides a compound of formula (II), an isomer thereof, or a pharmaceutically acceptable salt thereof,

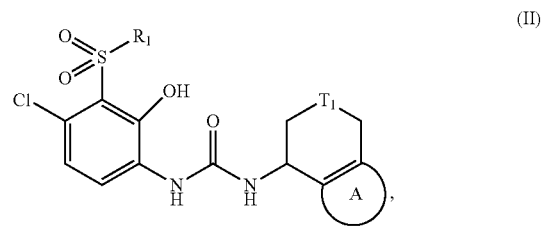

(II)

wherein, $T_1$ is selected from $C(R_2R_3)$ and $N(R_4)$;

ring A is selected from 5-6 membered heteroaryl and phenyl, wherein each of the 5-6 membered heteroaryl and phenyl is optionally substituted by one, two or three $R_a$;

$R_1$ is selected from $C_{1-6}$ alkyl, $NH_2$—(C=O)—$C_{1-3}$ alkyl-, 5-10 membered heteroaryl-$C_{1-3}$ alkyl-, $C_{3-7}$ cycloalkyl, 5-9 membered heterocycloalkyl, 5-10 membered heteroaryl, phenyl and —$C_{1-6}$ alkyl-phenyl, wherein each of the $C_{1-6}$ alkyl, $NH_2$—(C=O)—$C_{1-3}$ alkyl-, 5-10 membered heteroaryl-$C_{1-3}$ alkyl-, $C_{3-7}$ cycloalkyl, 5-9 membered heterocycloalkyl, 5-10 membered heteroaryl, phenyl and —$C_{1-6}$ alkyl-phenyl is optionally substituted by one, two or three R;

each of $R_2$ and $R_3$ is independently selected from H, F, Cl, Br, I, OH, $NH_2$ and $C_{1-3}$ alkyl optionally substituted by one, two or three $R_b$;

$R_4$ is selected from H and $C_{1-3}$ alkyl optionally substituted by one, two or three $R_c$; each $R_a$ is independently selected from H, F, Cl, Br, I, OH, $NH_2$ and $C_{1-3}$ alkyl optionally substituted by one, two or three R';

each of $R_b$ and $R_c$ is independently selected from H, F, Cl, Br, I, OH and $NH_2$;

each R is independently selected from H, F, Cl, Br, I, OH, $NH_2$, $C_{1-3}$ alkyl, $C_{1-3}$ alkyl-(C=O)—NH—, $C_{1-3}$ alkyl-O—(C=O)—NH—, $C_{3-6}$ cycloalkyl-(C=O)—NH— and $C_{1-6}$ alkyl-O—(C=O)—, wherein each of the $C_{1-3}$ alkyl, $C_{1-3}$ alkyl-(C=O)—NH—, C$_{3-6}$ cycloalkyl-(C=O)—NH— and C$_{1-6}$ 6 alkyl-O—(C=O)— is optionally substituted by one, two or three R';
each R' is independently selected from F, Cl, Br, I, OH and NH$_2$;
each of the 5-6 membered heteroaryl, 5-10 membered heteroaryl and 5-9 membered heterocycloalkyl contains one, two, three or four heteroatoms or heteroatomic groups independently selected from —NH—, —C(=O)—, —O—, —S— and N.

In some embodiments of the present disclosure, R is selected from F, Cl, Br, I, OH, NH$_2$, Me, Et,

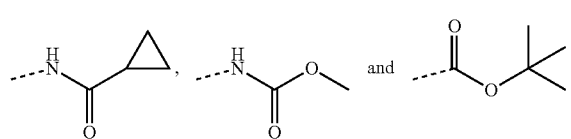

wherein each of the Me, Et,

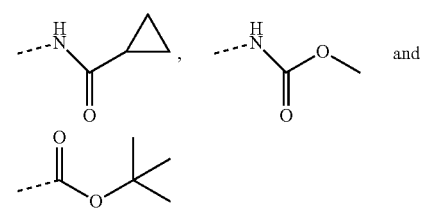

is optionally substituted by one, two or three R', and other variables are as defined in the present disclosure.

In some embodiments of the present disclosure, R is selected from F, Cl, Br, I, OH, NH$_2$, Me,

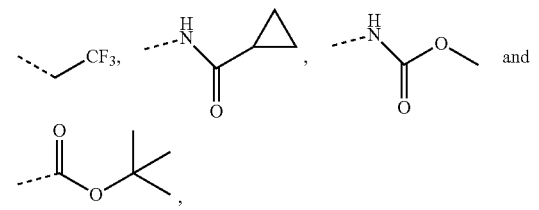

and other variables are as defined in the present disclosure.

In some embodiments of the present disclosure, each R$_a$ is independently selected from H, F, Cl, Br, I, OH, NH$_2$ and Me.

In some embodiments of the present disclosure, R$_1$ is selected from methyl, ethyl, propyl, isopropyl, butyl, tert-butyl, NH$_2$—(C=O)—CH$_2$—, isoindoline-1,3-dione-(CH$_2$)$_2$—, cyclopropyl, cyclobutyl, cyclopentyl, cyclohexyl, piperidinyl, tetrahydropyranyl, tetrahydrofuranyl, 1,4-diazepanyl, —C$_{1-4}$ alkyl-phenyl, 2-azaspiro[3.3]heptyl and 7-azaspiro[3.5]nonanyl, wherein each of the methyl, ethyl, propyl, isopropyl, butyl, tert-butyl, NH$_2$—(C=O)—CH$_2$—, isoindoline-1,3-dione-(CH$_2$)$_2$—, cyclopropyl, cyclobutyl, cyclopentyl, cyclohexyl, piperidinyl, tetrahydropyranyl, tetrahydrofuranyl, 1,4-diazepanyl, —C$_{1-4}$ alkyl-phenyl, 2-azaspiro[3.3]heptanyl and 7-azaspiro[3.5]nonanyl is optionally substituted by one, two or three R, and other variables are as defined in the present disclosure.

In some embodiments of the present disclosure, R$_1$ is selected from Me, Et,

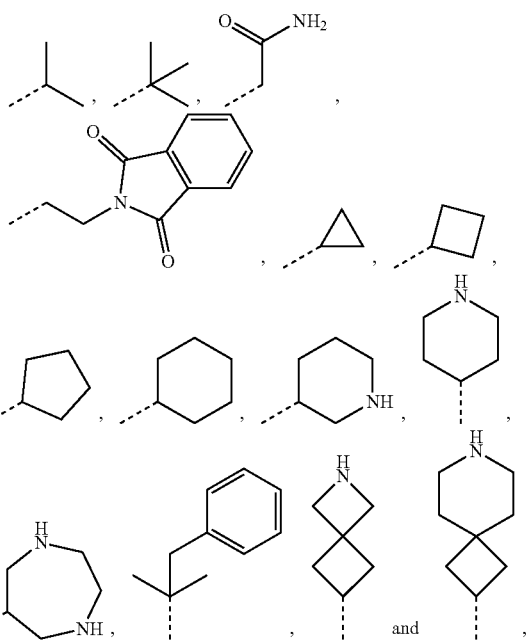

wherein each of the Me, Et,

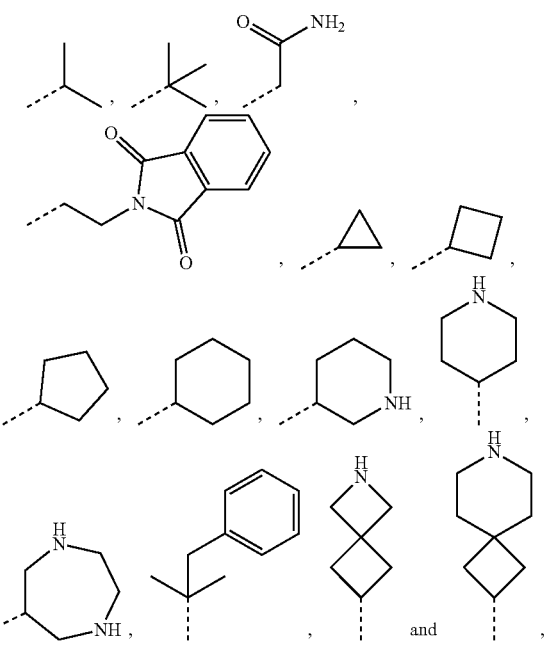

is optionally substituted by one, two or three R, and other variables are as defined in the present disclosure.

In some embodiments of the present disclosure, R$_1$ is selected from Me,

-continued

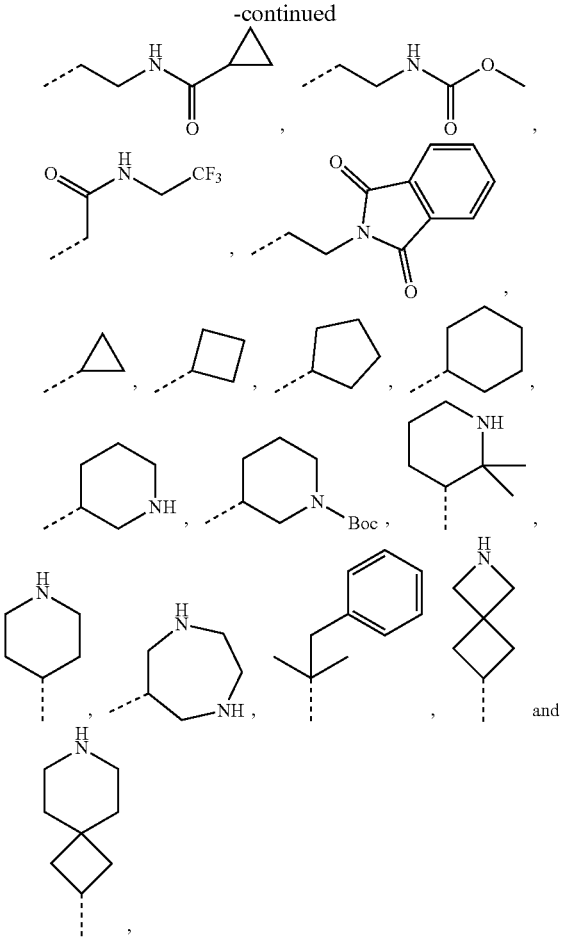

and other variables are as defined in the present disclosure.

In some embodiments of the present disclosure, each of $R_2$ and $R_3$ is independently selected from H, F, Cl, Br, I, OH, $NH_2$ and Me, and other variables are as defined in the present disclosure.

In some embodiments of the present disclosure, $R_4$ is selected from H and Me, and other variables are as defined in the present disclosure.

In some embodiments of the present disclosure, ring A is selected from furanyl, oxazolyl, isoxazolyl, thienyl, thiazolyl, isothiazolyl, pyridyl and phenyl, wherein each of the furanyl, oxazolyl, isoxazolyl, thienyl, thiazolyl, isothiazolyl, pyridyl and phenyl is optionally substituted by one, two or three $R_a$, and other variables are as defined in the present disclosure.

In some embodiments of the present disclosure, ring A is selected from

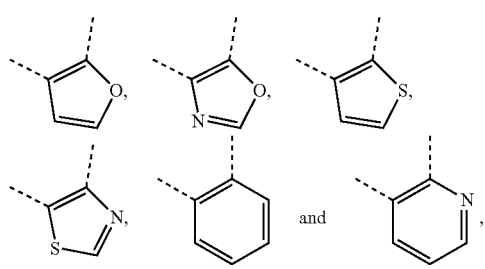

wherein each of the

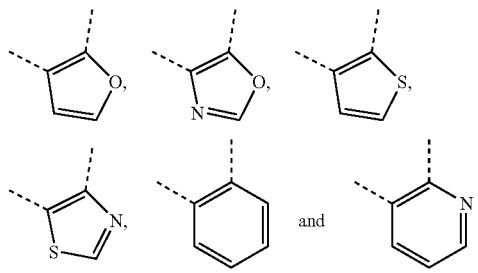

is optionally substituted by one, two or three $R_a$, and other variables are as defined in the present disclosure.

In some embodiments of the present disclosure, ring A is selected from

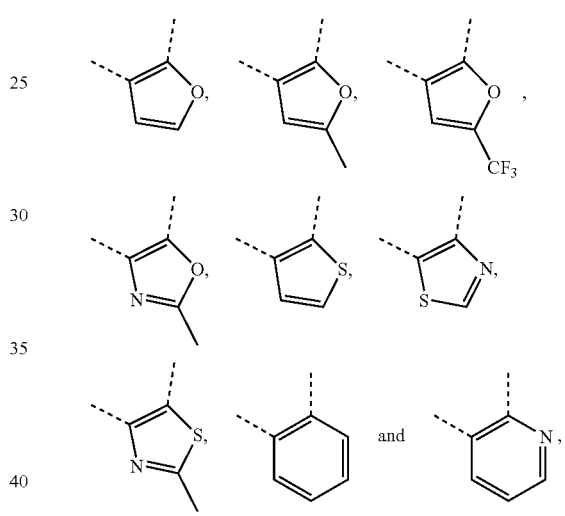

and other variables are as defined in the present disclosure.

In some embodiments of the present disclosure, in the compound, the isomer thereof or the pharmaceutically acceptable salt thereof, the moiety

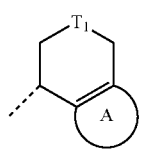

is selected from

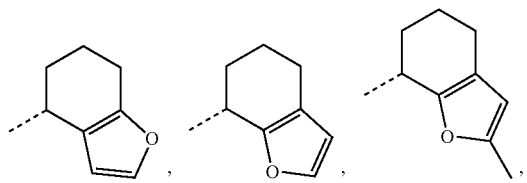

-continued

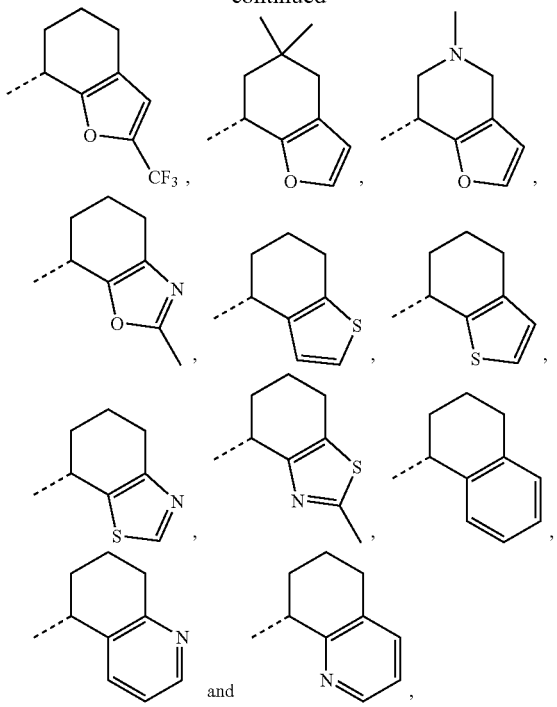

and other variables are as defined in the present disclosure.

The present disclosure also provides a compound of formula (I), an isomer thereof, or a pharmaceutically acceptable salt thereof,

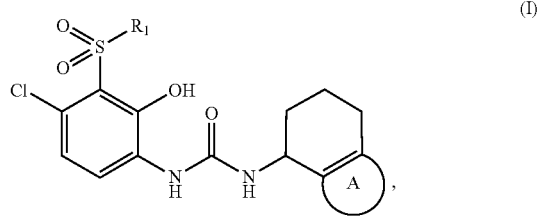
(I)

wherein,
ring A is selected from 5-6 membered heteroaryl;
$R_1$ is selected from $C_{1-6}$ alkyl, $NH_2$—(C═O)—$C_{1-3}$ alkyl-, 5-10 membered heteroaryl-$C_{1-3}$ alkyl-, $C_{3-7}$ cycloalkyl, 5-6 membered heterocycloalkyl, 5-10 membered heteroaryl and phenyl, wherein each of the $C_{1-6}$ alkyl, $NH_2$—(C═O)—$C_{1-3}$ alkyl-, 5-10 membered heteroaryl-$C_{1-3}$ alkyl-, $C_{3-7}$ cycloalkyl, 5-6 membered heterocycloalkyl, 5-10 membered heteroaryl and phenyl is optionally substituted by one, two or three R;
each R is independently selected from H, F, Cl, Br, I, OH, $NH_2$, $C_{1-3}$ alkyl, $C_{1-3}$ alkyl-(C═O)—NH—, $C_{1-3}$ alkyl-O—(C═O)—NH—, $C_{3-6}$ cycloalkyl-(C═O)—NH— and $C_{1-6}$ alkyl-O—(C═O)—, wherein each of the $C_{1-3}$ alkyl, $C_{1-3}$ alkyl-(C═O)—NH—, $C_{3-6}$ cycloalkyl-(C═O)—NH— and $C_{1-6}$ alkyl-O—(C═O)— is optionally substituted by one, two or three R';
each R' is independently selected from F, Cl, Br, I, OH and $NH_2$;
each of the 5-6 membered heteroaryl, 5-10 membered heteroaryl and 5-6 membered heterocycloalkyl contains one, two, three or four heteroatoms or heteroatomic groups independently selected from —NH—, —C(═O)—, —O—, —S— and N.

In some embodiments of the present disclosure, R is selected from F, Cl, Br, I, OH, $NH_2$, Me, Et,

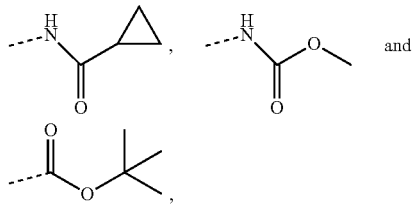

wherein each of the Me, Et,

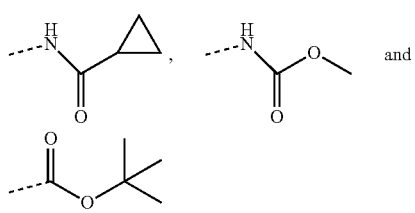

is optionally substituted by one, two or three R', and other variables are as defined in the present disclosure.

In some embodiments of the present disclosure, R is selected from F, Cl, Br, I, OH, $NH_2$,

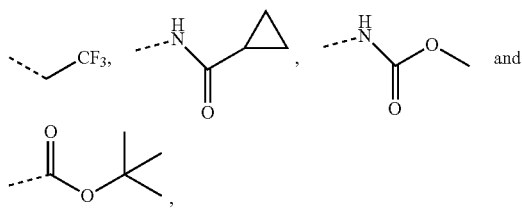

and other variables are as defined in the present disclosure.

In some embodiments of the present disclosure, $R_1$ is selected from methyl, ethyl, propyl, isopropyl, butyl, tert-butyl, $NH_2$—(C═O)—$CH_2$—, isoindoline-1,3-dione-$(CH_2)_2$—, cyclopropyl, cyclobutyl, cyclopentyl, cyclohexyl, piperidinyl, tetrahydropyranyl and tetrahydrofuranyl, wherein each of the methyl, ethyl, propyl, isopropyl, butyl, tert-butyl, $NH_2$—(C═O)—$CH_2$—, isoindoline-1,3-dione-$(CH_2)_2$—, cyclopropyl, cyclobutyl, cyclopentyl, cyclohexyl, piperidinyl, tetrahydropyranyl and tetrahydrofuranyl is optionally substituted by one, two or three R, and other variables are as defined in the present disclosure.

In some embodiments of the present disclosure, $R_1$ is selected from Me, Et,

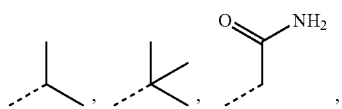

-continued

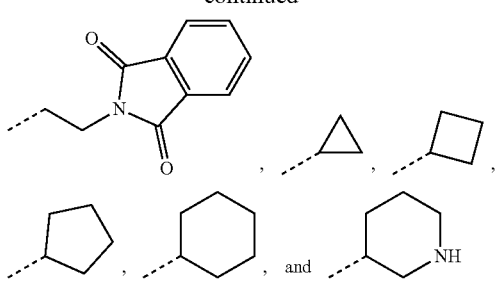

wherein each of the Me, Et,

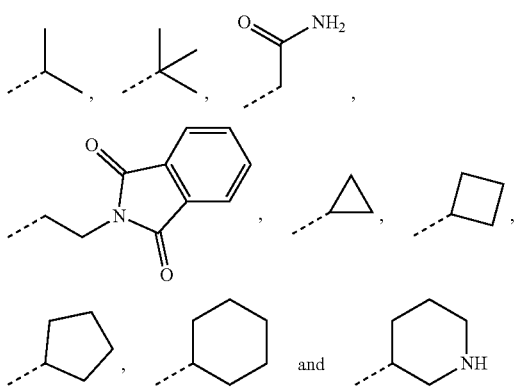

is optionally substituted by one, two or three R, and other variables are as defined in the present disclosure.

In some embodiments of the present disclosure, R₁ is selected from Me,

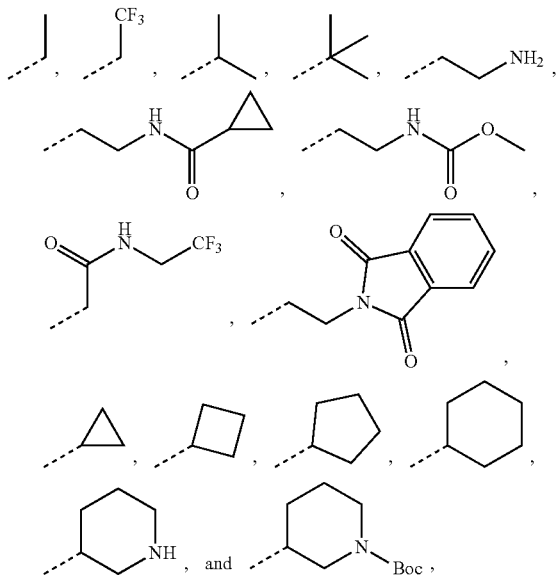

and other variables are as defined in the present disclosure.

In some embodiments of the present disclosure, ring A is furanyl, and other variables are as defined in the present disclosure.

In some embodiments of the present disclosure, the moiety

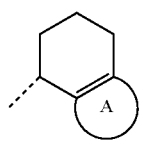

is selected from

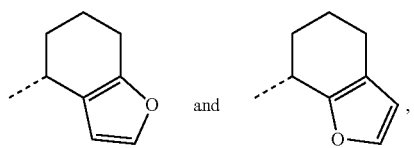

and other variables are as defined in the present disclosure.

Other embodiments of the present disclosure can be obtained by arbitrary combinations of the above variables.

In some embodiments of the present disclosure, the compound, the isomer thereof or the pharmaceutically acceptable salt thereof is selected from:

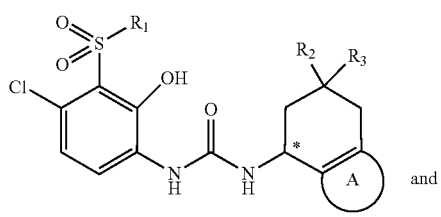

(II-A)

and (II-B)

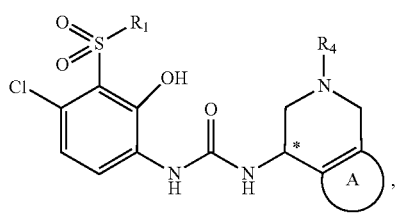

wherein,
R₁, R₂, R₃, R₄ and ring A are as defined in the present disclosure;
the carbon atom marked with "*" is a chiral carbon atom presented in the form of single (R) or (S) enantiomer or enriching in one enantiomer.

In some embodiments of the present disclosure, the compound, the isomer thereof or the pharmaceutically acceptable salt thereof is selected from:

(I-1)

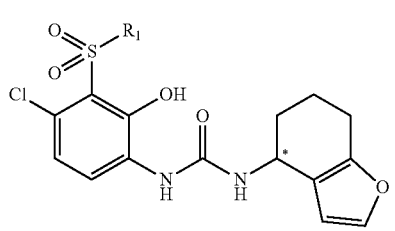

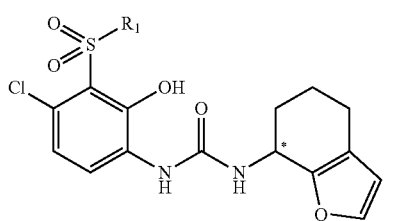
(I-2)
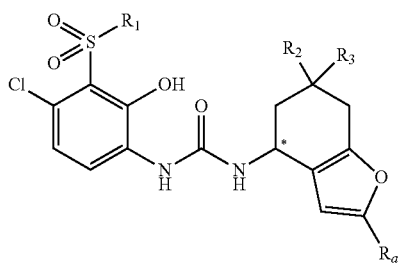
(II-1)
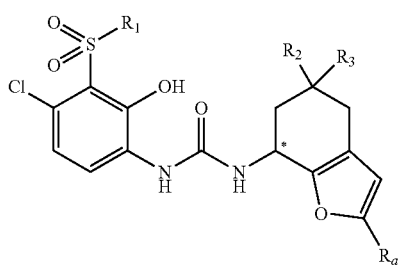
(II-2)
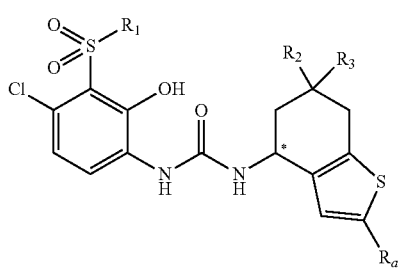
(II-3)
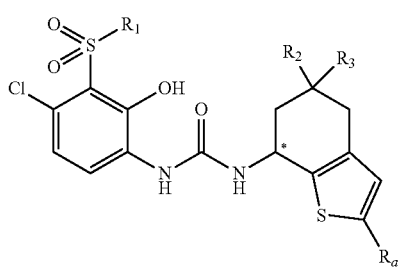
(II-4)
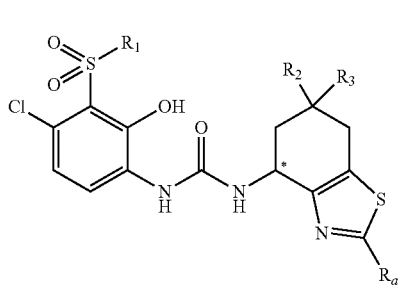
(II-5)
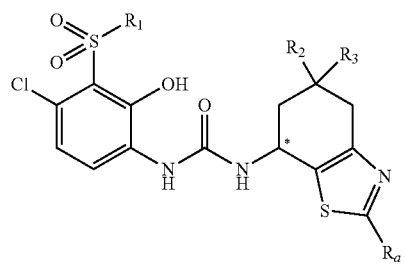
(II-6)
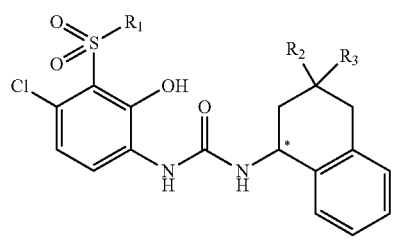
(II-7)
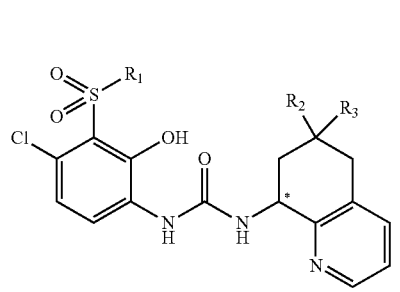
(II-8)
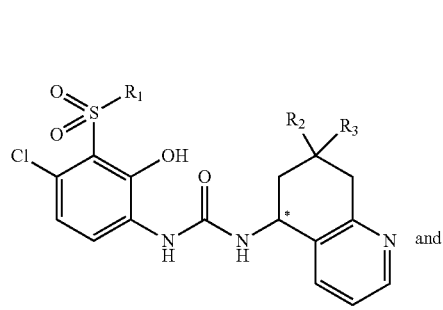
(II-9)
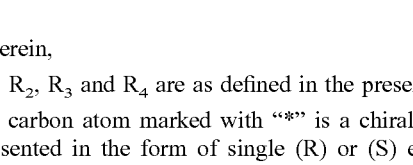
(II-10)
wherein,
$R_1$, $R_2$, $R_3$ and $R_4$ are as defined in the present disclosure;
the carbon atom marked with "*" is a chiral carbon atom presented in the form of single (R) or (S) enantiomer or enriching in one enantiomer of (R) or (S).

In some embodiments of the present disclosure, the compound, the isomer thereof or the pharmaceutically acceptable salt thereof is selected from:

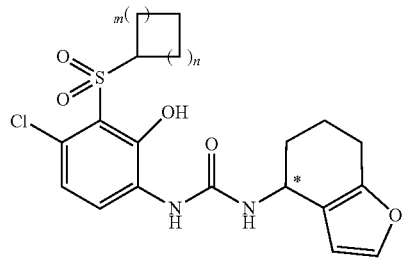
(I-3)

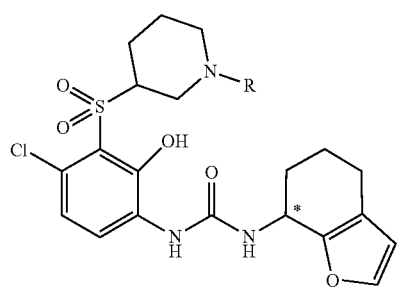
(I-4)

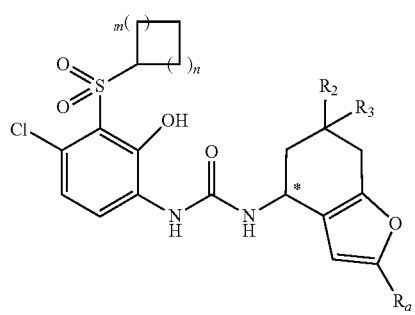
(II-11)

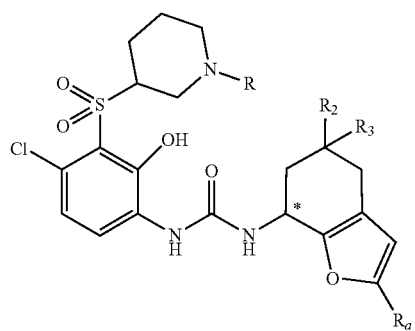
(II-12)

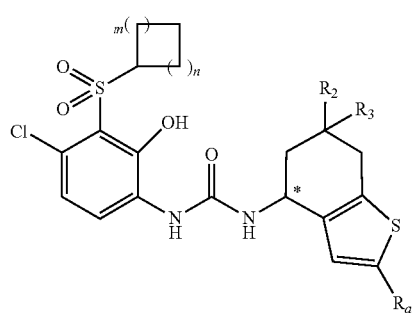
(II-13)

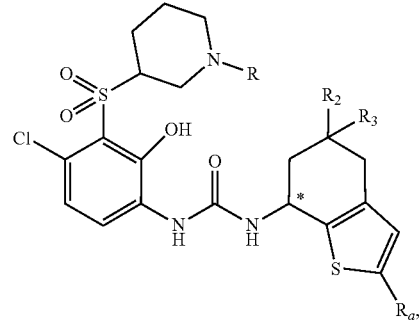
(II-14)

wherein, m is 0, 1 or 2;

n is 1 or 2;

$R_a$, $R_1$, $R_2$, $R_3$, $R_4$ and ring A are as defined in the present disclosure;

the carbon atom marked with "*" is a chiral carbon atom presented in the form of single (R) or (S) enantiomer or enriching in one enantiomer.

The present disclosure also provides a compound of any following formula, an isomer thereof, or a pharmaceutically acceptable salt thereof,

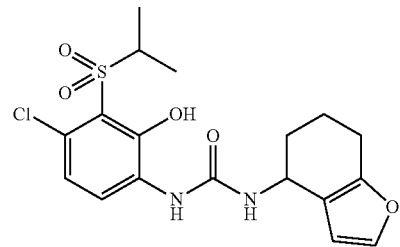

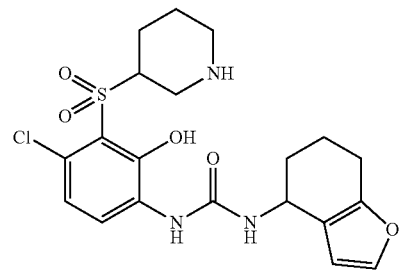

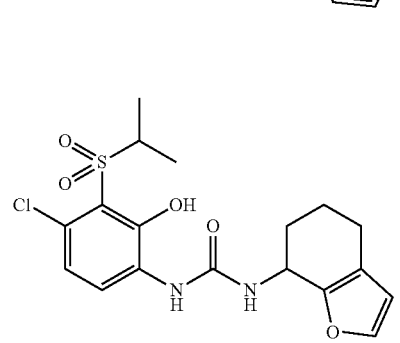

-continued
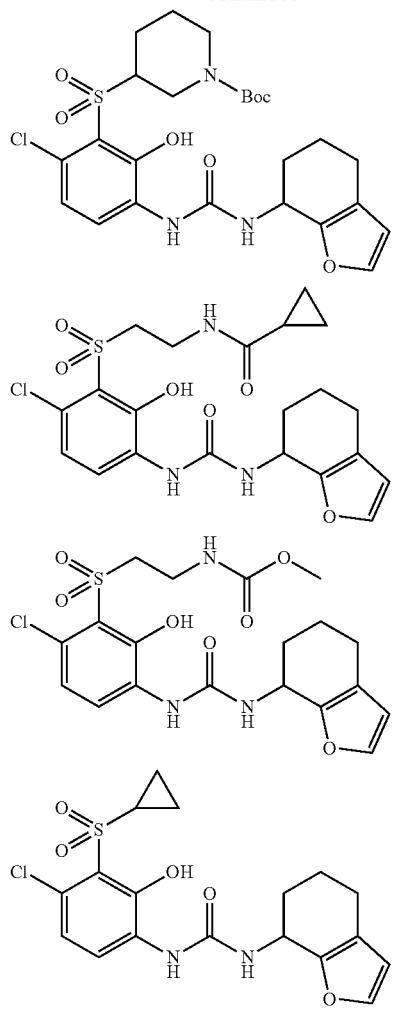
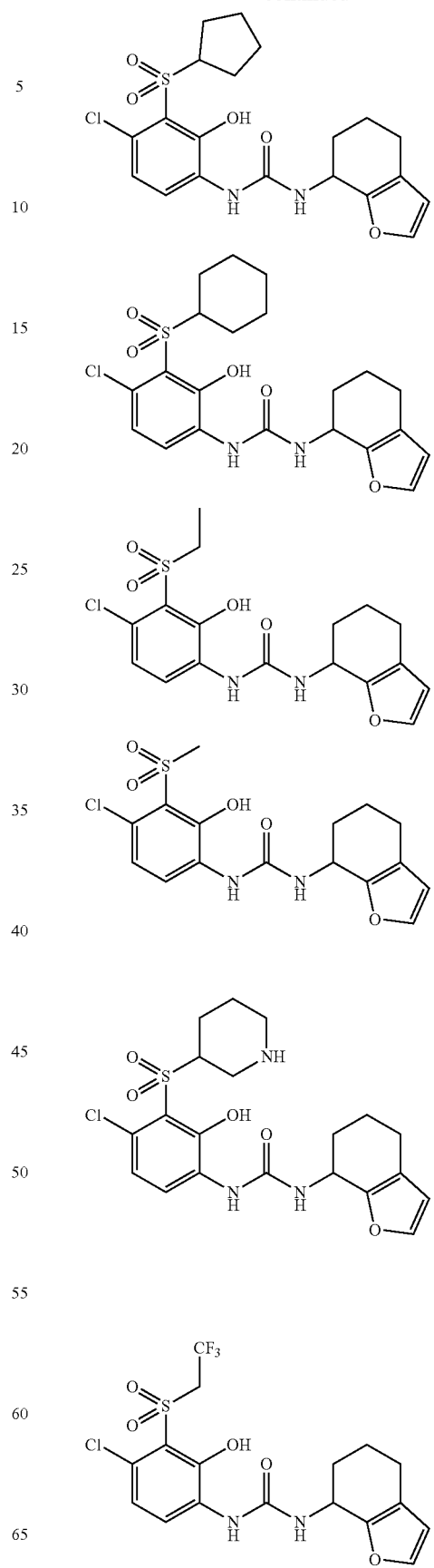

17
-continued
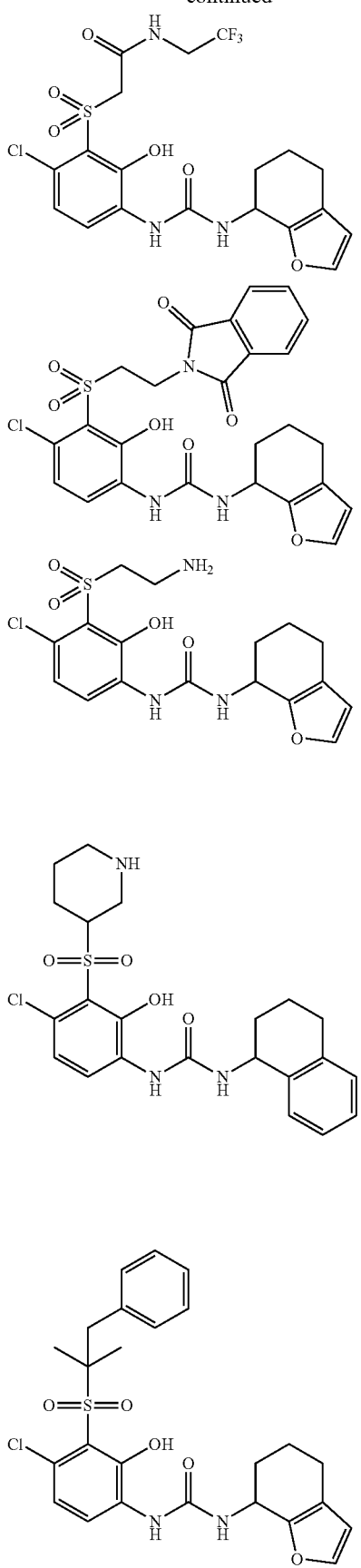
18
-continued
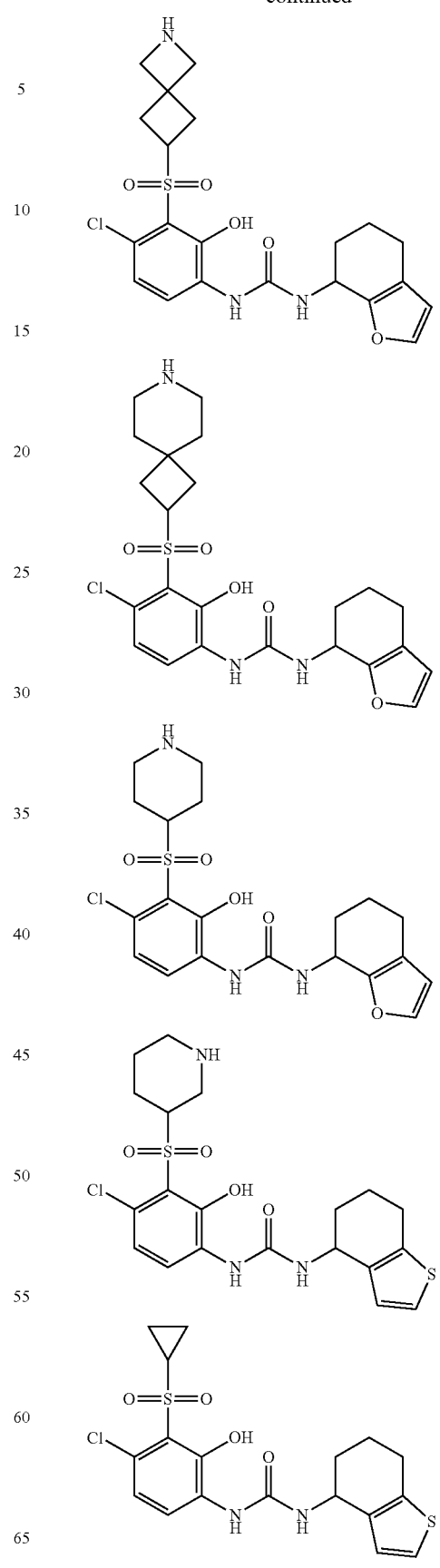

-continued
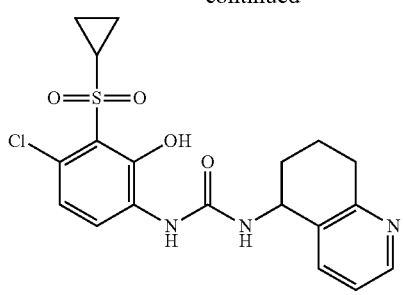
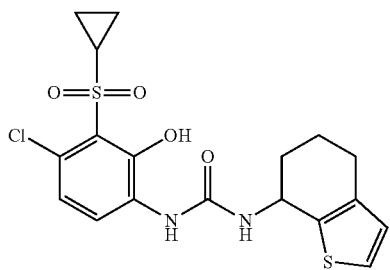
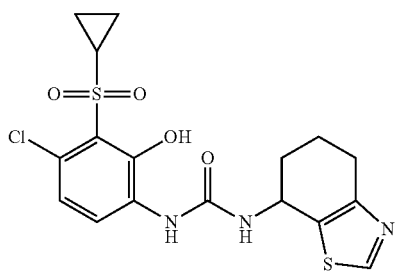
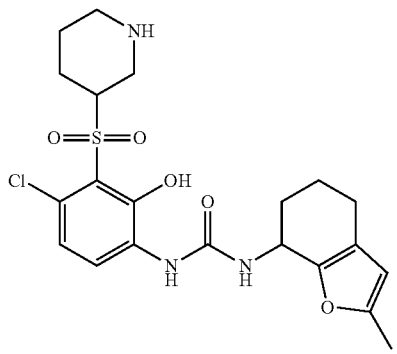
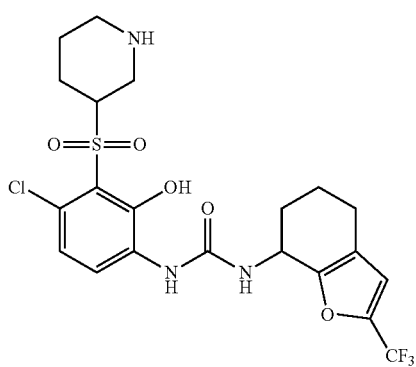
-continued
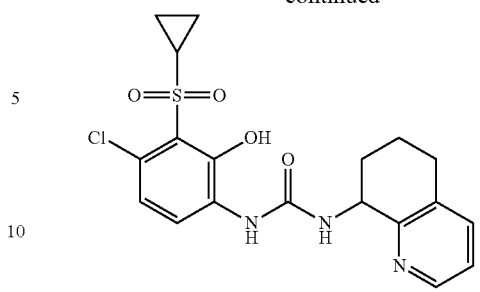
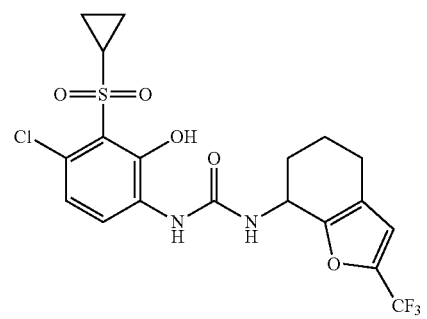
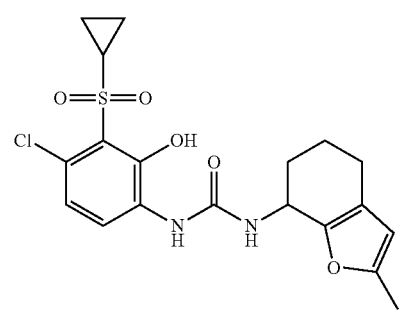
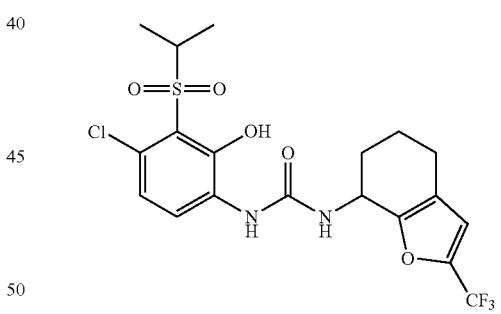
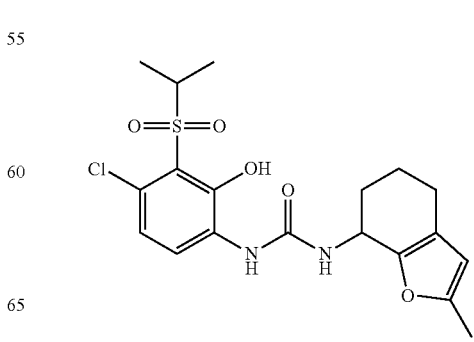

-continued
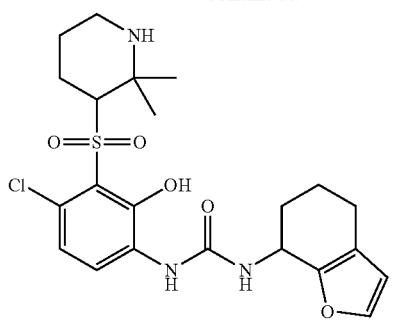
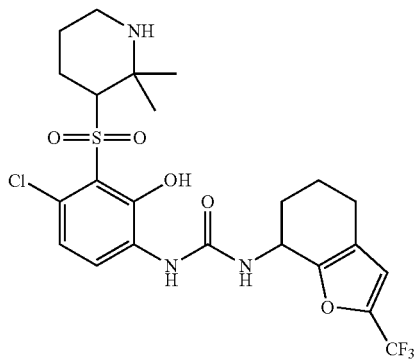
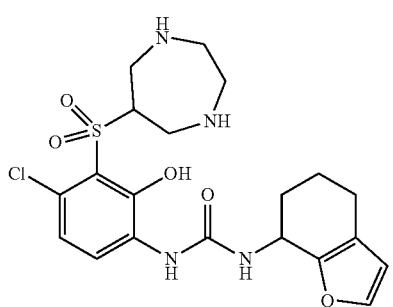
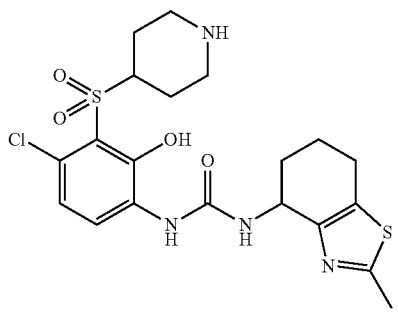
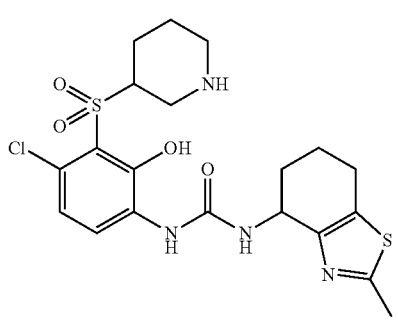
-continued
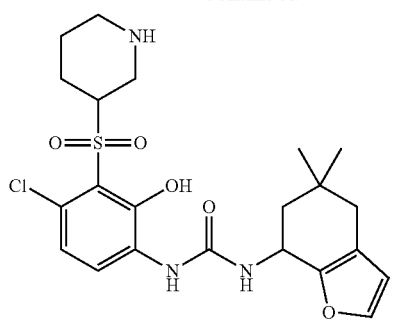
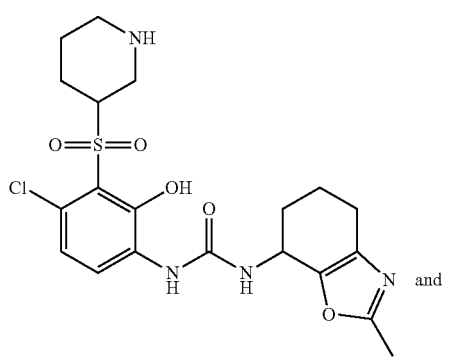
and
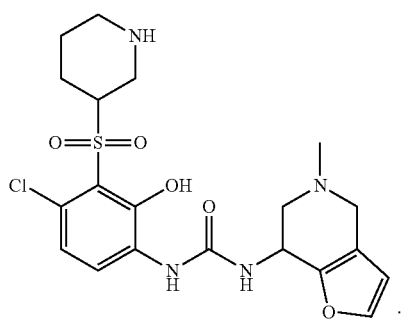 [SMILES: CN1Cc2ccoc2C(NC(=O)Nc2ccc(Cl)c(S(=O)(=O)[C@H]3CCCNC3)c2O)C1]
In some embodiments of the present disclosure, the compound, the isomer thereof or the pharmaceutically acceptable salt thereof is selected from
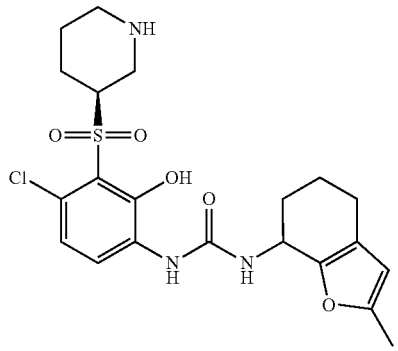

-continued
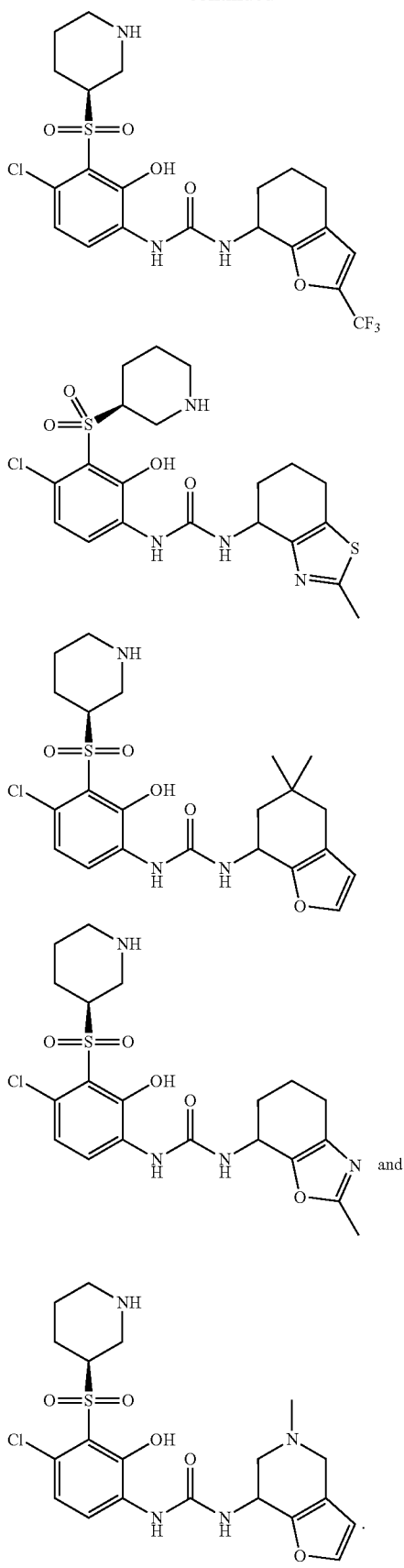
In some embodiments of the present disclosure, the compound, the isomer thereof or the pharmaceutically acceptable salt thereof is selected from

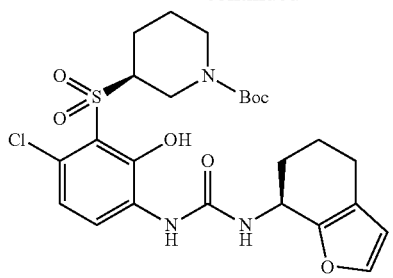
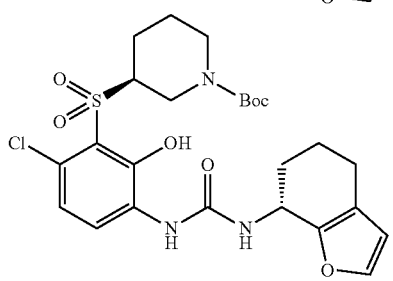
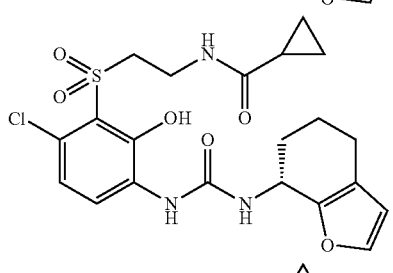
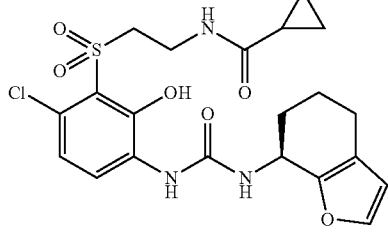
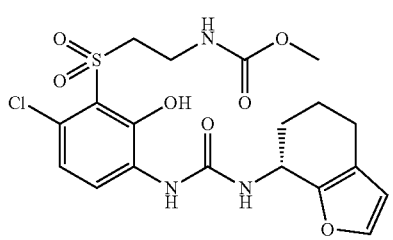
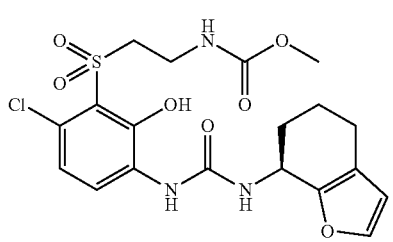
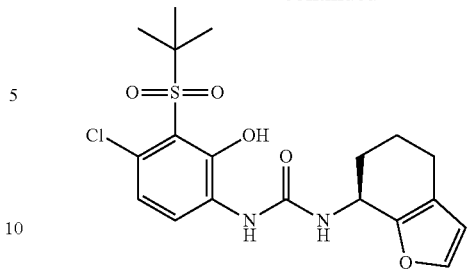
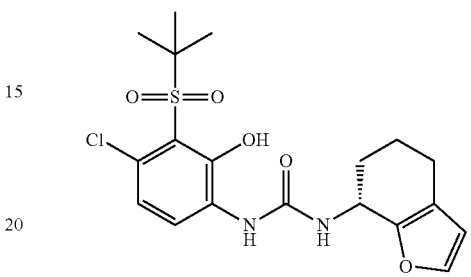
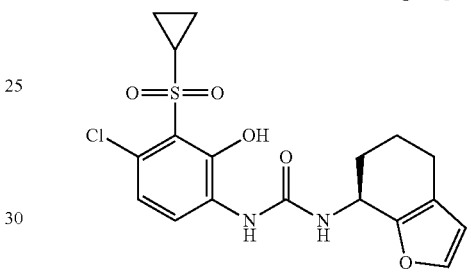
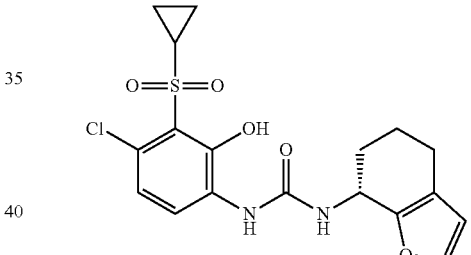
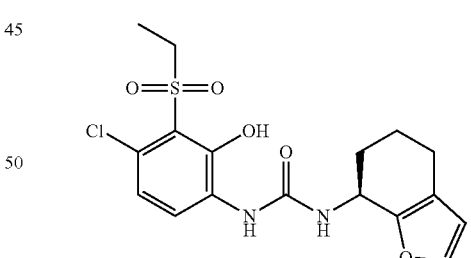
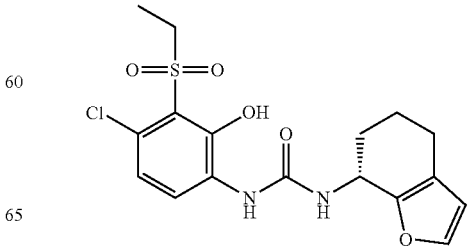

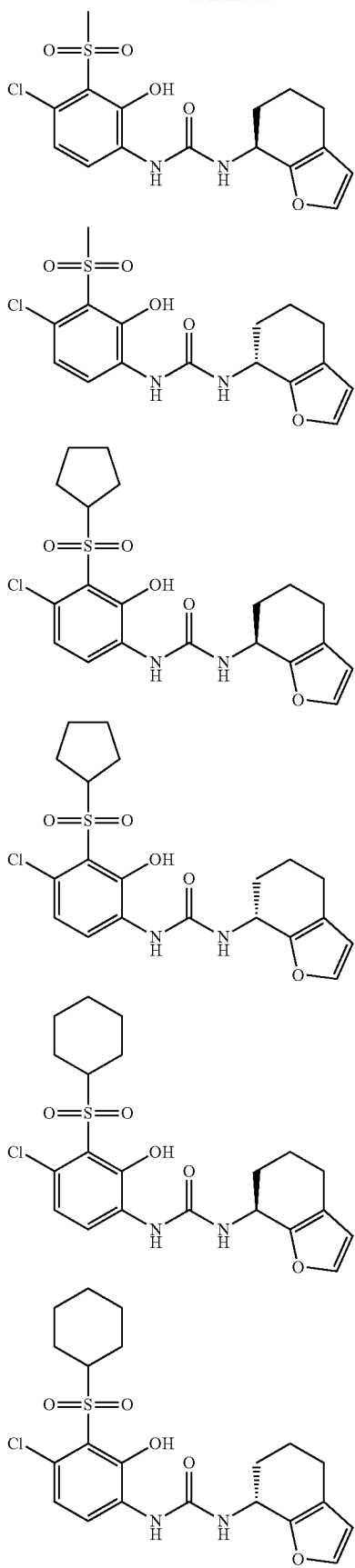
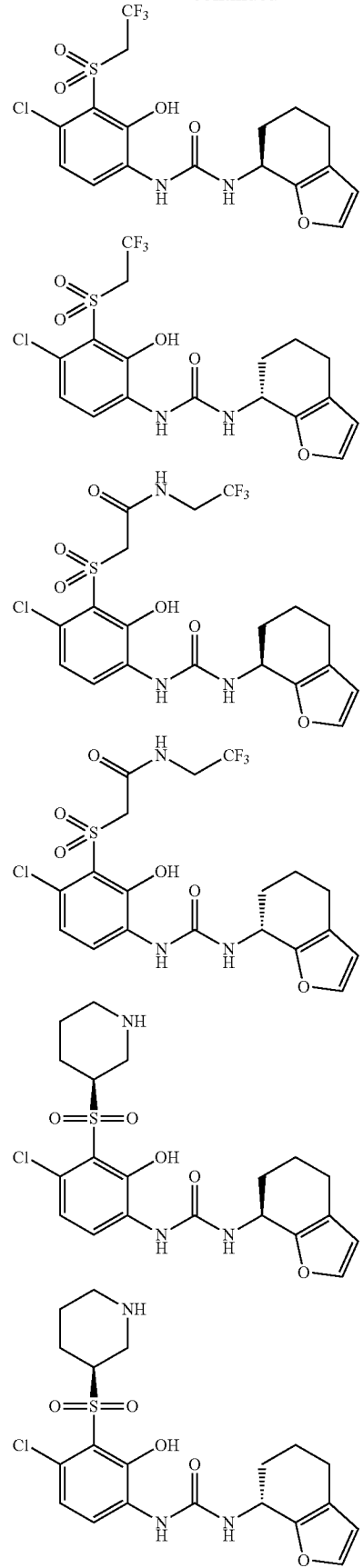

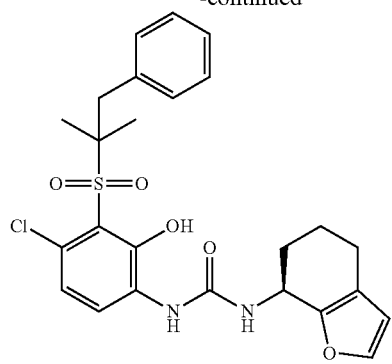
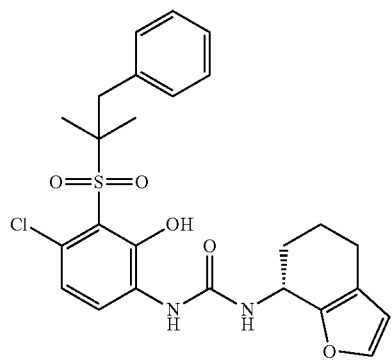
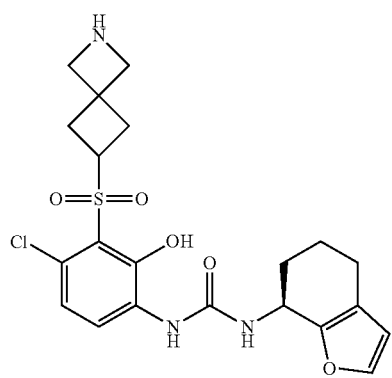
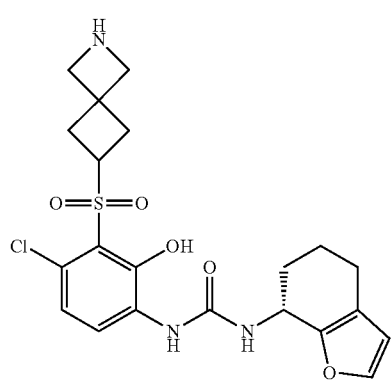
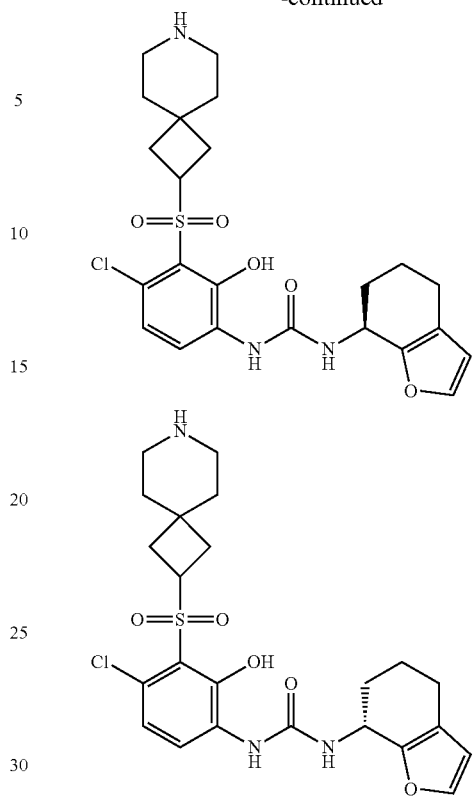
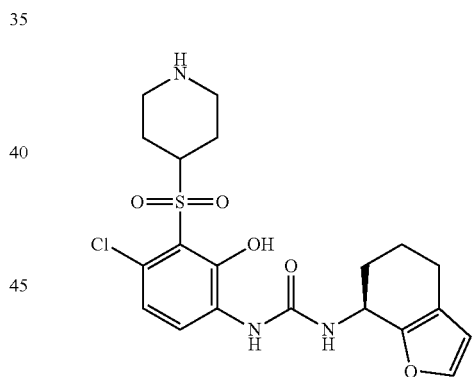
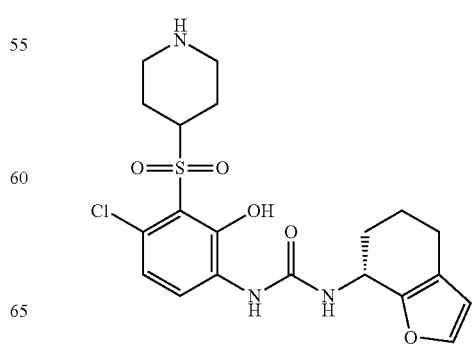

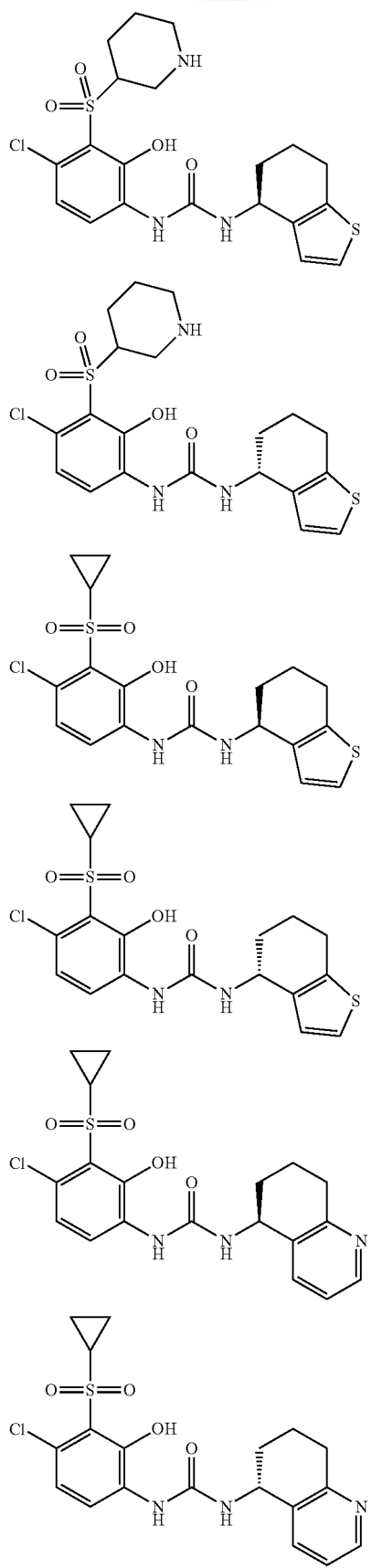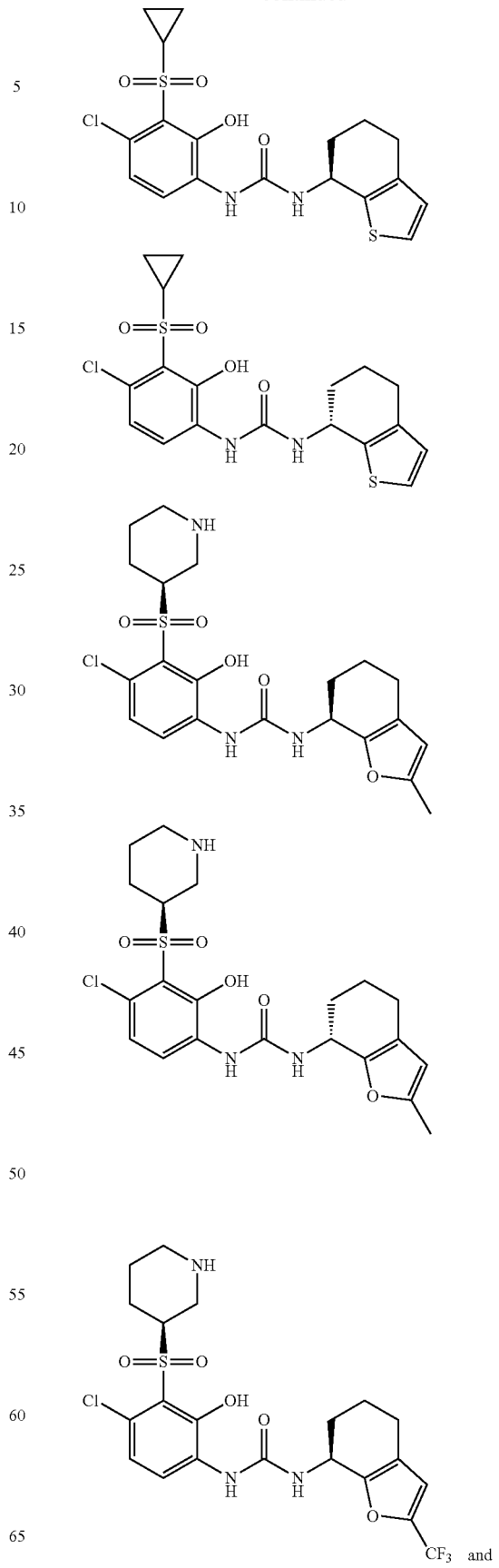

-continued

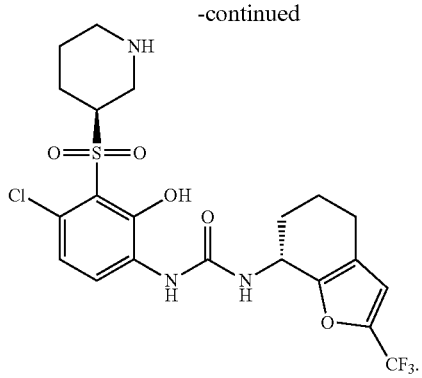

The present disclosure also provides a pharmaceutical composition, which comprises a therapeutically effective amount of the compound, the isomer thereof or the pharmaceutically acceptable salt thereof as an active ingredient, and a pharmaceutically acceptable carrier.

The present disclosure also provides a use of the compound or the pharmaceutically acceptable salt thereof, or the pharmaceutical composition in the manufacture of a medicament for the treatment of a CXCR2 related disease.

In some embodiments of the present disclosure, in the use, the medicament is a medicament for treating COPD.

Technical Effect

The compound of the present disclosure has a strong antagonistic effect on CXCR2; compared with the reference compound, the compound of the present disclosure has a decreased clearance rate, greatly reduced plasma exposure, as well as greatly improved bioavailability in mice.

Definition and Description

Unless otherwise indicated, the following terms used in the description and the claims of the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof. The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the neutral form of the compound into contact with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by bringing the neutral form of the compound into contact with a sufficient amount of acid in a pure solution or a suitable inert solvent.

Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and an salt of amino acid (such as arginine and the like), and a salt of an organic acid such as glucuronic acid and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

In addition to the salt form, the compound provided by the present disclosure also exists in prodrug form. The prodrug of the compound described herein is the compound that readily undergoes chemical change under physiological condition to convert into the compound of the present disclosure. Additionally, the prodrug can be converted to the compound of the present disclosure by a chemical or biochemical method in vivo environment.

Certain compounds of the present disclosure can also be presented in a nonsolvated form or a solvated form, including hydrated form. Generally, the solvated form is equivalent to the nonsolvated form, and both are encompassed within the scope of the present disclosure.

The compound of the present disclosure may have a specific geometric or stereoisomeric form. The present disclosure contemplates all such compounds, including cis and trans isomer, (−)- and (+)-enantiomer, (R)- and (S)-enantiomer, diastereomer, (D)-isomer, (L)-isomer, and racemic mixture and other mixtures, for example, an enantiomer or diastereomer enriched mixture, all of which are encompassed within the scope of the present disclosure. The substituent such as alkyl can have an additional asymmetric carbon atom. All these isomers and mixtures thereof are encompassed within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability of a double bond or a single bond of carbon atoms on the ring to freely rotate.

Unless otherwise specified, the term "diastereomer" refers to stereoisomers in which the molecules have two or more chiral centers and are not mirror images of each other.

Unless otherwise specified, "(D)" or "(+)" refers to dextrorotation, "(L)" or "(−)" refers to levorotation, "(DL)" or "(±)" refers to racemization.

Unless otherwise specified, the absolute configuration of a stereogenic center is represented by a wedged solid bond ( ◢ ) and a wedged dashed bond ( ◌ ), and the relative configuration of a stereogenic center is represented by a straight solid bond ( ◢ ) and a straight dashed bond ( ◌ ).

A wave line (⌒) represents a wedged solid bond (◆) or a wedged dashed bond (◇), or represents a straight solid bond (◆) or a straight dashed bond (◇).

The compounds of the present disclosure may be present in particular. Unless otherwise indicated, the term "tautomer" or "tautomeric form" refer to the fact that the isomers with different functional groups are in dynamic equilibrium at room temperature and can be rapidly converted into each other. If tautomers are possible (e.g., in solution), the chemical equilibrium of the tautomers can be achieved. For example, proton tautomers (also known as prototropic tautomers) include interconversions by proton migration, such as keto-enol isomerization and imine-enamine isomerization. Valence tautomers include the mutual transformation caused by bonding electrons transfer. A specific example of keto-enol tautomerization is the interconversion between two tautomers pentane-2,4-dione and 4-hydroxypent-3-en-2-one.

Unless otherwise specified, the term "enriched in one isomer", "isomer enriched", "enriched in one enantiomer" or "enantiomer enriched" refers to the content of one of the isomers or enantiomers is less than 100%, and the content of this isomer or enantiomer is 60% or more, or 70% or more, or 80% or more, or 90% or more, or 95% or more, or 96% or more, or 97% or more, or 98% or more, or 99% or more, or 99.5% or more, or 99.6% or more, or 99.7% or more, or 99.8% or more, or 99.9% or more.

Unless otherwise specified, the term "excess of isomer" or "excess of enantiomer" refers to the difference between the relative percentages of the two isomers or enantiomers. For example, wherein, the content of one of the isomers or enantiomers is 90%, and the other one is 10%, then the excess of isomer or enantiomer (ee value) is 80%.

Optically active (R)- and (S)-isomer, or D and L isomer can be prepared using chiral synthesis or chiral reagents or other conventional techniques. If one kind of enantiomers of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form salts in the form of diastereomers which are then subjected to diastereomeric resolution through conventional methods in the art to give the pure enantiomer. In addition, the enantiomer or diastereomer is generally isolated through chromatography which uses a chiral stationary phase and optionally combines with a chemical derivative method (such as carbamate generated from amine). The compound of the present disclosure may contain an unnatural proportion of atomic isotope at one or more atoms that constitute the compound. For example, the compound can be radiolabeled with a radioactive isotope, such as tritium ($^3$H), iodine-125 ($^{125}$I) or C-14 ($^{14}$C). For another example, hydrogen can be replaced by heavy hydrogen to form a deuterated drug, and the bond formed by deuterium and carbon atoms is stronger than the bond formed by ordinary hydrogen and carbon atoms. Compared with undeuterated drugs, deuterated drugs have advantages such as reduced side effects, increased drug stability, enhanced efficacy and prolonged biological half-life. All isotopic variations of the compound of the present disclosure, whether radioactive or not, are encompassed within the scope of the present disclosure.

"Optional" or "optionally" means that the subsequent event or condition may occur but not requisite, that the term includes the instance in which the event or condition occurs and the instance in which the event or condition does not occur.

The term "substituted" means one or more hydrogen atoms on a specific atom are substituted with a substituent, including deuterium and hydrogen variants, as long as the valence of the specific atom is normal and the substituted compound is stable. When the substituent is an oxygen (i.e., =O), it means two hydrogen atoms are substituted. Positions on an aromatic ring cannot be substituted with an oxo group. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound.

When the number of a linking group is 0, such as —(CRR)$_0$—, it means that the linking group is a single bond.

When a variable is selected from a single bond, it means that the two groups linked by the single bond are connected directly. For example, when L in A-L-Z represents a single bond, the structure of A-L-Z is actually A-Z.

When a substituent is vacant, it means that the substituent does not exist. For example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When an enumerative linking group does not indicate the direction for linking, the direction for linking is arbitrary, for example, the linking group L contained in

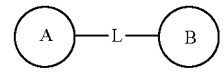

is -M-W—, then -M-W— can link ring A and ring B to form

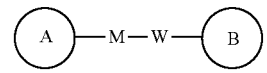

in the direction same as left-to-right reading order, and form

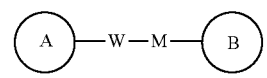

in the direction contrary to left-to-right reading order. A combination of substituents and/or variants thereof is allowed only when such combination can result in a stable compound.

Unless otherwise specified, the term "hetero" represents a heteroatom or a heteroatomic group (e.g., an atomic group containing a heteroatom), including the atom except carbon (C) and hydrogen (H) and the atomic group containing the above heteroatom, for example, including oxygen (O), nitrogen (N), sulfur (S), silicon (Si), germanium (Ge), aluminum (Al), boron (B), —O—, —S—, —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—, each of the —C(=O)N(H)—, —N(H)—, —C(=NH)—, —S(=O)$_2$N(H)— and —S(=O)N(H)— is optionally substituted.

Unless otherwise specified, the term "ring" refers to a substituted or unsubstituted cycloalkyl, heterocycloalkyl, cycloalkenyl, heterocycloalkenyl, cycloalkynyl, heterocycloalkynyl, aryl or heteroaryl. The so-called ring includes a monocyclic system, and also includes bicyclic and polycyclic systems, e.g., a spiro ring, a fused ring or a bridged ring. The number of the atom on the ring is usually defined as the membered number of the ring, for example, a "5-7 membered ring" means that 5 to 7 atoms are arranged on the ring. Unless otherwise specified, the ring optionally contains 1 to 3 heteroatoms. Therefore, a "5-7 membered ring" includes, for example, phenyl, pyridinyl and piperidinyl; on the other hand, the term "5-7 membered heterocycloalkyl" includes pyridyl and piperidinyl, but excluding phenyl. The term "ring" also includes a ring system containing at least one ring, wherein each ring independently meets the above definition.

Unless otherwise specified, the term "alkyl" refers to a linear chain or branched chain saturated hydrocarbon group. In some embodiments, the alkyl is $C_{1-12}$ alkyl; in some other embodiments, the alkyl is $C_{1-6}$ alkyl; in some other embodiments, the alkyl is $C_{1-3}$ alkyl. It can be mono-substituted (e.g., —CH$_2$F) or poly-substituted (e.g., —CF$_3$), can be monovalent (e.g. methyl), divalent (e.g., methylene) or multivalent (e.g., methylidyne). Examples of alkyl include methyl (Me), ethyl (Et), propyl (such as n-propyl and isopropyl), butyl (such as n-butyl, isobutyl, s-butyl, tert-butyl), pentyl (such as n-pentyl, isopentyl, neopentyl) and hexyl and the like.

Unless otherwise specified, the term "alkenyl" refers to a linear chain or branched chain hydrocarbon group having one or more carbon-carbon double bonds at any position of the group. In some embodiments, the alkenyl is $C_{2-8}$ alkenyl; in some other embodiments, the alkenyl is $C_{2-6}$ alkenyl; in some other embodiments, the alkenyl is $C_{2-4}$ alkenyl. It can be mono-substituted or poly-substituted, and can be monovalent, divalent or multivalent. Examples of the alkenyl include ethenyl, propenyl, butenyl, pentenyl, hexenyl, butadienyl, pentadienyl, hexadienyl, and the like.

Unless otherwise specified, the term "alkynyl" refers to a linear chain or branched chain hydrocarbon group having one or more carbon-carbon triple bonds at any position of the group. In some embodiments, the alkynyl is $C_{2-8}$ alkynyl; in some other embodiments, the alkynyl is $C_{2-6}$ alkynyl; in some other embodiments, the alkynyl is $C_{2-4}$ alkynyl. It can be mono-substituted or poly-substituted, and can be monovalent, divalent or multivalent. Examples of the alkynyl include ethynyl, propynyl, butynyl, pentynyl, and the like.

Unless otherwise specified, the term "heteroalkyl", by itself or in combination with another term, refers to a stable linear or branched chain hydrocarbon group or a combination thereof having a specified number of carbon atoms and at least one heteroatom or heteroatomic group. In some embodiments, the heteroatom is selected from B, O, N and S, wherein the nitrogen and sulfur atoms are optionally oxidized and the nitrogen atom is optionally quaternized. In some other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkyl is $C_{1-6}$ heteroalkyl; in some other embodiments, the heteroalkyl is $C_{1-3}$ heteroalkyl. The heteroatom or heteroatomic group can be located at any interior position of the heteroalkyl, including the position where the alkyl attaches to the rest of the molecule. But the terms "alkoxy", "alkylamino" and "alkylthio" (or thioalkoxy) are used in their conventional meanings and refer to an alkyl group connected to the rest of the molecule via an oxygen atom, an amino or a sulfur atom respectively. Examples of the heteroalkyl include, but not limited to, —OCH$_3$, —OCH$_2$CH$_3$, —OCH$_2$CH$_2$CH$_3$, —OCH$_2$(CH$_3$)$_2$, —CH$_2$—CH$_2$—O—CH$_3$, —NHCH$_3$, —N(CH$_3$)$_2$, —NHCH$_2$CH$_3$, —N(CH$_3$)(CH$_2$CH$_3$), —CH$_2$—CH$_2$—NH—CH$_3$, —CH$_2$—CH$_2$—N(CH$_3$)—CH$_3$, —SCH$_3$, —SCH$_2$CH$_3$, —SCH$_2$CH$_2$CH$_3$, —SCH$_2$(CH$_3$)$_2$, —CH$_2$—S—CH$_2$—CH$_3$, —CH$_2$—CH$_2$—, —S(=O)—CH$_3$, —CH$_2$—CH$_2$—S(=O)$_2$—CH$_3$, —CH=CH—O—CH$_3$, —CH$_2$—CH=N—OCH$_3$ and —CH=CH—N(CH$_3$)—CH$_3$. Up to two consecutive heteroatoms can be present, such as, —CH$_2$—NH—OCH$_3$.

Unless otherwise specified, the term "heteroalkenyl", by itself or in combination with another term, refers to a stable linear or branched chain alkenyl group or a combination thereof having a specified number of carbon atoms and at least one heteroatom or heteroatomic group. In some embodiments, the heteroatom is selected from B, O, N and S, wherein the nitrogen and sulfur atoms are optionally oxidized and the nitrogen atom is optionally quaternized. In some other embodiments, the heteroatomic group is selected from C(=O)O—, —C(=O)—, —C(=S)—, —S(=O), —S(=O)$_2$, —C(=O)N(H)—, —N(H)—, —C(=NH)—, —S(=O)$_2$N(H)— and —S(=O)N(H)—. In some embodiments, the heteroalkenyl is $C_{2-6}$ heteroalkenyl; in some other embodiments, the heteroalkenyl is $C_{2-4}$ heteroalkenyl. The heteroatom or heteroatomic group can be located at any interior position of the heteroalkenyl, including the position where the alkenyl attaches to the rest of the molecule. But the terms "alkenyloxy", "alkenylamino" and "alkenylthio" are used in their conventional meanings and refer to an alkenyl group connected to the rest of the molecule via an oxygen atom, an amino or a sulfur atom respectively. Examples of the heteroalkenyl include, but not limited to, —O—CH=CH$_2$, —O—CH=CHCH$_3$, —O—CH=C(CH$_3$)$_2$, —CH=CH—O—CH$_3$, —O—CH=CHCH$_2$CH$_3$, —CH$_2$CH=CH—OCH$_3$, —NH—CH=CH$_2$, —N(CH=CH$_2$)—CH$_3$, —CH=CH—NH—CH$_3$, —CH=CH—N(CH$_3$)$_2$, —S—CH=CH$_2$, —S—CH=CHCH$_3$, —S—CH=C(CH$_3$)$_2$, —CH$_2$—S—CH=CH$_2$, —S(=O)—CH=CH$_2$ and —CH=CH—S(=O)$_2$—CH$_3$. Up to two consecutive heteroatoms can be present, such as, —CH=CH—NH—OCH$_3$.

Unless otherwise specified, the term "heteroalkynyl", by itself or in combination with another term, refers to a stable linear or branched chain alkynyl group or a combination thereof having a specified number of carbon atoms and at least one heteroatom or heteroatomic group. In some embodiments, the heteroatom is selected from B, O, N and S, wherein the nitrogen and sulfur atoms are optionally oxidized and the nitrogen atom is optionally quaternized. In some other embodiments, the heteroatomic group is selected from —C(=O)O—, —C(=O)—, —C(=S)—, —S(=O), —S(=O)$_2$—, —C(=O)N(H)—, —N(H)—, —C(=NH)—, —S(=O)$_2$N(H)— and —S(=O)N(H)—. In some embodiments, the heteroalkynyl is C$_{2-6}$ heteroalkynyl; in some other embodiments, the heteroalkynyl is C$_{2-4}$ heteroalkynyl. The heteroatom or heteroatomic group can be located at any interior position of the heteroalkynyl, including the position where the alkynyl attaches to the rest of the molecule. But the terms "alkynyloxy", "alkynylamino" and "alkynylthio" are used in their conventional meanings and refer to an alkynyl group connected to the rest of the molecule via an oxygen atom, an amino or a sulfur atom respectively. Examples of the heteroalkynyl include, but not limited to,

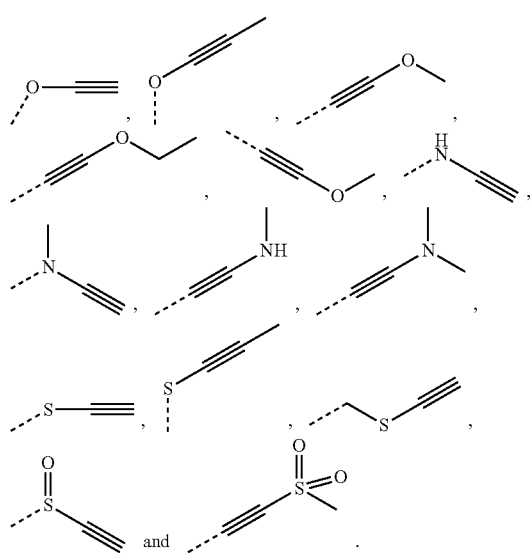

Up to two consecutive heteroatoms can be present, such as

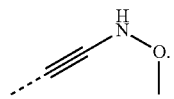

Unless otherwise specified, "cycloalkyl" includes any stable cyclic alkyl groups including monocyclic, bicyclic, or tricyclic systems, wherein the bicyclic and tricyclic systems include spiro, fused, and bridged rings. In some embodiments, the cycloalkyl is C$_{3-8}$ cycloalkyl; in some other embodiments, the cycloalkyl is C$_{3-6}$ cycloalkyl; in some other embodiments, the cycloalkyl is C$_{5-6}$ cycloalkyl. It can be mono-substituted or poly-substituted, and can be monovalent, divalent or multivalent. Examples of the cycloalkyl include, but not limited to, cyclopropyl, cyclobutyl, cyclopentyl, cyclohexyl, cycloheptyl, norbornanyl, [2.2.2]bicyclooctane, [4.4.0]bicyclodecane and the like.

Unless otherwise specified, "cycloalkenyl" includes any stable cyclic alkenyl group having one or more unsaturated carbon-carbon double bonds at any position of the group, including monocyclic, bicyclic, or tricyclic systems, wherein the bicyclic and tricyclic systems include spiro, fused, and bridged rings, but any ring in these systems is non-aromatic. In some embodiments, the cycloalkenyl is C$_{3-8}$ cycloalkenyl; in some other embodiments, the cycloalkenyl is C$_{3-6}$ cycloalkenyl; in some other embodiments, the cycloalkenyl is C$_{5-6}$ cycloalkenyl. It can be mono-substituted or poly-substituted, and can be monovalent, divalent or multivalent. Examples of the cycloalkenyl include, but not limited to, cyclopentenyl, cyclohexenyl and the like.

Unless otherwise specified, "cycloalkynyl" includes any stable cyclic alkynyl groups having one or more carbon-carbon triple bonds at any position of the group, including monocyclic, bicyclic, or tricyclic systems, wherein the bicyclic and tricyclic systems include spiro, fused, and bridged rings. It can be mono-substituted or poly-substituted, and can be monovalent, divalent or multivalent.

Unless otherwise specified, the term "heterocycloalkyl", by itself or in combination with another term, refers to a cyclized "heteroalkyl", including monocyclic, bicyclic, or tricyclic systems, wherein the bicyclic and tricyclic systems include spiro, fused, and bridged rings. In addition, in terms of the "heterocycloalkyl", the heteroatom can occupy the position through which the heterocycloalkyl is attached to the remainder of the molecule. In some embodiments, the heterocycloalkyl is a 4-6 membered heterocycloalkyl; in some other embodiments, the heterocycloalkyl is a 5-6 membered heterocycloalkyl. Examples of the heterocycloalkyl include, but not limited to, azetidinyl, oxetanyl, thiacyclobutanyl, pyrrolidinyl, pyrazolidinyl, imidazolidinyl, tetrahydrothiophenyl (including tetrahydrothiophen-2-yl and tetrahydrothiophen-3-yl etc.), tetrahydrofuranyl (including tetrahydrofuran-2-yl etc.), tetrahydropyranyl, piperidinyl (including 1-piperidinyl, 2-piperidinyl and 3-piperidinyl etc.), piperazinyl (including 1-piperazinyl and 2-piperazinyl etc.), morpholinyl (including 3-morpholinyl and 4-morpholinyl etc.), dioxanyl, dithianyl, isoxazolidinyl, isothiazolidinyl, 1,2-oxazinyl, 1,2-thiazinyl, hexahydropyridazinyl, homopiperazinyl, homopiperidinyl or oxepanyl.

Unless otherwise specified, the term "heterocycloalkenyl", by itself or in combination with another term, refers to a cyclized "heteroalkenyl", including monocyclic, bicyclic, or tricyclic systems, wherein the bicyclic and tricyclic systems include spiro, fused, and bridged rings, but any ring in these systems is non-aromatic. In addition, in terms of the "heterocycloalkenyl", the heteroatom can occupy the position through which the heteroalkenyl is attached to the remainder of the molecule. In some embodiments, the heterocycloalkenyl is a 4-6 membered heterocycloalkenyl; in other embodiments, the heterocycloalkenyl is a 5-6 membered heterocycloalkenyl. Examples of the heterocycloalkenyl include, but not limited

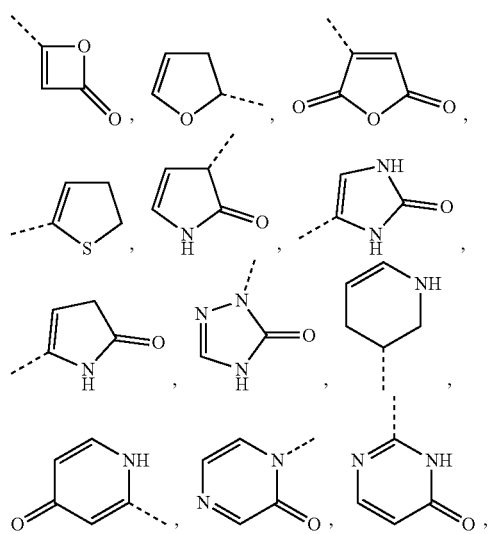

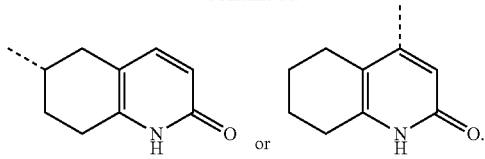

Unless otherwise specified, the term "heterocycloalkynyl", by itself or in combination with another term, refers to a cyclized "heteroalkynyl", including monocyclic, bicyclic, or tricyclic systems, wherein the bicyclic and tricyclic systems include spiro, fused, and bridged rings. In addition, in terms of the "heterocycloalkynyl", a heteroatom can occupy the position through which the heterocycloalkynyl is attached to the remainder of the molecule. In some embodiments, the heterocycloalkynyl is a 4-6 membered heterocycloalkynyl; in some other embodiments, the heterocycloalkynyl is a 5-6 membered heterocycloalkynyl. Unless otherwise specified, the term "halo" or "halogen" by itself or as part of another substituent refers to fluorine, chlorine, bromine or iodine atom. Furthermore, the term "haloalkyl" is meant to include monohaloalkyl and polyhaloalkyl. For example, the term "halo($C_1$-$C_4$)alkyl" is meant to include, but not limited to, trifluoromethyl, 2,2,2-trifluoroethyl, 4-chlorobutyl, 3-bromopropyl and the like. Unless otherwise specified, examples of the haloalkyl include, but not limited to trifluoromethyl, trichloromethyl, pentafluoroethyl and pentachloroethyl.

The term "alkoxy" refers to an alkyl defined above having a specified number of carbon atoms attached by an oxygen bridge. Unless otherwise specified, $C_{1-6}$ alkoxy includes $C_1$, $C_2$, $C_3$, $C_4$, $C_5$ and $C_6$ alkoxy. In some embodiments, the alkoxy is $C_{1-3}$ alkoxy. Examples of the alkoxy include, but not limited to methoxy, ethoxy, n-propoxy, isopropoxy, n-butoxy, sec-butoxy, tert-butoxy, n-pentyloxy and S-pentoxy.

Unless otherwise specified, the terms "aromatic ring" and "aryl" in the present disclosure can be used interchangeably. The term "aromatic ring" or "aryl" refers to a polyunsaturated carbocyclic system, which can be monocyclic, bicyclic or polycyclic systems, in which at least one ring is aromatic, and the rings in the bicyclic and polycyclic systems are fused together. It can also be mono- or poly-substituted, and can be monovalent, divalent or polyvalent. In some embodiments, the aryl is $C_{6-12}$ aryl; in some other embodiments, the aryl is $C_{6-10}$ aryl. Examples of the aryl include, but not limited to, phenyl, naphthyl (including 1-naphthyl, 2-naphthyl, etc.). The substituent of any one of the above aryl ring systems is selected from the acceptable substituents described in the present disclosure.

Unless otherwise specified, the terms "heteroaromatic ring" and "heteroaryl" in the disclosure can be used interchangeably. The term "heteroaryl" refers to an aryl (or an aromatic ring) containing 1, 2, 3 or 4 heteroatoms independently selected from B, N, O and S, which can be monocyclic, bicyclic, or tricyclic systems, wherein the nitrogen atom can be substituted or unsubstituted (i.e., N or NR, wherein R is H or the substituent as defined herein), and optionally quaternized and the nitrogen and sulfur heteroatoms can optionally be oxidized (i.e., NO and $S(O)_p$, p is 1 or 2). The heteroaryl can be connected to the rest of the molecule via a heteroatom. In some embodiments, the heteroaryl is a 5-10 membered heteroaryl; in some other embodiments, the heteroaryl is a 5-6 membered heteroaryl. Examples of the heteroaryl include, but not limited to, pyrrolyl (including N-pyrrolyl, 2-pyrrolyl and 3-pyrrolyl, etc.), pyrazolyl (including 2-pyrazolyl and 3-pyrazolyl, etc.), imidazolyl (including N-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thiophenyl (including 2-thiophenyl and 3-thiophenyl, etc.), pyridyl (including 2-pyridyl, 3-pyridyl and 4-pyridyl, etc.), pyrazinyl, pyrimidinyl (including 2-pyrimidinyl and 4-pyrimidinyl, etc.), benzothiazolyl (including 5-benzothiazolyl, etc.), purinyl, benzimidazolyl (including 2-benzimidazolyl, etc.), indolyl (including 5-indolyl, etc.), isoquinolinyl (including 1-isoquinolinyl and 5-isoquinolinyl, etc.), quinoxalinyl (including 2-quinoxalinyl and 5-quinoxalinyl, etc.), quinolinyl (including 3-quinolinyl and 6-quinolinyl, etc.), pyrazinyl, purinyl, benzoxazolyl. The substituent of any heteroaryl ring system is selected from the acceptable substituents of the present disclosure.

Unless otherwise specified, the term "aralkyl" is intended to include those groups in which an aryl is attached to an alkyl. In some embodiments, the aralkyl is $C_{6-10}$ aryl-$C_{1-4}$ alkyl; in some other embodiments, the aralkyl is $C_{6-10}$ aryl-$C_{1-2}$ alkyl. Examples of the aralkyl include, but not limited to, benzyl, phenethyl, naphthylmethyl, and the like. "Aryloxy" and "arylthio" represent those groups in which a carbon atom (such as methyl) in the aralkyl group is replaced by an oxygen atom and a sulfur atom, respectively. In some embodiments, the aryloxy is $C_{6-10}$ aryl-O—$C_{1-2}$ alkyl; in some other embodiments, the aryloxy is $C_{6-10}$ aryl-$C_{1-2}$ alkyl-O—. In some embodiments, the arylthio is $C_{6-10}$ aryl-S—$C_{1-2}$ alkyl; in some other embodiments, the arylthio is $C_{6-10}$ aryl-$C_{1-2}$ alkyl-S—. Examples of the aryloxy and the arylthio include, but not limited to, phenoxymethyl, 3-(1-naphthyloxy)propyl, phenylthiomethyl, and the like.

Unless otherwise specified, the term "heteroaralkyl" is intended to include those groups in which a heteroaryl is attached to an alkyl. In some embodiments, the heteroaralkyl is 5-8 membered heteroaryl-$C_{1-4}$ alkyl; in some other embodiments, the heteroaralkyl is 5-6 membered heteroaryl-$C_{1-2}$ alkyl. Examples of the heteroaralkyl include, but not limited to, pyrrolylmethyl, pyrazolylmethyl, pyridylmethyl, pyrimidinylmethyl, and the like. "Heteroaryloxy" and "heteroarylthio" refer to those groups in which a carbon atom (such as methyl) in the heteroaralkyl is replaced by an oxygen atom and a sulfur atom, respectively. In some embodiments, the heteroaryloxy is 5-8 membered heteroaryl-O—$C_{1-2}$ alkyl; in some other embodiments, the heteroaryloxy is 5-6 membered heteroaryl-$C_{1-2}$ alkyl-O—. In some embodiments, the heteroarylthio group is 5-8 membered heteroaryl-S—$C_{1-2}$ alkyl; in some other embodiments, the heteroarylthio group is 5-6 membered heteroaryl-$C_{1-2}$ alkyl-S—. Examples of the heteroaryloxy and the heteroarylthio include, but not limited to, pyrrolyloxymethyl, pyrazolyloxymethyl, 2-pyridyloxymethyl, pyrrolylthiomethyl, pyrazolylthiomethyl, 2-pyridylthiomethyl, and the like.

Unless otherwise specified, $C_{n-n+m}$ or $C_n$-$C_{n+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$ and $C_{12}$, and also includes any range between n and n+m, for example, $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, $C_{9-12}$ and the like; similarly, n-membered to n+m-membered means that the number of atoms arranged on the ring is n to n+m, for example, 3- to 12-membered ring means 3-membered ring, 4-membered ring, 5-membered ring, 6-membered ring, 7-membered ring, 8-membered ring, 9-membered ring, 10-membered ring, 11-membered ring and 12-membered ring, and also includes any range between n and n+m, for example, 3- to 12-membered includes 3- to 6-membered, 3- to 9-membered, 5- to 6-membered, 5- to 7-membered, 6- to 7-membered, 6- to 8-membered, 6- to 10-membered and the like.

The term "leaving group" refers to a functional group or atom which can be replaced by another functional group or atom through a substitution reaction (such as affinity substitution reaction). For example, representative leaving groups include triflate; chlorine, bromine and iodine; sulfonate group, such as mesylate, tosylate, p-bromobenzenesulfonate, p-toluenesulfonate and the like; acyloxy, such as acetoxy, trifluoroacetoxy and the like.

The term "protecting group" includes, but not limited to "amino protecting group", "hydroxyl protecting group" or "thiol protecting group". The term "amino protecting group" refers to a protecting group suitable for blocking the side reaction on the nitrogen atom of an amino group. Representative amino protecting groups include, but not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl)methyl; silyl such as trimethylsilyl (TMS) and tert-butyldimethylsilyl (TBS) and the like. The term "hydroxyl protecting group" refers to a protecting group suitable for blocking the side reaction on a hydroxyl group. Representative hydroxyl protecting groups include, but not limited to: alkyl such as methyl, ethyl and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyldimethylsilyl (TBS) and the like.

The compound of the present disclosure can be prepared by a variety of synthetic methods well known to those skilled in the art, including the following enumerative embodiments, embodiments formed by the following enumerative embodiments in combination with other chemical synthesis methods and equivalent replacements well known to those skilled in the art. The preferred embodiments includes, but not limited to the embodiments of the present disclosure.

The compound of the present disclosure can have various uses or indications, including but not limited to the specific uses or indications listed in this application.

All of the solvents used in the present disclosure are commercially available. The present disclosure adopts the abbreviating words as follows: "aq" refers to water; "HATU" refers to O-(7-azabenzotriazol-1-yl)-N,N,N',N'-tetramethyluronium hexafluorophosphate; "EDC" refers to N-(3-dimethylaminopropyl)-N'-ethylcarbodiimide hydrochloride; "m-CPBA" refers to 3-chloroperoxybenzoic acid; "eq" refers to equivalent; "CDI" refers to carbonyldiimidazole; "DCM" refers to dichloromethane; "PE" refers to petroleum ether; "DIAD" refers to diisopropyl azodicarboxylate; "DMF" refers to N,N-dimethylformamide; "DMSO" refers to dimethyl sulfoxide; "EtOAc" refers to ethyl acetate; "EtOH" refers to ethanol; "MeOH" refers to methanol; "CBz" refers to benzyloxycarbonyl, which is an amine protecting group; "BOC" refers to tert-butoxycarbonyl, which is an amine protecting group; "HOAc" refers to acetic acid; "NaCNBH$_3$" refers to sodium cyanoborohydride; "r.t." refers to room temperature; "O/N" refers to overnight; "THF" refers to tetrahydrofuran; "Boc$_2$O" refers to di-tert-butyldicarbonate; "TFA" refers to trifluoroacetic acid; "DIPEA" refers to diisopropylethylamine; "SOCl$_2$" refers to thionyl chloride; "CS$_2$" refers to carbon disulfide; "TsOH" refers to p-toluenesulfonic acid; "NFSI" refers to N-fluoro-N-(phenylsulfonyl)benzenesulfonamide; "NCS" refers to 1-chloropyrrolidine-2,5-dione; "n-Bu$_4$NF" refers to tetrabutylammonium fluoride; "iPrOH" refers to 2-propanol; "mp" refers to melting point; "LDA" refers to Lithium diisopropylamide; HPMC stands for hydroxypropyl methylcellulose; "HPβCD" refers to hydroxypropyl-β-cyclodextrin; "Ms" refers to mesyl; "FmocCl" refers to fluorenylmethoxycarbonyl chloride.

Compounds are named manually or by ChemDraw® software, and the commercially available compounds use their vendor directory names.

DETAILED DESCRIPTION OF THE EMBODIMENT

Figure 1:
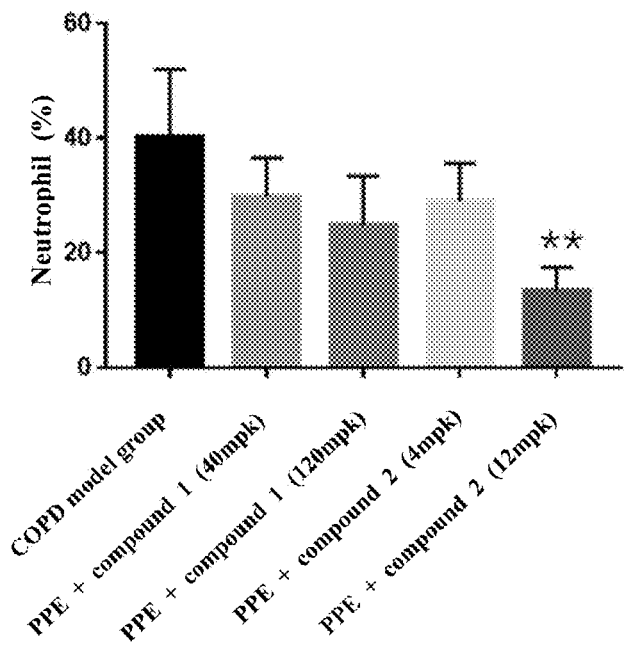
FIG. 1 shows the relationship between the proportion of neutrophils in the lung tissue of the animal in each group and the compound dose.

The following embodiments further illustrate the present disclosure, but the present disclosure is not limited thereto. The present disclosure has been described in detail herein, and specific embodiments thereof have also been disclosed. It will be apparent to those skilled in the art that various changes and modifications can be made to the specific embodiments of the present disclosure without departing from the spirit and scope of the present disclosure.

Fragment BB-1

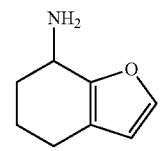

BB-1

Synthetic Route:

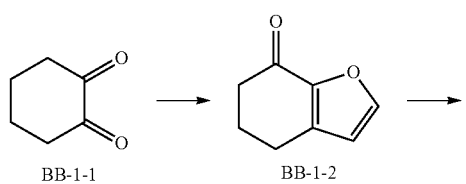

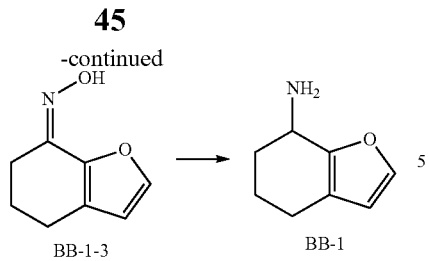

Step 1: Synthesis of Compound BB-1-2

Chloroacetaldehyde (40% aqueous solution, 21.89 mL) was dissolved in 250 mL of water, and $NaHCO_3$ (11.8 g, 140.47 mmol) was added at 0° C., followed by addition of compound BB-1-1 (10 g, 89.19 mmol) in portions. The reaction was allowed to run at 30° C. for 40 hours. After the reaction was completed, the mixture was adjusted to pH of 1 with 40% $H_2SO_4$, diluted with ethyl acetate (100 mL), and then extracted with ethyl acetate (100 mL×3). The obtained organic phases were combined, dried over anhydrous sodium sulfate and filtered, and the solvent was removed under reduced pressure to obtain a crude product, which was separated with a chromatography column (eluent: ethyl acetate/petroleum ether=0-40%) to obtain the target compound BB-1-2. $^1$H NMR (400 MHz, CHLOROFORM-d) δ ppm 7.50 (d, J=1.5 Hz, 1H), 6.35 (d, J=1.5 Hz, 1H), 2.71 (t, J=6.0 Hz, 2H), 2.56-2.46 (m, 2H), 2.14-2.03 (m, 2H).

Step 2: Synthesis of Compound BB-1-3

Compound BB-1-2 (3.8 g, 27.91 mmol) was dissolved in 100 mL of methanol, followed by addition of anhydrous sodium acetate (2.78 g, 33.84 mmol) and hydroxylamine hydrochloride (2.92 g, 41.99 mmol), and the mixture was stirred overnight at room temperature. After the reaction was completed, the solvent was removed under reduced pressure. To the residue was added 80 mL of water, followed by extraction with ethyl acetate (50 mL×3). The obtained organic phases were combined, and dried over anhydrous sodium sulfate. After the desiccant was removed by filtration, the solvent was removed under reduced pressure to obtain a crude product of the target compound BB-1-3, which was directly used in the next reaction.

Step 3: Synthesis of Compound BB-1

Compound BB-1-3 (3.0 g, 19.85 mmol) was dissolved in 120 mL of methanol, followed by addition of $NiCl_2 \cdot 6H_2O$ (5.21 g, 21.92 mmol) and $NaBH_4$ (7.45 g, 196.86 mmol), and the mixture was stirred at 0° C. for 3 hours. After the reaction was completed, 10 mL of saturated $NH_4Cl$ solution was added, and the resulting mixture was diluted with 40 mL of ethyl acetate, and extracted with ethyl acetate (50 mL×3). The obtained organic phases were combined, and dried over anhydrous sodium sulfate. After the desiccant was removed by filtration, the solvent was removed under reduced pressure to obtain the target compound BB-1. $^1$H NMR (400 MHz, METHANOL-$d_4$) δ ppm 7.39-7.32 (m, 1H), 6.23 (s, 1H), 3.97 (br s, 1H), 2.54-2.38 (m, 2H), 2.09 (br d, J=5.0 Hz, 1H), 1.96-1.87 (m, 1H), 1.77-1.65 (m, 2H).

Fragment BB-2

Synthetic Route:

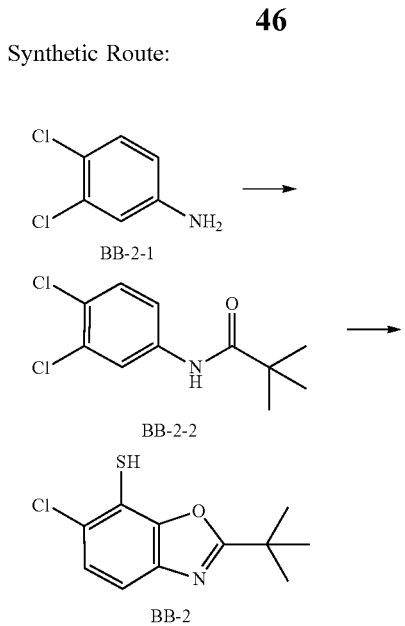

Step 1: Synthesis of Compound BB-2-2

Compound BB-2-1 (50 g, 308.60 mmol) was dissolved in 300 mL of tert-butyl methyl ether, followed by addition of a solution of 12.34 g of sodium hydroxide in 25 mL of water. Under an ice bath, trimethylacetyl chloride (39.07 g, 324.03 mmol, 39.87 mL) was added dropwise, and the reaction mixture was maintained at a temperature not exceeding 35° C. After the reaction was completed, to the mixture was added 200 mL of ethyl acetate for dilution and the resulting mixture was extracted with 100 mL of ethyl acetate. The extracted organic phase was washed with saturated brine (100 mL×2) and dried over anhydrous sodium sulfate, filtered and concentrated to obtain the target product BB-2-2. $^1$H NMR (400 MHz, DMSO-$d_6$) δ ppm 9.45 (s, 1H), 8.04 (d, J=2.5 Hz, 1H), 7.65 (dd, J=2.5, 8.8 Hz, 1H), 7.55 (d, J=8.8 Hz, 1H), 1.22 (s, 9H).

Step 2: Synthesis of Compound BB-2

Compound BB-2-2 (7.08 g, 28.76 mmol) was dissolved in 150 mL of THF, and n-butyllithium (2.5 M, 29 mL) was added dropwise at −60° C. After the dropwise addition was completed, the reaction mixture was cooled to 0° C. and stirred. After 15 minutes, sulfur powder (1.84 g, 57.53 mmol) was added at −60° C. The reaction mixture was stirred at room temperature overnight. After the reaction was completed, 2 N HCl (40 mL) was added to quench the reaction, and the resulting mixture was diluted with 100 mL of ethyl acetate and extracted with ethyl acetate (100 mL×3). The organic phases were combined, washed with saturated brine (80 mL×2), dried over anhydrous sodium sulfate, filtered and concentrated to obtain a crude product of BB-2, which was directly used in the subsequent reaction.

Fragment BB-3

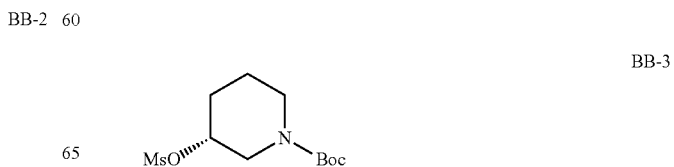

Synthetic Route:

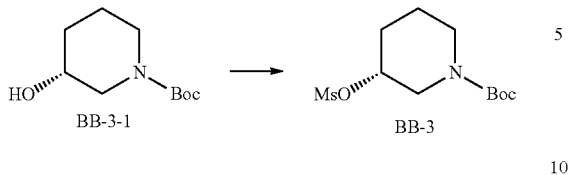

Step 1: Synthesis of Compound BB-3

Compound BB-3-1 (25 g, 124.22 mmol) was dissolved in 200 mL of DCM, and triethylamine (37.71 g, 372.65 mmol, 51.87 mL) was added dropwise at 0° C. Methanesulfonyl chloride (37.04 g, 323.35 mmol, 25.03 mL) was then added dropwise under an ice bath, and stirred at this temperature for 1 hour. After the reaction was completed, 100 mL of water was added to quench the reaction. The reaction mixture was diluted with 100 mL of DCM and extracted with DCM (100 mL×2). The organic phases were combined, dried over anhydrous sodium sulfate, filtered and concentrated to obtain a crude product, which was separated with a chromatography column (eluent: ethyl acetate/petroleum ether=0-30%) to obtain the target compound BB-3. $^1$H NMR (400 MHz, CHLOROFORM-d) δ ppm 4.74 (br s, 1H), 3.71-3.59 (m, 2H), 3.51-3.30 (m, 2H), 3.17 (s, 1H), 3.07 (s, 3H), 2.04-1.90 (m, 2H), 1.84 (tdd, J=4.3, 8.6, 12.9 Hz, 1H), 1.49 (s, 9H).

Fragment BB-4

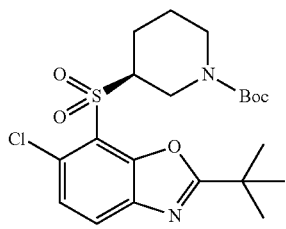

Synthetic Route:

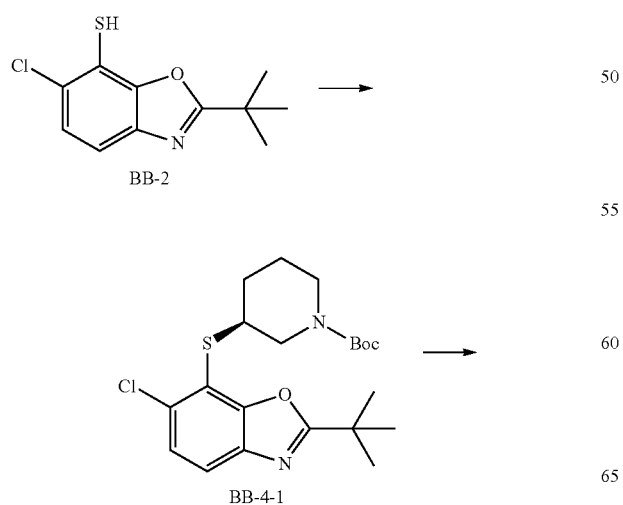

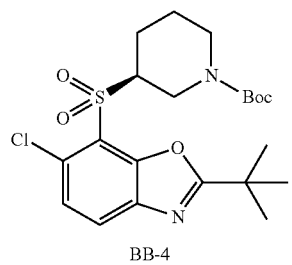

Step 1: Synthesis of Compound BB-4-1

Compound BB-2 (12.57 g, 52.00 mmol) was dissolved in 200 mL of DMF, followed by addition of potassium carbonate (7.19 g, 52.00 mmol) and compound BB-3 (9.44 g, 33.80 mmol), and the reaction mixture was stirred at 80° C. overnight. After the reaction was completed, 150 mL of water was added to quench the reaction, and then the resulting mixture was diluted with 100 mL of ethyl acetate and extracted with ethyl acetate (100 mL×3). The organic phases were combined, washed with saturated brine (100 mL×3), dried over anhydrous sodium sulfate, filtered and concentrated to obtain a crude product, which was separated with a chromatography column (eluent: ethyl acetate/petroleum ether=0-10%) to obtain compound BB-4-1. $^1$H NMR (400 MHz, CHLOROFORM-d) δ ppm 7.55 (br d, J=8.5 Hz, 1H), 7.41 (br d, J=8.3 Hz, 1H), 3.85 (br d, J=12.5 Hz, 1H), 3.51 (br s, 1H), 2.91 (br s, 2H), 2.12 (br s, 1H), 1.83 (br s, 1H), 1.69-1.61 (m, 1H), 1.53 (s, 9H), 1.47 (s, 2H), 1.36 (br s, 9H).

Step 2: Synthesis of Compound BB-4

Compound BB-4-1 (6.10 g, 14.35 mmol) was dissolved in 150 mL of DCM, followed by addition of m-CPBA (85%, 17.48 g, 86.12 mmol) in portions at −10° C., and the resulting mixture was stirred at −10° C. for 5 hours. After the reaction was completed, 100 mL of saturated sodium sulfite solution and 100 mL of saturated sodium bicarbonate solution were added. The mixture was diluted with 100 mL of DCM, and extracted with DCM (100 mL×3). The organic phases were combined, washed with saturated brine (50 mL×2) and dried over anhydrous sodium sulfate. The desiccant was removed by filtration, and the solvent was removed under reduced pressure to obtain a crude product, which was separated with a chromatography column (eluent: ethyl acetate/petroleum ether=0-25%) to obtain the target compound BB-4. $^1$H NMR (400 MHz, CHLOROFORM-d) δ ppm 7.85 (d, J=8.5 Hz, 1H), 7.51 (d, J=8.3 Hz, 1H), 4.24 (br s, 1H), 4.07 (br s, 1H), 3.57 (br s, 1H), 3.07 (br s, 1H), 2.71 (br t, J=12.3 Hz, 1H), 2.25 (br s, 1H), 2.03-1.80 (m, 3H), 1.54 (s, 9H), 1.38 (br s, 9H).

Fragment BB-5

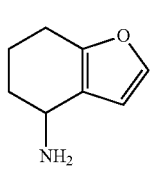

Synthetic Route:

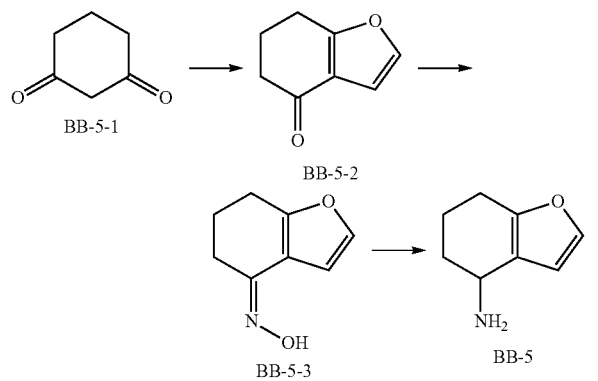

Fragment BB-6

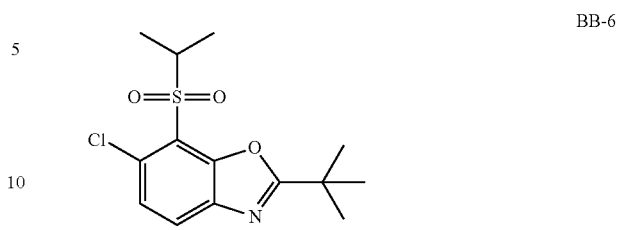

Synthetic Route:

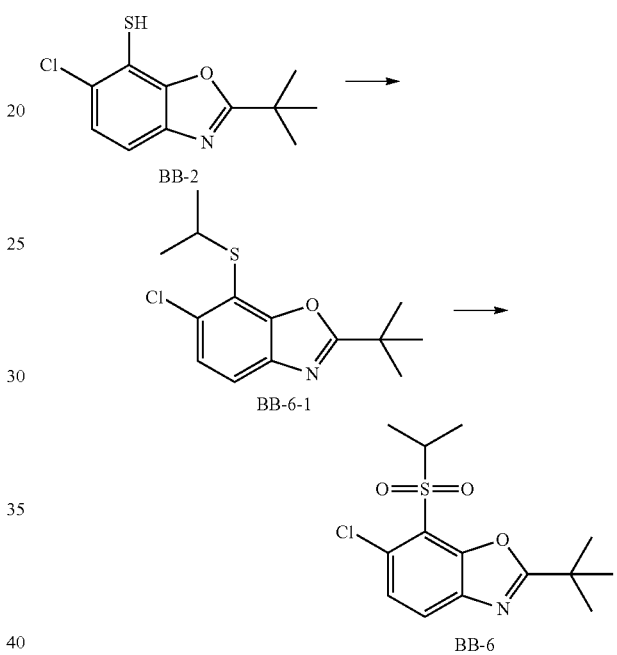

Step 1: Synthesis of Compound BB-5-2

Chloroacetaldehyde (40% aqueous solution, 22.38 mL) and NaHCO$_3$ (9 g, 107.13 mmol) were dissolved in 50 mL of water, followed by addition of compound BB-5-1 (10 g, 89.18 mmol) at 0° C., and the reaction mixture was stirred at 0-25° C. for 18 hours. After the reaction was completed, the mixture was adjusted to pH of 1 with 40% H$_2$SO$_4$ and extracted with ethyl acetate (100 mL×3). The organic phases were combined, dried over anhydrous sodium sulfate, filtered and concentrated to obtain a crude product, which was separated with a chromatography column (eluent: ethyl acetate/petroleum ether=0 to 30%) to obtain the target compound BB-5-2. $^1$H NMR (400 MHz, CHLOROFORM-d) δ ppm 2.17-2.24 (m, 2H) 2.52 (dd, J=7.28, 5.77 Hz, 2H) 2.90 (t, J=6.27 Hz, 2H) 6.69 (d, J=2.01 Hz, 1H) 7.34 (d, J=2.01 Hz, 1H).

Step 2: Synthesis of Compound BB-5-3

Compound BB-5-2 (1 g, 7.34 mmol), anhydrous sodium acetate (0.8 g, 9.76 mmol) and hydroxylamine hydrochloride (698.78 mg, 10.06 mmol) were dissolved in 15 mL of methanol, and the reaction mixture was stirred at room temperature overnight. After the reaction was completed, the solvent was evaporated under reduced pressure, and 5 mL of ethyl acetate and 3 mL of water were added to the residue, which was then extracted with ethyl acetate (5 mL×3). The organic phases were combined, washed with water (5 mL×2) and saturated brine (5 mL), and dried over anhydrous sodium sulfate. After the desiccant was removed by filtration, the solvent was removed under reduced pressure to obtain a crude product of the target compound BB-5-3, which was directly used in the next reaction.

Step 3: Synthesis of Compound BB-5

Compound BB-5-3 (400 mg, 2.65 mmol) was dissolved in 5 mL of methanol, followed by addition of NiCl$_2$.6H$_2$O (628.98 mg, 2.65 mmol), and the temperature was lowered to 0° C. NaBH$_4$ (1 g, 26.46 mmol) was added thereto in portions, and the resulting mixture was stirred at 0° C. for half an hour. After the reaction was completed, the solvent was evaporated under reduced pressure, and then the residue was diluted with 20 mL of ethyl acetate and 15 mL of water, and extracted with ethyl acetate (20 mL×3). The organic phases were combined, washed with saturated brine (10 mL×2) and dried over anhydrous sodium sulfate. After the desiccant was removed by filtration, the filtrate was concentrated under reduced pressure to remove the solvent to obtain a crude product of the target compound BB-5, which was directly used in the subsequent reaction. $^1$H NMR (400 MHz, CHLOROFORM-d) δ ppm 1.33-1.48 (m, 1H) 1.72-1.77 (m, 1H) 1.86-1.96 (m, 2H) 2.37-2.57 (m, 2H) 3.73-3.90 (m, 1H) 6.31 (d, J=1.76 Hz, 1H) 7.16-7.22 (m, 1H).

Step 1: Synthesis of Compound BB-6-1

BB-2 (12.00 g, 49.64 mmol) and 2-bromoisopropane (9.17 g, 74.56 mmol, 7.00 mL) were dissolved in 120 mL of DMF, followed by addition of potassium carbonate (10 g, 72.35 mmol), and the mixture was stirred at 80° C. overnight. After the reaction was completed, to the mixture 150 mL of water was added, and the resulting mixture was extracted with ethyl acetate (150 mL×3). The organic phases were combined, washed successively with water (80 mL×3) and saturated brine (80 mL×3), dried over anhydrous sodium sulfate, filtered and concentrated to obtain a crude product, which was separated with a chromatography column (eluent: ethyl acetate/petroleum ether=0-20%) to obtain compound BB-6-1. $^1$H NMR (400 MHz, CHLOROFORM-d) δ ppm 1.31 (d, J=6.78 Hz, 6H) 1.51 (s, 9H) 3.80 (spt, J=6.69 Hz, 1H) 7.39 (d, J=8.53 Hz, 1H) 7.51 (d, J=8.53 Hz, 1H).

Step 2: Synthesis of Compound BB-6

Compound BB-6-1 (10 g, 35.23 mmol) was dissolved in 150 mL of DCM, followed by addition of m-CPBA (30.00 g, 147.77 mmol) at 0° C., and the resulting mixture was stirred and reacted at 0° C. for 1 hour, and then warmed to 30° C. and reacted for 5 hours. After the reaction was completed, to the mixture was added saturated sodium sulfite solution at 0° C. until the potassium iodide starch test paper did not turn blue. Saturated sodium bicarbonate solution was added to obtain pH>7, and the mixture was stirred at room temperature for half an hour. The mixture was extracted with ethyl acetate (150 mL×3). The organic phases were combined, washed with saturated brine (100 mL×2) and dried over anhydrous sodium sulfate. After the desiccant was removed by filtration, the crude product obtained by concentration was separated with a chromatography column (eluent: ethyl acetate/petroleum ether=0 to 30%) to obtain the target compound BB-6. $^1$H NMR (400 MHz, CHLOROFORM-d) δ ppm 1.40 (d, J=6.78 Hz, 6H) 1.54 (s, 9H) 3.68-3.78 (m, 1H) 7.50 (d, J=8.28 Hz, 1H) 7.84 (d, J=8.53 Hz, 1H).

Fragment BB-7

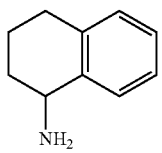 [SMILES: NC1CCCc2ccccc21]

Synthetic Route:

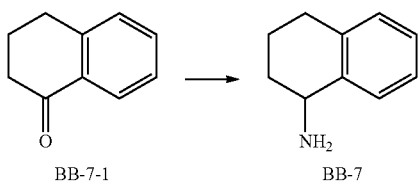

Step 1: Synthesis of Compound BB-7

According to the steps 2 and 3 in the synthesis of BB-1, BB-7 was synthesized using BB-7-1.

Fragment BB-8

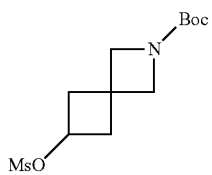

Synthetic Route:

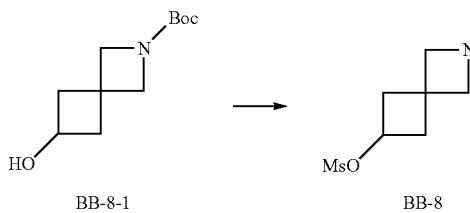

Step 1: Synthesis of Compound BB-8

According to the step 1 in the synthesis of BB-3, BB-8 was synthesized using BB-8-1.

Fragment BB-9

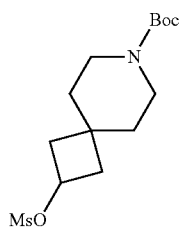

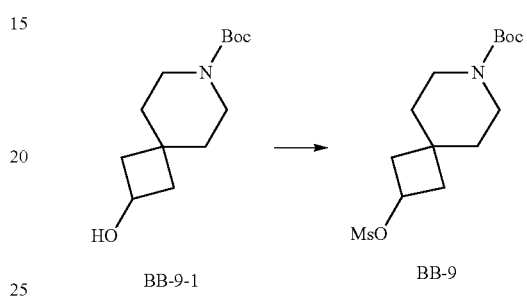

Step 1: Synthesis of Compound BB-9

According to the step 1 in the synthesis of BB-3, BB-9 was synthesized using BB-9-1.

Fragment BB-10

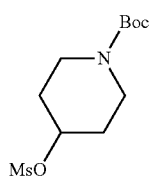

Synthetic Route:

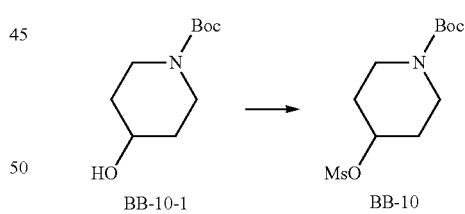

Step 1: Synthesis of Compound BB-10

According to the step 1 in the synthesis of BB-3, BB-10 was synthesized using BB-10-1.

Fragment BB-11

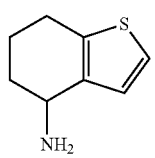

Synthetic Route:

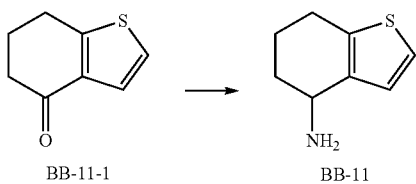

Step 1: Synthesis of Compound BB-11

According to the steps 2 and 3 in the synthesis of BB-1, BB-11 was synthesized using BB-11-1. $^1$H NMR (400 MHz, METHANOL-$d_4$) δ ppm 7.14 (d, J=5.2 Hz, 1H), 7.05 (d, J=5.2 Hz, 1H), 3.93 (br d, J=5.6 Hz, 1H), 2.82-2.75 (m, 2H), 1.88-1.80 (m, 2H), 1.69-1.59 (m, 2H)

Fragment BB-12

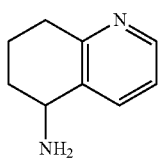 [SMILES: NC1CCCc2ncccc21]

Synthetic Route:

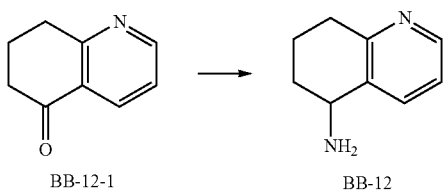

Step 1: Synthesis of Compound BB-12

According to the steps 2 and 3 in the synthesis of BB-1, BB-12 was synthesized using BB-12-1. $^1$H NMR (400 MHz, METHANOL-$d_4$) δ ppm 8.36-8.30 (m, 1H), 7.91 (d, J=7.6 Hz, 1H), 7.27 (t, J=6.4 Hz, 1H), 4.05-3.98 (m, 1H), 2.97-2.86 (m, 2H), 2.13-2.07 (m, 2H), 1.76-1.71 (m, 2H).

Fragment BB-13

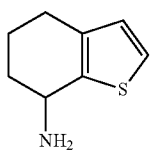

Synthetic Route:

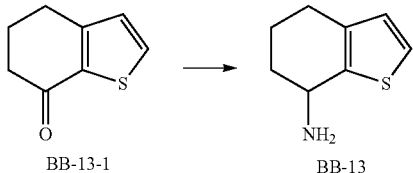

Step 1: Synthesis of Compound BB-13

According to the steps 2 and 3 in the synthesis of BB-1, BB-13 was synthesized using BB-13-1.

Fragment BB-14

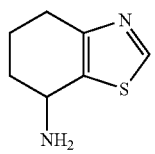

Synthetic Route:

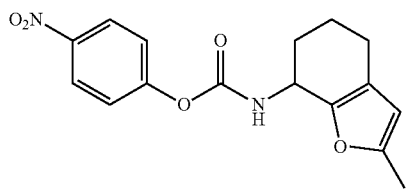 [SMILES: Cc1cc2c(o1)C(NC(=O)Oc1ccc([N+](=O)[O-])cc1)CCC2]

Step 1: Synthesis of Compound BB-14

Compound BB-14-1 (50 mg, 326.37 μmol) was dissolved in 5 mL of methanol, followed by addition of ammonium acetate (251.57 mg, 3.26 mmol) and sodium cyanoborohydride (51.27 mg, 815.92 μmol), and the reaction mixture was heated to 80° C. and stirred for 16 hours. After the reaction was completed, the reaction mixture was directly concentrated to dryness to obtain a crude product. The crude product was separated and purified with a thin layer chromatography preparative plate to obtain compound BB-14. $^1$H NMR (400 MHz, METHANOL-$d_4$) δ ppm 8.97 (s, 1H), 4.51 (t, J=5.6 Hz, 1H), 2.93-2.81 (m, 2H), 2.28-2.18 (m, 1H), 2.14-2.03 (m, 1H), 1.94 (br d, J=6.0 Hz, 2H)

Fragment BB-15

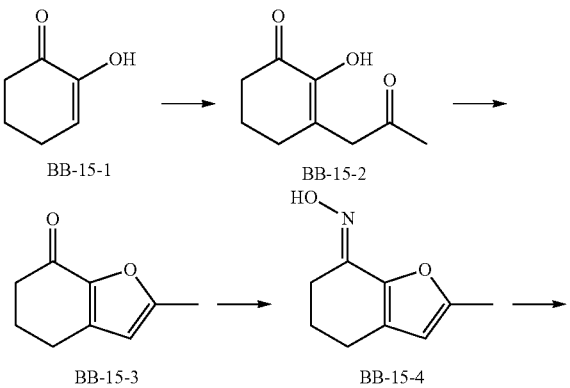

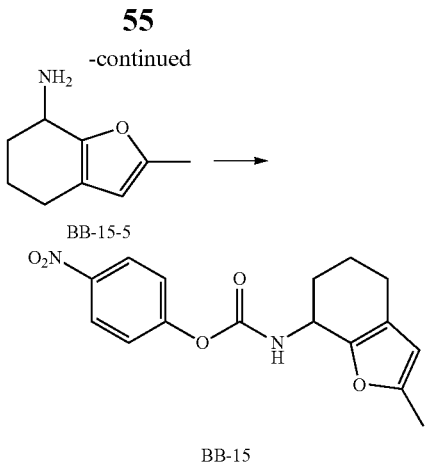

Step 1: Synthesis of Compound BB-15-2

Cerium ammonium nitrate (195.57 g, 356.74 mmol) was dissolved in methanol (400 mL), and a solution of dimethoxypropene (38.58 g, 535.11 mmol) and compound BB-15-1 (20 g, 178.37 mmol) in methanol (400 mL) was slowly added dropwise at −35° C. under nitrogen atmosphere over 0.5 hour. The reaction mixture was further stirred at −35° C. for 0.5 hour. After the reaction was completed, 400 mL of water and 80 mL of saturated sodium thiosulfate solution were added to quench the reaction mixture. The mixture was concentrated under reduced pressure to remove methanol, and the residue was extracted with ethyl acetate (750 mL×2). The organic phases were combined, washed with saturated brine (750 mL×1), dried over anhydrous sodium sulfate, filtered, and concentrated under reduced pressure. The residue was separated and purified with a flash preparative chromatography (eluent: ethyl acetate/petroleum ether=0-25%) to obtain compound BB-15-2. $^1$H NMR (400 MHz, CHLOROFORM-d) δ ppm 6.18 (s, 1H), 3.70-3.64 (m, 2H), 2.55-2.50 (m, 2H), 2.40-2.35 (m, 2H), 2.21 (s, 3H), 2.03-1.97 (m, 2H).

Step 2: Synthesis of Compound BB-15-3

Compound BB-15-2 (9.90 g, 58.86 mmol) and sulfonated poly(divinylbenzene-co-styrene) (10 g) were dissolved in toluene (500 mL), and the reaction mixture was heated to 120° C. and stirred for 12 hours. After the reaction was completed, the reaction mixture was filtered, and the filtrate was concentrated to dryness under reduced pressure. The residue was separated and purified with a flash preparative chromatography (eluent: ethyl acetate/petroleum ether=0-20%) to obtain compound BB-15-3. $^1$H NMR (400 MHz, CHLOROFORM-d) δ ppm 6.02 (s, 1H), 2.68 (t, J=6.2 Hz, 2H), 2.54-2.47 (m, 2H), 2.34 (s, 3H), 2.13-2.06 (m, 2H).

Step 3: Synthesis of Compound BB-15-4

Compound BB-15-3 (380 mg, 2.53 mmol) was dissolved in methanol (15 mL), followed by addition of sodium acetate (622.71 mg, 7.59 mmol) and hydroxylamine hydrochloride (351.67 mg, 5.06 mmol), and the reaction mixture was stirred at 50° C. for 3 hours. After the reaction was completed, the reaction mixture was concentrated to dryness, followed by addition of 80 mL of ethyl acetate and 30 mL of water. The resulting mixture was stirred thoroughly, and allowed to stand for liquid separation. The organic phase was washed with saturated brine (30 mL*1), dried over anhydrous sodium sulfate, filtered, and concentrated under reduced pressure to obtain a crude product of the compound BB-15-4, which was directly used in the next step.

Step 4: Synthesis of Compound BB-15-5

Compound BB-15-4 (420 mg, 2.54 mmol) was dissolved in methanol (15 mL), followed by addition of nickel chloride hexahydrate (664.77 mg, 2.80 mmol) and sodium borohydride (961.85 mg, 25.43 mmol) at 25° C. The reaction mixture was heated to 80° C., and stirred at 80° C. for 0.5 hour. After the reaction was completed, the reaction mixture was concentrated to dryness, followed by addition of 80 mL of ethyl acetate and 50 mL of water. The resulting mixture was stirred thoroughly, filtered, and allowed to stand for liquid separation. The organic phase was washed with saturated brine (50 mL*1), dried over anhydrous sodium sulfate, filtered, and concentrated under reduced pressure to obtain compound BB-15-5, which was directly used in the next step. $^1$H NMR (400 MHz, CHLOROFORM-d) δ ppm 5.76 (s, 1H), 3.91 (br t, J=5.6 Hz, 1H), 2.46-2.31 (m, 2H), 2.25 (s, 3H), 2.07-2.01 (m, 1H), 1.88-1.77 (m, 1H), 1.74-1.66 (m, 2H), 1.62-1.51 (m, 2H)

Step 5: Synthesis of Compound BB-15

Compound BB-15-5 (735 mg, 4.86 mmol) was dissolved in dichloromethane (50 mL), followed by addition of sodium carbonate (618.25 mg, 5.83 mmol) and 4-nitrobenzyl chloroformate (1.08 g, 5.35 mmol). The mixture was stirred at 25° C. for 0.5 hour. After the reaction was completed, the reaction mixture was poured into water (50 mL) and extracted with dichloromethane (50 mL). The organic phase was washed with saturated brine (50 mL), dried over anhydrous sodium sulfate, filtered, and concentrated to dryness under reduced pressure to obtain the intermediate compound BB-15, which was directly used in the subsequent reaction without purification.

$^1$H NMR (400 MHz, CHLOROFORM-d) δ ppm (d, J=9.2 Hz, 2H), 7.28 (d, J=9.2 Hz, 2H), 5.75 (s, 1H), 5.34 (br d, J=7.6 Hz, 1H), 4.84-4.73 (m, 1H), 2.43-2.27 (m, 2H), 2.20 (s, 3H), 2.04-1.95 (m, 1H), 1.92-1.83 (m, 1H), 1.78-1.67 (m, 2H).

Fragment BB-16

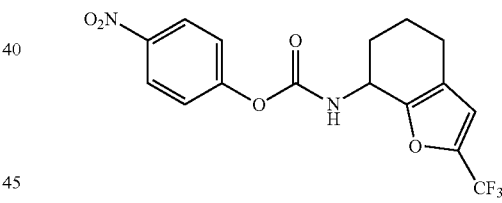

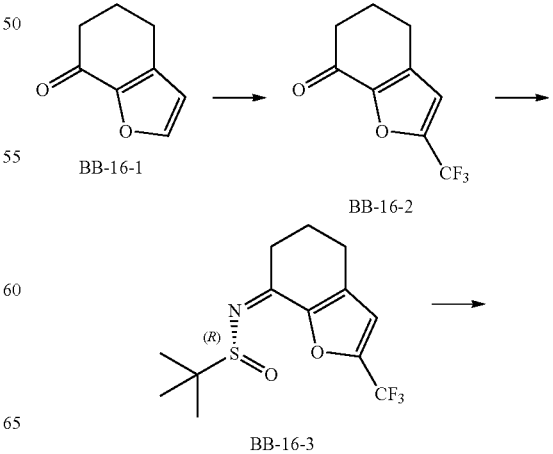

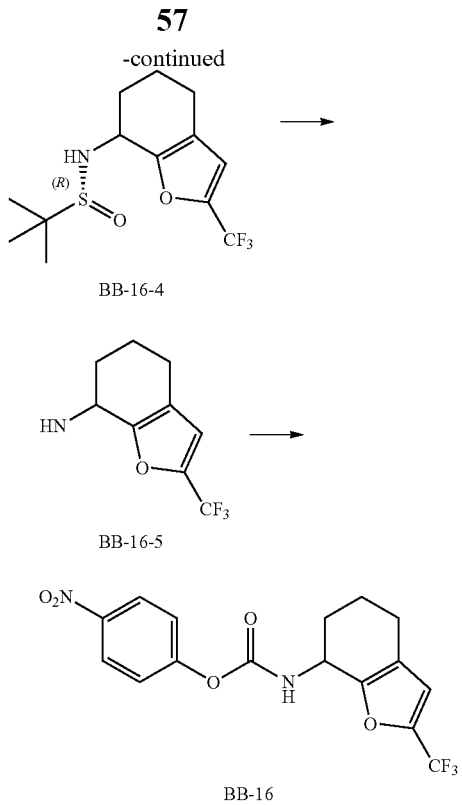

Step 1: Synthesis of Compound BB-16-2

Compound BB-16-1 (20.00 g, 146.90 mmol) was dissolved in 1,2-dichloroethane (300 mL), followed by addition of 1-trifluoromethyl-1,2-benzoiodoxol-3(H)-one (51.06 g, 161.59 mmol) and cuprous iodide (41.97 g, 220.35 mmol). The reaction mixture was stirred at 60° C. for 14 hours. After the reaction mixture was filtered, the filtrate was washed with saturated aqueous sodium bicarbonate solution (200 mL×2), and then filtered. The filtrate was extracted with dichloromethane (100 mL×2). The organic phases were combined, washed with saturated brine (200 mL), dried over anhydrous sodium sulfate, filtered, and concentrated under reduced pressure. The residue was separated and purified with a silica gel chromatography column (eluent: petroleum ether/ethyl acetate, 100:1 to 5:1) to obtain compound BB-16-2. $^1$H NMR (400 MHz, CDCl$_3$) δ ppm 6.80 (s, 1H), 2.83-2.79 (m, 2H), 2.65-2.61 (m, 2H), 2.24-2.17 (m, 2H).

Step 2: Synthesis of Compound BB-16-3

Compound BB-16-2 (8.50 g, 41.64 mmol) was dissolved in anhydrous toluene (150 mL), followed by addition of (R)-(−)-2-methyl-2-propanesulfinamide (7.57 g, 62.46 mmol) and tetraethyl titanate (28.49 g, 124.91 mmol). The reaction mixture was stirred at 90° C. for 3 hours. Water (100 mL) and ethyl acetate (100 mL) were added to the reaction mixture, which was then thoroughly stirred and filtered, and the filtrate was extracted with ethyl acetate (60 mL×2). The organic phases were combined, washed with saturated brine (100 mL), dried over anhydrous sodium sulfate, filtered, and concentrated under reduced pressure. The residue was separated and purified with a silica gel chromatography column (eluent: petroleum ether/ethyl acetate, 10:1 to 1:1) to obtain compound BB-16-3.

Step 3: Synthesis of Compound BB-16-4

Compound BB-16-3 (8.30 g, 27.01 mmol) was dissolved in tetrahydrofuran (150 mL), and diisobutylaluminum hydride solution (1 M solution in toluene, 41 mL, 40.5 mmol) was slowly added dropwise at 0° C. under nitrogen atmosphere. The reaction mixture was stirred at 0° C. for 1 hour. Water (200 mL) was added to the reaction mixture to quench the reaction. The resulting mixture was thoroughly stirred and filtered, and the filtrate was extracted with ethyl acetate (100 mL×2). The organic phases were combined, washed with saturated brine (100 mL), dried over anhydrous sodium sulfate, filtered, and concentrated under reduced pressure. The residue was separated and purified with a silica gel chromatography column (eluent: petroleum ether/ethyl acetate, 10:1 to 1:1) to obtain compound BB-16-4.

Step 4: Synthesis of Compound BB-16-5

Compound BB-16-4 (6.20 g, 20.04 mmol) was dissolved in anhydrous tetrahydrofuran (60 mL), and concentrated hydrochloric acid (8 mL, 12 N) was added dropwise at 0° C. The reaction mixture was stirred at 0° C. for 1 hour. The reaction mixture was adjusted to pH of 8-9 with sodium carbonate aqueous solution and filtered, and the filtrate was concentrated under reduced pressure. To the residue was added water (30 mL) and the mixture was extracted with dichloromethane (40 mL×2). The organic phases were combined, washed with saturated brine (100 mL), dried over anhydrous sodium sulfate, filtered, and concentrated under reduced pressure. The residue was separated and purified with a silica gel chromatography column (eluent: dichloromethane/methanol, 100:1 to 10:1) to obtain compound BB-16-5. $^1$H NMR (400 MHz, CDCl$_3$) δ ppm 6.58 (s, 1H), 3.40-3.98 (m, 1H), 2.47-2.41 (m, 2H), 2.15-2.11 (m, 1H), 1.89-1.86 (m, 1H), 1.74-1.65 (m, 2H) Two enantiomers with a retention time of 1.785 min and 2.006 min and a ratio of 88.3:11.7 were detected by supercritical fluid chromatography analysis.

Analytical conditions: column: ChiralPak IC-3 150×4.6 mm I.D., 3 μm; mobile phase, A: carbon dioxide, B: ethanol (0.05% diethylamine); gradient, from 5% to 40% of B in 5.5 min, then 5% of B for 1.5 min; flow rate: 2.5 mL/min; column temperature: 40° C.; detection wavelength: 220 nm Step 5: Synthesis of Compound BB-16

Compound BB-16-5 (300 mg, 1.46 mmol) was dissolved in dichloromethane (10 mL), followed by addition of sodium carbonate (232.46 mg, 2.19 mmol) and 4-nitrobenzyl chloroformate (265.25 mg, 1.32 mmol). The mixture was stirred at 20° C. for 1 hour. After the reaction was completed, the reaction mixture was diluted with dichloromethane (40 mL) and washed with water (50 mL). The organic phase was washed with saturated brine (50 mL), dried over anhydrous sodium sulfate, filtered, and concentrated to dryness under reduced pressure to obtain a crude product. The crude product was separated and purified with a flash preparative chromatography (eluent: ethyl acetate/petroleum ether=0-20%) to obtain the intermediate compound BB-16.

Fragment BB-17

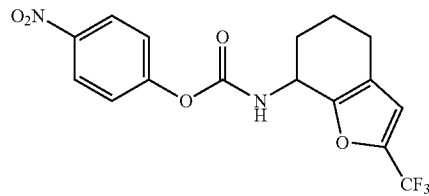 [SMILES: O=C(NC1CCCc2cc(C(F)(F)F)oc21)Oc1ccc([N+](=O)[O-])cc1]

Synthetic Route:

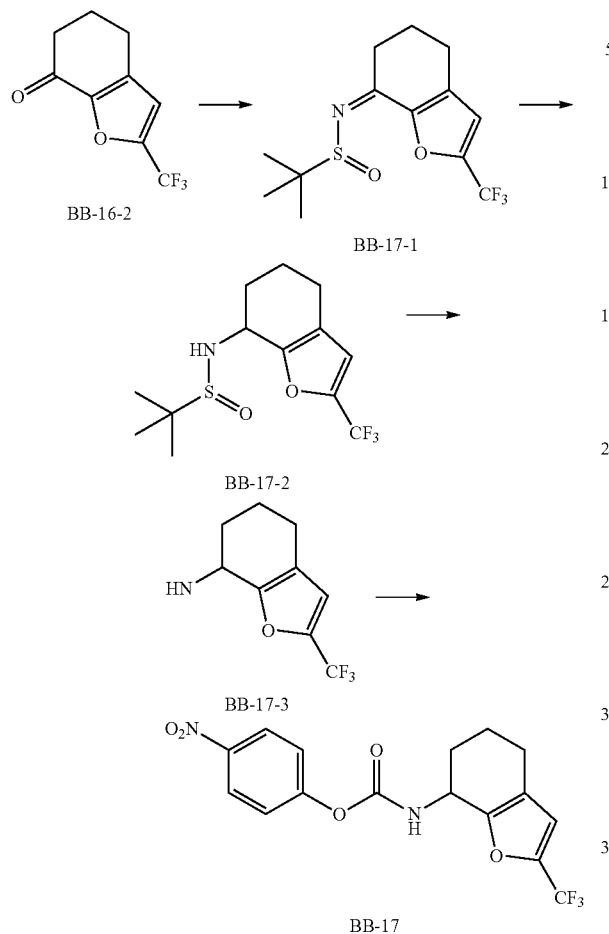

Step 1: Synthesis of Compound BB-17-1

According to the method for synthesizing the fragment BB-16-3, compound BB-17-1 was synthesized using compound BB-16-2. $^1$H NMR (400 MHz, CDCl$_3$) δ ppm 6.76 (s, 1H), 3.27-3.21 (m, 1H), 3.12-3.06 (m, 1H), 2.72-2.69 (m, 2H), 2.09-2.03 (m, 2H), 1.32 (s, 9H).

Step 2: Synthesis of Compound BB-17-2

Compound BB-17-1 (0.35 g, 1.14 mmol) was dissolved in tetrahydrofuran (2 mL), and sodium borohydride (86.2 mg, 2.28 mmol) was added at 0° C. under nitrogen atmosphere. The reaction mixture was stirred at 26° C. for 1 hour. Saturated brine (30 mL) was added to the reaction mixture to quench the reaction, and the resulting mixture was extracted with dichloromethane (50 mL×3). The organic phases were combined, washed with saturated brine (20 mL), dried over anhydrous sodium sulfate, filtered, and concentrated under reduced pressure to obtain a crude product of compound BB-17-2, which was directly used in the next step.

Step 3: Synthesis of Compound BB-17-3.

According to the method for synthesizing the fragment BB-16-5, compound BB-17-3 was synthesized using compound BB-17-2.

Step 4: Synthesis of Compound BB-17.

According to the method for synthesizing the fragment BB-16, compound BB-17 was synthesized using compound BB-17-3.

Fragment BB-18

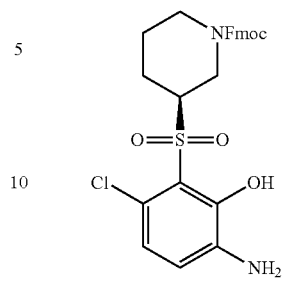

Synthetic Route:

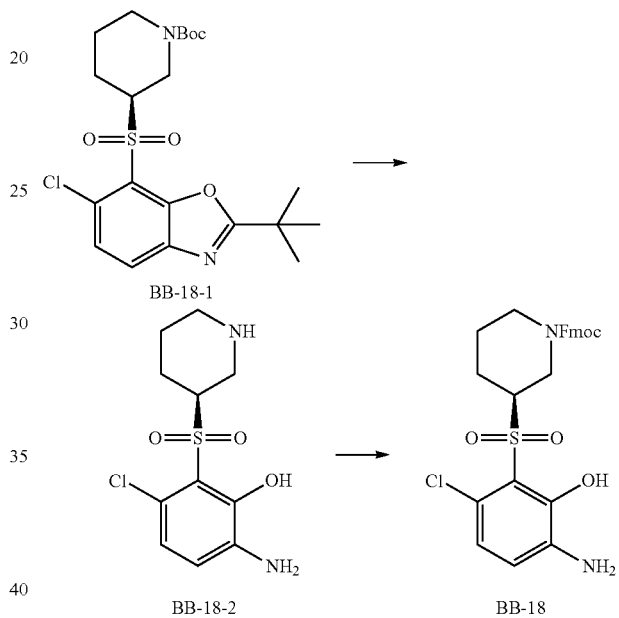

Step 1: Synthesis of Compound BB-18-2

Compound BB-18-1 (1.10 g, 2.41 mmol) was dissolved in toluene (10 mL), then concentrated hydrochloric acid (12 M, 4.01 mL) was added to the reaction mixture, and the mixture was heated to 80° C. and stirred for 12 hours. After completion of the reaction as indicated by thin layer chromatography and liquid chromatography, the reaction mixture was concentrated to obtain a crude product of BB-18-2 as a brown solid.

Step 2: Synthesis of Compound BB-18

The above compound BB-18-2 (0.70 g, 2.41 mmol) was dissolved in dichloromethane (10 mL), followed by addition of saturated NaHCO$_3$ solution to obtain pH>7, and FmocCl (465.81 mg, 1.44 mmol) was added at 0° C. The mixture was stirred at 25° C. for 1 hour. After completion of the reaction as indicated by thin layer chromatography and liquid chromatography, the reaction mixture was separated into layers, and the aqueous phase was extracted three times with ethyl acetate (20 mL*3). The organic phases were combined, dried over anhydrous sodium sulfate, filtered and concentrated, and the residue was purified by column chromatography (SiO$_2$, petroleum ether/ethyl acetate=3/1) to obtain BB-18. $^1$H NMR (400 MHz, CHLOROFORM-d) δ ppm 10.47 (br s, 1H), 7.77 (d, J=7.2 Hz, 2H), 7.55 (br d, J=7.2 Hz, 2H), 7.44-7.38 (m, 2H), 7.37-7.29 (m, 2H), 6.87 (br d, J=8.0 Hz, 1H), 6.78 (br s, 1H), 4.43 (br s, 2H), 4.21 (br s, 1H), 4.02

(br s, 2H), 3.73 (br s, 1H), 3.37-2.99 (m, 1H), 2.88-2.77 (m, 1H), 2.15 (br s, 1H), 1.99-1.78 (m, 2H), 1.32-1.19 (m, 1H)

Fragment BB-19

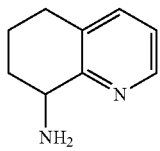

Synthetic Route:

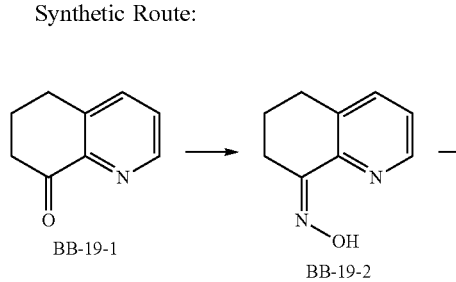

BB-19

Step 1: Synthesis of Compound BB-19-2

Compound BB-19-1 (0.6 g, 4.08 mmol) was dissolved in methanol (20 mL), followed by addition of sodium acetate (1.00 g, 12.23 mmol) and hydroxylamine hydrochloride (424.95 mg, 6.12 mmol), and the reaction mixture was stirred at 20° C. for 1 hour. After the reaction was completed, the reaction mixture was quenched by adding 20 mL of saturated sodium bicarbonate solution, concentrated under reduced pressure to remove methanol, and extracted with dichloromethane (30 mL*2). The organic phase was dried over anhydrous sodium sulfate, filtered and concentrated under reduced pressure to dryness to obtain a crude product of the compound BB-19-2, which was directly used in the next step.

Step 2: Synthesis of Compound BB-19

Compound BB-19-2 (440 mg, 2.71 mmol) was dissolved in methanol (35 mL), followed by addition of wet palladium on carbon (50 mg, 10% purity). The reaction mixture was stirred at 25° C. for 16 hours under hydrogen (50 psi) atmosphere. After the reaction was completed, the reaction mixture was filtered through diatomite, and the filtrate was concentrated under reduced pressure to dryness to obtain a crude product of the compound BB-19, which was directly used in the next step.

$^1$H NMR (400 MHz, METHANOL-d$_4$) δ ppm 8.32 (br d, J=4.4 Hz, 1H), 7.50 (br d, J=7.6 Hz, 1H), 7.16 (m, 1H), 4.02-3.89 (m, 1H), 2.84-2.74 (m, 2H), 2.11-1.91 (m, 2H), 1.82-1.67 (m, 2H).

Fragment BB-20

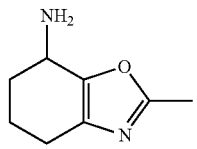

Synthetic Route:

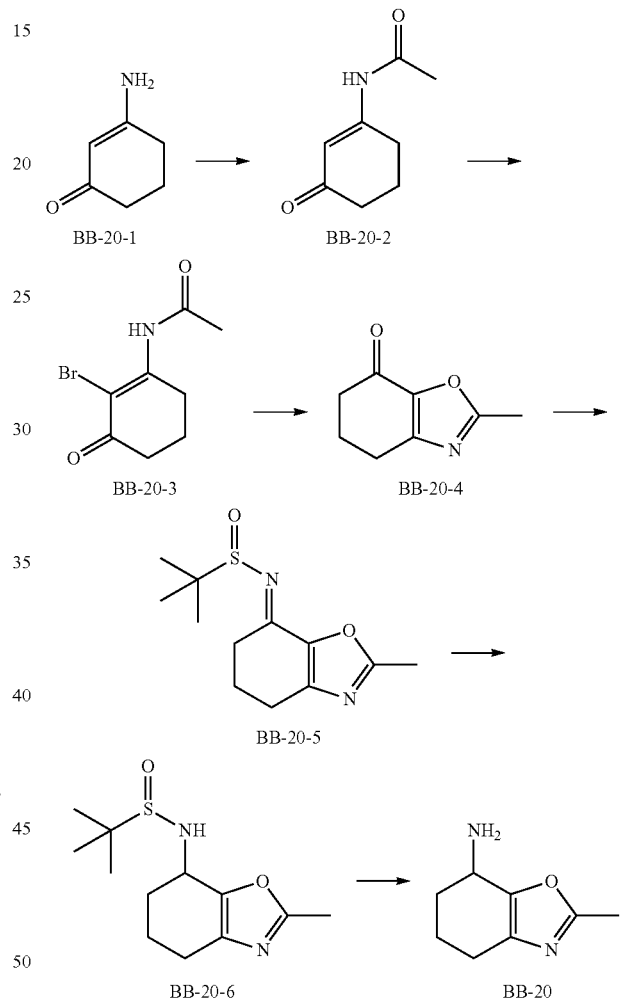

Step 1: Synthesis of Compound BB-20-2

At room temperature, BB-20-1 (2.00 g, 18.00 mmol) was dissolved in anhydrous tetrahydrofuran (50 mL), followed by addition of pyridine (2.85 g, 35.99 mmol) and acetyl chloride (2.83 g, 35.99 mmol). The reaction mixture was heated to 60° C. and stirred for 2 hours. After the reaction mixture was filtered, the filtrate was concentrated under reduced pressure, and the residue was separated and purified by silica gel column chromatography (petroleum ether/ethyl acetate=0:1, then dichloromethane/methanol=20:1) to obtain compound BB-20-2. $^1$H NMR (400 MHz, CDCl$_3$) δ ppm 7.82 (br.s, 1H), 6.59 (s, 1H), 2.60-2.56 (m, 2H), 2.39-2.35 (m, 2H), 2.15 (s, 3H), 2.07-2.02 (m, 2H).

Step 2: Synthesis of Compound BB-20-3

At 0° C., compound BB-20-2 (1.00 g, 6.53 mmol) was dissolved in anhydrous N,N-dimethylformamide (15 mL), followed by addition of N-bromosuccinimide (1.39 g, 7.83 mmol). The reaction mixture was heated to 25° C. and stirred for 4 hours. The reaction mixture was added to water (30 mL) to quench the reaction, and extracted with ethyl acetate (40 mL×2). The organic phases were combined, washed with saturated brine (100 mL), dried over anhydrous sodium sulfate, filtered, and concentrated under reduced pressure. The residue was separated and purified by silica gel column chromatography (petroleum ether/ethyl acetate, 3:1 to 1:1) to obtain compound BB-20-3. $^1$H NMR (400 MHz, CDCl$_3$) δ ppm 7.95 (s, 1H), 3.27-3.23 (m, 2H), 2.61-2.57 (m, 2H), 2.23 (s, 3H), 2.07-2.00 (m, 2H).

Step 3: Synthesis of Compound BB-20-4

Compound BB-20-3 (1.20 g, 5.17 mmol) was dissolved in anhydrous dioxane (15 mL), followed by addition of cesium carbonate (3.54 g, 10.86 mmol), cuprous iodide (196 mg, 1.03 mmol) and dimethylglycine hydrochloride (433 mg, 3.10 mmol). The reaction mixture was heated to 90° C. and stirred for 3 hours. The reaction mixture was filtered, concentrated under reduced pressure, and the residue was separated and purified by silica gel column chromatography (dichloromethane/methanol, 100:1 to 40:1) to obtain compound BB-20-4. $^1$H NMR (400 MHz, CDCl$_3$) δ ppm 2.85-2.82 (m, 2H), 2.61-2.54 (m, 5H), 2.22-2.15 (m, 2H).

Step 4: Synthesis of Compound BB-20-5

Compound BB-20-4 (540 mg, 3.57 mmol) was dissolved in anhydrous toluene (10 mL), followed by addition of 2-methyl-2-propanesulfinamide (563 mg, 4.64 mmol) and tetraethyl titanate (2.44 g, 10.72 mmol). The reaction mixture was stirred at 100° C. for 3 hours. Water (30 mL) and ethyl acetate (30 mL) were added to the reaction mixture, and the resulting mixture was thoroughly stirred and filtered, and the filtrate was extracted with ethyl acetate (20 mL×2). The organic phases were combined, washed with saturated brine (40 mL), dried over anhydrous sodium sulfate, filtered, and concentrated under reduced pressure. The residue was separated and purified by silica gel column chromatography (dichloromethane/methanol, 100:1 to 40:1) to obtain compound BB-20-5.

Step 5: Synthesis of Compound BB-20-6

Compound BB-20-5 (570 mg, 2.24 mmol) was dissolved in anhydrous methanol (10 mL), followed by addition of sodium borohydride (84 mg, 2.24 mmol) at 0° C. The reaction mixture was stirred at 40° C. for 1 hour. Water (2 mL) was added to the reaction mixture to quench the reaction, and the resulting mixture was concentrated under reduced pressure to obtain a crude product of the compound BB-20-6.

Step 6: Synthesis of Compound BB-20

Compound BB-20-6 (580 mg, 2.26 mmol) was dissolved in methanol (5 mL), followed by addition of concentrated hydrochloric acid (1 mL, 12 N). The reaction mixture was stirred at 25° C. for 0.5 hour. The reaction mixture was adjusted to pH of 8-9 with sodium carbonate solid, and filtered. The filtrate was concentrated under reduced pressure. To the residue was added dichloromethane/methanol=10:1 (30 mL), and the mixture was stirred for 3 minutes, filtered, and the filtrate was concentrated under reduced pressure. The residue was separated and purified by silica gel column chromatography (dichloromethane/methanol, 50:1 to 20:1) to obtain compound BB-20. $^1$H NMR (400 MHz, CDCl$_3$) δ ppm 4.00-3.97 (m, 1H), 2.50-2.41 (m, 5H), 2.11-2.08 (m, 1H), 1.87-1.84 (m, 1H), 1.75-1.72 (m, 1H), 1.63-1.56 (m, 3H).

Fragment BB-21

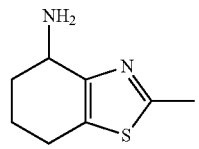

Synthetic Route:

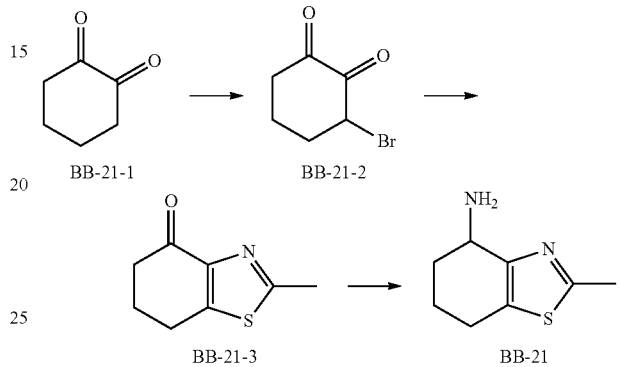

Step 1: Synthesis of Compound BB-21-2

Compound BB-21-1 (10 g, 89.19 mmol) was dissolved in dichloromethane (200 mL), and a solution of liquid bromine (14.25 g, 89.19 mmol, 4.60 mL) in dichloromethane (150 mL) was slowly added dropwise at 0° C. over half an hour. After the dropwise addition was completed, the reaction mixture was stirred at 25° C. for 1 hour. After the reaction was completed, the reaction mixture was concentrated to dryness to obtain a crude product, which was separated and purified with a flash preparative chromatography (eluent: ethyl acetate/petroleum ether=0-20%) to obtain compound BB-21-2. $^1$H NMR (400 MHz, CHLOROFORM-d) δ ppm 6.41 (s, 1H), 2.88 (t, J=6.0 Hz, 2H), 2.61-2.54 (m, 2H), 2.13-2.02 (m, 2H)

Step 2: Synthesis of Compound BB-21-3

A solution of compound BB-21-2 (1 g, 5.23 mmol) and thioacetamide (393.32 mg, 5.23 mmol) in ethanol (30 mL) was heated to 90° C. and stirred for 12 hours. After the reaction was completed, the reaction mixture was concentrated to dryness to obtain a crude product, which was separated and purified with a flash preparative chromatography (eluent: ethyl acetate/petroleum ether=0-40%) to obtain compound BB-21-3. $^1$H NMR (400 MHz, CHLOROFORM-d) δ ppm 3.05 (t, J=6.0 Hz, 2H), 2.70 (s, 3H), 2.67-2.61 (m, 2H), 2.28-2.20 (m, 2H).

Step 3: Synthesis of Compound BB-21

Compound BB-21-3 (170 mg, 1.02 mmol) was dissolved in methanol (20 mL), followed by addition of ammonium acetate (783.58 mg, 10.17 mmol) and sodium cyanoborohydride (319.41 mg, 5.08 mmol). The reaction mixture was heated to 80° C. and stirred for 12 hours. After the reaction was completed, the reaction mixture was concentrated to dryness to obtain a crude product, which was separated and purified with a flash preparative chromatography (eluent: methanol/dichloromethane=0-10%) to obtain compound BB-21. $^1$H NMR (400 MHz, METHANOL-d$_4$) δ ppm 4.43-4.35 (m, 1H), 3.35 (s, 3H), 2.86-2.79 (m, 2H), 2.33-2.23 (m, 1H), 2.13-2.04 (m, 1H), 1.92-1.82 (m, 2H)

Fragment BB-22

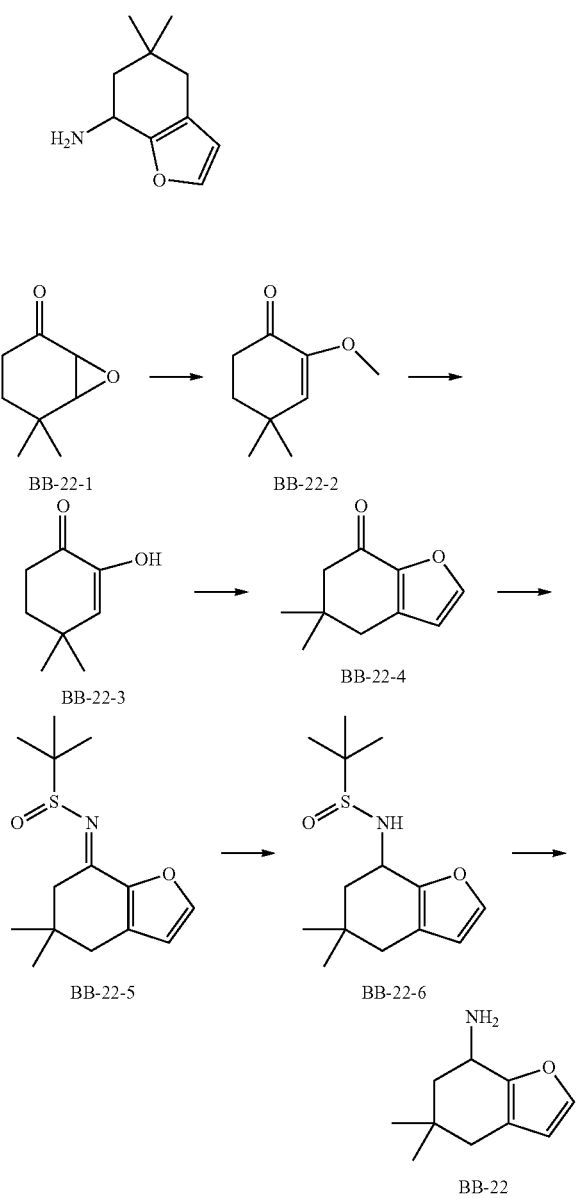

Step 1: Synthesis of Compound BB-22-2

At 25° C., sodium hydroxide (5.14 g, 128.41 mmol) was dissolved in water (150.00 mL), followed by addition of compound BB-22-1 (18 g, 128.41 mmol), and the reaction was allowed to run at 100° C. for 2 hours. The reaction mixture was extracted with ethyl acetate (200 mL×2). The organic phase was washed with saturated brine (200 mL), dried over anhydrous sodium sulfate, filtered, and concentrated, and the residue was separated and purified by flash silica gel column chromatography (petroleum ether/ethyl acetate 100-75%) to obtain compound BB-22-2.

Step 2: Synthesis of Compound BB-22-3

At 25° C., sulfuric acid (3.18 g, 32.42 mmol) was dissolved in water (150.00 mL), followed by addition of a solution of compound BB-22-2 (5.00 g, 32.42 mmol) in tetrahydrofuran (50.00 mL), and the reaction was allowed to run for 48 hours at 100° C. The reaction mixture was extracted with ethyl acetate (50 mL×2). The organic phase was washed with saturated brine (200 mL), dried over anhydrous sodium sulfate, filtered, and concentrated, and the residue was separated and purified by flash silica gel column chromatography (petroleum ether/ethyl acetate 100-83%) to obtain compound BB-22-3. $^1$H NMR (400 MHz, CDCl$_3$) δ ppm 6.00 (m, 1H), 5.90 (s, 1H), 2.40 (s, 2H), 2.30 (m, 2H), 1.09 (s, 6H).

Step 3: Synthesis of Compound BB-22-4

At 25° C., chloroacetaldehyde (1.79 g, 9.12 mmol) and sodium bicarbonate (0.72 g, 8.56 mmol) were dissolved in water (20.00 mL), followed by addition of a solution of compound BB-22-3 (1.00 g, 7.13 mmol) in methanol (10.00 mL) at 0° C. The reaction was allowed to run for 60 hours at 25° C. The reaction mixture was diluted with ethyl acetate (10 mL), adjusted to pH of 1 with 10% sulfuric acid aqueous solution, and extracted with ethyl acetate (10 mL×2). The organic phase was washed with saturated brine (20 mL), dried over anhydrous sodium sulfate, filtered, concentrated, was and the residue was separated and purified with a thin layer chromatography silica gel plate (petroleum ether/ethyl acetate=80%) to obtain compound BB-22-4.

Step 4: Synthesis of Compound BB-22-5

At 25° C., BB-22-4 (733 mg, 4.46 mmol) and tert-butylsulfinamide (0.65 g, 5.36 mmol) were dissolved in toluene (10.00 mL), followed by addition of tetraethyl titanate (5.09 g, 22.32 mmol). The reaction was allowed to run for 16 hours at 110° C. Water (10 mL) was added to the reaction mixture, and the resulting mixture was extracted with ethyl acetate (10 mL×2). The organic phase was washed with saturated brine (20 mL), dried over anhydrous sodium sulfate, filtered, concentrated, and the residue was separated and purified by flash silica gel column chromatography (petroleum ether/ethyl acetate 100-75%) to obtain compound BB-22-5.

Step 5: Synthesis of Compound BB-22-6

According to the method for synthesizing the fragment BB-20-6, compound BB-22-6 was synthesized using compound BB-22-5.

Step 6: Synthesis of Compound BB-22

According to the method for synthesizing the fragment BB-20, compound BB-22 was synthesized using compound BB-22-6. $^1$H NMR (400 MHz, CDCl$_3$) δ ppm (d, J=1.2 Hz, 1H), 6.17 (d, J=1.6 Hz, 1H), 3.89 (m, 1H), 2.34 (m, 1H), 2.22-2.13 (m, 1H), 1.88 (m, 1H), 1.37 (m, 1H), 1.09 (s, 3H), 0.93 (s, 3H).

Fragment BB-23

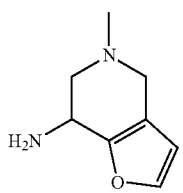

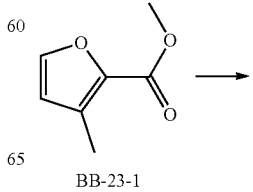

BB-23-1

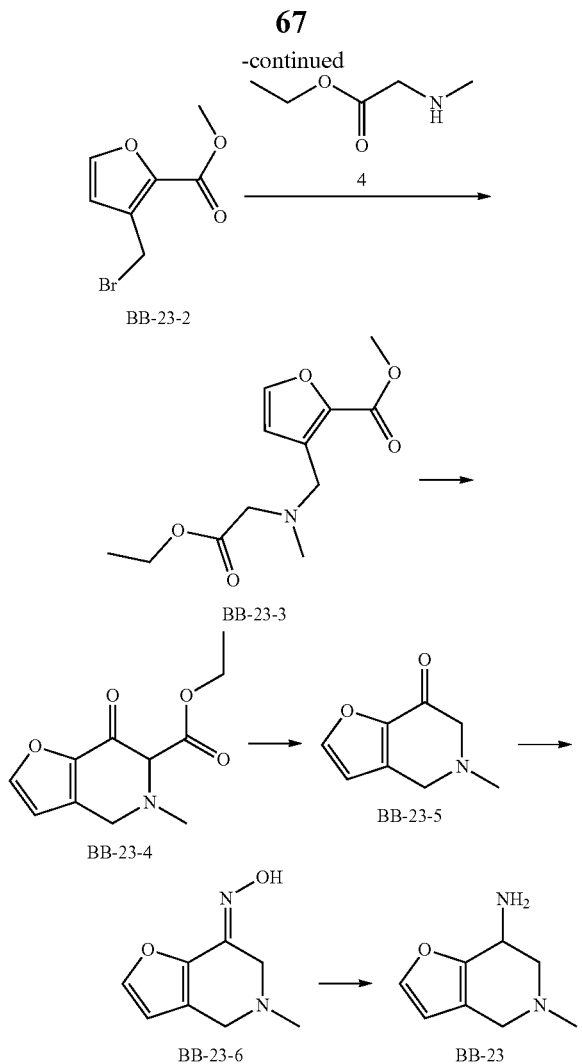

Step 1: Synthesis of Compound BB-23-2

Compound BB-23-1 (9 g, 64.22 mmol) was dissolved in tetrachloromethane (400 mL), followed by addition of N-bromosuccinimide (11.43 g, 64.22 mmol) and 2,2'-azobis (2-methylpropionitrile) (1.05 g, 6.42 mmol), and then the reaction system was purged with nitrogen three times. The reaction mixture was reacted at 75° C. for three hours. After completion of the reaction as indicated by thin layer chromatography, dichloromethane (300 mL) and deionized water (300 mL) were added to the reaction mixture. The organic phase was isolated, washed with brine (100 mL), dried over anhydrous sodium sulfate, filtered, and concentrated to obtain BB-23-2, which was directly used in the next step.

Step 2: Synthesis of Compound BB-23-3

Compound BB-23-2 (13 g, 59.35 mmol) was dissolved in N,N-dimethylformamide (200 mL), followed by addition of ethyl 2-(methylamino)acetate hydrochloride (9.12 g, 59.35 mmol) and potassium carbonate (24.61 g, 178.06 mmol). The reaction mixture was reacted at 25° C. for 2 hours. After completion of the reaction as indicated by thin layer chromatography, to the reaction mixture were added ethyl acetate (500 mL) and deionized water (500 mL). The organic phase was isolated, dried over anhydrous sodium sulfate, filtered, and concentrated to obtain a crude product, which was purified by silica gel column chromatography (petroleum ether/ethyl acetate=5:1 to 1:1) to obtain BB-23-3. $^1$H NMR (400 MHz, CHLOROFORM-d) δ ppm 7.50 (d, J=2.0 Hz 1H), 6.66 (d, J=1.6 Hz 1H), 4.19 (q, J=14.4 Hz, 2H), 3.93 (s, 2H), 3.90 (s, 3H), 3.28 (s, 2H), 2.41 (s, 3H), 1.28 (t, J=7.2 Hz, 3H).

Step 3: Synthesis of Compound BB-23-4

Compound BB-23-3 (10 g, 39.17 mmol) was dissolved in tetrahydrofuran (300 mL). The mixture was cooled to −78° C., and a solution of potassium tert-butoxide (8.79 g, 78.35 mmol) in tetrahydrofuran (100 mL) was slowly added dropwise to the above reaction mixture. The reaction was allowed to run for 14 hours at −78° C. After completion of the reaction as indicated by thin layer chromatography, to the reaction mixture were added dilute hydrochloric acid (1 M, 78 mL), saturated ammonium chloride (200 mL) and ethyl acetate (500 mL). The organic phase was isolated, washed with brine, dried over anhydrous sodium sulfate, filtered and concentrated to obtain BB-23-4.

Step 4: Synthesis of Compound BB-23-5

Compound BB-23-4 (4 g, 17.92 mmol) was added to dilute hydrochloric acid (1 M, 100 mL), and the reaction mixture was heated to 100° C. and reacted for 6 hours. After completion of the reaction as indicated by thin layer chromatography, to the reaction mixture were added saturated sodium carbonate (20 mL) and dichloromethane (100 mL). The organic phase was isolated, washed with saturated brine, dried over anhydrous sodium sulfate, filtered, and concentrated to obtain BB-23-5. $^1$H NMR (400 MHz, CHLOROFORM-d) δ ppm 7.62 (d, J=1.6 Hz 1H), 6.44 (d, J=1.6 Hz 1H), 3.70 (s, 2H), 3.30 (s, 2H), 2.52 (s, 3H).

Step 5: Synthesis of compound BB-23

Compound BB-23-5 (1 g, 6.62 mmol) was dissolved in ethanol (30 mL), followed by addition of sodium acetate (1.09 g, 13.23 mmol). The reaction mixture was reacted at 80° C. for 12 hours. After completion of the reaction as indicated by thin layer chromatography, to the reaction mixture were added dichloromethane (100 mL) and deionized water (50 mL). The organic phase was isolated, washed with saturated brine (20 mL), dried over anhydrous sodium sulfate, filtered and concentrated to obtain BB-23-6. $^1$H NMR (400 MHz, CD$_3$OD) δ ppm 7.55 (d, J=2.0 Hz 1H), 6.47 (d, J=2.0 Hz, 1H), 3.69 (s, 2H), 3.60 (s, 2H), 2.53 (s, 3H).

Step 5: Synthesis of Compound BB-23

Compound BB-23-6 (0.25 g, 1.50 mmol) was dissolved in tetrahydrofuran (30 mL), followed by addition of lithium aluminum hydride (285.50 mg, 7.52 mmol). The reaction mixture was then heated to 80° C. and reacted for 2 hours. After completion of the reaction as indicated by thin layer chromatography, to the reaction mixture were added deionized water (10 mL) and tetrahydrofuran (10 mL). The mixture was filtered through diatomite, and concentrated to obtain a crude product. The crude product was purified by column chromatography to obtain BB-23. $^1$H NMR (400 MHz, CHLOROFORM-d) δ ppm 7.28 (d, J=1.2 Hz 1H), 6.18 (d, J=1.6 Hz 1H), 3.96 (s, 1H), 3.46-3.42 (m, 1H), 3.21-3.17 (m, 1H). 2.82-2.78 (m, 1H), 2.63-2.59 (m, 1H), 2.46 (s, 3H).

Fragment BB-24

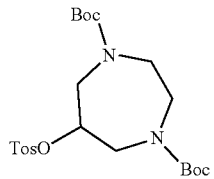

Synthetic Route:

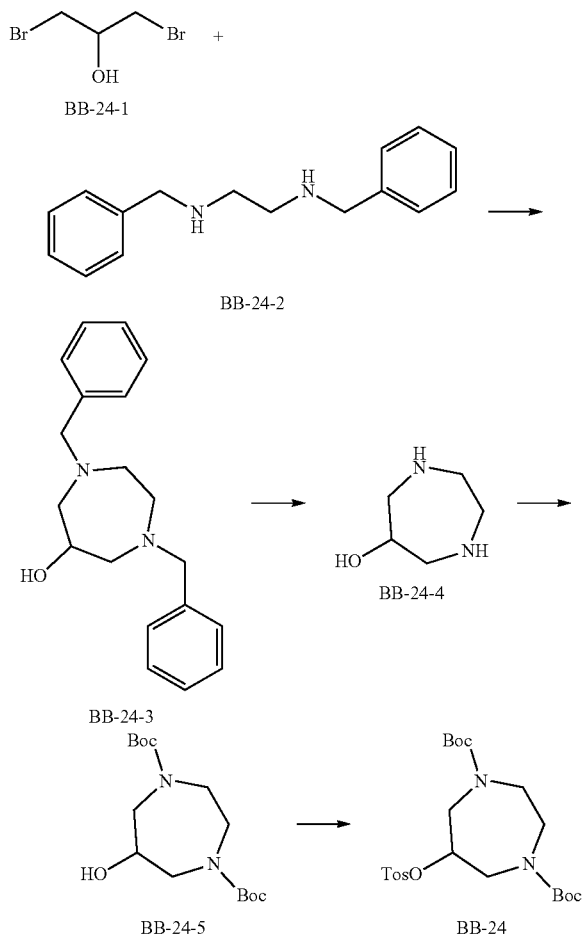

Step 1: Synthesis of Compound BB-24-3

Compound BB-24-2 (10.00 g, 45.90 mmol) was dissolved in toluene (400 mL), and then compound BB-24-1 (11.03 g, 45.90 mmol) and triethylamine (19.16 mL, 137.69 mmol) were added into the reaction mixture. The mixture was heated to 120° C. and stirred for 12 hours. After completion of the reaction as indicated by thin layer chromatography, the reaction mixture was concentrated, followed by addition of water (30 mL) and ethyl acetate (30 mL). The aqueous phase was extracted three times with ethyl acetate (30 mL×3). The organic phases were combined and dried over anhydrous sodium sulfate, filtered, and concentrated, and the residue was purified by column chromatography (dichloromethane/methanol=20/1) to obtain BB-24-3. $^1$H NMR (400 MHz, CHLOROFORM-d) δ ppm 7.36-7.26 (m, 10H), 3.85-3.77 (m, 1H), 3.75-3.62 (m, 4H), 2.94-2.80 (m, 4H), 2.79-2.68 (m, 2H), 2.53-2.41 (m, 2H)

Step 2: Synthesis of Compound BB-24-4

Compound BB-24-3 (8.10 g, 27.33 mmol) was dissolved in methanol (300 mL), and then palladium hydroxide on carbon (2.00 g) was added to the reaction mixture. The mixture was stirred at room temperature for 3 hours under hydrogen atmosphere (15 psi). After completion of the reaction as indicated by thin layer chromatography, the reaction mixture was filtered through diatomite at room temperature to remove the catalyst, and the filtrate was rotary-evaporated to obtain a crude product of the compound BB-24-4.

Step 3: Synthesis of Compound BB-24-5

Compound BB-24-4 (2.60 g, 22.38 mmol) was dissolved in methanol (26 mL), followed by addition of triethylamine (7.48 mL, 53.72 mmol) and Boc$_2$O (9.77 g, 44.77 mmol), and the mixture was stirred at 25° C. for 1 hour. After completion of the reaction as indicated by thin layer chromatography and liquid chromatography, the reaction mixture was concentrated at room temperature and quenched with water (20 mL), and then extracted with dichloromethane (20 mL×3). The organic phases were combined, dried over anhydrous sodium sulfate, filtered, and concentrated, and the residue was purified by column chromatography (petroleum ether/ethyl acetate=1:1) to obtain BB-24-5. $^1$H NMR (400 MHz, CHLOROFORM-d) δ ppm 4.31-4.08 (m, 1H), 4.03-3.86 (m, 3H), 3.86-3.54 (m, 1H), 3.54-3.27 (m, 2H), 3.12-3.11 (m, 1H), 3.03 (m, 1H), 2.78 (m, 1H), 1.48 (s, 9H), 1.47 (s, 9H).

Step 4: Synthesis of Compound BB-24

Compound BB-24-5 (1.00 g, 3.16 mmol) was dissolved in dichloromethane (10 mL), followed by addition of triethylamine (1.10 mL, 3.90 mmol), DMAP (193.06 mg, 1.58 mmol) and p-toluenesulfonyl chloride (1.21 g, 6.32 mmol) to the reaction mixture at 0° C. The mixture was heated to 40° C. and stirred for 1 hour. After completion of the reaction as indicated by thin layer chromatography, the reaction mixture was quenched with water (20 mL) at room temperature, and extracted with dichloromethane (20 mL×3). The organic phases were combined, dried over anhydrous sodium sulfate, filtered, and concentrated, and the residue was purified by column chromatography (petroleum ether/ethyl acetate=7:3) to obtain compound BB-24. $^1$H NMR (400 MHz, CHLOROFORM-d) δ=7.88-7.75 (m, 2H), 7.36 (br d, J=7.2 Hz, 2H), 4.79-4.57 (m, 1H), 3.88-3.27 (m, 8H), 2.46 (s, 3H), 1.52-1.38 (m, 18H).

Fragment BB-25

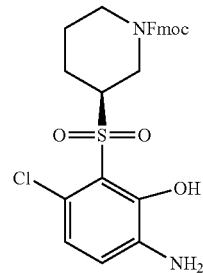

Synthetic Route:

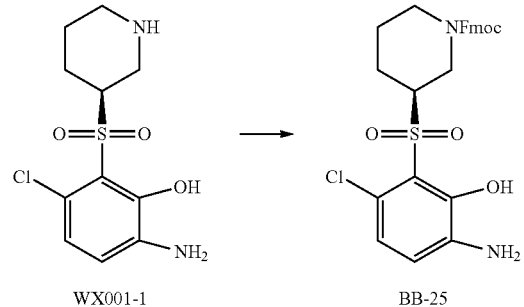

Compound WX001-1 (0.70 g, 2.41 mmol) was dissolved in dichloromethane (10 mL), and saturated NaHCO$_3$ solution was added to obtain pH>7, followed by addition of FmocCl (465.81 mg, 1.44 mmol) at 0° C. The mixture was stirred at 25° C. for 1 hour. After completion of the reaction as indicated by thin layer chromatography and liquid chromatography, the reaction mixture was separated into layers, and the aqueous phase was extracted three times with ethyl acetate (20 mL×3). The organic phases were combined, dried over anhydrous sodium sulfate, filtered and concentrated, and the residue was purified by column chromatography (SiO$_2$, petroleum ether/ethyl acetate=3/1) to obtain BB-25. $^1$H NMR (400 MHz, CHLOROFORM-d) δ ppm 10.47 (br s, 1H), 7.77 (d, J=7.2 Hz, 2H), 7.55 (br d, J=7.2 Hz, 2H), 7.44-7.38 (m, 2H), 7.37-7.29 (m, 2H), 6.87 (br d, J=8.0 Hz, 1H), 6.78 (br s, 1H), 4.43 (br s, 2H), 4.21 (br s, 1H), 4.02 (br s, 2H), 3.73 (br s, 1H), 3.37-2.99 (m, 1H), 2.88-2.77 (m, 1H), 2.15 (br s, 1H), 1.99-1.78 (m, 2H), 1.32-1.19 (m, 1H).

Fragment BB-26

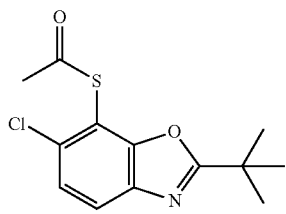 [SMILES: CC(=O)Sc1c(Cl)ccc2nc(C(C)(C)C)oc12]

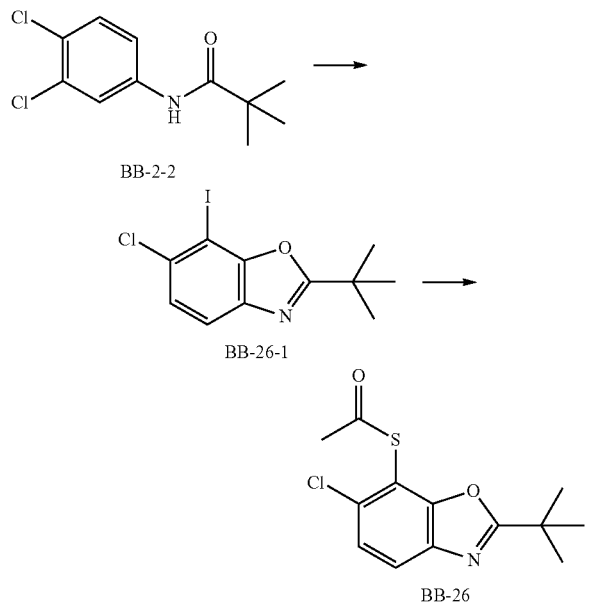

Step 1: Synthesis of Compound BB-26-1

At 25° C., compound BB-2-2 (50.00 g, 203.14 mmol) was dissolved in tetrahydrofuran (500.00 mL). The mixture was cooled to −25° C., followed by dropwise addition of n-butyllithium (2.5 M, 138.14 mL, 345.34 mmol) under nitrogen atmosphere while maintaining the internal temperature below −10° C. After the dropwise addition was completed, the reaction was allowed to run for 5 minutes at −10° C., followed by dropwise addition of a solution of iodine (103.12 g, 406.29 mmol) in tetrahydrofuran (250.00 mL) while maintaining the internal temperature below −5° C. After the dropwise addition was completed, the reaction was allowed to run for 8 minutes at −5° C. The mixture was quenched with saturated aqueous solution of sodium thiosulfate (200 mL), and extracted with ethyl acetate (200 mL×2). The organic phase was washed with saturated aqueous solution of sodium thiosulfate (200 mL) and saturated brine (200 mL×2), dried over anhydrous sodium sulfate, filtered, and concentrated, and the residue was separated and purified by flash silica gel column chromatography (petroleum ether/ethyl acetate 100-96%) to obtain compound BB-26-1.

Step 2: Synthesis of Compound BB-26

At 25° C., compound BB-26-1 (10.00 g, 29.80 mmol), cuprous iodide (1.14 g, 5.96 mmol), 1,10-phenanthroline (1.07 g, 5.96 mmol) and potassium thioacetate (6.81 g, 59.60 mmol) were dissolved in toluene (100.00 mL) and reacted at 90° C. for 20 hours under nitrogen atmosphere. After cooling to room temperature, the mixture was quenched with water (100 mL), diluted with ethyl acetate (100 mL), filtered, and extracted with ethyl acetate (200 mL×2). The organic phase was washed with saturated brine (100 mL), dried over anhydrous sodium sulfate, filtered, and concentrated, and the residue was separated and purified by flash silica gel column chromatography (petroleum ether/ethyl acetate 100-94%) to obtain compound BB-26.

Fragment BB-27

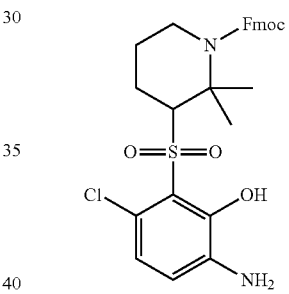

Synthetic Route:

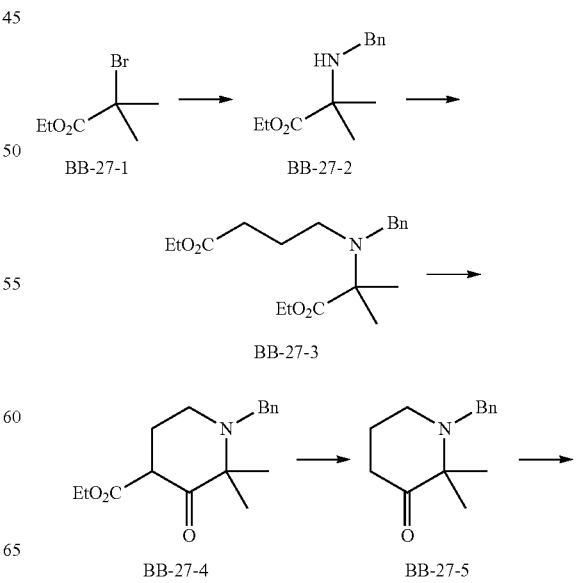

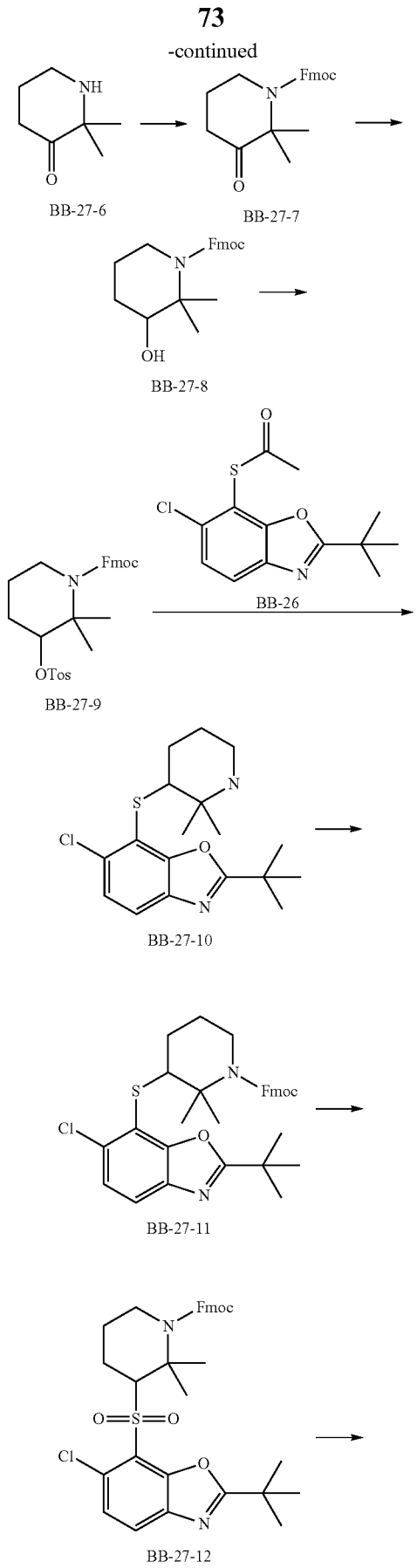

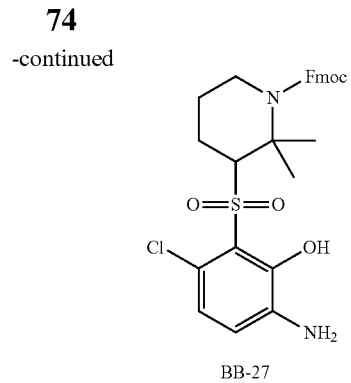

BB-27

Step 1: Synthesis of Compound BB-27-2

Compound BB-27-1 (83.79 g, 429.57 mmol) was dissolved in ethanol (500 mL), followed by addition of potassium carbonate (69.66 g, 504.00 mmol), potassium iodide (836.65 mg, 5.04 mmol) and benzylamine (54.00 g, 504.00 mmol). The mixture was heated to 85° C. and stirred for 16 hours. After the reaction was completed, the precipitated solid was removed by filtration under reduced pressure, and the filtrate was collected. The filtrate was concentrated to dryness under reduced pressure, and the residue was separated and purified with a flash preparative chromatography (eluent: ethyl acetate/petroleum ether=0-20%) to obtain compound BB-27-2. $^1$H NMR (400 MHz, CHLOROFORM-d) δ ppm 7.38-7.26 (m, 5H), 4.20 (q, J=7.2 Hz, 2H), 3.62 (s, 2H), 1.37 (s, 6H), 1.31 (t, J=7.2 Hz, 3H).

Step 2: Synthesis of Compound BB-27-3

A mixture of compound BB-27-2 (25.3 g, 114.33 mmol), ethyl bromobutyrate (23.41 g, 120.04 mmol) and potassium iodide (948.93 mg, 5.72 mmol) was heated to 120° C. and stirred for 24 hours. After the reaction was completed, the reaction mixture was diluted by adding ethyl acetate (250 mL). The precipitated solid was removed by filtration under reduced pressure, and the filtrate was collected. The filtrate was concentrated to dryness under reduced pressure, and the residue was separated and purified with a flash preparative chromatography (eluent: ethyl acetate/petroleum ether=0-10%) to obtain compound BB-27-3. $^1$H NMR (400 MHz, CHLOROFORM-d) δ ppm 7.40-7.26 (m, 4H), 7.22-7.16 (m, 1H), 4.20-4.14 (m, 2H), 4.10-4.01 (m, 2H), 3.82 (s, 2H), 2.70-2.61 (m, 2H), 2.17 (t, J=7.2 Hz, 2H), 1.56-1.48 (m, 2H), 1.36 (s, 6H), 1.29 (t, J=7.2 Hz, 3H), 1.20 (t, J=7.2 Hz, 3H).

Step 3: Synthesis of Compound BB-27-4

Compound BB-27-3 (8.5 g, 25.34 mmol) was dissolved in tetrahydrofuran (250 mL), followed by addition of sodium hydride (3.04 g, 76.02 mmol, 60% purity), and the mixture was heated to 80° C. and stirred for 4 hours. After the reaction was completed, the reaction mixture was concentrated to dryness under reduced pressure, followed by addition of 100 mL of water and adjusting the pH to 5 with dilute hydrochloric acid, during which the temperature was kept below 10° C. with an ice bath. The mixture was neutralized with sodium bicarbonate solid to obtain a neutral pH, and extracted with ethyl acetate (250 mL×2). The organic phase was washed with saturated brine (200 mL), dried over anhydrous sodium sulfate, filtered, and concentrated to dryness under reduced pressure to obtain compound BB-27-4, which was directly used in the next step without purification. $^1$H NMR (400 MHz, CHLOROFORM-d) δ ppm 12.41 (s, 1H), 7.40-7.29 (m, 5H), 4.23-4.18 (m, 2H), 3.61 (s, 2H), 2.51 (t, J=5.6 Hz, 2H), 2.16 (t, J=5.6 Hz, 2H), 1.39 (s, 6H), 1.28 (t, J=7.2 Hz, 3H)

Step 4: Synthesis of Compound BB-27-5

Compound BB-27-4 (7.1 g, 24.54 mmol) was dissolved in 6 M hydrochloric acid (177.50 mL), and the reaction mixture was heated to 110° C. and stirred for 3 hours. After the reaction was completed, the reaction mixture was cooled to room temperature, adjusted to pH 8 by addition of sodium hydroxide solid, and extracted with ethyl acetate (250 mL×2). The organic phases were combined, washed with saturated brine (250 mL), dried over anhydrous sodium sulfate, filtered, and concentrated to dryness under reduced pressure to obtain compound BB-27-5, which was directly used in the next step without purification. $^1$H NMR (400 MHz, CHLOROFORM-d) δ ppm 7.39-7.24 (m, 5H), 3.62 (s, 2H), 2.65 (t, J=6.0 Hz, 2H), 2.49 (t, J=7.2 Hz, 2H), 1.87-1.77 (m, 2H), 1.30 (s, 6H).

Step 5: Synthesis of Compound BB-27-6

Compound BB-27-5 (2.5 g, 11.50 mmol) was dissolved in methanol (10 mL), followed by addition of wet palladium on carbon (100 mg, 10% purity), and the reaction mixture was stirred at 25° C. for 3 hours under hydrogen atmosphere (30 psi). After the reaction was completed, the reaction mixture was filtered through diatomite, and the filtrate was concentrated to dryness under reduced pressure to obtain compound BB-27-6, which was directly used in the next step. $^1$H NMR (400 MHz, CHLOROFORM-d) δ ppm 3.08-2.99 (m, 2H), 2.49 (t, J=6.8 Hz, 2H), 2.08-1.98 (m, 2H), 1.25 (s, 6H).

Step 6: Synthesis of Compound BB-27-7

Compound BB-27-6 (1.25 g, 9.83 mmol) was dissolved in dichloromethane (35 mL), followed by addition of 35 mL of aqueous sodium bicarbonate solution (2.48 g, 29.48 mmol) and FmocCl (2.54 g, 9.83 mmol). The reaction mixture was stirred at 25° C. for 2 hours. After the reaction was completed, the reaction mixture was extracted with dichloromethane (30 mL×2). The organic phases were combined, washed with saturated brine (50 mL), dried over anhydrous sodium sulfate, and filtered. The filtrate was concentrated to dryness under reduced pressure, and the residue was separated and purified with a flash preparative chromatography (eluent: ethyl acetate/petroleum ether=0-30%) to obtain compound BB-27-7.

Step 7: Synthesis of Compound BB-27-8

Compound BB-27-7 (497 mg, 1.42 mmol) was dissolved in methanol (10 mL), followed by addition of sodium borohydride (53.81 mg, 1.42 mmol) at 0° C., and the reaction mixture was warmed to 25° C. and stirred for 1 hour. After the reaction was completed, 10 mL of acetone was added to quench the reaction, and the reaction mixture was concentrated to dryness under reduced pressure, followed by addition of 10 mL of water and extraction with dichloromethane (25 mL×2). The organic phases were combined, washed with saturated brine (20 mL), dried over anhydrous sodium sulfate, and filtered. The filtrate was concentrated to dryness under reduced pressure, and the residue was separated and purified with a flash preparative chromatography (eluent: ethyl acetate/petroleum ether=0-35%) to obtain compound BB-27-8.

Step 8: Synthesis of Compound BB-27-9

Compound BB-27-8 (790 mg, 2.25 mmol) was dissolved in dichloromethane (80 mL), followed by addition of triethylamine (568.66 mg, 5.62 mmol), 4-dimethylaminopyridine (274.63 mg, 2.25 mmol) and p-toluenesulfonyl chloride (642.85 mg, 3.37 mmol). The reaction mixture was stirred at 40° C. for 12 hours. After the reaction was completed, the reaction mixture was directly concentrated to dryness, and the residue was separated and purified with a flash preparative chromatograph (eluent: ethyl acetate/petroleum ether=0-20%) to obtain compound BB-27-9.

Step 9: Synthesis of Compound BB-27-10

Compound BB-26 (285 mg, 1.00 mmol) was dissolved in methanol (15 mL), followed by addition of potassium carbonate (347.01 mg, 2.51 mmol), and the reaction mixture was heated to 60° C. and stirred for 0.5 hour. The reaction mixture was concentrated to dryness under reduced pressure, and dissolved in dimethylformamide (35 mL), followed by addition of potassium carbonate (340.18 mg, 2.46 mmol) and compound BB-27-9 (497.81 mg, 984.54 μmol). The reaction mixture was heated to 60° C. and stirred for 1 hour. After the reaction was completed, the reaction mixture was poured into 150 mL of water to quench the reaction, and the resulting mixture was extracted with ethyl acetate (50 mL×3). The organic phases were combined, washed with saturated brine (100 mL), dried over anhydrous sodium sulfate, and filtered. The filtrate was concentrated to dryness under reduced pressure, and the residue was separated and purified with a flash preparative chromatography (eluent: methanol/dichloromethane=0-20%) to obtain compound BB-27-10.

Step 10: Synthesis of Compound BB-27-11

Compound BB-27-10 (20 mg, 56.67 μmol) was dissolved in dichloromethane (5 mL), followed by addition of 2 mL of an aqueous solution of sodium bicarbonate (14.28 mg, 170.01 μmol) and FmocCl (14.66 mg, 56.67 μmol). The reaction mixture was stirred at 25° C. for 2 hours. After the reaction was completed, the reaction mixture was poured into 10 mL of water, and extracted with dichloromethane (10 mL×2). The organic phases were combined, washed with saturated brine (10 mL), dried over anhydrous sodium sulfate, and filtered. The filtrate was concentrated and dried under reduced pressure to obtain compound BB-27-11, which was directly used in the next step.

Step 11: Synthesis of Compound BB-27-12

Compound BB-27-11 (35 mg, 60.85 μmol) was dissolved in dichloromethane (5 mL), and m-chloroperoxybenzoic acid (98.83 mg, 486.82 μmol, 85% purity) was added in portions. The reaction mixture was stirred at 25° C. for 16 hours. After the reaction was completed, 2 mL of saturated sodium thiosulfate solution and 5 mL of saturated sodium bicarbonate solution were added to quench the reaction, and the resulting mixture was extracted with dichloromethane (10 mL×2). The organic phases were combined, washed with saturated brine (10 mL), dried over anhydrous sodium sulfate, and filtered. The filtrate was concentrated to dryness under reduced pressure to obtain compound BB-27-12, which was directly used in the next step.

Step 12: Synthesis of Compound BB-27

Compound BB-27-12 (35 mg, 57.65 μmol) was dissolved in ethanol (5 mL), followed by addition of concentrated hydrochloric acid (12 M, 480.38 μL). The reaction mixture was heated to 85° C. and stirred for 16 hours. After the reaction was completed, the reaction mixture was concentrated to dryness under reduced pressure, dissolved in 30 mL of ethyl acetate, washed with saturated sodium bicarbonate solution (10 mL) and saturated brine (10 mL), dried over anhydrous sodium sulfate, and filtered. The filtrate was concentrated to dryness under reduced pressure to obtain compound BB-27, which was directly used in the next step.

Embodiment 1: WX001, WX001A, WX001B

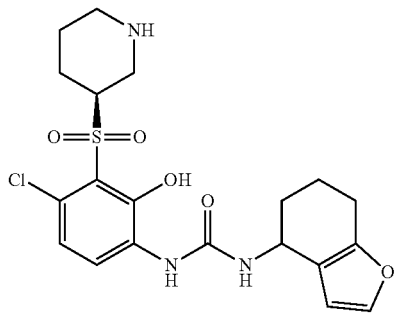 [SMILES: O=C(Nc1ccc(Cl)c(S(=O)(=O)[C@H]2CCCNC2)c1O)NC1CCCc2occc21]

Synthetic Route:

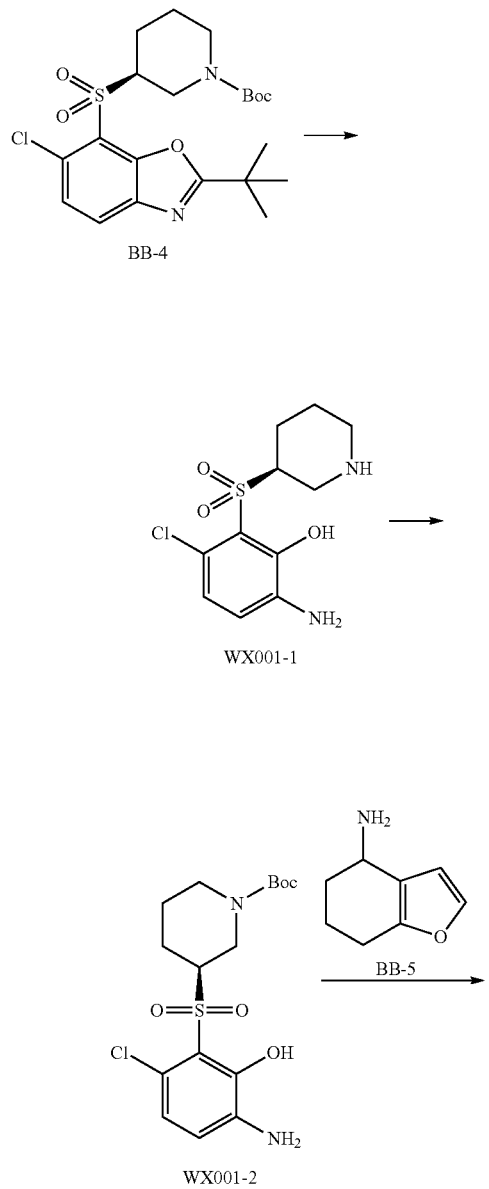

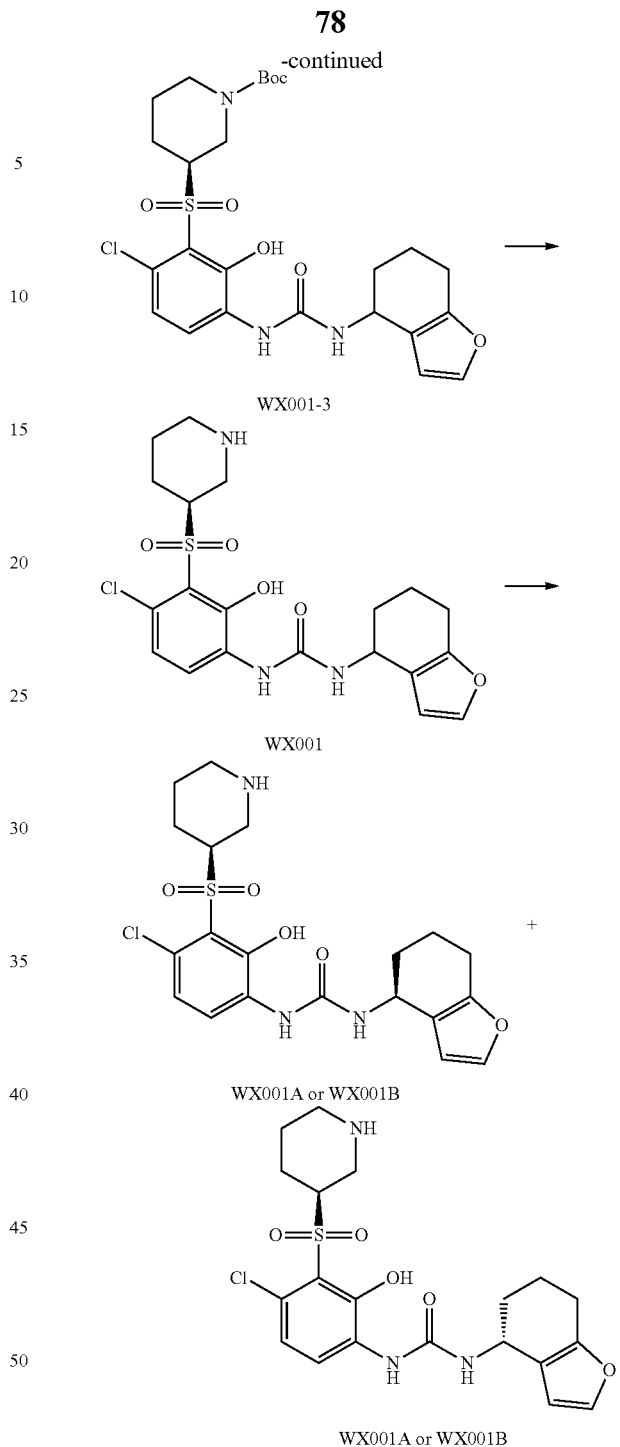

Step 1: Synthesis of Compound WX001-1

Compound BB-4 (3.25 g, 7.11 mmol) was dissolved in 15 mL of ethanol, followed by addition of concentrated hydrochloric acid (12 M, 9.5 mL), and the resulting mixture was heated to 80° C. and stirred overnight. After the reaction was completed, the solvent was removed under reduced pressure, and the pH value was adjusted to 12 with 2 M NaOH to obtain a crude product solution, which was directly used in the next reaction.

Step 2: Synthesis of Compound WX001-2

To the above crude product solution were added 10 mL of ethyl acetate and Boc$_2$O (1.55 g, 7.12 mmol, 1.64 mL), and the reaction was allowed to run for 1.5 hours at 0° C. After the reaction was completed, the mixture was diluted with 20 mL of ethyl acetate and extracted with ethyl acetate (20 mL×3). The organic phases were combined, washed with saturated brine (15 mL×3), dried over anhydrous sodium sulfate, filtered and concentrated to obtain a crude product, which was separated by a chromatography column (eluent: ethyl acetate/petroleum ether=0-25%) to obtain the target compound WX001-2. $^1$H NMR (400 MHz, CHLOROFORM-d) δ ppm 10.47 (br s, 1H), 6.92-6.86 (m, 1H), 6.81 (d, J=8.2 Hz, 1H), 4.26 (br s, 1H), 4.04 (br s, 3H), 3.76-3.66 (m, 1H), 3.08 (br s, 1H), 2.76 (br t, J=12.6 Hz, 1H), 2.21 (br d, J=10.4 Hz, 1H), 1.98-1.84 (m, 2H), 1.58 (s, 1H), 1.42 (s, 9H).

Step 3: Synthesis of Compound WX001-3

Triphosgene (158 mg, 532.43 μmol) was dissolved in 5 mL of DCM, followed by addition of BB-5 (220 mg, 1.60 mmol) and triethylamine (54.36 mg, 537.25 μmol, 74.47 μL). After stirring at room temperature for 30 minutes, the reaction mixture was concentrated. The obtained crude product was dissolved in 5 mL of DCM, followed by addition of WX001-2 (200 mg, 511.67 μmol) and triethylamine (117.01 mg, 1.16 mmol, 160.29 μL), and the resulting mixture was stirred at room temperature overnight. After the reaction was completed, the reaction mixture was concentrated to obtain a crude product of WX001-3, which was directly used in the next reaction.

Step 4: Synthesis of Compound WX001

Compound WX001-3 (300.00 mg, 541.47 μmol) was dissolved in 5 mL of ethyl acetate, followed by addition of HCl/EtOAc (4 M, 4.00 mL), and the reaction mixture was stirred at room temperature overnight. After the reaction was completed, the reaction mixture was concentrated to obtain a crude product, which was separated by high performance liquid chromatography to obtain the target compound WX001. $^1$H NMR (400 MHz, DMSO-d$_6$) δ ppm 1.57-1.75 (m, 2H) 1.74-1.93 (m, 7H) 1.96 (br d, J=13.2 Hz, 2H) 2.89 (br s, 2H) 3.11 (br t, J=11.6 Hz, 1H) 3.24 (br d, J=12.0 Hz, 1H) 3.42-3.46 (m, 1H) 4.16 (br t, J=11.4 Hz, 1H) 4.63-4.71 (m, 1H) 6.37 (s, 1H) 7.17 (d, J=9.0 Hz, 1H) 7.36-7.49 (m, 2H) 8.22 (d, J=8.8 Hz, 1H) 8.56 (s, 1H) 8.82-9.59 (m, 2H) 10.92 (br s, 1H).

Step 5: Synthesis of Compounds WX001A and WX001B

Compound WX001 was resolved by supercritical fluid chromatography (separation conditions: column, Chiralpak AD-3 100×4.6 mm ID., 3 μm; mobile phase, A: carbon dioxide, B: methanol (0.05% diethylamine); flow rate: 2.8 mL/min; column temperature: 40° C.; detection wavelength: 220 nm) to obtain the chiral isomers WX001A and WX001B with a retention time of 4.883 min and 5.875 min, respectively, and a ratio of 1:1.

Embodiment 2: WX002, WX002A, WX002B

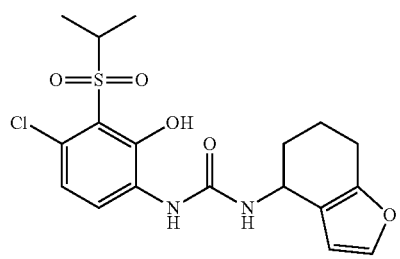 [SMILES: CC(C)S(=O)(=O)c1c(Cl)ccc(NC(=O)NC2CCCc3occc32)c1O]

Synthetic Route:

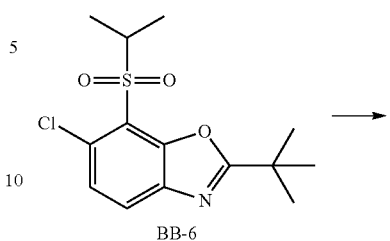
BB-6

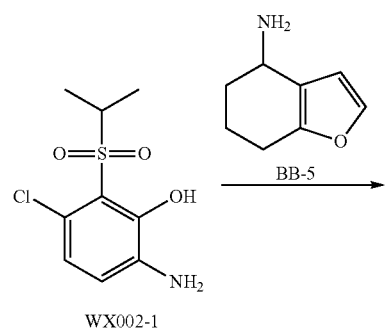
WX002-1

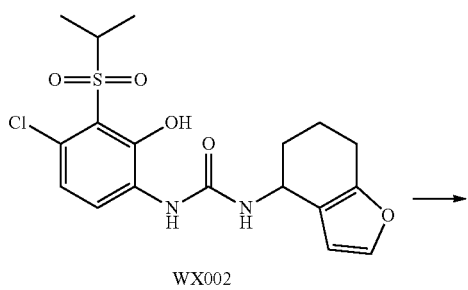
WX002

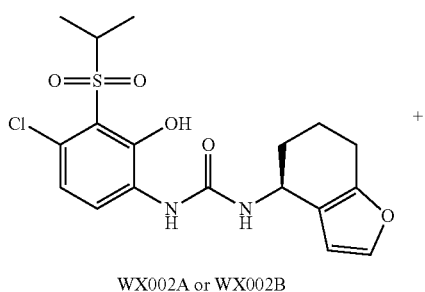
WX002A or WX002B

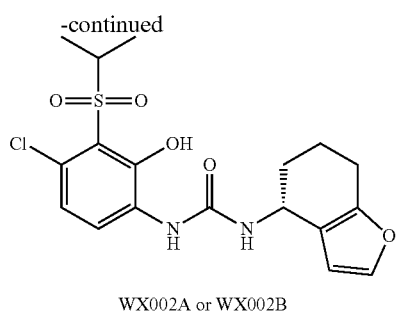

WX002A or WX002B

Step 1: Synthesis of Compound WX002-1

Compound BB-6 (10.80 g, 34.20 mmol) was dissolved in 60 mL of ethanol, followed by addition of concentrated hydrochloric acid (12 M, 20 mL), and the resulting mixture was heated to 80° C. and reacted with stirring overnight. After the reaction was completed, the solvent was evaporated under reduced pressure. The residue was adjusted to pH of 7 with 1 M NaOH, and extracted with ethyl acetate (40 mL×3). The organic phases were combined, washed with saturated brine (30 mL×3), dried over anhydrous sodium sulfate, filtered and concentrated to obtain a crude product, which was then separated with a chromatography column (eluent: ethyl acetate/petroleum ether=0-30%) to obtain the target compound WX002-1. $^1$H NMR (400 MHz, CHLOROFORM-d) δ ppm 1.40 (d, J=7.0 Hz, 6H) 3.89 (spt, J=6.8 Hz, 1H) 6.78-6.83 (m, 1H) 6.85-6.91 (m, 1H) 10.62 (s, 1H).

Step 2: Synthesis of Compound WX002

BB-5 (219.74. mg, 1.60 mmol) was dissolved in 5 mL of DCM, followed by addition of triphosgene (156.87 mg, 528.61 μmol) and triethylamine (81.05 mg, 800.93 μmol, 111.03 μL). After the reaction mixture was stirred at room temperature for 30 minutes, the reaction mixture was concentrated. The obtained crude product was dissolved in 5 mL of DCM, followed by addition of WX002-1 (200 mg, 800.93 μmol) and triethylamine (162.09 mg, 1.60 mmol, 222.04 μL), and the resulting mixture was stirred at room temperature overnight. After the reaction was completed, the reaction mixture was concentrated, and the obtained crude product was separated by high-performance liquid chromatography to obtain the target compound WX002.

Step 3: Synthesis of Compounds WX002A and WX002B.

Compound WX002 was resolved by supercritical fluid chromatography (separation conditions: column, Chiralpak AD (250 mm×30 mm, 5 μm); mobile phase, A: carbon dioxide, B: methanol (0.1% ammonium hydroxide)) to obtain the chiral isomers WX002A and WX002B, with a retention time of 4.803 min and 5.672 min, respectively, and a ratio of 1:1.

According to the steps 1 to 3 in the synthesis of Embodiment 2, the embodiments in Table 1 were synthesized using BB-1 in the step 2. The structures in the table also represent their potential isomers.

TABLE 1

| Embodiment | Fragment in the step 2 | Structure | Compound |
|---|---|---|---|
| 3 | BB-1 | | WX003<br>WX003A<br>WX003B |

Embodiment 4: WX004, WX004A, WX004B

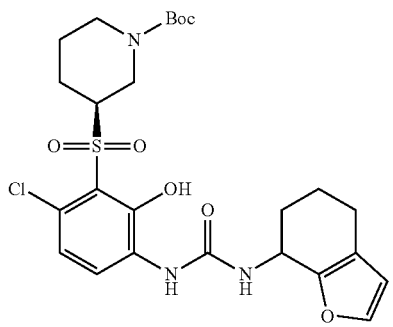 [SMILES: CC(C)(C)OC(=O)N1CCC[C@H](S(=O)(=O)c2c(Cl)ccc(NC(=O)NC3CCCc4ccoc43)c2O)C1]

Synthetic Route:

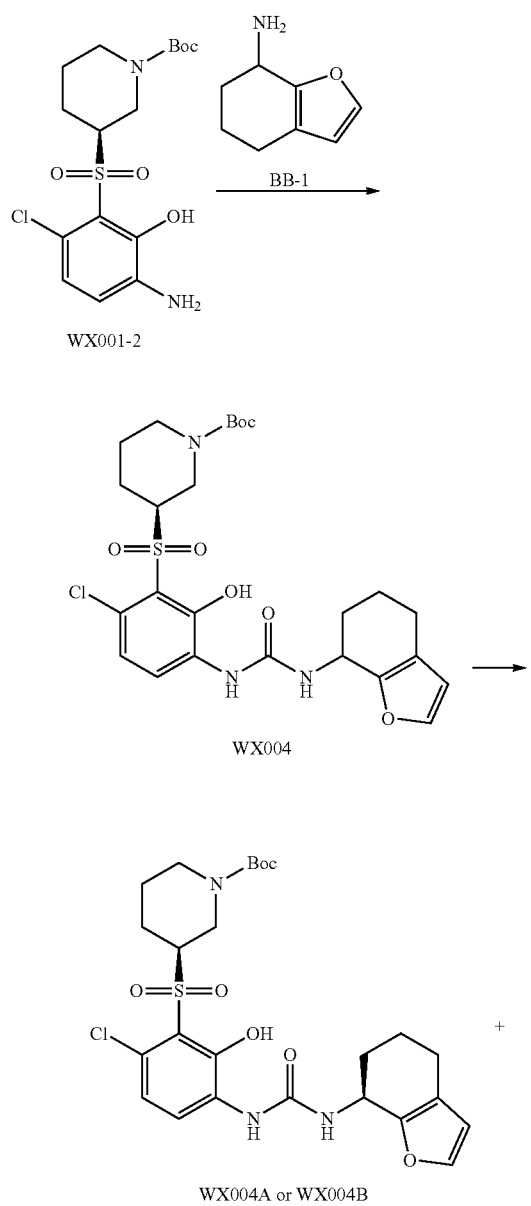

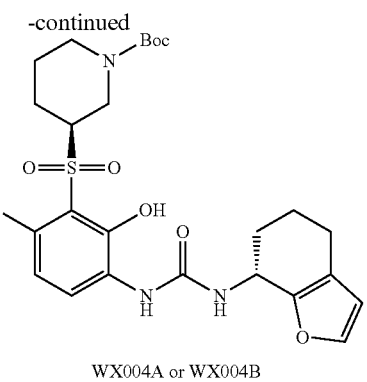

WX004A or WX004B

Step 1: Synthesis of Compound WX004

BB-1 (105.28 mg, 767.50 μmol) was dissolved in 5 mL of DCM, followed by addition of triphosgene (75.16 mg, 253.28 μmol) and triethylamine (77.66 mg, 767.50 μmol, 106.83 μL). After stirring at room temperature for 30 minutes, the reaction mixture was concentrated. The obtained crude product was dissolved in 5 mL of DCM, followed by addition of WX001-2 (150.00 mg, 383.75 μmol) and triethylamine (38.83 mg, 383.75 μmol, 53.41 μL), and the resulting mixture was stirred at room temperature overnight. After the reaction was completed, the reaction mixture was concentrated, and the obtained crude product was separated by high performance liquid chromatography to obtain the target compound WX004.

Step 2: Synthesis of Compounds WX004A and WX004B

Compound WX004 was resolved by supercritical fluid chromatography (separation conditions: column, ChiralCel OD-H 150×4.6 mm I.D., 5 μm; mobile phase, A: carbon dioxide, B: ethanol (0.05% diethylamine); flow rate: 2.5 mL/min; column temperature: 40° C.; detection wavelength: 220 nm) to obtain the chiral isomers WX004A and WX004B with a retention time of 4.499 min and 5.163 min, respectively, and a ratio of 1:1.

Embodiment 5: WX005, WX005A, WX005B

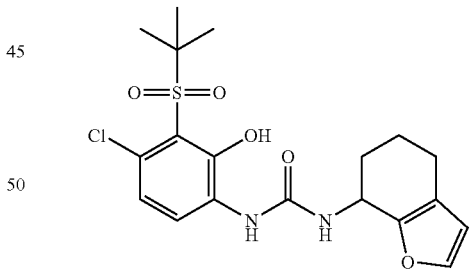

Synthetic Route:

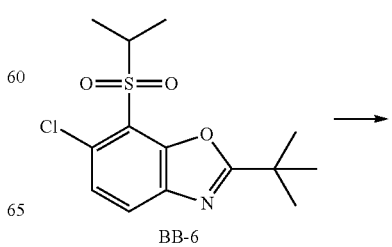

BB-6

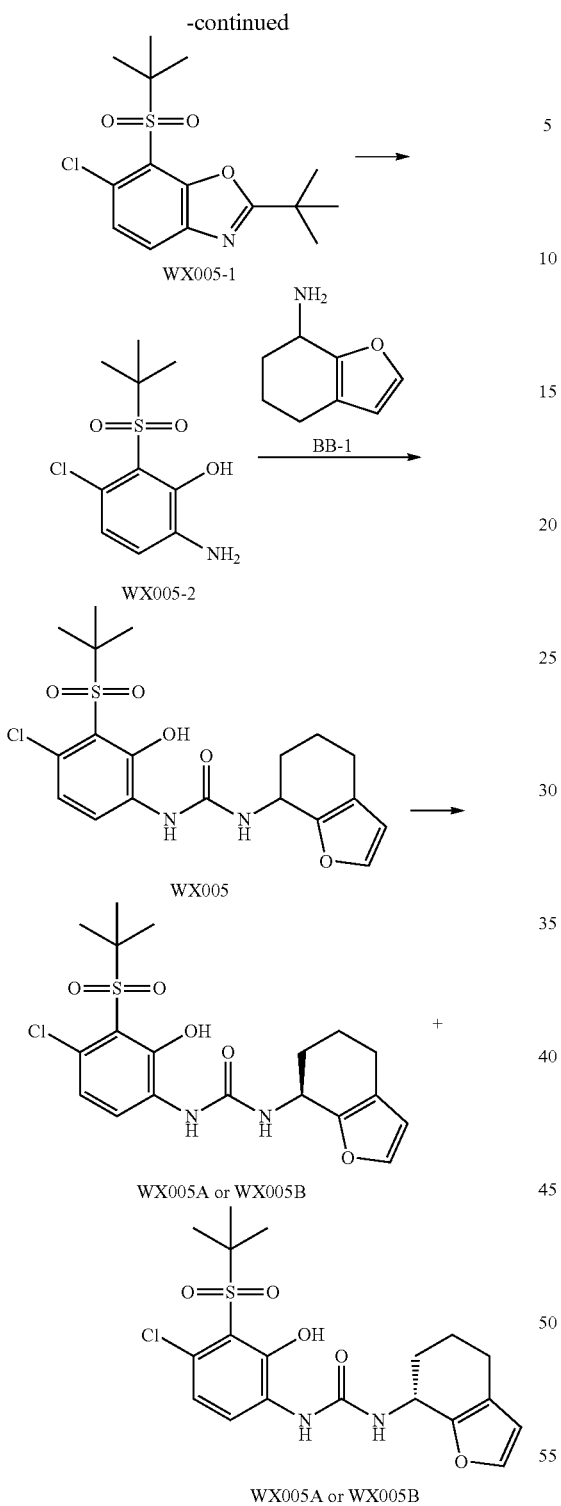

Step 1: Synthesis of Compound WX005-1

Compound BB-6 (1 g, 3.17 mmol) was dissolved in 30 mL of THF, and LiHMDS (1 M, 6.33 mL) was added dropwise at −70° C. After stirring at −70° C. for 0.5 hour, iodomethane (3.7 g, 26.07 mmol, 1.62 mL) was added and the reaction was allowed to run for 3 hours. After the reaction was completed, 20 mL of saturated ammonium chloride solution was added to quench the reaction. The mixture was diluted with 25 mL of ethyl acetate, and then extracted with ethyl acetate (25 mL×3). The organic phases were combined, dried over anhydrous sodium sulfate, filtered and concentrated to obtain a crude product, which was then separated with a chromatography column (eluent: ethyl acetate/petroleum ether=0-25%) to obtain the target compound WX005-1. $^1$H NMR (400 MHz, CHLOROFORM-d) δ ppm 7.66 (dd, J=1.1, 8.4 Hz, 1H), 7.36-7.31 (m, 1H), 1.35 (s, 9H), 1.29 (s, 9H).

Step 2: Synthesis of Compound WX005-2

Compound WX005-1 (0.447 g, 1.36 mmol) was dissolved in 10 mL of ethanol, followed by addition of concentrated hydrochloric acid (12 M, 2 mL). The reaction mixture was heated to 80° C. and reacted under stirring overnight. After the reaction was completed, the solvent was evaporated under reduced pressure, and the residue was adjusted to pH of 12 with 2 M NaOH, and extracted with ethyl acetate (10 mL×3). The organic phases were combined, dried over anhydrous sodium sulfate, filtered and concentrated to obtain a crude product, which was then separated with a chromatography column (eluent: ethyl acetate/petroleum ether=0-25%) to obtain the target compound WX005-2. $^1$H NMR (400 MHz, CHLOROFORM-d) δ ppm 10.36 (s, 1H), 6.93-6.87 (m, 1H), 6.83 (d, J=8.0 Hz, 1H), 1.47 (s, 9H).

Step 3: Synthesis of Compound WX005

Compound BB-1 (208.05 mg, 1.52 mmol) was dissolved in 5 mL of DCM, followed by addition of triphosgene (148.52 mg, 500.49 μmol) and triethylamine (153.47 mg, 1.52 mmol, 211.10 μL). The reaction mixture was stirred at room temperature for 30 minutes, and then concentrated. The obtained crude product was dissolved in 5 mL of DCM, followed by addition of compound WX005-2 (200.00 mg, 758.32 μmol) and triethylamine (76.73 mg, 758.32 μmol, 105.55 μL), and the reaction mixture was stirred at room temperature overnight. After the reaction was completed, the reaction mixture was concentrated, and the obtained crude product was separated by high performance liquid chromatography to obtain the target compound WX005.

Step 4: Synthesis of WX005A and WX005B.

Compound WX005 was resolved by supercritical fluid chromatography (separation conditions: column, ChiralCel OD-H 150×4.6 mm 5 μm; mobile phase, A: carbon dioxide, B: ethanol (0.05% diethylamine); flow rate: 2.5 mL/min; column temperature: 40° C.; detection wavelength: 220 nm) to obtain the chiral isomers WX005A and WX005B with a retention time of 4.205 min and 5.142 min, respectively, and a ratio of 1:1.

Embodiment 6: WX006, WX006A, WX006B

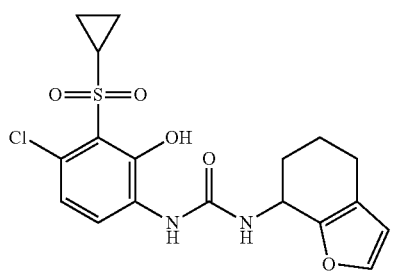 [SMILES: O=C(Nc1ccc(Cl)c(S(=O)(=O)C2CC2)c1O)NC1CCCc2ccoc21]

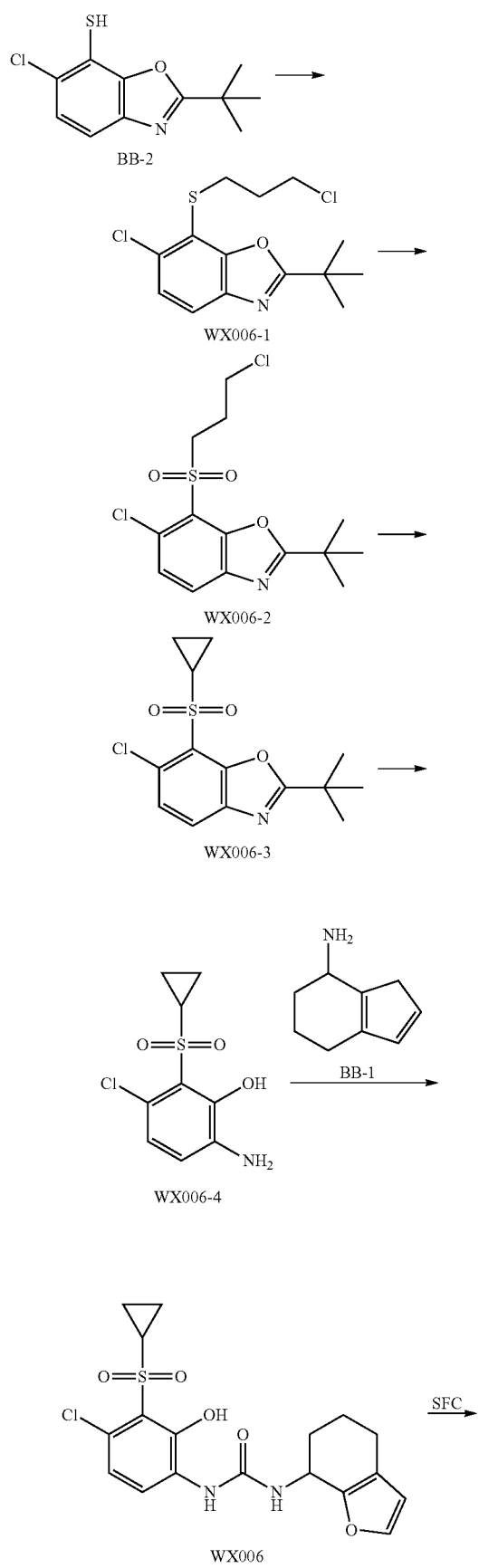

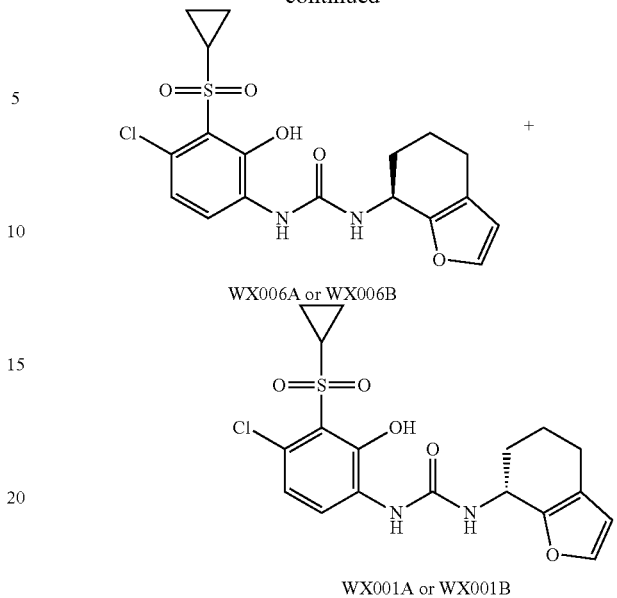

WX006A or WX006B

WX001A or WX001B

Step 1: Synthesis of Compound WX006-1

The crude compound BB-2 (6.95 g, 28.75 mmol) was dissolved in 120 mL of DMF, followed by addition of potassium carbonate (3.98 g, 28.80 mmol) and 1-bromo-3-chloropropane (5.44 g, 34.55 mmol), and the reaction mixture was stirred at 80° C. for 16 hours. After the reaction was completed, the solvent was evaporated under reduced pressure. To the residue was added 100 mL of water, followed by extraction with ethyl acetate (80 mL×3). The obtained organic phases were combined and dried over anhydrous sodium sulfate. After the desiccant was removed by filtration, the crude product obtained after concentration was separated with a chromatography column (eluent: ethyl acetate/petroleum ether=0-10%) to obtain the target compound WX006-1. $^1$H NMR (400 MHz, CHLOROFORM-d) δ ppm 7.53 (d, J=8.4 Hz, 1H), 7.39 (d, J=8.4 Hz, 1H), 3.72 (t, J=6.2 Hz, 2H), 3.29 (t, J=6.8 Hz, 2H), 2.13-1.93 (m, 2H), 1.53 (s, 9H).

Step 1: Synthesis of Compound WX006-2

Compound WX006-1 (3.28 g, 10.31 mmol) was dissolved in 100 mL of DCM, followed by addition of m-CPBA (12.55 g, 61.84 mmol) at −10° C., and the reaction mixture was stirred at −10° C. for 5 hours. After the reaction was completed, 50 mL of saturated sodium sulfite solution, 50 mL of saturated sodium bicarbonate solution and 50 mL of DCM were added. The aqueous phase was extracted with DCM (50 mL×3), and the organic phases were combined and dried over anhydrous sodium sulfate. After the desiccant was removed by filtration, the crude product obtained after concentration was separated with a chromatography column (eluent: ethyl acetate/petroleum ether=0-15%) to obtain the target compound WX006-2. $^1$H NMR (400 MHz, CHLOROFORM-d) δ ppm 7.85 (d, J=8.4 Hz, 1H), 7.51 (d, J=8.4 Hz, 1H), 3.74-3.64 (m, 4H), 2.44-2.28 (m, 2H), 1.54 (s, 9H).

Step 3: Synthesis of Compound WX006-3

The compound WX006-2 (2.61 g, 7.45 mmol) was dissolved in 60 mL of tetrahydrofuran, and cooled to −70° C., followed by addition of KHMDS (1.64 g, 8.20 mmol). The reaction mixture was stirred at −70° C. for 1 hour. After the reaction was completed, 20 mL of water was added to quench the reaction, and the mixture was diluted with 30 mL of ethyl acetate. The aqueous phase was extracted with ethyl acetate (30 mL×3). The organic phases are combined, dried over anhydrous sodium sulfate, filtered and concentrated to obtain a crude product, which was then separated with a chromatography column (developing solvent: ethyl acetate/petroleum ether=0-15%) to obtain the target compound WX006-3. $^1$H NMR (400 MHz, CHLOROFORM-d) δ ppm 7.81 (d, J=8.4 Hz, 1H), 7.50 (d, J=8.4 Hz, 1H), 3.09 (tt, J=4.6, 8.0 Hz, 1H), 1.53 (s, 9H), 1.51-1.48 (m, 2H), 1.15-1.09 (m, 2H).

Step 4: Synthesis of Compound WX006-4

Compound WX006-3 (2.05 g, 6.53 mmol) was dissolved in 40 mL of ethanol, followed by addition of concentrated hydrochloric acid (12 M, 9 mL). The mixture was heated to 80° C. and reacted with stirring overnight. After the reaction was completed, the solvent was removed under reduced pressure, and the residue was adjusted to pH of 9 by addition of saturated sodium bicarbonate solution. The aqueous phase was extracted with ethyl acetate (50 mL×3). The organic phases were combined, dried over anhydrous sodium sulfate, filtered and concentrated to obtain a crude product, which was then separated with a chromatography column (developing solvent: ethyl acetate/petroleum ether=0-25%) to obtain the target compound WX006-4. $^1$H NMR (400 MHz, CHLOROFORM-d) δ ppm 10.34 (s, 1H), 6.90-6.86 (m, 1H), 6.79 (d, J=8.3 Hz, 1H), 4.09-3.93 (m, 2H), 3.22 (tt, J=4.6, 8.0 Hz, 1H), 1.46-1.39 (m, 2H), 1.18-1.10 (m, 2H).

Step 5: Synthesis of Compound WX006

Compound BB-1 (0.84 g, 6.12 mmol) was dissolved in 20 mL of DCM, followed by addition of triphosgene (0.55 g, 1.85 mmol) and triethylamine (620.95 mg, 6.14 mmol). The reaction mixture was stirred at room temperature for 30 minutes, and then concentrated. The obtained crude product was dissolved in 20 mL of DCM, followed by addition of compound WX006-4 (0.76 g, 3.07 mmol) and triethylamine (310.48 g, 3.07 mmol), and the reaction mixture was stirred at room temperature overnight. After the reaction was completed, the reaction mixture was concentrated, and the obtained crude product was separated by high performance liquid chromatography, and then further separated with a chromatography column (eluent: ethyl acetate/petroleum ether=0-40%) to obtain the target compound WX006.

Step 6: Synthesis of Compounds WX006A and WX006B

Compound WX006 was resolved by supercritical fluid chromatography (separation conditions: column, Chiralpak AD-3 150×4.6 mm 3 μm; mobile phase, A: carbon dioxide, B: methanol (0.05% diethylamine); flow rate: 2.5 mL/min; column temperature: 40° C.; detection wavelength: 220 nm) to obtain the chiral isomers WX006A and WX006B with a retention time of 6.531 min and 7.085 min, respectively, and a ratio of 1:1.

Embodiment 7: WX007, WX007A, WX007B

Synthetic Route:

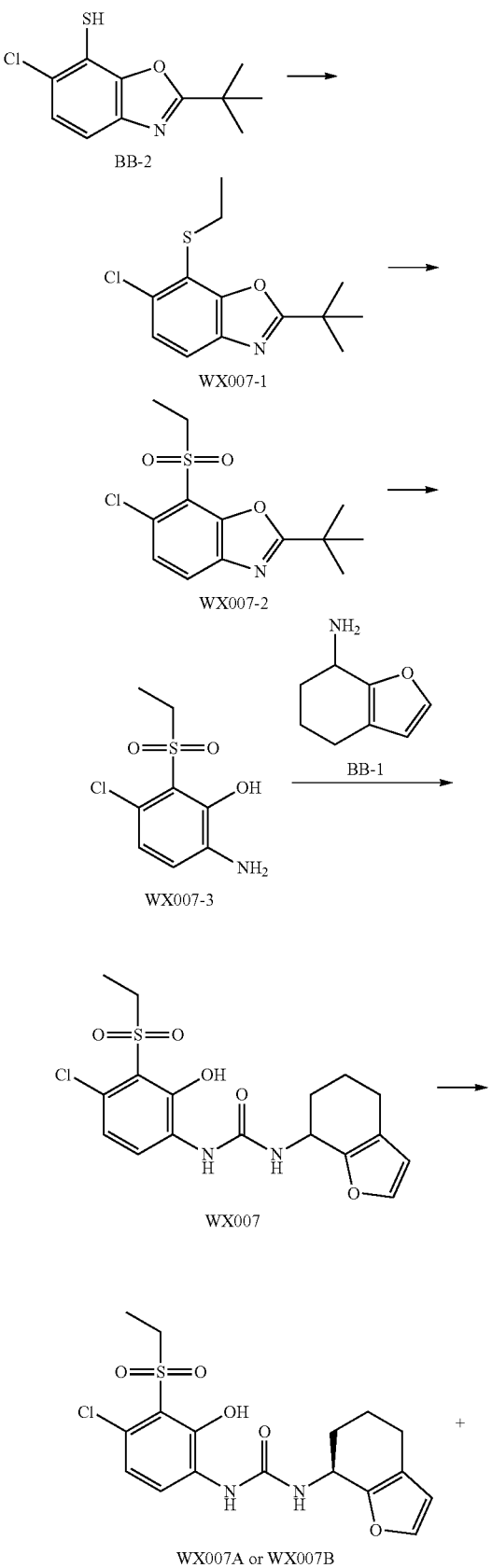

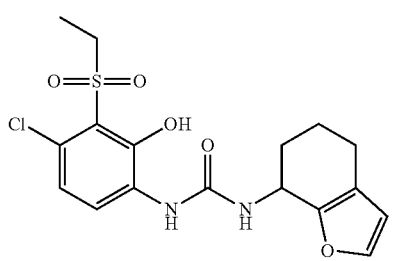 [SMILES: CCS(=O)(=O)c1c(Cl)ccc(NC(=O)NC2CCCc3ccoc32)c1O]

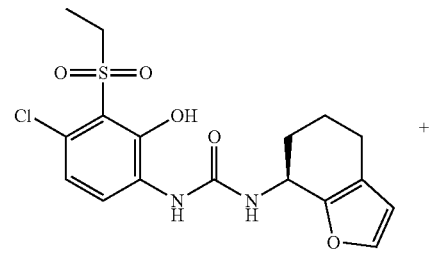

WX007A or WX007B

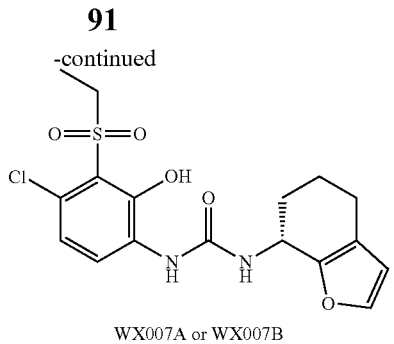

WX007A or WX007B

Step 1: Synthesis of Compound WX007-1

Compound BB-2 (1.5 g, 6.21 mmol) was dissolved in 30 mL of DMF, followed by addition of potassium carbonate (1 g, 7.24 mmol) and bromoethane (730 mg, 6.70 mmol, 0.5 mL), and the reaction mixture was stirred at 80° C. overnight. After the reaction was completed, the solvent was evaporated under reduced pressure. To the residue was added 50 mL of water, and the mixture was extracted with ethyl acetate (30 mL×3). The organic phases were combined, washed with saturated sodium chloride solution (50 mL×2), dried over anhydrous sodium sulfate, filtered and concentrated to obtain a crude product, which was then separated with a chromatography column (eluent: ethyl acetate/petroleum ether=0-5%) to obtain compound WX007-1. $^1$H NMR (400 MHz, CHLOROFORM-d) δ ppm 7.50 (d, J=8.4 Hz, 1H), 7.38 (d, J=8.4 Hz, 1H), 3.20 (q, J=7.4 Hz, 2H), 1.53 (s, 9H), 1.33-1.29 (m, 3H).

Step 2: Synthesis of Compound WX007-2

Compound WX007-1 (0.84 g, 3.11 mmol) was dissolved in 20 mL of DCM, followed by addition of m-CPBA (3.79 g, 18.68 mmol), and the reaction mixture was stirred at −10° C. for 5 hours. After the reaction was completed, 40 mL of saturated sodium sulfite solution, 40 mL of saturated sodium bicarbonate solution and 30 mL of DCM were added. The mixed solution was extracted with DCM (30 mL×3), and the obtained organic phases were combined and dried over anhydrous sodium sulfate. After the desiccant was removed by filtration, the filtrate was evaporated under reduced pressure to remove the solvent, and the obtained crude product was separated with a chromatography column (eluent: ethyl acetate/petroleum ether=0-25%) to obtain the target compound WX007-2. $^1$H NMR (400 MHz, CHLOROFORM-d) δ ppm 7.83 (d, J=8.4 Hz, 1H), 7.49 (d, J=8.4 Hz, 1H), 3.50 (q, J=7.4 Hz, 2H), 1.53 (s, 9H), 1.37 (t, J=7.4 Hz, 3H).

Step 3: Synthesis of Compound WX007-3

Compound WX007-2 (0.82 g, 2.72 mmol) was dissolved in 10 mL of ethanol, followed by addition of concentrated hydrochloric acid (12 M, 3 mL). The mixture was heated to 80° C. and reacted with stirring overnight. After the reaction was completed, the solvent was evaporated under reduced pressure, followed by addition of saturated sodium bicarbonate solution to obtain a pH of 9, and the mixture was extracted with ethyl acetate (30 mL×3). The organic phases were combined, dried over anhydrous sodium sulfate, filtered and concentrated to obtain a crude product, which was then separated with a chromatography column (eluent: ethyl acetate/petroleum ether=0-35%) to obtain the target compound WX007-3. $^1$H NMR (400 MHz, CHLOROFORM-d) δ ppm 10.60 (s, 1H), 6.89-6.84 (m, 1H), 6.84-6.79 (m, 1H), 3.54 (q, J=7.4 Hz, 2H), 1.36 (t, J=7.4 Hz, 3H).

Step 4: Synthesis of Compound WX007

Compound BB-1 (93.13 mg, 678.86 μmol) was dissolved in 5 mL of DCM, followed by addition of triphosgene (60.44 mg, 203.66 μmol) and triethylamine (68.69 mg, 678.86 μmol, 94.49 μL). The reaction mixture was stirred at room temperature for 30 minutes, and then concentrated. The obtained crude product was dissolved in 5 mL of DCM, followed by addition of compound WX007-3 (0.08 g, 339.43 μmol) and triethylamine (34.35 mg, 339.43 μmol, 47.24 μL), and the reaction mixture was stirred at room temperature overnight. After the reaction was completed, the reaction mixture was concentrated, and the obtained crude product was separated by high performance liquid chromatography to obtain the target compound WX007.

Step 5: Synthesis of Compounds WX007A and WX007B

Compound WX007 was resolved by supercritical fluid chromatography (separation conditions: column, column, AD (250 mm×30 mm, 5 μm); mobile phase, isopropanol (0.1% ammonium hydroxide)) to obtain the chiral isomers WX007A and WX007B with a retention time of 5.048 min and 5.605 min, respectively, and a ratio of 1:1.

According to the steps 1 to 5 in the synthesis of Embodiment 7, the embodiments in Table 2 were synthesized using different fragments in the step 1. The structures in the table also represent their potential isomers.

TABLE 2

| Embodiment | Fragment in the step 1 | Structure | Compound |
|---|---|---|---|
| 8 | H₃C—I | (structure) | WX008<br>WX008A<br>WX008B |

TABLE 2-continued
| Embodiment | Fragment in the step 1 | Structure | Compound |
|---|---|---|---|
| | | 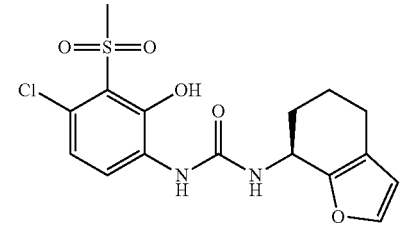 [SMILES: CS(=O)(=O)c1c(Cl)ccc(NC(=O)N[C@H]2CCCc3ccoc32)c1O] | |
| | |  | |
| 9 | 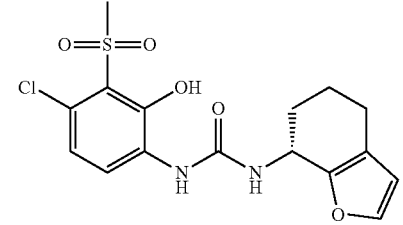 [SMILES: CS(=O)(=O)c1c(Cl)ccc(NC(=O)N[C@@H]2CCCc3ccoc32)c1O] | 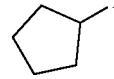 | WX009 |
| 10 | 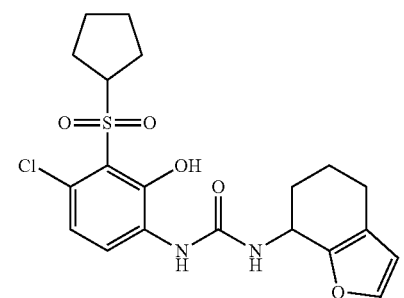 [SMILES: O=C(Nc1ccc(Cl)c(S(=O)(=O)C2CCCC2)c1O)NC1CCCc2ccoc21] | 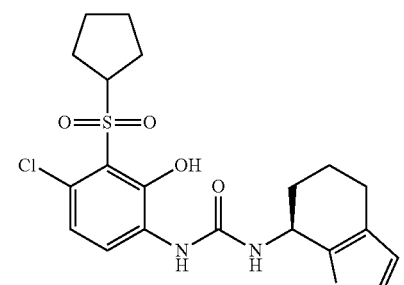 | WX010<br>WX010A<br>WX010B |

TABLE 2-continued
| Embodiment | Fragment in the step 1 | Structure | Compound |
|---|---|---|---|
| | | 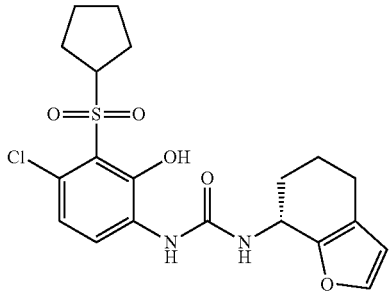 [SMILES: O=C(Nc1ccc(Cl)c(S(=O)(=O)C2CCCC2)c1O)N[C@@H]1CCCc2ccoc21] | |
| 11 | 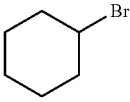 | 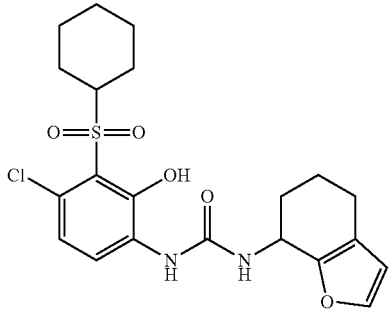 | WX011<br>WX011A<br>WX011B |
| 12 | 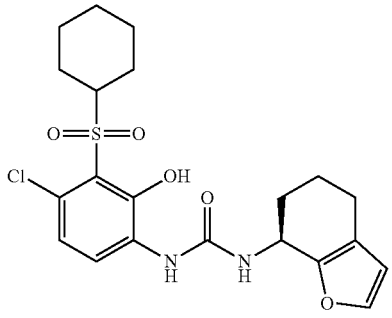 [SMILES: O=C(Nc1ccc(Cl)c(S(=O)(=O)C2CCCCC2)c1O)N[C@H]1CCCc2ccoc21] | 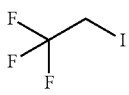 | WX012<br>WX012A<br>WX012B |
| | | 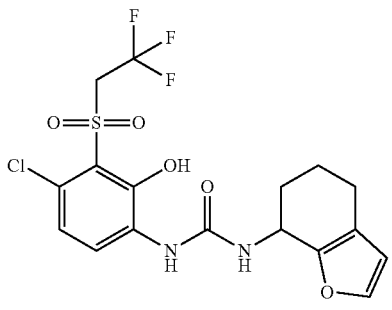 [SMILES: O=C(Nc1ccc(Cl)c(S(=O)(=O)CC(F)(F)F)c1O)N[C@@H]1CCCc2ccoc21] | |

TABLE 2-continued
| Embodiment | Fragment in the step 1 | Structure | Compound |
|---|---|---|---|
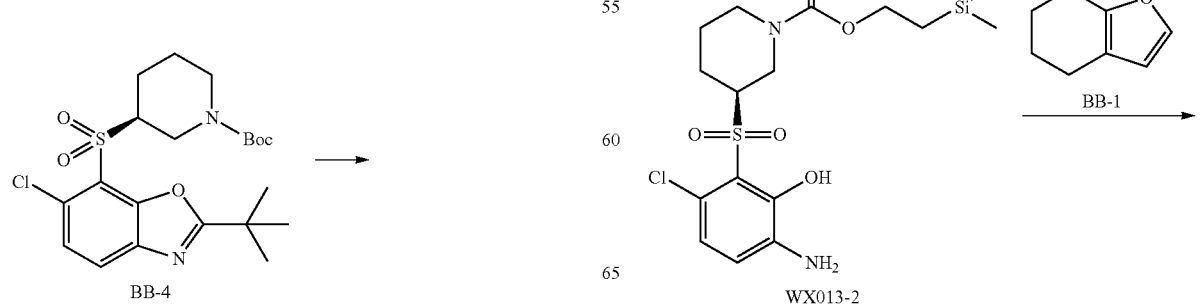
Embodiment 13: WX013, WX013A, WX013B
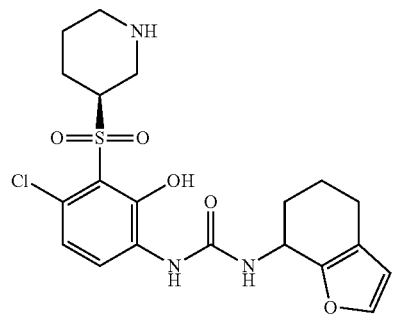 [SMILES: O=C(Nc1ccc(Cl)c(S(=O)(=O)[C@H]2CCCNC2)c1O)NC1CCCc2ccoc21]
Synthetic Route:
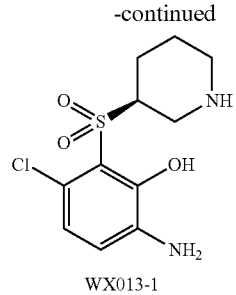

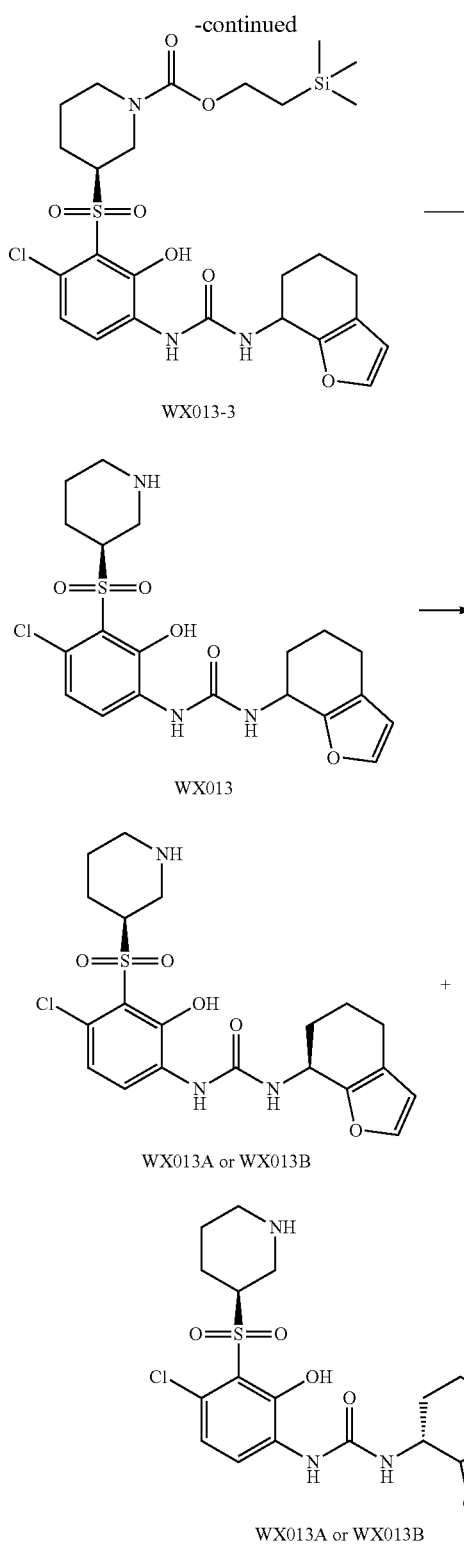

acetate (30 mL×3). The organic phases were combined, dried over anhydrous sodium sulfate, filtered and concentrated to obtain a crude product, which was then separated with a chromatography column (eluent: methanol/dichloromethane=0-5%) to obtain compound WX013-1. $^1$H NMR (400 MHz, METHANOL-$d_4$) δ ppm 6.92-6.85 (m, 2H), 4.60 (br s, 2H), 3.89-3.79 (m, 1H), 3.27 (br s, 1H), 3.01 (br d, J=11.8 Hz, 1H), 2.91 (dd, J=10.6, 12.4 Hz, 1H), 2.65-2.55 (m, 1H), 2.11-2.03 (m, 1H), 1.90-1.80 (m, 2H), 1.55 (br d, J=14.6 Hz, 1H).

Step 2: Synthesis of Compound WX013-2

Compound WX013-1 (0.2 g, 687.84 μmol) was dissolved in 3 mL of water, followed by addition of a solution of triethylamine (174.48 mg, 1.72 mmol, 240 μL) and N-[2-(trimethylsilyl)ethoxycarbonyloxy]succinimide (0.17 g, 655.53 μmol) in dioxane (3 mL), and the reaction mixture was stirred at room temperature overnight. After the reaction was completed, the solvent was evaporated under reduced pressure, and the residue was diluted with 10 mL of water and extracted with ethyl acetate (10 mL×3). The organic phases were combined, dried over anhydrous sodium sulfate, filtered and concentrated to obtain a crude product, which was then separated with a chromatography column (eluent: ethyl acetate/petroleum ether=0-30%) to obtain the target compound WX013-2. $^1$H NMR (400 MHz, CHLOROFORM-d) δ ppm 10.41 (s, 1H), 6.86-6.81 (m, 1H), 6.81-6.76 (m, 1H), 4.36 (br d, J=12.4 Hz, 1H), 4.10-4.06 (m, 1H), 4.00 (br s, 2H), 3.73-3.63 (m, 1H), 3.09 (br s, 1H), 2.81-2.71 (m, 1H), 2.13 (br d, J=12.8 Hz, 1H), 1.93-1.79 (m, 2H), 1.51-1.43 (m, 1H), 0.94 (t, J=8.4 Hz, 2H), 0.00 (s, 9H).

Step 3: Synthesis of Compound WX013-3.

Compound BB-5 (0.35 g, 2.55 mmol) was dissolved in 10 mL of DCM, followed by addition of triphosgene (0.23 g, 775.07 μmol) and triethylamine (259.13 mg, 2.56 mmol, 356.44 μL). The reaction mixture was stirred at room temperature for 30 minutes, and then concentrated. The obtained crude product was dissolved in 10 mL of DCM, followed by addition of compound WX013-2 (0.557 g, 1.28 mmol) and triethylamine (129.57 mg, 1.28 mmol, 178.22 μL), and the reaction mixture was stirred at room temperature overnight. After the reaction was completed, the reaction mixture was concentrated, and the obtained crude product of WX013-3 was directly used in the next reaction.

Step 4: Synthesis of Compound WX013.

Compound WX013-3 (0.765 g, 1.28 mmol) was dissolved in 15 mL of THF, and the reaction system was purged with nitrogen three times, followed by addition of TBAF (1 M, 5 mL). The reaction mixture was stirred at 50° C. for 48 hours. After completion of the reaction, the solvent was evaporated under reduced pressure, and the residue was diluted with 20 mL of water and extracted with ethyl acetate (15 mL×3). The organic phases were combined, dried over anhydrous sodium sulfate, filtered and concentrated to obtain a crude product, which was then separated by high performance liquid chromatography to obtain compound WX013.

Step 5: Synthesis of Compounds WX013A and WX013B

The compound WX013 was resolved by supercritical fluid chromatography (separation conditions: column, AD (250 mm×30 mm, 10 μm); mobile phase, ethanol (0.1% ammonium hydroxide) to obtain the chiral isomers WX013A and WX013B with a retention time of 3.126 min and 5.932 min, respectively, and a ratio of 1:1.

Step 1: Synthesis of Compound WX013-1

Compound BB-4 (0.58 g, 1.27 mmol) was dissolved in 10 mL of ethanol, followed by addition of concentrated hydrochloric acid (12 M, 1.5 mL). The mixture was heated to 80° C. and reacted with stirring overnight. After the reaction was completed, the solvent was evaporated under reduced pressure, and the residue was adjusted to pH of 9 with saturated sodium bicarbonate solution, and extracted with ethyl

Embodiment 14: WX014

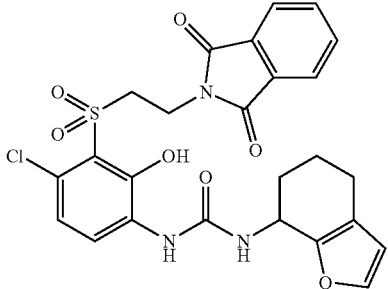 [SMILES: O=C(Nc1ccc(Cl)c(S(=O)(=O)CCN2C(=O)c3ccccc3C2=O)c1O)NC1CCCc2ccoc21]

Synthetic Route:

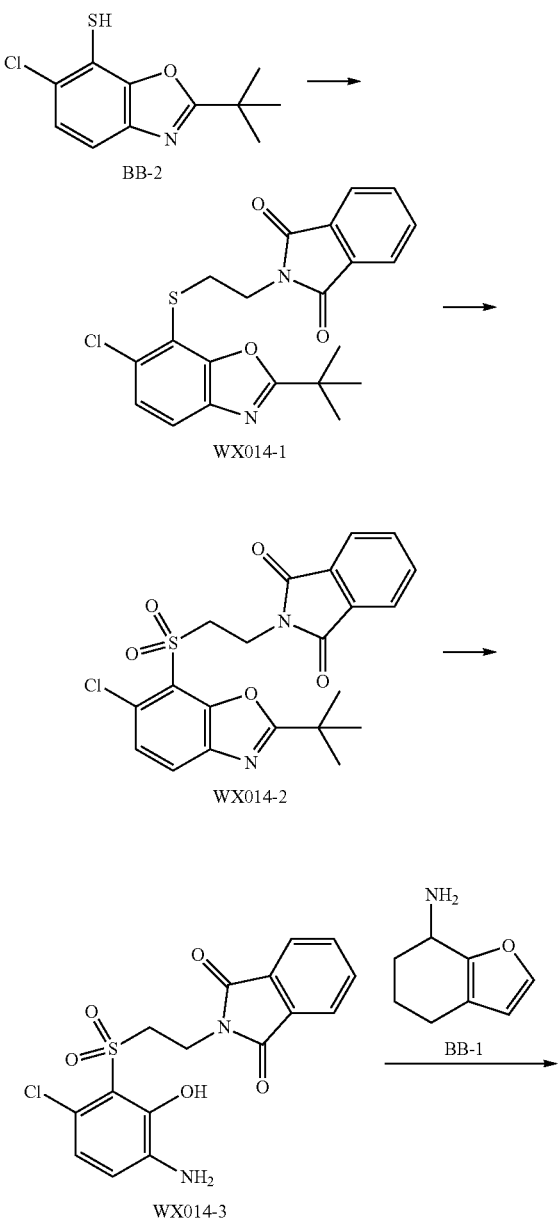

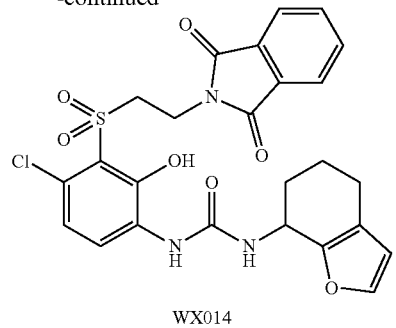

Step 1: Synthesis of Compound WX014-1

The crude product of compound BB-2 (5 g, 20.68 mmol) and potassium carbonate (2.86 g, 20.68 mmol) were dissolved in 100 mL of DMF, followed by addition of N-(2-bromoethyl)phthalimide (5.25 g, 20.68 mmol), and the reaction mixture was stirred at 80° C. for 18 hours. After the reaction was completed, the solvent was evaporated under reduced pressure. To the residue were added 50 mL of water and 50 mL of ethyl acetate, and the mixture was extracted with ethyl acetate (40 mL×3). The obtained organic phases were combined, washed with water (20 mL×3) and 30 mL of saturated brine sequentially, and dried over anhydrous sodium sulfate. After removing the desiccant by filtration, the filtrate was distilled under reduced pressure to remove the solvent, and the obtained crude product was separated with a chromatography column (eluent: ethyl acetate/petroleum ether=0-20%) to obtain the target compound WX014-1. $^1$H NMR (400 MHz, CHLOROFORM-d) δ ppm 1.45 (s, 9H) 3.47 (t, J=6.6 Hz, 2H) 3.85 (t, J=6.6 Hz, 2H) 7.13 (d, J=8.4 Hz, 1H) 7.27 (d, J=8.4 Hz, 1H) 7.57-7.62 (m, 2H) 7.63-7.68 (m, 2H).

Step 2: Synthesis of Compound WX014-2

Compound WX014-1 (2 g, 4.82 mmol) was dissolved in 50 mL of DCM, followed by addition of m-CPBA (5.87 g, 28.92 mmol) in portions at −10° C., and the reaction mixture was stirred at −10° C. to 20° C. for 20 hours. After the reaction was completed, 40 mL of saturated sodium sulfite solution, 40 mL of saturated sodium bicarbonate solution and 50 mL of ethyl acetate were added, followed by extraction with ethyl acetate (30 mL×3). The organic phases were combined, washed with saturated brine (30 mL×2), and dried over anhydrous sodium sulfate. After the desiccant was removed by filtration, the filtrate was evaporated under reduced pressure to remove the solvent, and slurried with a mixed solvent (PE:EA=20:1) to obtain the target compound WX014-2. $^1$H NMR (400 MHz, CHLOROFORM-d) δ ppm 1.57 (s, 9H) 4.00-4.12 (m, 2H) 4.17 (t, J=6.2 Hz, 2H) 7.26 (s, 1H) 7.59 (d, J=8.6 Hz, 1H) 7.70 (s, 4H).

Step 3: Synthesis of Compound WX014-3

Compound WX014-2 (2 g, 4.48 mmol) was dissolved in 10 mL of ethanol, followed by addition of concentrated hydrochloric acid (12 M, 10 mL). The mixture was heated to 80° C. and reacted with stirring overnight. After the reaction was completed, the solvent was evaporated under reduced pressure, and saturated sodium bicarbonate solution was added to the residue to adjust pH to 7, followed by extraction with ethyl acetate (20 mL×3). The obtained organic phases were combined, washed with 10 mL of saturated brine, dried over anhydrous sodium sulfate, filtered and concentrated to obtain a crude product, which was then separated with a chromatography column (eluent: ethyl acetate/petroleum ether=20/1 to 2/1) to obtain the target compound WX014-3. ¹H NMR (400 MHz, CHLOROFORM-d) δ ppm 4.05-4.09 (m, 2H) 4.11 (br d, J=6.8 Hz, 2H) 4.15 (d, J=7.2 Hz, 2H) 6.58 (d, J=8.4 Hz, 1H) 6.66-6.72 (m, 1H) 7.75-7.78 (m, 2H) 7.80-7.84 (m, 2H) 10.40 (s, 1H).

Step 4: Synthesis of Compound WX014

Compound BB-1 (111.31 mg, 811.44 μmol) was dissolved in 5 mL of DCM, followed by addition of triphosgene (79.49 mg, 267.86 μmol) and triethylamine (159.44 mg, 1.58 mmol, 219.31 μL). The reaction mixture was stirred at room temperature for 30 minutes, and then concentrated. The obtained crude product was dissolved in 5 mL of DCM, followed by addition of compound WX014-3 (0.3 g, 787.81 μmol) and triethylamine (79.72 mg, 787.81 μmol, 109.65 μL), and the reaction mixture was stirred at room temperature overnight. After the reaction was completed, the reaction mixture was concentrated, and the obtained crude product was separated by high performance liquid chromatography to obtain the target compound WX014. ¹H NMR (400 MHz, DMSO-$d_6$) δ ppm 10.54 (br s, 1H), 8.03 (br s, 1H), 7.89 (br s, 1H), 7.74 (br d, J=9.2 Hz, 4H), 7.57 (br s, 1H), 7.41 (br d, J=7.0 Hz, 1H), 6.86 (br s, 1H), 6.35 (br s, 1H), 4.80 (br s, 1H), 4.20 (br s, 2H), 4.02 (br s, 2H), 3.17 (br s, 1H), 2.39 (br s, 1H), 1.94 (br s, 1H), 1.76 (br s, 3H).

Embodiment 15: WX015

(2.06 g, 34.98 mmol, 2 mL), and the reaction mixture was stirred at 80° C. for half an hour. After the reaction was completed, the solvent was evaporated under reduced pressure, and the crude product was separated by high performance liquid chromatography to obtain the target product WX015. ¹H NMR (400 MHz, DMSO-$d_6$) δ ppm 1.64-1.82 (m, 4H) 1.88 (br s, 1H), 2.41 (br s, 1H), 3.08 (br s, 2H), 3.64 (br t, J=5.8 Hz, 2H), 4.81 (br s, 1H), 6.08 (d, J=8.4 Hz, 1H), 6.30 (s, 1H), 7.37 (br d, J=8.4 Hz, 1H), 7.50 (s, 1H), 7.78 (d, J=8.4 Hz, 1H), 8.17 (s, 1H).

Embodiment 16: WX016, WX016A, WX016B

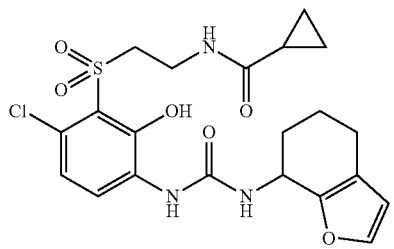 [SMILES: O=C(Nc1ccc(Cl)c(S(=O)(=O)CCNC(=O)C2CC2)c1O)NC1CCCc2ccoc21]

Synthetic Route:

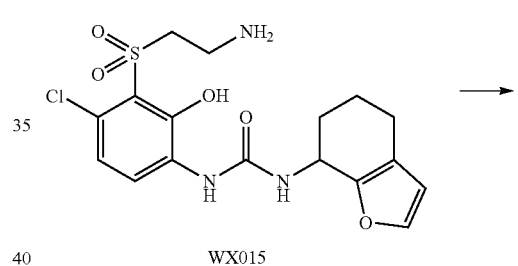

WX015

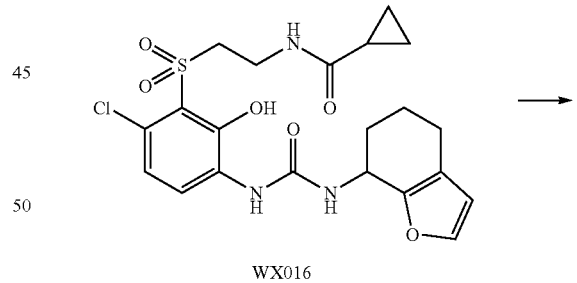

WX016

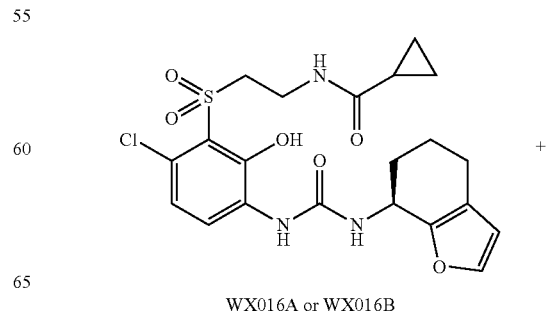

WX016A or WX016B

Synthetic Route:

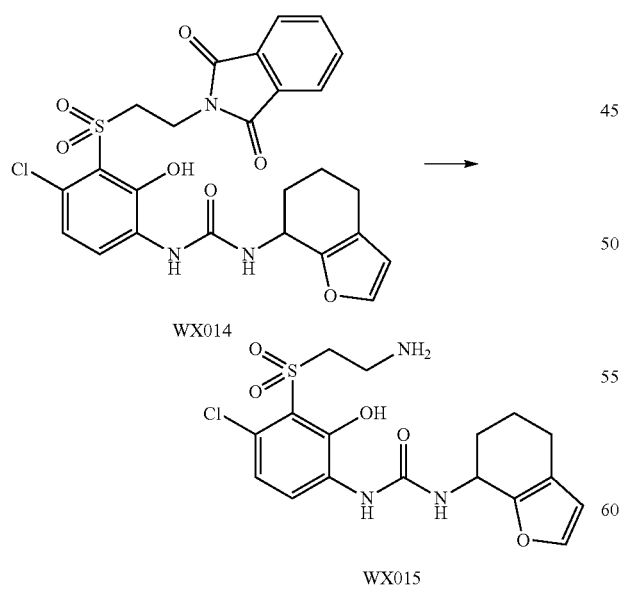

Step 1: Synthesis of Compound WX015

Compound WX014 (0.428 g, 786.80 μmol) was added to 5 mL of ethanol, followed by addition of hydrazine hydrate

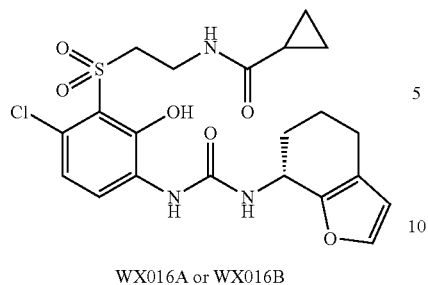

WX016A or WX016B

Step 1: Synthesis of Compound WX016

Compound WX015 (0.080 g, 193.30 μmol) and cyclopropylformyl chloride (60.62 mg, 579.89 μmol, 52.71 μL) were added to 5 mL of DCM, followed by addition of triethylamine (58.68 mg, 579.89 μmol, 80.71 μL). The reaction mixture was stirred at room temperature overnight. After the reaction was completed, the solvent was evaporated under reduced pressure, and the obtained crude product was separated by high performance liquid chromatography to obtain the product WX016.

Step 2: Synthesis of Compounds WX016A and WX016B.

Compound WX016 was resolved by supercritical fluid chromatography (separation conditions: column, ChiralPak AD-3 150×4.6 mm I.D., 3 μm; mobile phase, A: carbon dioxide, B: ethanol (0.05% diethylamine); flow rate: 2.5 mL/min; column temperature: 40° C.; detection wavelength: 220 nm) to obtain the chiral isomers WX006A and WX006B with a retention time of 7.007 min and 7.668 min, respectively, and a ratio of 1:1.

Embodiment 17: WX017, WX017A, WX017B

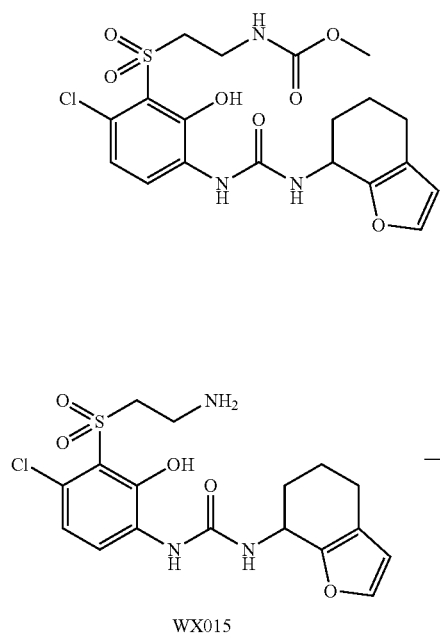

WX015

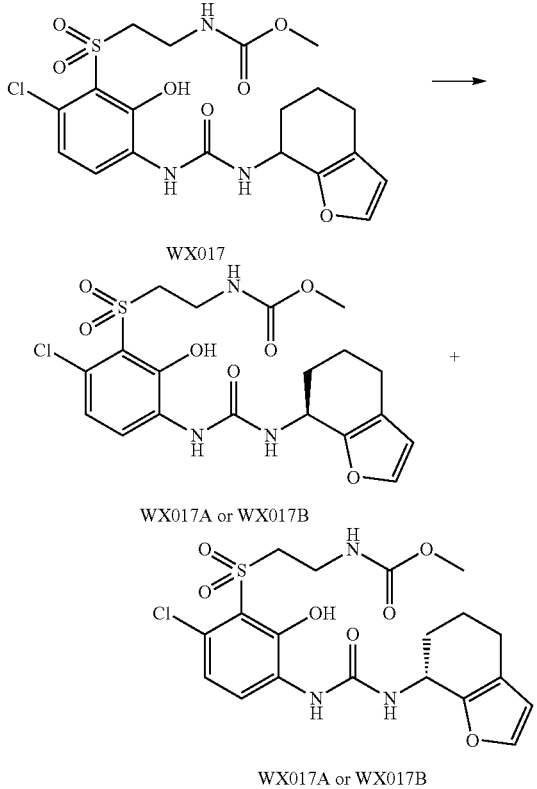

WX017

WX017A or WX017B

WX017A or WX017B

Step 1: Synthesis of Compound WX017

Compound WX015 (0.04 g, 96.65 μmol) and methyl chloroformate (1.3 g, 13.76 mmol, 1.07 mL) were added to 2 mL of DCM, followed by addition of triethylamine (29.34 mg, 289.94 μmol, 40.36 μL). The reaction mixture was stirred at room temperature overnight. After the reaction was completed, the solvent was evaporated under reduced pressure, and the crude product was separated by high-performance liquid chromatography to obtain the product WX017.

Step 2: Synthesis of Compounds WX017A and WX017B.

Compound WX017 was resolved by supercritical fluid chromatography (separation conditions: column, ChiralPak AS-3 150×4.6 mm I.D., 3 μm; mobile phase, A: carbon dioxide, B: ethanol (0.05% diethylamine); flow rate: 2.5 mL/min; column temperature: 40° C.; detection wavelength: 220 nm) to obtain the chiral isomers WX017A and WX017B with a retention time of 4.776 min and 5.215 min, respectively, and a ratio of 1:1.

Embodiment 18: WX018, WX018A, WX018B

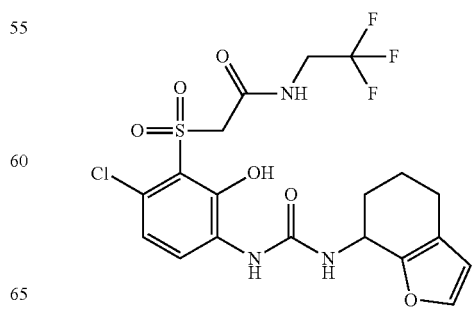

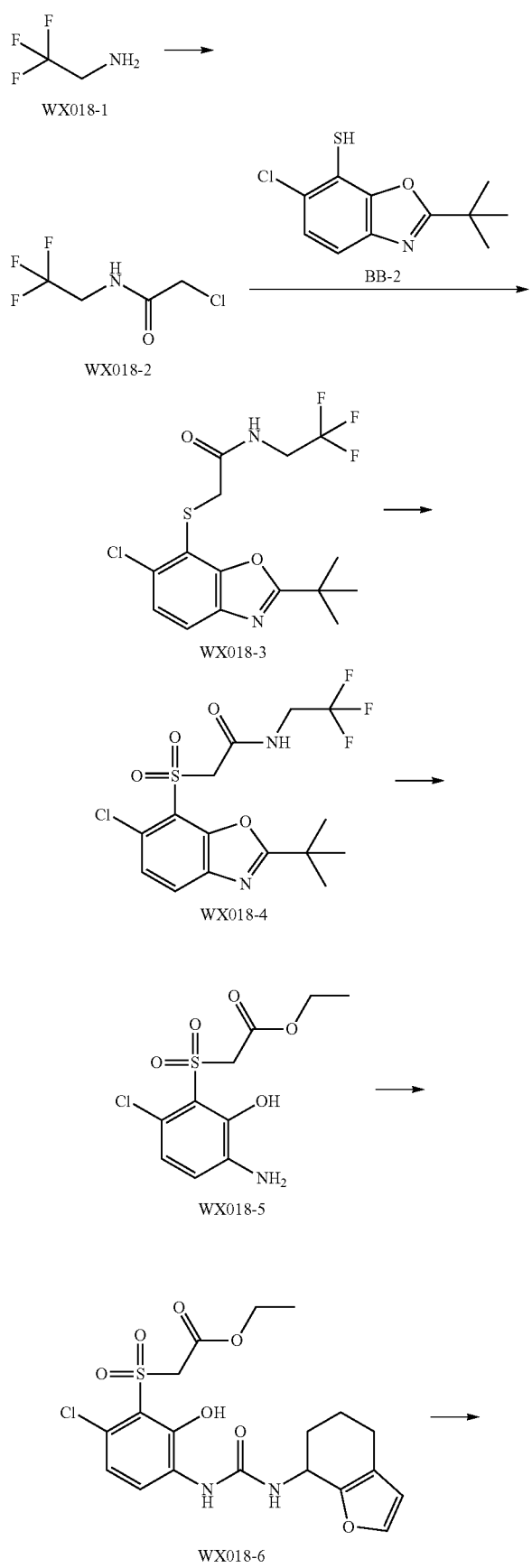
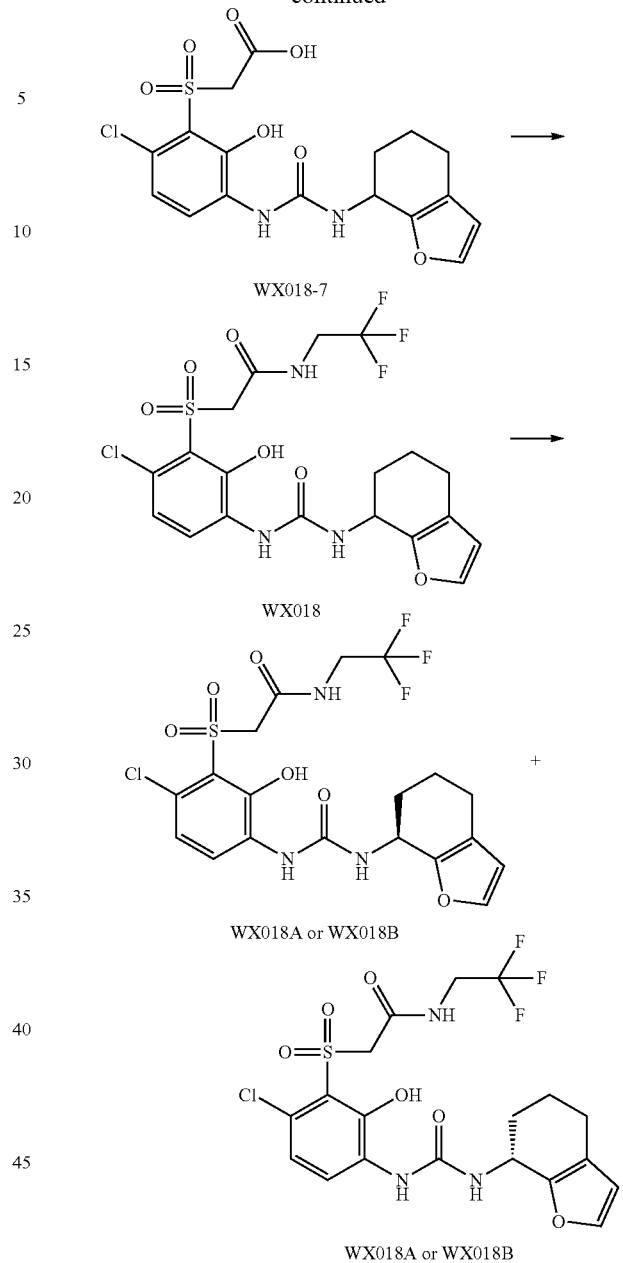

Step 1: Synthesis of Compound WX018-2

Compound WX018-1 (1.26 g, 12.72 mmol, 1 mL) was dissolved in 20 mL of DCM, followed by addition of triethylamine (1.45 g, 14.37 mmol, 2 mL) and chloroacetyl chloride (2.13 g, 18.86 mmol, 1.5 mL). The reaction mixture was stirred at 0° C. for 2 hours. After the reaction was completed, 50 mL of water was added to quench the reaction, and the mixture was diluted with 50 mL of DCM and extracted with DCM (50 mL×3). The organic phases were combined, dried over anhydrous sodium sulfate, filtered and concentrated to obtain compound WX018-2. $^1$H NMR (400 MHz, CHLOROFORM-d) δ ppm 6.83 (br s, 1H), 4.10-4.00 (m, 2H), 3.96-3.84 (m, 2H).

Step 2: Synthesis of Compound WX018-3

Compound BB-2 (2.47 g, 10.22 mmol) was dissolved in 50 mL of DMF, followed by addition of potassium carbonate (1.5 g, 10.85 mmol), potassium iodide (1 g, 6.02 mmol) and WX018-2 (1.84 g, 10.49 mmol). The reaction mixture was stirred at 80° C. for 2 hours. After the reaction was completed, the solvent was evaporated under reduced pressure, followed by addition of 50 mL of water and extraction with ethyl acetate (40 mL×3). The organic phases were combined, washed with saturated brine (50 mL×2), dried over anhydrous sodium sulfate, filtered and concentrated to obtain a crude product, which was then separated with a chromatography column (eluent: ethyl acetate/petroleum ether=0-20%) to obtain compound WX018-3. $^1$H NMR (400 MHz, CHLOROFORM-d) δ ppm 7.57 (d, J=8.4 Hz, 1H), 7.41 (d, J=8.4 Hz, 1H), 7.30 (br s, 1H), 3.94 (s, 2H), 3.86 (dq, J=6.8, 9.0 Hz, 2H), 1.52 (s, 9H).

Step 3: Synthesis of Compound WX018-4

Compound WX018-3 (0.788 g, 2.07 mmol) was dissolved in 20 mL of DCM, followed by addition of m-CPBA (2.52 g, 12.42 mmol) in portions, and the reaction mixture was stirred at −10° C. for 5 hours. After the reaction was completed, 20 mL of saturated sodium sulfite solution, 20 mL of saturated sodium bicarbonate solution and 20 mL of DCM were added, followed by extraction with DCM (20 mL×3). The obtained organic phases were combined and dried over anhydrous sodium sulfate. After filtering to remove the desiccant, the filtrate was distilled under reduced pressure to remove the solvent, and the crude product was separated with a chromatography column (eluent: ethyl acetate/petroleum ether=0-30%) to obtain compound WX018-4. $^1$H NMR (400 MHz, CHLOROFORM-d) δ ppm 7.89 (d, J=8.4 Hz, 1H), 7.53 (d, J=8.4 Hz, 1H), 7.11 (br s, 1H), 4.51 (s, 2H), 3.92-3.83 (m, 2H), 1.54 (s, 9H).

Step 4: Synthesis of Compound WX018-5

Compound WX018-4 (0.61 g, 1.48 mmol) was dissolved in 10 mL of ethanol, followed by addition of concentrated hydrochloric acid (12 M, 5 mL). The mixture was heated to 80° C. and stirred with stirring overnight. After the reaction was completed, the solvent was evaporated under reduced pressure, followed by addition of 30 mL of saturated sodium bicarbonate solution and extraction with ethyl acetate (15 mL×2). The organic phases were combined, dried over anhydrous sodium sulfate, filtered and concentrated to obtain a crude product, which was then separated with a chromatography column (eluent: ethyl acetate/petroleum ether=0-50%) to obtain compound WX018-5. $^1$H NMR (400 MHz, CHLOROFORM-d) δ ppm 10.29 (s, 1H), 6.92-6.87 (m, 1H), 6.85-6.81 (m, 1H), 4.51 (s, 2H), 4.19 (q, J=7.2 Hz, 2H), 1.20 (t, J=7.2 Hz, 3H).

Step 5: Synthesis of Compound WX018-6

Triphosgene (235.40 mg, 793.26 μmol) was dissolved in 10 mL of DCM, followed by addition of compound BB-1 (326.46 mg, 2.38 mmol) and triethylamine (240.81 mg, 2.38 mmol, 331.24 μL). The reaction mixture was stirred at room temperature for 30 minutes, and then concentrated. The obtained crude product was dissolved in 10 mL of DCM, followed by addition of compound WX018-5 (0.233 g, 793.26 μmol) and triethylamine (80.27 mg, 793.26 μmol, 110.41 μL), and the mixture was stirred at room temperature overnight. After the reaction was completed, the reaction mixture was concentrated to obtain a crude product of compound WX018-6, which was directly used in the next reaction.

Step 6: Synthesis of Compound WX018-7

Compound WX018-6 (0.362 g, 792.30 μmol) was dissolved in 5 mL of THF, 5 mL of ethanol and 1 mL of water, followed by addition of LiOH.H$_2$O (166.24 mg, 3.96 mmol), and the reaction mixture was stirred at room temperature overnight. After the reaction was completed, the reaction mixture was concentrated, followed by addition of 20 mL of water and 30 mL of ethyl acetate for liquid separation. The aqueous phase was adjusted to pH of 2 with 2 N hydrochloric acid, and then extracted with ethyl acetate (30 mL×3). The organic phases were combined, dried over anhydrous sodium sulfate, filtered and concentrated to obtain a crude product of compound WX018-7, which was directly used in the next reaction.

Step 7: Synthesis of Compound WX018

Compound WX018-7 (0.27 g, 629.60 μmol) was dissolved in 5 mL of DMF, followed by addition of 2,2,2-trifluoroethylamine (74.84 mg, 755.52 μmol, 59.40 μL), HATU (0.36 g, 946.80 μmol) and triethylamine (127.42 mg, 1.26 mmol, 175.27 μL), and the reaction mixture was stirred at 40° C. overnight. After the reaction was completed, the solvent was evaporated under reduced pressure, followed by addition of 40 mL of water and extraction with ethyl acetate (30 mL×2). The organic phases were combined, washed with saturated brine (30 mL×2), dried over anhydrous sodium sulfate, filtered and concentrated to obtain a crude compound, which was then separated with a chromatography column (eluent: ethyl acetate/petroleum ether=0-50%) to obtain the target compound WX018.

Step 8: Synthesis of Compounds WX018A and WX018B.

Compound WX018 was resolved by supercritical fluid chromatography (separation conditions: column, DAICEL CHIRALPAK AS-H (250 mm×30 mm, 5 μm); mobile phase, ethanol (0.1% ammonium hydroxide)) to obtain the chiral isomers WX018A and WX018B, with a retention time of 4.070 min and 4.755 min, respectively, and a ratio of 1:1.

Table 3. NMR and MS Data of Each Embodiment

According to the steps 3 to 4 in the synthesis of Embodiment 1, the embodiment in Table 3 was synthesized using BB-7 in the step 3. The structures in the table also represent their potential isomers.

TABLE 3

| Embodiment | Fragment in the step 3 | Structure | Compound |
|---|---|---|---|
| 19 | | 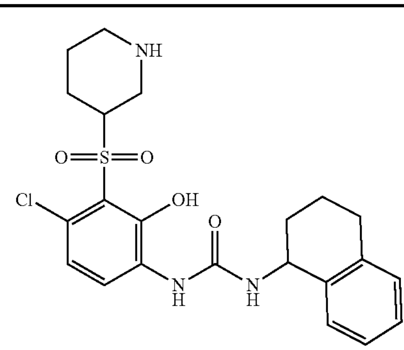 | WX019 |

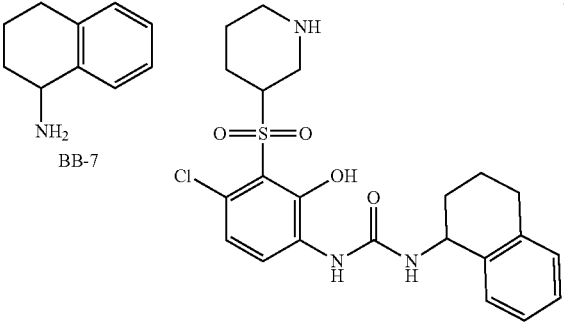

WX019 ¹H NMR (400 MHz, DMSO-d₆) δ ppm 8.54 (s, 1H), 8.22 (d, J=8.8 Hz, 1H), 7.58 (br d, J=8.4 Hz, 1H), 7.29-7.24 (m, 1H), 7.20-7.15 (m, 2H), 7.14-7.08 (m, 2H), 4.91-4.81 (m, 1H), 4.18 (br t, J=11.6 Hz, 1H), 3.24 (br d, J=12.4 Hz, 1H), 3.11 (br t, J=12.0 Hz, 1H), 2.94-2.70 (m, 6H), 2.04-1.66 (m, 10H)

[M+H]⁺: 464.0

According to the steps 1 to 4 in the synthesis of Embodiment 5, the embodiments in Table 4 were synthesized using benzyl bromide in the step 1. The structures in the table also represent their potential isomers.

TABLE 4

| Embodiment | Fragment in the step 1 | Structure | Compound |
|---|---|---|---|
| 20 | (benzyl bromide) | (structure 1) | WX020 WX020A WX020B |
|  |  | (structure 2) |  |
|  |  | (structure 3) |  |

Compound WX020 was resolved by supercritical fluid chromatography (separation conditions: column, DAICEL CHIRALPAK AY 250 mm×30 mm, 20 μm; mobile phase, A: carbon dioxide, B: ethanol (0.1% ammonium hydroxide); gradient, B %: 50%-50%) to obtain the chiral isomers WX020A and WX020B with a retention time of 2.214 min, 4.890 min, respectively, and a ratio of 1:1.

Analytical conditions: column: Lux Cellulose-2 150×4.6 mm I.D., 3 μm; mobile phase, A: carbon dioxide, B: ethanol (0.05% diethylamine); gradient, 40% of B; flow rate: 2.5 mL/min; column temperature: 40° C.; detection wavelength: 220 nm.

WX020A ¹H NMR (400 MHz, DMSO-d₆) δ ppm 10.41 (br s, 1H), 8.43 (br d, J=8.4 Hz, 1H), 8.19 (s, 1H), 7.54-7.45 (m, 2H), 7.36-7.22 (m, 5H), 7.15 (br s, 1H), 6.32 (d, J=1.6 Hz, 1H), 4.82 (br d, J=7.6 Hz, 1H), 3.06 (s, 2H), 2.47-2.41 (m, 1H), 2.37 (br d, J=6.8 Hz, 1H), 1.91 (m, 1H), 1.79-1.67 (m, 3H), 1.22 (s, 6H)

[M+H]⁺: 503.1

WX020B ¹H NMR (400 MHz, DMSO-d₆) δ ppm 10.40 (br s, 1H), 8.44 (br d, J=8.8 Hz, 1H), 8.19 (s, 1H), 7.54-7.44 (m, 2H), 7.36-7.23 (m, 5H), 7.17 (br d, J=8.8 Hz, 1H), 6.32 (d, J=1.6 Hz, 1H), 4.88-4.78 (m, 1H), 3.06 (s, 2H), 2.43 (br s, 1H), 2.39-2.30 (m, 1H), 1.98-1.87 (m, 1H), 1.79-1.66 (m, 3H), 1.22 (s, 6H)

[M+H]⁺: 503.1

Embodiment 21: WX021, WX021A, WX021B
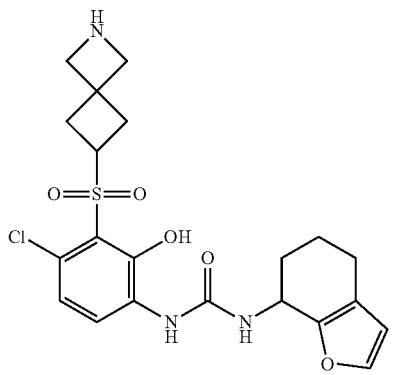 [SMILES: O=C(Nc1ccc(Cl)c(S(=O)(=O)C2CC3(CNC3)C2)c1O)NC1CCCc2ccoc21]
Synthetic Route:
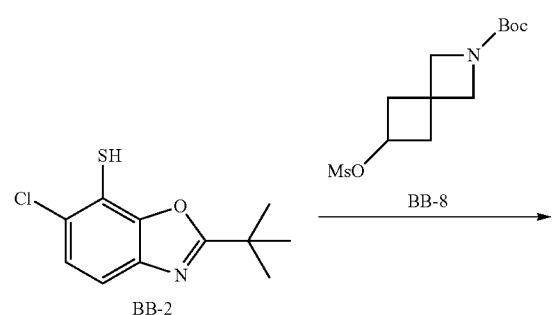
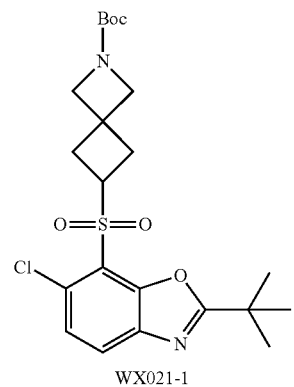
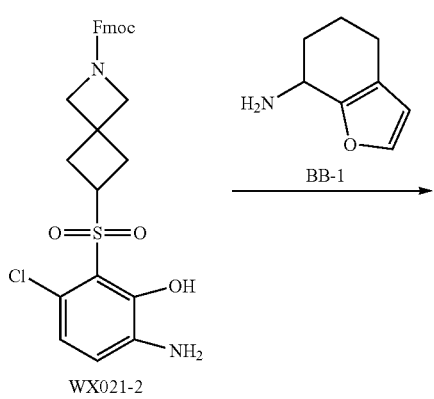
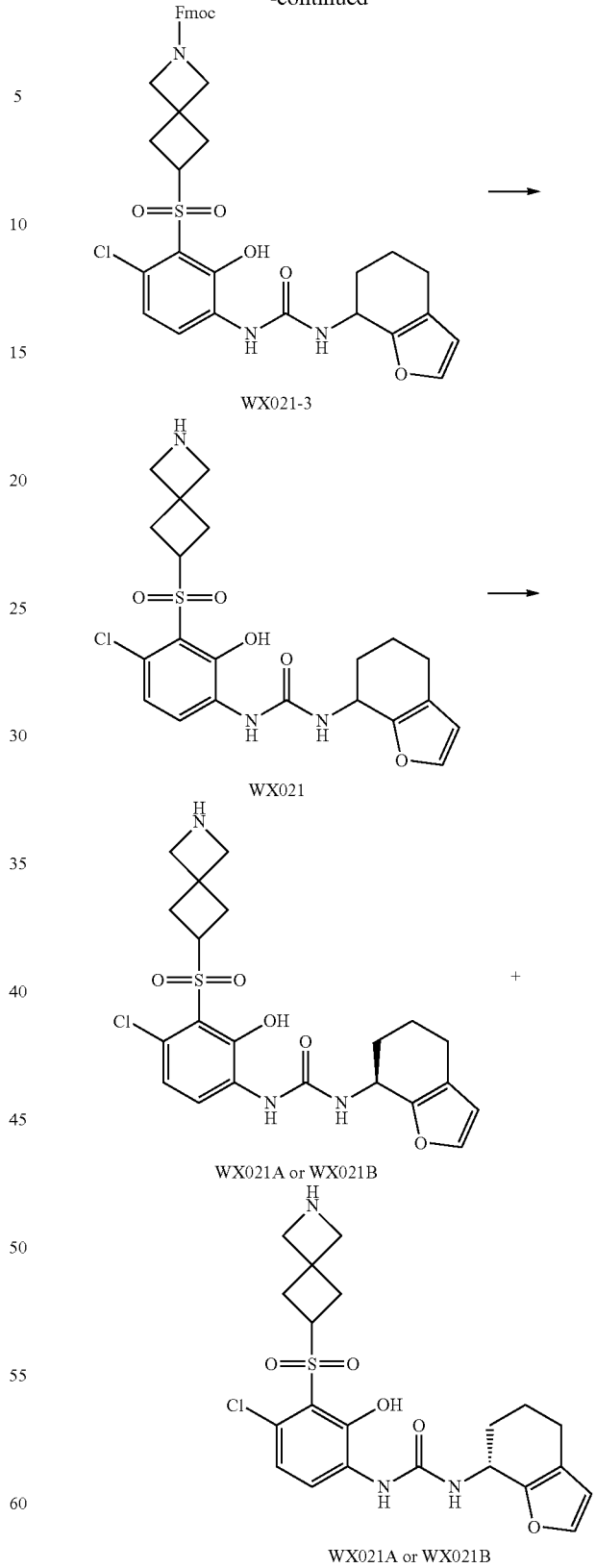
Step 1: Synthesis of Compound WX021-1
According to the steps 1 to 2 in the synthesis of BB-4, the target compound WX021-1 was synthesized using BB-8 in the step 1. $^1$H NMR (400 MHz, CHLOROFORM-d) δ ppm 7.83 (d, J=8.4 Hz, 1H), 7.49 (d, J=8.4 Hz, 1H), 4.26-4.18 (m, 1H), 4.03 (s, 2H), 3.94 (s, 2H), 2.82 (m, 2H), 2.51 (m, 2H), 1.55 (s, 9H), 1.45 (s, 9H).

Step 2: Synthesis of Compound WX021-2

Compound WX021-1 (0.29 g, 0.62 mmol) was dissolved in 5 mL of ethanol, followed by addition of 5 mL of hydrochloric acid (12 M). The reaction mixture was stirred at 85° C. for 14 hours. The reaction mixture was concentrated to dryness under reduced pressure, and dissolved in 5 mL of dichloromethane, followed by addition of 5 mL of saturated aqueous sodium bicarbonate solution and FmocCl (0.141 g, 0.55 mmol). The reaction mixture was stirred at 0° C. for 15 minutes. After the reaction was completed, the reaction mixture was diluted by adding 10 mL of dichloromethane, followed by liquid separation, and the organic phase was retained. The aqueous phase was extracted with dichloromethane (20 mL×3).

The organic phases were combined, washed with saturated brine (15 mL×2), dried over anhydrous sodium sulfate, filtered and concentrated to obtain a crude product, which was then separated with a chromatography column (eluent: ethyl acetate/petroleum ether=0-40%) to obtain compound WX021-2. $^1$H NMR (400 MHz, CHLOROFORM-d) δ ppm 10.47 (s, 1H), 7.70 (d, J=7.6 Hz, 2H), 7.50 (d, J=7.6 Hz, 2H), 7.36-7.30 (m, 2H), 7.28-7.22 (m, 2H), 6.81-6.76 (m, 1H), 6.75-6.70 (m, 1H), 4.35-4.25 (m, 3H), 4.16-4.10 (m, 1H), 3.99 (s, 2H), 3.94 (s, 2H), 2.68 (m, 2H), 2.53-2.41 (m, 2H).

Step 3: Synthesis of Compound WX021-3

Triphosgene (93.83 mg, 316.18 μmol) was dissolved in 5 mL of dichloromethane, followed by addition of compound BB-1 (130.12 mg, 948.54 μmol) and triethylamine (72.70 mg, 718.45 μmol, 0.1 mL). The reaction mixture was stirred at room temperature (18° C.) for 30 minutes, and then concentrated. The obtained crude product was dissolved in 5 mL of dichloromethane, followed by addition of compound WX021-2 (166 mg, 316.18 μmol) and triethylamine (145.40 mg, 1.44 mmol, 0.2 mL), and the mixture was stirred at room temperature (18° C.) for 3.5 hours. After completion of the reaction, the reaction mixture was directly concentrated to dryness to obtain a crude product. The crude product of WX021-3 was directly used in the next reaction.

Step 4: Synthesis of Compound WX021

Compound WX021-3 (0.2 g, 290.62 μmol) was dissolved in 10 mL of dichloromethane, followed by addition of diethylamine (7.10 g, 97.08 mmol), and the reaction mixture was stirred at 15° C. for 1 hour. After the reaction was completed, the reaction mixture was directly concentrated to dryness to obtain a crude product. The crude product was separated by high performance liquid chromatography to obtain the target compound WX021.

Step 5: Synthesis of Compounds WX021A and WX021B

Compound WX021 was resolved by supercritical fluid chromatography (separation conditions: column, DAICEL CHIRALPAK IC 250 mm×30 mm, 10 μm; mobile phase, A: carbon dioxide, B: isopropanol (0.1% ammonium hydroxide); gradient, B %: 50%-50%) to obtain the chiral isomers WX021A and WX021B with a retention time of 7.251 min and 10.541 min, respectively, and a ratio of 1:1.

Analytical conditions: Column: ChiralPak IC-3 150×4.6 mm I.D., 3 um; mobile phase, A: carbon dioxide, B: isopropanol (0.1% ethanolamine); gradient, B %: 40%; flow rate: 2.5 mL/min; column temperature: 40° C.; detection wavelength: 220 nm.

WX021A $^1$H NMR (400 MHz, DMSO-d$_6$) δ ppm 8.47 (br s, 1H), 8.18 (s, 1H), 7.72 (br s, 1H), 7.49 (d, J=1.6 Hz, 1H), 7.36 (br d, J=8.4 Hz, 1H), 6.30 (d, J=1.6 Hz, 1H), 6.05 (br s, 1H), 4.80 (br d, J=4.1 Hz, 1H), 4.75-4.61 (m, 1H), 3.93 (br d, J=6.4 Hz, 4H), 2.44 (br d, J=5.6 Hz, 2H), 1.93-1.84 (m, 1H), 1.80-1.66 (m, 3H), 1.51 (br s, 2H), 0.87-0.83 (m, 2H)

[M+H]$^+$: 466.0

WX021B $^1$H NMR (400 MHz, DMSO-d$_6$) δ ppm 8.48 (br s, 1H), 8.18 (s, 1H), 7.75 (br s, 1H), 7.50 (d, J=1.6 Hz, 1H), 7.37 (br d, J=8.0 Hz, 1H), 6.30 (d, J=1.6 Hz, 1H), 4.81 (br s, 1H), 4.73-4.63 (m, 1H), 3.97-3.90 (m, 4H), 2.44 (br s, 2H), 1.89 (br d, J=4.8 Hz, 1H), 1.77-1.67 (m, 3H), 1.51 (br s, 2H), 0.87-0.84 (m, 2H)

[M+H]$^+$: 466.0

According to the steps 1 to 4 in the synthesis of Embodiment 21, the embodiments in Table 5 were synthesized using different fragments in the step 1. The structures in the table also represent their potential isomers.

TABLE 5

| Embodiment | Fragment in the step 1 | Structure | Compound |
|---|---|---|---|
| 22 | BB-9 | 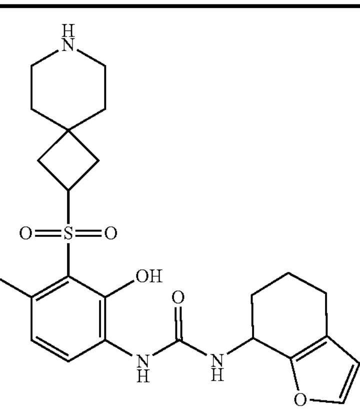 | WX022<br>WX022A<br>WX022B |

TABLE 5-continued
| Embodiment | Fragment in the step 1 | Structure | Compound |
|---|---|---|---|
| | | 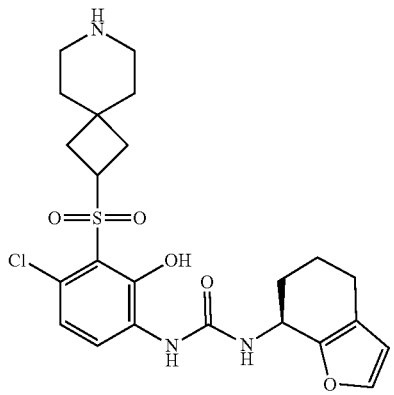 [SMILES: O=C(Nc1ccc(Cl)c(S(=O)(=O)C2CC3(CCNCC3)C2)c1O)N[C@H]1CCCc2ccoc21] | |
| | | 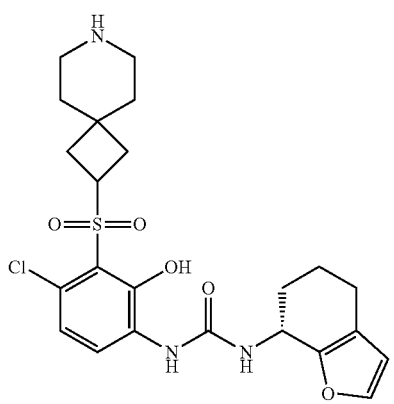 [SMILES: O=C(Nc1ccc(Cl)c(S(=O)(=O)C2CC3(CCNCC3)C2)c1O)N[C@@H]1CCCc2ccoc21] | |
| 23 | 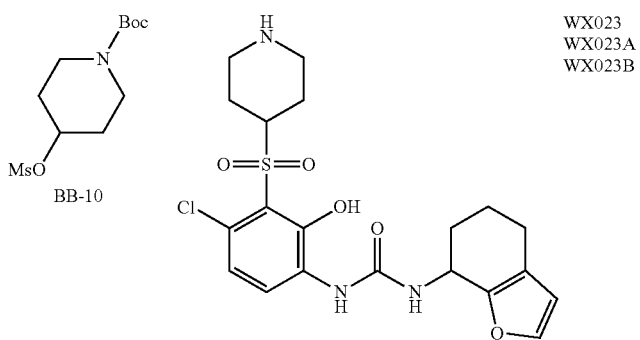 BB-10 | 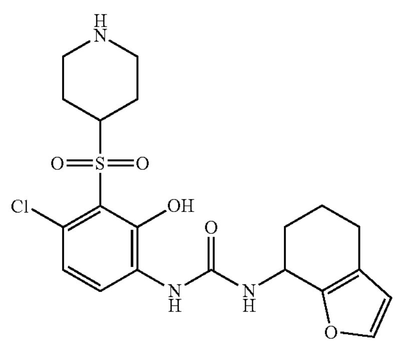 | WX023<br>WX023A<br>WX023B |
| | | 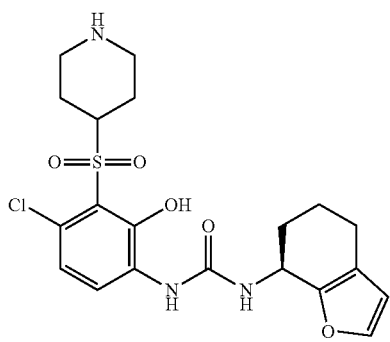 [SMILES: O=C(Nc1ccc(Cl)c(S(=O)(=O)C2CCNCC2)c1O)N[C@H]1CCCc2ccoc21] | |

TABLE 5-continued

| Embodiment | Fragment in the step 1 | Structure | Compound |
|---|---|---|---|

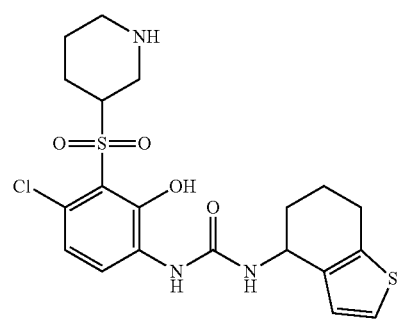 [SMILES: O=C(Nc1ccc(Cl)c(S(=O)(=O)C2CCCNC2)c1O)NC1CCCc2sccc21]

Compound WX022 was resolved by supercritical fluid chromatography (separation conditions: column, DAICEL CHIRALPAK AD 250 mm×30 mm, 10 μm; mobile phase, A: carbon dioxide, B: isopropanol (0.1% ammonium hydroxide); gradient, B %: 40%-40%) to obtain the chiral isomers WX022A and WX022B with a retention time of 6.755 min and 8.006 min, respectively, and a ratio of 1:1.

Analytical conditions: column: ChiralPak AD-3 150×4.6 mm I.D., 3 um; mobile phase, A: carbon dioxide, B: isopropanol (0.1% ethanolamine); gradient, mobile phase B from 5% to 40% within 5.5 minutes, then 40% for 3 min, then 5% for 1.5 minutes; flow rate: 2.5 mL/min; column temperature: 40° C.; detection wavelength: 220 nm.

WX022A $^1$H NMR (400 MHz, METHANOL-$d_4$) δ ppm 7.94 (d, J=8.4 Hz, 1H), 7.37 (d, J=1.6 Hz, 1H), 6.52 (br d, J=7.6 Hz, 1H), 6.26 (d, J=1.6 Hz, 1H), 4.81-4.69 (m, 1H), 4.63 (s, 1H), 3.13-3.02 (m, 4H), 2.57-2.49 (m, 1H), 2.47-2.40 (m, 1H), 2.39-2.30 (m, 2H), 2.13 (br t, J=10.0 Hz, 2H), 2.01 (br s, 1H), 1.93-1.89 (m, 1H), 1.84-1.77 (m, 2H), 1.37-1.33 (m, 3H), 1.12 (br s, 1H)

[M+H]$^+$: 494.0

WX022B $^1$H NMR (400 MHz, METHANOL-$d_4$) δ ppm 7.94 (br d, J=8.8 Hz, 1H), 7.37 (s, 1H), 6.53 (br s, 1H), 6.26 (s, 1H), 4.75 (s, 1H), 3.06 (br s, 4H), 2.51 (s, 1H), 2.44 (br d, J=7.6 Hz, 1H), 2.35 (br s, 2H), 2.12 (br s, 2H), 2.01 (br s, 1H), 1.94-1.90 (m, 1H), 1.84-1.77 (m, 2H), 1.39-1.35 (m, 2H), 1.14 (br s, 2H)

[M+H]$^+$: 494.0

Compound WX023 was resolved by supercritical fluid chromatography (separation conditions: column, DAICEL CHIRALPAK AS-H 250 mm×30 mm, 5 μm; mobile phase, A: carbon dioxide, B: isopropanol (0.1% ammonium hydroxide); gradient, B %: 50%-50%) to obtain the chiral isomers WX023A and WX023B with a retention time of 2.129 min and 3.461 min, respectively, and a ratio of 1:1.

Analytical conditions: column: ChiralPak AS-3 150×4.6 mm I.D., 3 um; mobile phase, A: carbon dioxide, B: isopropanol (0.05% diethylamine); gradient, mobile phase B was 40%; flow rate: 2.5 mL/min; column temperature: 40° C.; detection wavelength: 220 nm WX023A $^1$H NMR (400 MHz, DMSO-$d_6$) δ ppm 8.40 (br s, 1H), 8.13 (s, 1H), 7.72 (d, J=8.4 Hz, 1H), 7.51-7.47 (m, 1H), 7.37 (br d, J=8.4 Hz, 1H), 6.30 (d, J=1.6 Hz, 1H), 5.99 (d, J=8.4 Hz, 1H), 4.81 (br d, J=4.4 Hz, 1H), 4.35 (br s, 1H), 2.84 (br t, J=10.8 Hz, 2H), 2.47-2.29 (m, 3H), 1.96-1.66 (m, 9H).

[M+H]$^+$: 453.9

WX023B $^1$H NMR (400 MHz, DMSO-$d_6$) δ ppm 8.50 (br s, 1H), 8.14 (s, 1H), 7.78 (br d, J=8.4 Hz, 1H), 7.50 (d, J=1.6 Hz, 1H), 7.38 (d, J=8.4 Hz, 1H), 6.30 (d, J=1.6 Hz, 1H), 6.09 (br s, 1H), 4.82 (br s, 1H), 4.33 (br s, 1H), 2.92-2.82 (m, 2H), 2.46-2.38 (m, 1H), 2.48-2.29 (m, 2H), 2.00-1.62 (m, 9H).

[M+H]$^+$: 453.9

Embodiment 24: WX024, WX024A, WX024B

Synthetic Route:

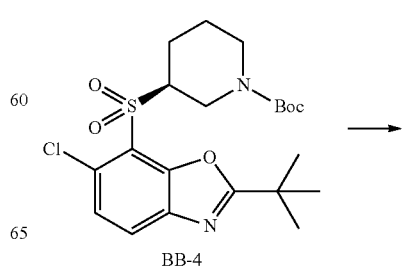

121
-continued

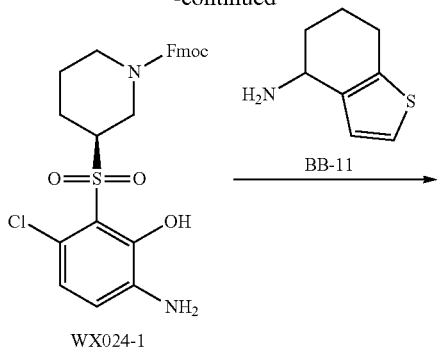

WX024-1

122
-continued

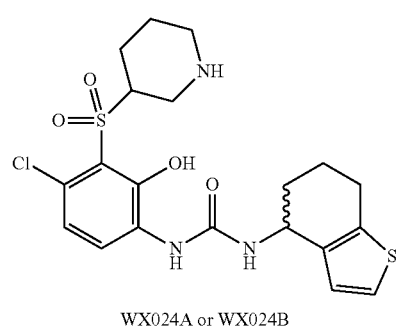

WX024A or WX024B

Step 1: Synthesis of Compound WX024-1

According to the step 2 in the synthesis of Embodiment 21, the target compound WX024-1 was synthesized.

Step 2: Synthesis of Compound WX024-2

According to the step 5 in the synthesis of Embodiment 6, the target compound WX024-1 was synthesized using BB-11.

Step 3: Synthesis of Compound WX024

According to the step 4 in the synthesis of Embodiment 21, the target compound WX024 was synthesized.

Step 4: Synthesis of Compounds WX024A and WX024B

Compound WX024 was resolved by supercritical fluid chromatography (separation conditions: column, DAICEL CHIRALCEL OD-H 250 mm×30 mm, 5 μm; mobile phase, A: carbon dioxide, B: ethanol (0.1% ammonium hydroxide); gradient, B %: 45%-45%) to obtain the chiral isomers WX024A and WX024B with a retention time of 4.376 min and 4.794 min, respectively, and a ratio of 1:1.

Analytical conditions: column: Chiralcel OD-3 150×4.6 mm I.D., 3 um; mobile phase, A: carbon dioxide, B: ethanol (0.1% ethanolamine); gradient, mobile phase B from 5% to 40% within 4.5 minutes, then maintained at 40% for 2.5 minutes, then maintained at 5% for 1 minute; flow rate: 2.8 mL/min; column temperature: 40° C.; detection wavelength: 220 nm WX024A $^1$H NMR (400 MHz, DMSO-$d_6$) δ ppm 7.88-7.75 (m, 2H), 7.39 (br d, J=8.4 Hz, 1H), 7.22 (d, J=5.2 Hz, 1H), 6.85 (d, J=5.2 Hz, 1H), 6.16 (br d, J=8.4 Hz, 1H), 4.75 (br s, 1H), 4.48 (br s, 1H), 3.12-2.98 (m, 2H), 2.78 (br d, J=13.2 Hz, 2H), 2.74-2.66 (m, 2H), 1.88 (br s, 2H), 1.78 (br s, 4H), 1.73-1.67 (m, 1H), 1.64-1.55 (m, 1H)

$[M+H]^+$: 470.0

WX024B $^1$H NMR (400 MHz, DMSO-$d_6$) δ ppm 8.01 (br s, 1H), 7.82-7.72 (m, 1H), 7.41-7.28 (m, 1H), 7.22 (br d, J=5.2 Hz, 1H), 6.86 (br d, J=5.2 Hz, 1H), 6.07 (br d, J=8.0 Hz, 1H), 4.75 (br s, 1H), 4.40 (br s, 1H), 3.08-2.86 (m, 2H), 2.69 (br d, J=11.2 Hz, 4H), 1.90 (br d, J=8.4 Hz, 2H), 1.84-1.71 (m, 4H), 1.63 (br s, 2H)

$[M+H]^+$: 470.0

According to the steps 5 to 6 in the synthesis of Embodiment 6, the embodiments in Table 6 were synthesized using different fragments in the step 5. The structures in the table also represent their potential isomers.

TABLE 6
| Embodiment | Fragment in the step 1 | Structure | Compound |
|---|---|---|---|
| 25 | 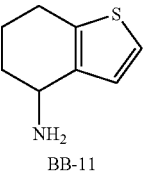 BB-11 | 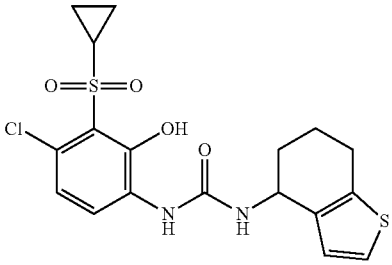 [SMILES: O=C(Nc1ccc(Cl)c(S(=O)(=O)C2CC2)c1O)NC1CCCc2sccc21] | WX025 WX025A WX025B |
| 26 | 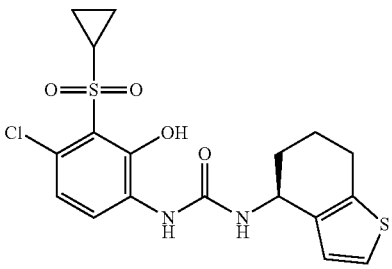 [SMILES: O=C(Nc1ccc(Cl)c(S(=O)(=O)C2CC2)c1O)N[C@H]1CCCc2sccc21] BB-12 | 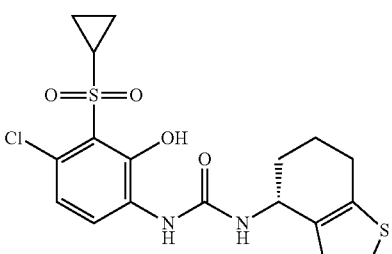 | WX026 WX026A WX026B |

TABLE 6-continued

| Embodiment | Fragment in the step 1 | Structure | Compound |
|---|---|---|---|
| 27 | BB-13 | | WX027 WX027A WX027B |
| 28 | BB-14 | 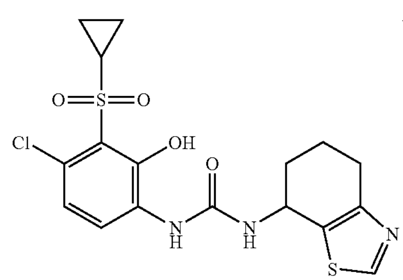 | WX028 |

Compound WX025 was resolved by supercritical fluid chromatography (separation conditions: column, DAICEL CHIRALCEL OJ-H 250 mm×30 mm, 5 μm; mobile phase, A: carbon dioxide, B: ethanol (0.1% ammonium hydroxide); gradient, B %: 40%-40%) to obtain the chiral isomers WX025A and WX025B with a retention time of 3.994 min and 4.753 min, respectively, and a ratio of 1:1.

Analytical conditions: column: Chiralcel OJ-3 100×4.6 mm I.D., 3 um; mobile phase, A: carbon dioxide, B: ethanol (0.05% diethylamine); gradient, mobile phase B from 5% to 40 within 4.5 minutes, then maintained at 40% for 2.5 minutes, then maintained at 5% for 1 minute; flow rate: 2.8 mL/min; column temperature: 40° C.; detection wavelength: 220 nm WX025A ¹H NMR (400 MHz, DMSO-d₆) δ ppm 8.26-8.17 (m, 2H), 7.40 (d, J=8.4 Hz, 1H), 7.27 (d, J=5.2 Hz, 1H), 6.90 (d, J=5.2 Hz, 2H), 4.82-4.74 (m, 1H), 3.47 (br s, 1H), 2.84-2.64 (m, 2H), 1.98-1.78 (m, 3H), 1.73-1.62 (m, 1H), 1.18 (br d, J=3.6 Hz, 2H), 1.15-1.05 (m, 2H)

[M+H]⁺: 427.0

WX025B ¹H NMR (400 MHz, DMSO-d₆) δ ppm 8.28-8.16 (m, 2H), 7.40 (br d, J=8.0 Hz, 1H), 7.27 (d, J=5.4 Hz, 1H), 6.90 (d, J=5.2 Hz, 2H), 4.78 (br d, J=5.6 Hz, 1H), 3.46 (br d, J=4.4 Hz, 1H), 2.85-2.61 (m, 2H), 1.98-1.76 (m, 3H), 1.75-1.61 (m, 1H), 1.21-1.07 (m, 4H)

[M+H]⁺: 427.0

Compound WX026 was resolved by supercritical fluid chromatography (separation conditions: column, DAICEL CHIRALCEL OD 250 mm×30 mm, 10 μm; mobile phase, A: carbon dioxide, B: methanol (0.1% ammonium hydroxide); gradient, B %: 35%-35%) to obtain the chiral isomers WX026A and WX026B with a retention time of 3.351 min and 4.422 min, respectively, and a ratio of 1:1.

Analytical conditions: column: Chiralcel OD-3 100×4.6 mm I.D., 3 um; mobile phase, A: carbon dioxide, B: methanol (0.05% diethylamine); gradient, mobile phase B from 5% to 40% within 4.5 minutes, then maintained at 40% for 2.5 minutes, then maintained at 5% for 1 minute; flow rate: 2.8 mL/min; column temperature: 40° C.; detection wavelength: 220 nm WX026A ¹H NMR (400 MHz, DMSO-d₆) δ ppm 8.38 (d, J=3.6 Hz, 1H), 8.30 (d, J=8.8 Hz, 1H), 8.22 (s, 1H), 7.65 (d, J=7.6 Hz, 1H), 7.51 (d, J=8.4 Hz, 1H), 7.21 (m, 1H), 7.06 (br d, J=8.8 Hz, 1H), 4.95-4.86 (m, 1H), 2.93-2.81 (m, 2H), 2.01-1.81 (m, 4H), 1.78-1.69 (m, 1H), 1.22 (br d, J=4.4 Hz, 2H), 1.16 (br d, J=7.6 Hz, 2H)

[M+H]⁺: 422.0

WX026B ¹H NMR (400 MHz, DMSO-d₆) δ ppm 8.38 (br d, J=3.6 Hz, 1H), 8.30 (br d, J=8.8 Hz, 1H), 8.22 (s, 1H), 7.65 (br d, J=7.6 Hz, 1H), 7.50 (br d, J=8.4 Hz, 1H), 7.21 (dd, J=4.8, 7.6 Hz, 1H), 7.05 (br d, J=8.8 Hz, 1H), 4.95-4.86 (m, 1H), 2.93-2.79 (m, 2H), 2.04-1.79 (m, 4H), 1.78-1.68 (m, 1H), 1.22 (br d, J=4.0 Hz, 2H), 1.16 (br d, J=7.6 Hz, 2H)

[M+H]⁺: 422.0

Compound WX027 was resolved by supercritical fluid chromatography (separation conditions: column, DAICEL CHIRALCEL OD-H 250 mm×30 mm, 5 μm; mobile phase, A: carbon dioxide, B: methanol (0.1% ammonium hydroxide); gradient, B %: 40%-40%) to obtain the chiral isomers WX027A and WX027B with a retention time of 2.212 min and 3.034 min, respectively, and a ratio of 1:1.

Analytical conditions: Column: Chiralcel OD-3 150×4.6 mm I.D., 3 um; mobile phase, A: carbon dioxide, B: methanol (0.05% diethylamine); gradient, 40% mobile phase B; flow rate: 2.5 mL/min; column temperature: 35° C.; detection wavelength: 220 nm WX027A ¹H NMR (400 MHz, METHANOL-d₄) δ ppm 8.30 (d, J=8.8 Hz, 1H), 7.22 (d, J=5.2 Hz, 1H), 7.07 (br d, J=8.8 Hz, 1H), 6.76 (d, J=5.2 Hz, 1H), 5.08-5.00 (m, 1H), 4.62 (s, 2H), 3.37-3.32 (m, 1H), 2.74-2.56 (m, 2H), 2.17-2.06 (m, 1H), 1.98-1.79 (m, 3H), 1.36-1.30 (m, 2H), 1.18 (br d, J=5.6 Hz, 2H)

[M+H]⁺: 427.0

WX027B ¹H NMR (400 MHz, METHANOL-d₄) δ ppm 8.31 (d, J=8.8 Hz, 1H), 7.22 (d, J=5.2 Hz, 1H), 7.09 (d, J=8.8 Hz, 1H), 6.76 (d, J=5.2 Hz, 1H), 5.08-5.00 (m, 1H), 4.62 (br s, 2H), 3.35-3.32 (m, 1H), 2.73-2.57 (m, 2H), 2.11 (dt, J=5.2, 9.3 Hz, 1H), 1.99-1.78 (m, 3H), 1.38-1.30 (m, 2H), 1.19 (m, 2H)

[M+H]⁺: 427.0

WX028 ¹H NMR (400 MHz, METHANOL-d₄) δ ppm 8.86 (s, 1H), 8.29 (d, J=8.8 Hz, 1H), 7.07 (br d, J=8.8 Hz, 1H), 5.11 (m, 1H), 4.61 (s, 3H), 2.87-2.78 (m, 2H), 2.23-1.79 (m, 5H), 1.32 (br s, 2H), 1.18 (br d, J=5.6 Hz, 2H)

[M+H]⁺: 428.0

Embodiment 29: WX029, WX029A, WX029B

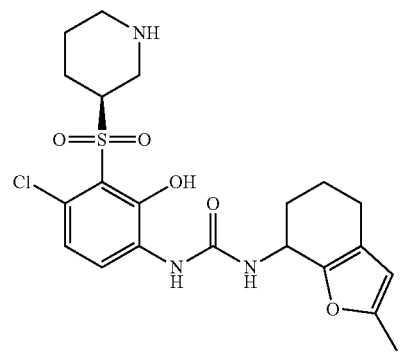 [SMILES: Cc1cc2c(o1)C(NC(=O)Nc1ccc(Cl)c(S(=O)(=O)[C@H]3CCCNC3)c1O)CCC2]

Synthetic Route:

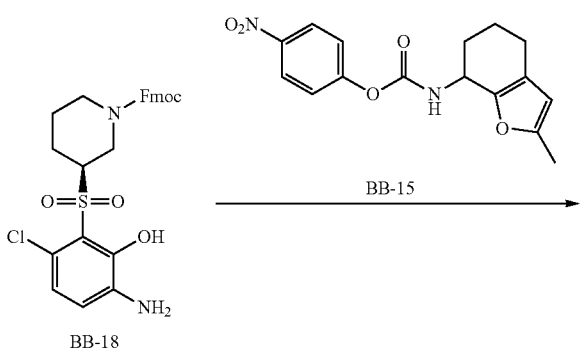

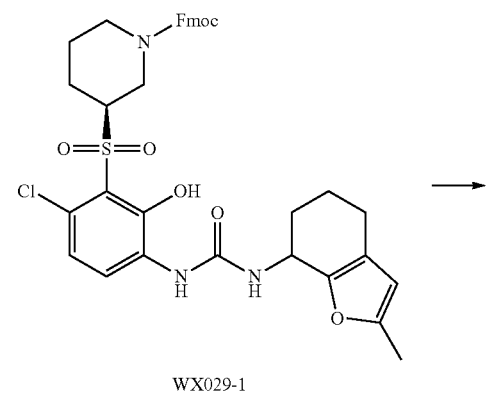

WX029-1

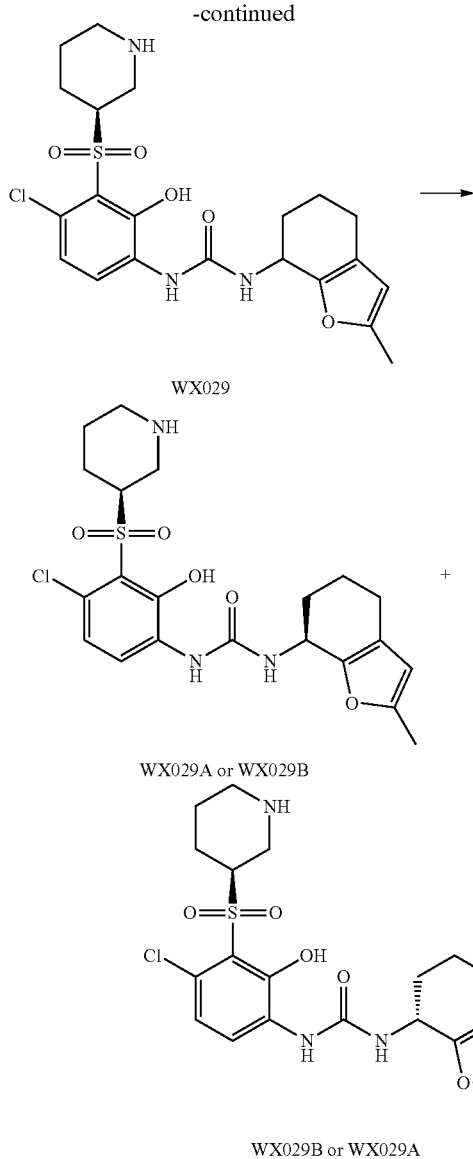

WX029

WX029A or WX029B

WX029B or WX029A

Step 1: Synthesis of Compound WX029-1

Compound BB-18 (750 mg, 1.46 mmol) was dissolved in dichloromethane (60 mL), followed by addition of triethylamine (369.84 mg, 3.65 mmol) and the intermediate compound BB-15 (1.62 g, 5.12 mmol). The mixture was stirred at 40° C. for 16 hours. After completion of the reaction, the reaction mixture was diluted with dichloromethane (100 mL) and washed with water (100 mL). The organic phase was washed with saturated brine (100 mL), dried over anhydrous sodium sulfate, filtered, concentrated to dryness under reduced pressure to obtain a crude product, which was then separated and purified with a flash preparative chromatography (eluent: ethyl acetate/petroleum ether=0-30%) to obtain compound WX029-1.

Step 2: Synthesis of Compound WX029

Compound WX029-1 (40 mg, 57.95 μmol) was dissolved in dichloromethane (5 mL), followed by addition of diethylamine (355.00 mg, 4.85 mmol, 0.5 mL), and the reaction mixture was stirred at 25° C. for 1 hour. After the reaction was completed, the reaction mixture was diluted with 20 mL of dichloromethane, washed with 20 mL of water and 20 mL of saturated brine, dried over anhydrous sodium sulfate, filtered, and concentrated under reduced pressure to obtain a crude product. The crude product was separated by high performance liquid chromatography (neutral condition) to obtain WX029. $^1$H NMR (400 MHz, METHANOL-$d_4$) δ ppm 8.07-7.96 (m, 1H), 6.63 (br d, J=8.4 Hz, 1H), 5.81 (s, 1H), 4.15 (br s, 1H), 3.47 (m, 1H), 3.16-3.07 (m, 2H), 2.85-2.73 (m, 1H), 2.48-2.32 (m, 2H), 2.21 (s, 3H), 2.04 (m, 1H), 1.99-1.63 (m, 8H)

Step 3: Synthesis of Compounds WX029A and WX029B

Compound WX029 (58 mg, 123.94 μmol) was resolved by supercritical fluid chromatography (separation conditions: column, DAICEL CHIRALPAK AD-H 250 mm×30 mm, 5 μm; mobile phase, A: carbon dioxide, B: ethanol (0.1% ammonium hydroxide); gradient, B %: 40%-40%) to obtain the chiral isomers WX029A and WX029B with a retention time of 5.922 min and 7.134 min, respectively, and a ratio of 1:1.

Embodiment 30: WX030, WX030A, WX030B

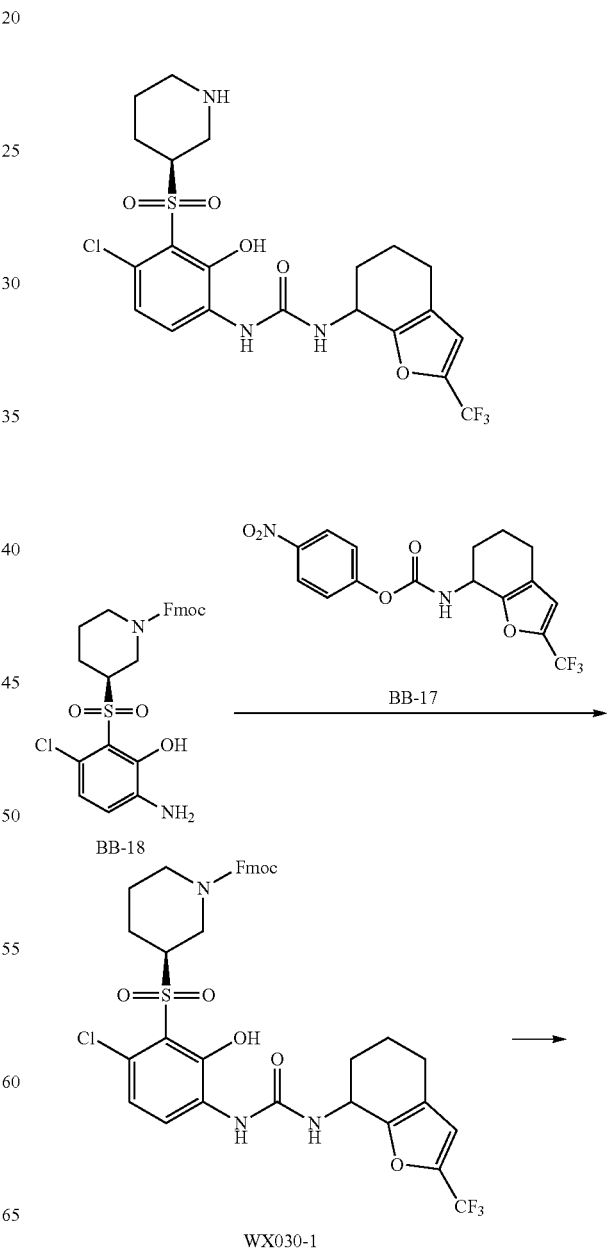

BB-18

WX030-1

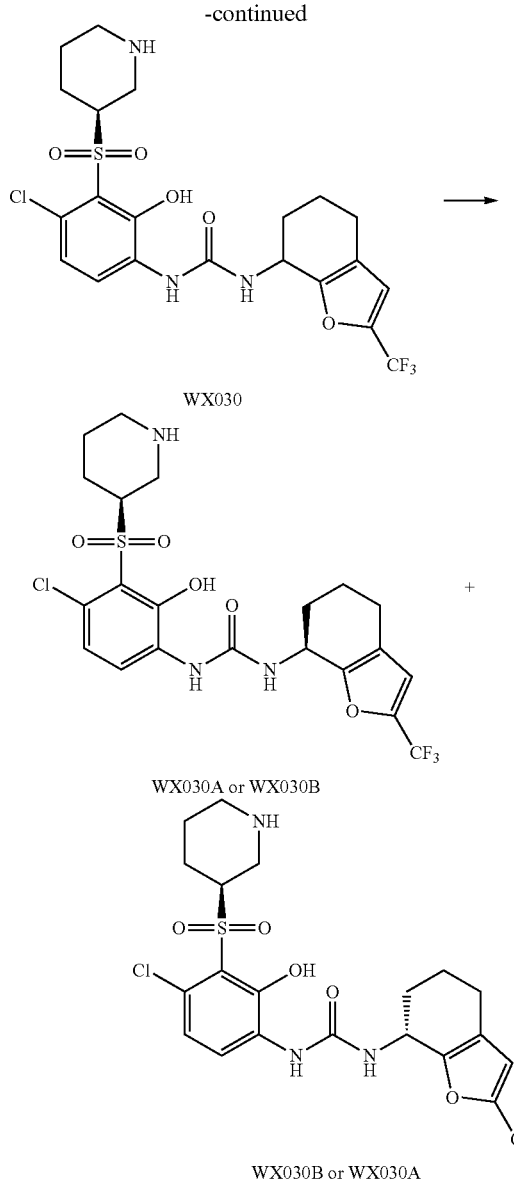

WX030

WX030A or WX030B

WX030B or WX030A

Step 1: Synthesis of Compound WX030-1

According to the synthesis method for WX029-1 in Embodiment 29, the target compound WX030-1 was synthesized.

Step 2: Synthesis of Compound WX030

According to the synthesis method for WX029 in Embodiment 29, the target compound WX030 was synthesized using WX030-1. $^1$H NMR (400 MHz, METHANOL-$d_4$) δ ppm 7.99-7.93 (m, 1H), 6.79 (s, 1H), 6.60-6.56 (m, 1H), 4.96 (s, 1H), 4.27 (br s, 1H), 3.58-3.54 (m, 1H), 3.16-3.08 (m, 2H), 2.82-2.79 (m, 1H), 2.54-2.46 (m, 2H), 2.03 (br s, 2H), 1.94-1.85 (m, 6H)

[M+H]$^+$:522.1

Step 3: Synthesis of Compounds WX030A and WX030B

Compound WX029 (70 mg, 134.12 μmol) was resolved by supercritical fluid chromatography (separation conditions: column, DAICEL CHIRALPAK AS-H 250 mm×30 mm, 5 μm; mobile phase, A: carbon dioxide, B: ethanol (0.1% ammonium hydroxide); gradient, B %: 30%-30%) to obtain the chiral isomers WX030A and WX030B with a retention time of 3.548 min and 3.847 min, respectively, and a ratio of 1:1.

Embodiment 31: WX031

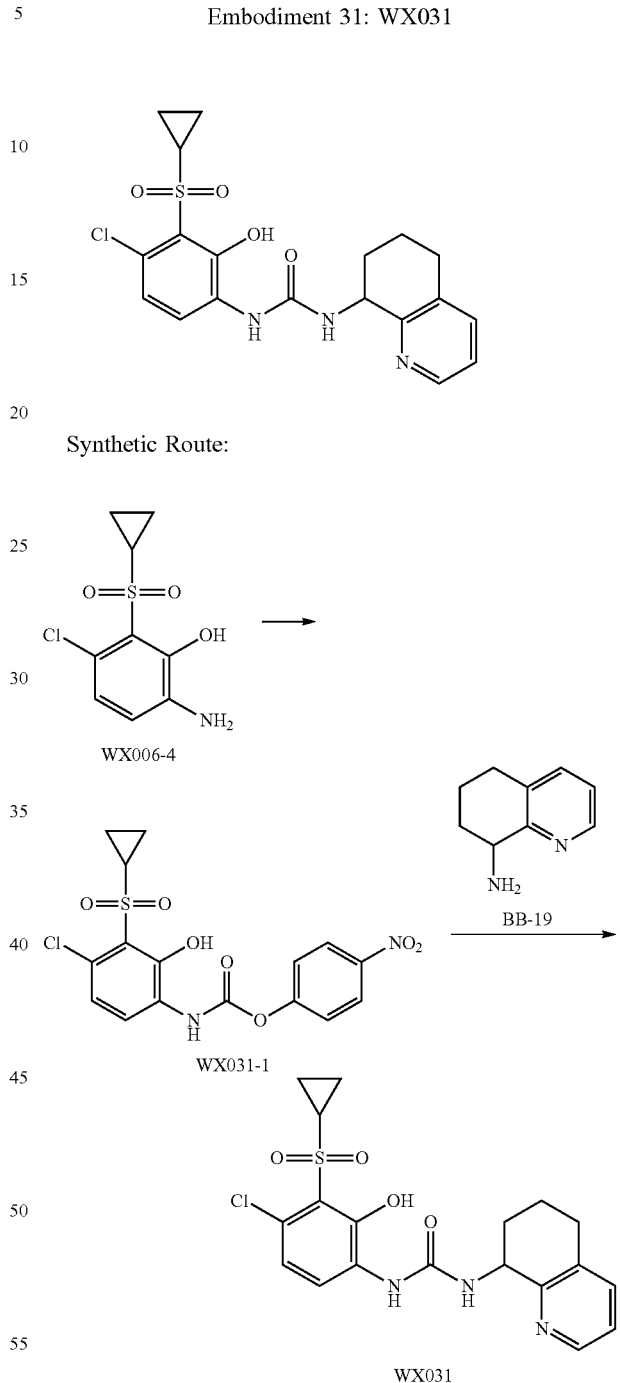

Step 1: Synthesis of Compound WX031-1

Compound WX006-4 (50 mg, 201.86 μmol) was dissolved in dichloromethane (5 mL), followed by addition of triethylamine (51.07 mg, 504.65 μmol) and p-nitrophenyl chloroformate (48.82 mg, 242.23 μmol) at 0° C. The reaction mixture was stirred at 25° C. for 2 hours. After the reaction was completed, the reaction mixture was directly concentrated to dryness to obtain a crude product of compound WX031-1, which was directly used in the next step.

Step 2: Synthesis of Compound WX031

Compound WX031-1 (80 mg, 193.80 μmol) was dissolved in tetrahydrofuran (10 mL), followed by addition of triethylamine (39.22 mg, 387.60 μmol) and compound BB-19 (43.08 mg, 290.70 μmol). The reaction mixture was heated to 60° C. and stirred for 14 hours. After the reaction was completed, the reaction mixture was concentrated under reduced pressure to obtain a crude product. The crude product was separated by high performance liquid chromatography (neutral condition) to obtain WX031.

Embodiment 32: WX032

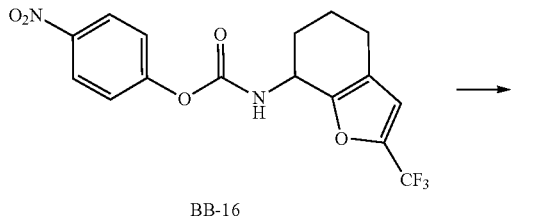
BB-16

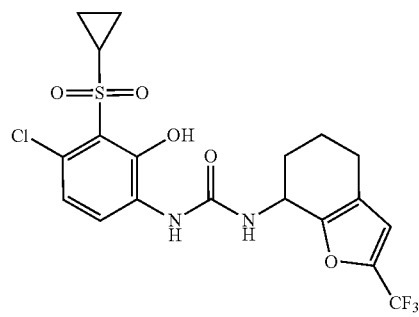

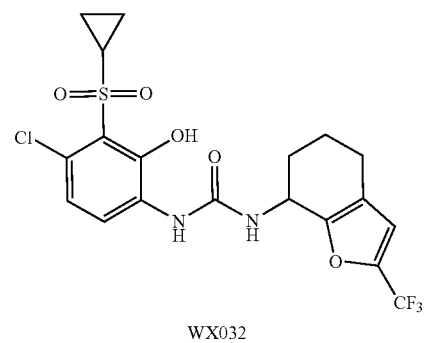
WX032

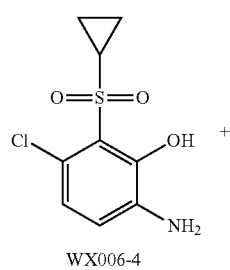
WX006-4

Step 1: Synthesis of Compound WX032

Compound WX006-4 (100 mg, 403.72 μmol) was dissolved in dichloromethane (10 mL), followed by addition of triethylamine (122.56 mg, 1.21 mmol) and the intermediate compound BB-16 (194.33 mg, 524.83 μmol). The mixture was stirred at 5-20° C. for 16 hours. After the reaction was completed, the reaction mixture was diluted with dichloromethane (40 mL) and washed with water (50 mL). The organic phase was washed with saturated brine (50 mL×2), dried over anhydrous sodium sulfate, filtered, and concentrated to dryness under reduced pressure to obtain a crude product. The crude product was separated and purified with a thin layer chromatography plate (eluent: dichloromethane/methanol=20:1) to obtain compound WX032. The structure also represents its potential isomers.

According to the step 1 in the synthesis of Embodiment 32, the embodiment in Table 7 was synthesized using BB-15 in the step 1. The structure in the table also represents its potential isomers.

TABLE 7

| Embodiment | Fragment in the step 1 | Structure | Compound |
|---|---|---|---|
| 33 | ![BB-15] BB-15 | ![structure] | WX033 |

According to the step 1 in the synthesis of Embodiment 32, the embodiments in Table 8 were synthesized using WX002-1 in the step 1. The structures in the table also represent their potential isomers.
TABLE 8
| Embodiment | Fragment in the step 1 | Structure | Compound |
|---|---|---|---|
| 34 | | 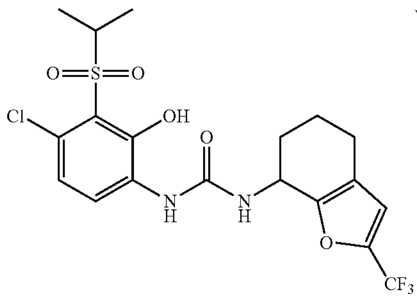 | WX034 |
| 35 | | 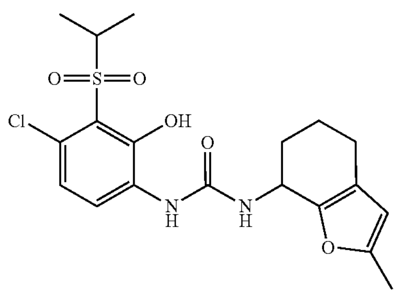 [SMILES: Cc1cc2c(o1)C(NC(=O)Nc1ccc(Cl)c(S(=O)(=O)C(C)C)c1O)CCC2] | WX035 |
Embodiment 36: WX036
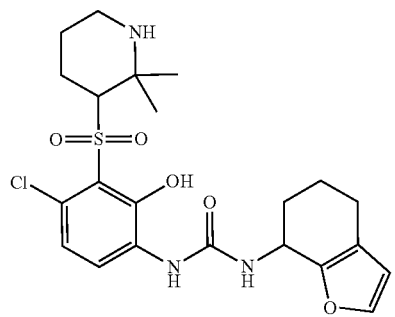 [SMILES: CC1(C)NCCCC1S(=O)(=O)c1c(Cl)ccc(NC(=O)NC2CCCc3ccoc32)c1O]
Synthetic Route:
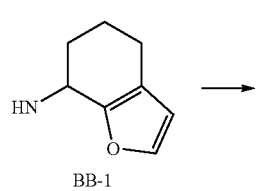
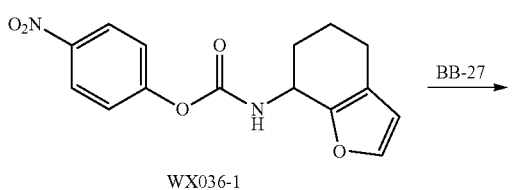
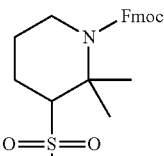
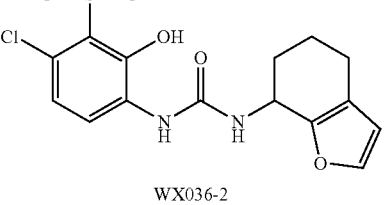

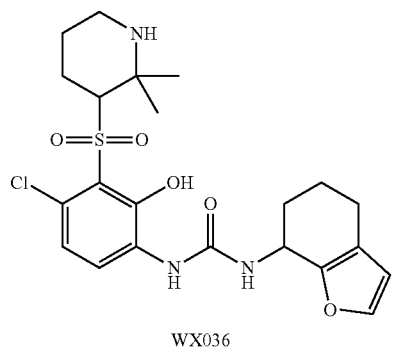

WX036

Step 1: Synthesis of Compound WX036-1

According to the step 5 in the synthesis of fragment BB-15, the intermediate compound WX036-1 was synthesized using fragment BB-1.

Step 2: Synthesis of Compound WX036-2

Compound BB-27 (130 mg, 240.27 μmol) was dissolved in dichloromethane (10 mL), followed by addition of triethylamine (72.94 mg, 720.81 μmol) and the intermediate compound WX036-1 (145.26 mg, 480.54 μmol). The mixture was stirred at 20° C. for 15 hours. After the reaction was completed, the reaction mixture was diluted with dichloromethane (50 mL) and washed with water (50 mL). The organic phase was washed with saturated brine (50 mL×2), dried over anhydrous sodium sulfate, filtered, and concentrated to dryness under reduced pressure to obtain a crude product. The crude product was separated and purified with thin-layer chromatography plates twice (eluent: dichloromethane/methanol=20:1 and petroleum ether/ethyl acetate=2:1) to obtain compound WX036-2.

Step 2: Synthesis of Compound WX036

Compound WX036-2 (86 mg, 122.12 μmol) was dissolved in dichloromethane (4 mL), followed by addition of diethylamine (446.59 mg, 6.11 mmol), and the reaction mixture was stirred at 20° C. for 12 hours. After the reaction was completed, the reaction mixture was diluted with dichloromethane (20 mL) and washed with water (20 mL). The organic phase was washed with saturated brine (20 mL), dried over anhydrous sodium sulfate, filtered, and concentrated to dryness under reduced pressure to obtain a crude product. The crude product was separated by high performance liquid chromatography (neutral condition) to obtain WX036. The structure also represents its potential isomers.

According to the steps 2 to 3 in the synthesis of Embodiment 36, Embodiment 37 in Table 9 was synthesized using BB-16 in the step 2. The structure in the table also represents its potential isomers.

TABLE 9

| Embodiment | Fragment in the step 2 | Structure | Compound |
|---|---|---|---|
| 37 | BB-16 | 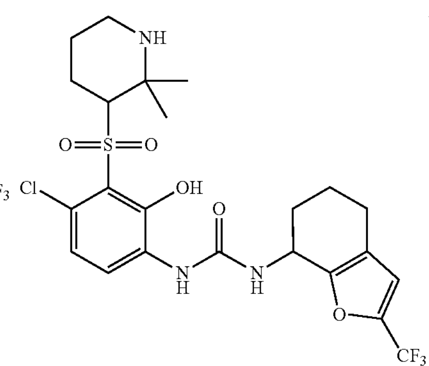 | WX037 |

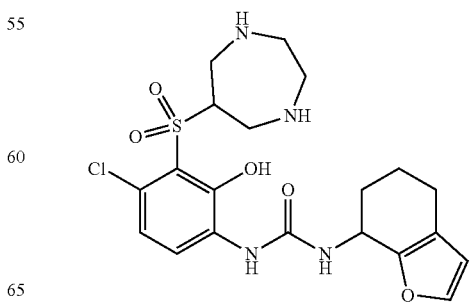

Embodiment 38: WX038

Synthetic Route:

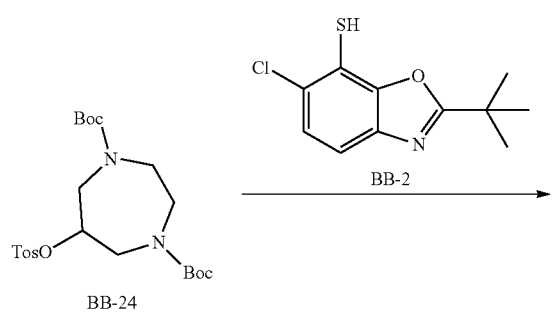

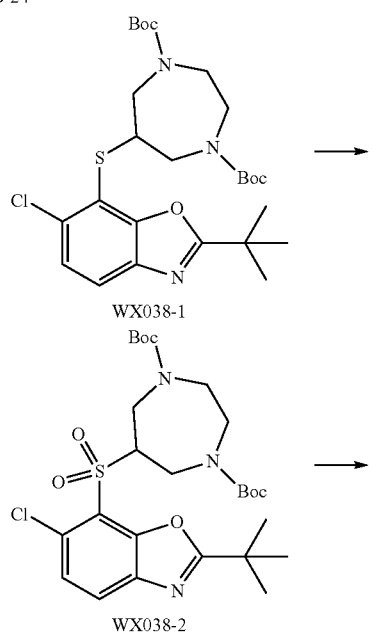

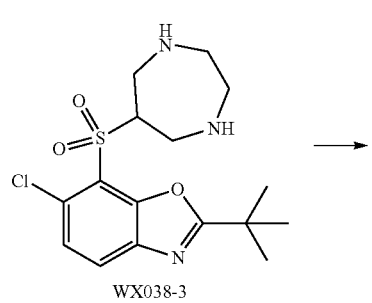

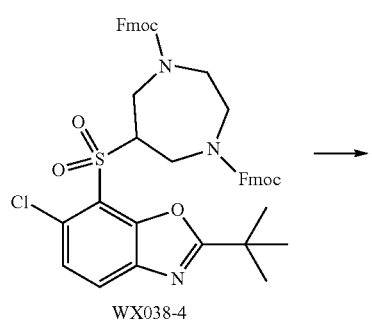

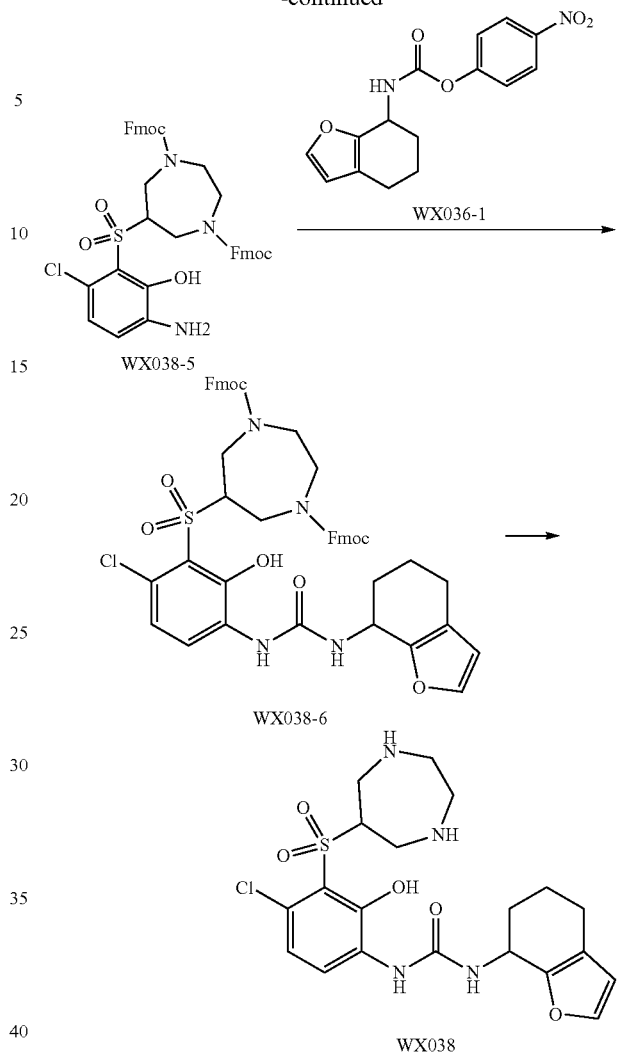

Step 1: Synthesis of Compound WX038-1

According to the step 1 in the synthesis of fragment BB-4, the target compound WX038-1 was synthesized using BB-24 and BB-2. $^1$H NMR (400 MHz, CHLOROFORM-d) δ ppm (br d, J=8.4 Hz, 1H), 7.40 (br d, J=8.4 Hz, 1H), 4.01-3.78 (m, 2H), 3.77-3.58 (m, 2H), 3.44-3.30 (m, 1H), 3.27-3.03 (m, 2H), 3.01-2.87 (m, 1H), 1.61 (br s, 1H), 1.57-1.40 (m, 18H), 1.34 (s, 5H), 1.24 (m, 4H).

Step 2: Synthesis of Compound WX038-2

According to the step 2 in the synthesis of fragment BB-4, the target compound WX038-2 was synthesized using WX038-1. $^1$H NMR (400 MHz, CHLOROFORM-d) δ ppm 7.82 (m, 1H), 7.53-7.44 (m, 1H), 4.18 (m, 1H), 4.07-3.88 (m, 2H), 3.82 (m, 2H), 3.61 (m, 1H), 3.40-3.22 (m, 1H), 3.20-2.98 (m, 1H), 1.61-1.60 (m, 1H), 1.53 (s, 9H), 1.50-1.33 (m, 18H).

Step 3: Synthesis of Compound WX038-3

Compound WX038-2 (0.85 g, 1.49 mmol) was added to a mixed solvent of dichloromethane (9 mL) and trifluoroacetic acid (3 mL), and the mixture was stirred at 25° C. for 1 hour. After completion of the reaction as indicated by liquid chromatography, the reaction mixture was rotary-evaporated to dryness to obtain a crude product of WX038-3, which was directly used in the next step.

Step 4: Synthesis of Compound WX038-4

Compound WX038-3 (0.55 g, 1.48 mmol) was dissolved in dichloromethane (20 mL), and saturated aqueous NaHCO₃ solution was added to obtain pH>7, followed by the addition of 9-fluorenylmethyl chloroformate (0.77 g, 2.97 mmol). The mixture was stirred at 25° C. for 1 hour. After completion of the reaction as indicated by thin layer chromatography and liquid chromatography, the reaction mixture was extracted with dichloromethane (10 mL×3) at 25° C. The organic phases were combined, dried over anhydrous sodium sulfate, filtered and concentrated, and the residue was purified by silica gel column chromatography (petroleum ether/ethyl acetate=3:1) to obtain compound WX038-4. ¹H NMR (400 MHz, CHLOROFORM-d) δ ppm 7.89-7.66 (m, 5H), 7.60-7.44 (m, 4H), 7.44-7.34 (m, 5H), 7.34-7.28 (m, 3H), 7.23 (m, 1H), 4.57-4.47 (m, 1H), 4.47-4.30 (m, 2H), 4.29-4.14 (m, 4H), 4.06 (br s, 2H), 4.01-3.91 (m, 1H), 3.89-3.68 (m, 1H), 3.64-3.43 (m, 2H), 3.39-3.25 (m, 1H), 3.23-3.11 (m, 1H), 1.51 (s, 9H).

Step 5: Synthesis of Compound WX038-5

Compound WX038-4 (1.20 g, 1.47 mmol) was dissolved in ethanol (20 mL), followed by addition of concentrated hydrochloric acid (7.35 mL). The mixture was then stirred at 90° C. for 24 hours. After completion of the reaction as indicated by thin layer chromatography and liquid chromatography, the reaction mixture was concentrated with a rotary evaporator, followed by the addition of saturated NaHCO₃ solution (30 mL) and ethyl acetate (30 mL). The mixture was extracted with ethyl acetate (30 mL*3). The organic phases were combined, dried over anhydrous sodium sulfate, filtered and concentrated to obtain WX038-5. ¹H NMR (400 MHz, CHLOROFORM-d) δ ppm 7.77 (m, 4H), 7.59-7.46 (m, 4H), 7.41 (m, 4H), 7.34 (m, 5H), 6.81 (br s, 1H), 4.59 (br s, 2H), 4.46-4.16 (m, 5H), 3.94 (m, 3H), 3.75-3.37 (m, 3H), 3.30-3.11 (m, 1H), 2.92 (br s, 1H), 2.13-2.08 (m, 2H).

Step 6: Synthesis of Compound WX038-6

According to the step 1 in the synthesis of Embodiment 29, the target compound WX038-6 was synthesized using WX036-1 and WX038-5 in step 1.

Step 7: Synthesis of Compound WX038

According to the step 2 in the synthesis of Embodiment 29, the target compound WX038 was synthesized using WX038-6 in step 1.

According to the steps 1 to 2 in the synthesis of Embodiment 29, the embodiments in Table 10 were synthesized using different fragments in the step 1. The structures in the table also represent their potential isomers.

TABLE 10

| Embodiment | Fragment in the step 1 | Structure | Compound |
|---|---|---|---|
| 39 | BB-21 | 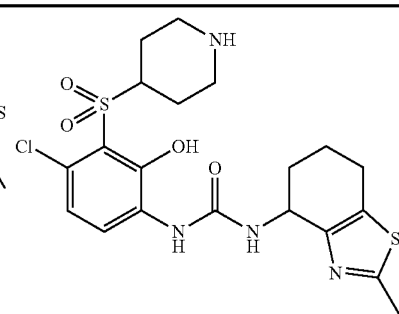 | WX039 |
| 40 | | 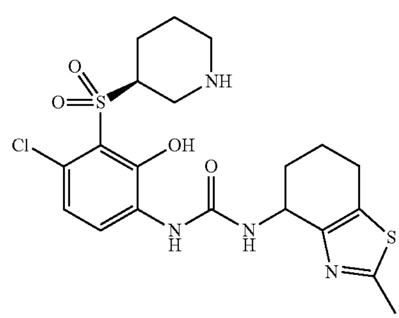 [SMILES: Cc1nc2c(s1)CCCC2NC(=O)Nc1ccc(Cl)c(S(=O)(=O)[C@H]2CCCNC2)c1O] | WX040 |
| 41 | BB-23 | 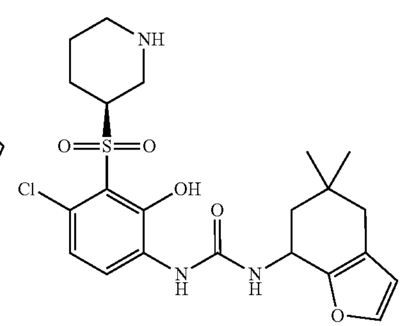 | WX041 |

TABLE 10-continued

| Embodiment | Fragment in the step 1 | Structure | Compound |
|---|---|---|---|
| 42 | BB-20 | 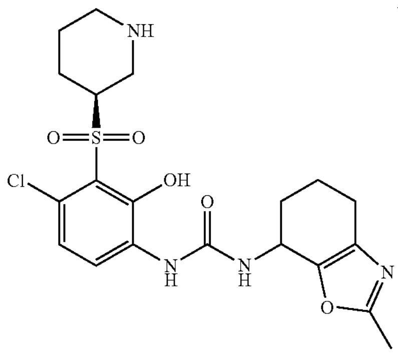 | WX042 |
| 43 | BB-23 | 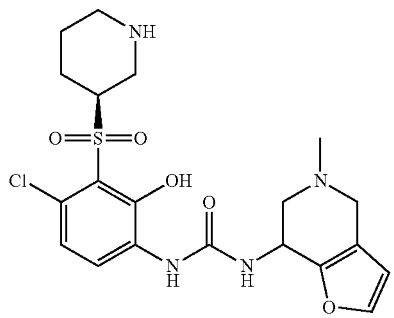 [SMILES: CN1Cc2ccoc2C(NC(=O)Nc2ccc(Cl)c(S(=O)(=O)[C@H]3CCCNC3)c2O)C1] | WX043 |

TABLE 11

NMR and MS data of each embodiment

| Embodiment | Compound | NMR | MS m/z: |
|---|---|---|---|
| 29 | WX029 WX029A WX029B | SFC detection method: column, Chiralpak AD-3 150 × 4.6 mm I.D., 3 μm; mobile phase, A: carbon dioxide, B: ethanol (0.05% diethylamine); flow rate: 2.5 mL/min; column temperature: 35° C.; detection wavelength: 220 nm. The retention time of chiral isomers WX029A and WX029B was 5.922 min and 7.134 min, respectively, and the ratio was 1:1. WX029A: $^1$H NMR (400 MHz, METHANOL-d$_4$) δ ppm 7.93 (br d, J = 8.4 Hz, 1H), 6.54 (br d, J = 8.4 Hz, 1H), 5.80 (s, 1H), 4.34 (br s, 1H), 3.65 (br s, 1H), 3.19-3.02 (m, 2H), 2.78 (br t, J = 10.4 Hz, 1H), 2.47-2.28 (m, 2H), 2.21 (s, 3H), 2.03-1.68 (m, 9H) WX029B: $^1$H NMR (400 MHz, METHANOL-d$_4$) Shift = 7.91 (d, J = 8.4 Hz, 1H), 6.54 (d, J = 8.4 Hz, 1H), 5.80 (s, 1H), 4.33 (br s, 1H), 3.63 (br d, J = 12.4 Hz, 1H), 3.18-3.03 (m, 2H), 2.78 (br t, J = 10.4 Hz, 1H), 2.46-2.29 (m, 2H), 2.19 (s, 3H), 2.02-1.71 (m, 9H). | 468.0 (M + H)$^+$ |
| 30 | WX030 WX030A WX030B | SFC detection method: column, Chiralpak AS-3 (150 mm × 4.6 mm, 3 μm); mobile phase, A: carbon dioxide, B: ethanol (0.05% diethylamine). The retention time of chiral isomers WX030A and WX030B was 3.548 min and 3.847 min, respectively, and the ratio was 1:1. WX030A: $^1$H NMR (400 MHz, METHANOL-d$_4$) δ ppm 8.01 (d, J = 8.8 Hz, 1H), 6.80 (s, 1H), 6.64 (d, J = 8.8 Hz, 1H), 4.96 (s, 1H), 4.15 (br s, 1H), 3.46-3.43 (m, 1H), 3.15-3.09 (m, 2H), 2.82-2.80 (m, 1H), 2.55-2.47 (m, 2H), 2.07 (br s, 2H), 1.96-1.85 (m, 6H). WX030B: $^1$H NMR (400 MHz, METHANOL-d$_4$) δ ppm 8.03 (d, J = 8.0 Hz, 1H), 6.80 (s, 1H), 6.65 (d, J = 8.4 Hz, 1H), 4.96 (s, 1H), 4.08 (br s, 1H), 3.48-3.41 (m, 1H), 3.14-3.09 (m, 2H), 2.84-2.79 (m, 1H), 2.58-2.47 (m, 2H), 2.06 (br s, 2H), 1.93-1.86 (m, 6H). | 522.0 (M + H)$^+$ |
| 31 | WX031 | $^1$H NMR (400 MHz, METHANOL-d$_4$) δ ppm 8.38-8.34 (m, 1H), 8.32 (d, J = 8.8 Hz, 1H), 7.60 (d, J = 7.2 Hz, 1H), 7.25 (m, 1H), 7.07 (d, J = 8.8 Hz, 1H), 4.93 (t, J = 5.6 Hz, 1H), 2.86 (m, 2H), 2.23-2.10 (m, 1H), 2.01 (m, 1H), 1.95-1.84 (m, 2H), 1.36-1.27 (m, 3H), 1.23-1.15 (m, 2H) | 422.1 (M + H)$^+$ |
| 32 | WX032 | 1H NMR (400 MHz, METHANOL-d$_4$) δ ppm 8.26 (d, J = 8.8 Hz, 1H), 7.02 (d, J = 8.8 Hz, 1H), 6.80 (s, 1H), 4.97 (m, 1H), 3.39-3.33 (m, 1H), 2.59-2.44 (m, 2H), 2.14-2.02 (m, 1H), 1.93-1.82 (m, 3H), 1.32 (m, 2H), 1.16 (m, 2H) | 479.0 (M + H)$^+$ |
| 33 | WX033 | $^1$H NMR (400 MHz, METHANOL-d$_4$) δ ppm 8.27 (d, J = 8.0 Hz, 1H), 7.04 (d, J = 7.6 Hz, 1H), 5.82 (s, 1H), 5.08-4.93 (m, 1H), 3.47- | 447.0 (M + Na)$^+$ |

TABLE 11-continued

NMR and MS data of each embodiment

| Embodiment | Compound | NMR | MS m/z: |
|---|---|---|---|
| | | 3.32 (m, 1H), 2.44-2.28 (m, 2H), 2.21 (s, 3H), 2.09-1.66 (m, 4H), 1.32-1.17 (m, 4H) | |
| 34 | WX034 | $^1$H NMR (400 MHz, METHANOL-$d_4$) δ ppm 8.35 (d, J = 8.8 Hz, 1H), 7.09 (d, J = 8.8 Hz, 1H), 6.80 (s, 1H), 4.98-4.96 (m, 1H), 3.97-3.88 (m, 1H), 2.55-2.48 (m, 2H), 2.09-2.07 (m, 1H), 1.90-1.83 (m, 3H), 1.34-1.32 (m, 6H). | 481.0 $(M + H)^+$ |
| 35 | WX035 | $^1$H NMR (400 MHz, CDCl$_3$) δ ppm 10.87 (s, 1H), 8.42 (d, J = 8.8 Hz, 1H), 7.04-7.01 (m, 2H), 5.80 (s, 1H), 5.03-4.95 (m, 2H), 3.92-3.85 (m, 1H), 2.44-2.34 (m, 2H), 2.25 (s, 3H), 2.06-2.01 (m, 1H), 1.94-1.89 (m, 1H), 1.80-1.74 (m, 2H),1.38-1.36 (m, 6H). | 449.0 $(M + H)^+$ |
| 36 | WX036 | $^1$H NMR (400 MHz, METHANOL-$d_4$) δ ppm 8.02 (d, J = 8.4 Hz, 1H), 7.34 (s, 1H), 6.63 (d, J = 7.2 Hz, 1H), 6.23 (s, 1H), 4.07 (br d, J = 9.4 Hz, 1H), 3.01 (m, 2H), 2.57-2.36 (m, 2H), 2.14 (m, 1H), 1.92 (m, 4H), 1.81 (m, 2H), 1.61 (br s, 2H), 1.59 (br s, 3H), 1.54 (br s, 3H) | 482.1 $(M + H)^+$ |
| 37 | WX037 | 1H NMR (400 MHz, METHANOL-$d_4$) δ ppm 7.97 (t, J = 8.8 Hz, 1H), 7.91 (s, 1H), 6.79 (s, 1H), 6.56 (t, J = 8.4 Hz, 1H), 5.49 (s, 1H), 4.96 (m, 1H), 4.09 (br d, J = 8.4 Hz, 1H), 3.00 (m, 2H), 2.60-2.42 (m, 2H), 2.18-2.02 (m, 2H), 1.99-1.78 (m, 4H), 1.65-1.51 (m, 6H) | 550.1 $(M + H)^+$ |

Test example 1: In vitro activity evaluation

| | | | |
|---|---|---|---|
| 38 | WX038 | $^1$H NMR (400 MHz, METHANOL-$d_4$) δ ppm 8.26 (d, J = 7.2 Hz, 1H), 7.37 (br s, 1H), 7.17 (d, J = 7.2 Hz, 1H), 6.26 (br s, 1H), 5.52-5.13 (m, 1H), 3.93 (m, 1H), 3.55-3.35 (m, 4H), 3.12 (m, 4H), 2.60-2.37 (m, 2H), 2.03 (m, 1H), 1.84 (m, 3H) | 469.1 $(M + H)^+$ |
| 39 | WX039 | $^1$H NMR (400 MHz, DMSO-$d_6$) δ ppm 9.28 (br d, J = 9.6 Hz, 1H), 8.92 (br d, J = 10.4 Hz, 1H), 8.41 (s, 1H), 8.28 (d, J = 8.8 Hz, 1H), 7.58 (br d, J = 8.0 Hz, 1H), 7.17 (d, J = 8.8 Hz, 1H), 4.90-4.74 (m, 1H), 4.05-3.98 (m, 1H), 3.36 (br d, J = 12.0 Hz, 2H), 2.97 (br d, J = 11.2 Hz, 2H), 2.84-2.64 (m, 2H), 2.60 (s, 3H), 2.02-1.87 (m, 5H), 1.85-1.72 (m, 3H) | 485.0 $(M + H)^+$ |
| 40 | WX040 | $^1$H NMR (400 MHz, METHANOL-$d_4$) δ ppm 8.34 (br d, J = 8.4 Hz, 1H), 7.15 (d, J = 8.8 Hz, 1H), 4.96 (br s, 1H), 4.15 (m, 1H), 3.65 (m, 1H), 3.42-3.33 (m, 2H), 3.05 (m,1H), 2.90-2.80 (m, 1H), 2.79-2.69 (m, 1H), 2.65 (s, 3H), 2.12 (m, 2H), 2.06-1.68 (m, 6H) | 485.0 $(M + H)^+$ |
| 41 | WX041 | $^1$H NMR (400 MHz, METHANOL-$d_4$) δ ppm 8.06-7.95 (m, 1H), 7.35 (s, 1H), 6.62 (br d, J = 8.0 Hz, 1H), 6.21 (s, 1H), 4.60 (br s, 1H), 4.23 (br s, 1H), 3.56 (m, 1H), 3.16-3.04 (m, 2H), 2.80 (m, 1H), 2.42-2.16 (m, 2H), 2.06-1.86 (m, 4H), 1.75 (br s, 1H), 1.57-1.49 (m, 1H), 1.09 (s, 3H), 0.99 (s, 3H) | 482.0 $(M + H)^+$ |
| 42 | WX042 | $^1$H NMR (400 MHz, DMSO-$d_6$) δ ppm 8.01(s, 1H), 7.76-7.73 (m, 1H), 7.44-7.38 (m, 1H), 6.12-6.11 (m, 1H), 4.87-4.84 (m, 1H), 4.46-4.43 (m, 1H), 3.11-3.07 (m, 3H), 2.85-2.82 (m, 1H), 2.68-2.66 (m, 1H), 2.36-2.32 (m, 4H), 1.77-1.69 (m, 8H). | 469.0 $(M + H)^+$ |
| 43 | WX043 | $^1$H NMR (400 MHz, METHANOL-$d_4$) δ ppm 7.98-7.91(m, 1 H), 7.42 (s, 1 H), 6.59-6.56 (m, 1 H), 6.30 (s, 1 H), 4.98 (m, 1 H),4.36-4.34 (m, 1 H),3.56-3.53(m, 2 H), 3.17-2.77(m, 6 H), 2.50(s, 3 H), 1.98-1.87(m, 4H). | 469.1 $(M + H)^+$ |

Experimental Purpose:

The $IC_{50}$ values were determined to evaluate the antagonistic activity of the test compounds against CXCR2.

Experimental Method:

PathHunter® CXCR2 β-arrestin cells (DiscoverX) were grown under normal conditions and seeded on a white-walled 384-microwell plate at 20 μL/well. Before testing, the cells were incubated at 37° C. for an appropriate time. The test compounds were serially diluted in DMSO at a three-fold dilution factor to obtain 8 serially diluted test compounds. Shortly before the test, the above serially diluted test compounds were further diluted with test buffer to 5 times the test concentration. 5 μL of the further diluted test compounds was added to the cells and then the cells were incubated at 37° C. for 30 minutes. The vehicle concentration was 1%. 5 μL of 6×EC80 agonist (CXCL8) buffer was added to the cells and then the cells were incubated at 37° C. for 90 minutes. 15 μL (50% v/v) of PathHunter detection reagent mixture was added in one portion, followed by one-hour incubation to generate the test signal. The microplates were read on a PerkinElmer Envision™ instrument for chemiluminescence signal. The biological activity of the test compounds was analyzed by CBIS data analysis suite (ChemInnovation, CA) and shown as $IC_{50}$ values. The experimental results are shown in Table 12:

TABLE 12

Test results of in vitro activity of the compounds of the present disclosure

| Compound | CXCR2 $IC_{50}$ (nM) |
|---|---|
| WX001A | 152 |
| WX002A | 45 |
| WX003A | 17 |
| WX004A | 43 |
| WX005A | 14 |
| WX006A | 22 |
| WX007A | 42 |
| WX008A | 122 |
| WX009 | 177 |
| WX010A | 61 |
| WX011A | 70 |
| WX012A | 17 |
| WX013A | 14 |
| WX014 | 232 |
| WX015 | 186 |
| WX016A | 134 |
| WX017A | 72 |
| WX018A | 133 |
| WX020A | 177 |
| WX021A | 720 |
| WX022A | 366 |
| WX023A | 36 |
| WX024A | 525 |
| WX024B | 667 |
| WX025B | 139 |
| WX027A | 269 |
| WX028 | 472 |
| WX029 | 15 |

TABLE 12-continued

Test results of in vitro activity of the
compounds of the present disclosure

| Compound | CXCR2 IC$_{50}$ (nM) |
|---|---|
| WX029A | 2 |
| WX029B | 245 |
| WX030B | 22 |
| WX032 | 144 |
| WX033 | 6 |
| WX034 | 55 |
| WX036 | 23 |

Conclusion: The compounds of the present disclosure have a strong antagonistic effect on CXCR2.

Test Example 2: Pharmacokinetic Evaluation of the Compounds

Experimental Purpose:
The pharmacokinetic parameters of the compounds in C57BL/6 mice were investigated.

Experimental Materials:
C57BL/6 mice (male, 18-30 g, 7-9 weeks old, Shanghai Lingchang Biotechnology Co., Ltd.)

Experimental Procedure:
Formulations containing an aqueous solution of 1% DMSO/10% hydroxypropyl-β-cyclodextrin as the vehicle were administered by intravenous injection (1 mpk), formulations containing an aqueous solution of 1% DMSO/1% hydroxypropyl methylcellulose/0.2% Tween 80 as the vehicle were administered by gavage (5 mpk). Before the animal experiment, all animals were fasted, and fed 4 hours after administration; all animals were free to drink water. The time points of blood collection: intravenous injection administration group: 0.083, 0.25, 0.5, 1, 2, 4, 6, 8 and 24 hours; gavage administration group: 0.25, 0.5, 1, 2, 4, 6, 8 and 24 hours.

Whole blood samples (0.03 mL) were collected through the saphenous vein (or other suitable blood collection sites) at the prescribed time points, and all blood samples were added to labeled plastic centrifuge tubes containing K2-EDTA anticoagulant. After the blood samples were collected, the plasma was isolated by centrifugation, immediately placed in dry ice and stored at low temperature. All samples were analyzed by LC-MS/MS with a minimum detection limit of 2 nM. The non-compartmental model of WinNonlin™ Version 6.3 (Pharsight, Mountain View, Calif.) pharmacokinetic software was used to process the mean plasma concentration, and the linear-log trapezoid method was used to calculate the pharmacokinetic parameters.

The experimental results are shown in Table 13:

TABLE 13

Pharmacokinetic test results

| Sample to be tested (compound prepared in each embodiment) (nM · hr) | Clearance (mL/min/kg) | Half-life T$_{1/2}$ (h) | Area under the drug concentration time curve (AUC) | Bioavailability (F) (%) |
|---|---|---|---|---|
| Danirixin | 42.5 | 7.43 | 1580 | 34.3 |
| WX003A | 11.2 | 2.22 | 12689 | 70.3 |
| WX006A | 8.3 | 3.09 | 20091 | 83.8 |

TABLE 13-continued

Pharmacokinetic test results

| Sample to be tested (compound prepared in each embodiment) (nM · hr) | Clearance (mL/min/kg) | Half-life T$_{1/2}$ (h) | Area under the drug concentration time curve (AUC) | Bioavailability (F) (%) |
|---|---|---|---|---|
| WX012A | 15.8 | 0.94 | 9392 | 82.5 |
| WX013A | 30.8 | 2.21 | 4438 | 75.5 |

Conclusion: The compounds of the present disclosure can significantly improve single or partial pharmacokinetic indices in mice.

Test Example 3: Evaluation of Pharmacokinetic and Tissue Distribution of the Compounds Experimental Purpose:
The pharmacokinetic and tissue distribution of the compounds in Lewis rats was tested.

Experimental Materials:
Lewis rats (male, 202-239 g, 7-9 weeks old, Beijing Viton Lihua)

Experimental Procedure:
Formulations containing an aqueous solution of 1% hydroxypropyl methylcellulose/0.2% Tween 80 as the vehicle were administered by gavage (5 mpk). Before the animal experiment, all animals were fasted overnight, and fed 4 hours after administration; all animals were free to drink water. The time points of blood collection: danirixin administration group: 0.25, 1, 8 hours; gavage administration group: 0.5, 1, 4 hours.

Whole blood samples (0.2 mL) were collected through the saphenous vein (or other suitable blood collection sites) at the prescribed time points, and all blood samples were added to labeled plastic centrifuge tubes containing K2-EDTA anticoagulant. After the blood samples were collected, the plasma was separated by centrifugation, immediately placed in dry ice and stored at low temperature. All samples were analyzed by LC-MS/MS with a minimum detection limit of 2 nM. The non-compartmental model of WinNonlin™ Version 6.3 (Pharsight, Mountain View, Calif.) pharmacokinetic software was used to process the mean plasma concentration, and the log-linear trapezoid method was used to calculate the pharmacokinetic parameters.

The experimental results are shown in Table 14:

TABLE 14

Pharmacokinetic test results

| Positive control and the compound of the present disclosure | Danirixin | WX030B |
|---|---|---|
| Ratio in lung blood | 1.57 | 2.17 |

Conclusion: The compound of the present disclosure significantly improves the distribution ratio in lung tissue of rats.

Test Example 4: Therapeutic Effect of the Compounds on PPE-Induced COPD Model

Experimental Purpose:
The therapeutic effect of the compounds on PPE-induced COPD model in C57BL/6 mice was tested.

Experimental Materials:

Animals: C57BL/6 mice (female, 17.5-18.5 g, 6-8 weeks old)

Figure 2:
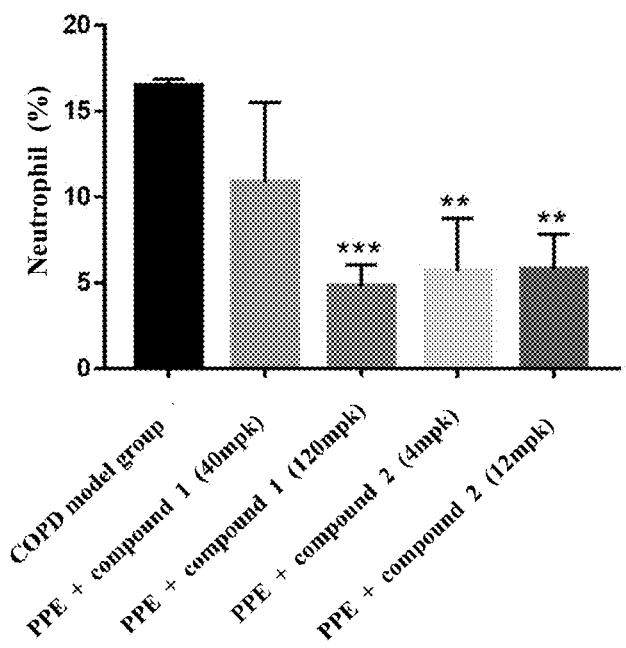
FIG. 2 shows the relationship between the proportion of neutrophils in the alveolar lavage fluid of the animal in each group and the compound dose.
Figure 3:
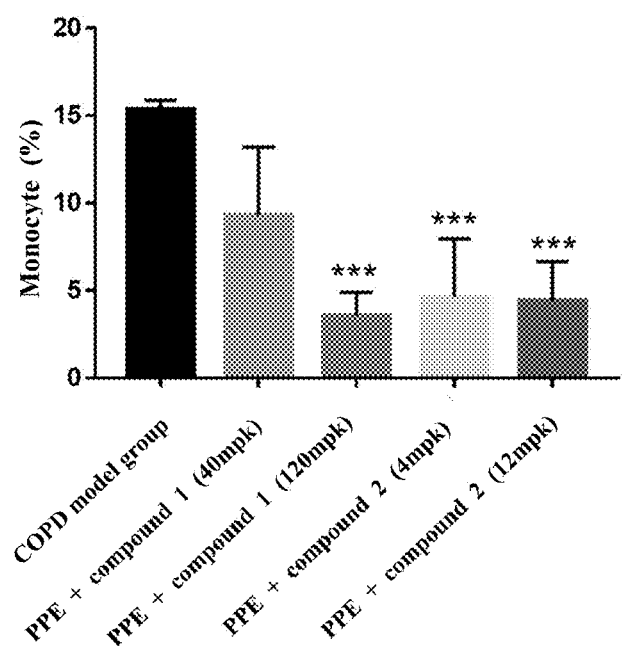
FIG. 3 shows the relationship between the proportion of monocytes in the alveolar lavage fluid of the animal in each group and the compound dose.

Drugs: Porcine pancreas elastase (PPE) (sigma, 0.068 U/μL); compound 1 in FIG. 1, FIG. 2 and FIG. 3 is danirixin; compound 2 is WX006A.

Grouping: (1) COPD model group (porcine pancreatic elastase model group)

(2) PPE+ danirixin (40 mpk)

(3) PPE+ danirixin (120 mpk)

(4) PPE+WX006A (4 mpk)

(5) PPE+WX006A (12 mpk)

Experimental Procedure:

1. Modeling method: PPE was administered through by drip transfusion at the back of the tongue.

2. Administration method: an aqueous solution of 1% DMSO/1% hydroxypropyl methylcellulose/0.2% Tween 80 was used as the vehicle; the animals were daily administered with a volume of 200 μL/animal by gavage for 4 weeks.

3. End point of the experiment: On the 29$^{th}$ day, the mice were euthanized, samples were collected, and flow cytometry was performed.

Flow Cytometry

The blood, alveolar lavage fluid and lung tissue of the mice were collected after 4 weeks of administration to determine the percentage of inflammatory cells.

1) Alveolar lavage cells: the mice were euthanized. The neck was dissected, and the trachea was exposed and intubated, followed by lavage with 1 mL of sulphate buffer precooled at 4° C. for three times. The lavage fluids were combined, and centrifuged at 1200 rpm for 5 minutes. The supernatant was discarded and the cell suspension was collected.

2) The blood and lung tissue of the mice were collected. The blood was subjected to erythrocyte lysis and washed to prepare a cell suspension; the lung tissue was cut into small pieces, and then digested with type I collagenase at 37° C. for 1.5 hours, filtered and subjected to erythrocyte lysis to prepare a cell suspension.

3) The cells were counted and the cell suspensions were transferred into flow cytometry tubes.

4) After dividing into flow cytometry tubes, CD45, Lytic, Ly6g, and CD11b fluorescent antibodies for flow cytometry were used for marking.

5) After washing the cells, the percentage of neutrophils and monocytes in CD45$^+$ cells was determined using a flow cytometer.

The experimental results are shown in FIG. 1, FIG. 2 and FIG. 3. It is concluded that in the PPE-induced mouse COPD model, the compound of the present disclosure significantly reduces the proportion of neutrophils in lung tissue, which is superior to the positive control danirixin. The compound of the present disclosure and danirixin both have a significant effect of reducing the proportions of neutrophils and monocytes in the alveolar lavage fluid at a high dose (120 mpk), and exhibit a good inhibitory effect on inflammation. Moreover, the compound of the present disclosure can achieve a comparable anti-inflammatory effect at a low dose (4 mpk).

What is claimed is:

1. A compound of formula (II), a tautomer or stereoisomer thereof, or a pharmaceutically acceptable salt thereof,

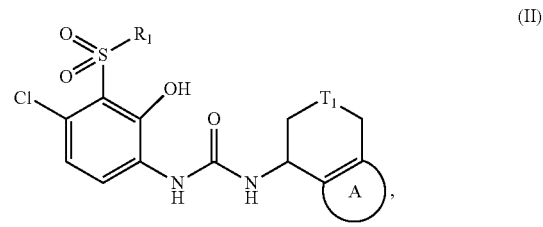

(II)

wherein, $T_1$ is selected from $C(R_2R_3)$ and $N(R_4)$;

ring A is selected from 5-6 membered heteroaryl and phenyl, wherein each of the 5-6 membered heteroaryl and phenyl is optionally substituted by one, two or three $R_a$;

$R_1$ is selected from $C_{1-6}$ alkyl, $NH_2$—(C=O)—$C_{1-3}$ alkyl—, 5-10 membered heteroaryl—$C_{1-3}$ alkyl—, $C_{3-7}$ cycloalkyl, 5-9 membered heterocycloalkyl, 5-10 membered heteroaryl, phenyl and —$C_{1-6}$ alkyl—phenyl, wherein each of the $C_{1-6}$ alkyl, $NH_2$—(C=O)—$C_{1-3}$ alkyl—, 5-10 membered heteroaryl—$C_{1-3}$ alkyl—, $C_{3-7}$ cycloalkyl, 5-9 membered heterocycloalkyl, 5-10 membered heteroaryl, phenyl and —$C_{1-6}$ alkyl—phenyl is optionally substituted by one, two or three R;

each of $R_2$ and $R_3$ is independently selected from H, F, Cl, Br, I, OH, $NH_2$ and $C_{1-3}$ alkyl optionally substituted by one, two or three $R_b$;

$R_4$ is selected from H and $C_{1-3}$ alkyl optionally substituted by one, two or three $R_c$;

each $R_a$ is independently selected from H, F, Cl, Br, I, OH, $NH_2$ and $C_{1-3}$ alkyl optionally substituted by one, two or three R';

each of $R_b$ and $R_c$ is independently selected from H, F, Cl, Br, I, OH and $NH_2$;

each R is independently selected from H, F, Cl, Br, I, OH, $NH_2$, $C_{1-3}$ alkyl, $C_{1-3}$ alkyl—(C=O)—NH—, $C_{1-3}$ alkyl—O—(C=O)—NH—, $C_{3-6}$ cycloalkyl—(C=O)—NH—and $C_{1-6}$ alkyl—O—(C=O)—, wherein each of the $C_{1-3}$ alkyl, $C_{1-3}$ alkyl—(C=O)—NH—, $C_{3-6}$ cycloalkyl—(C=O)—NH—and $C_{1-6}$ alkyl—O—(C=O)—is optionally substituted by one, two or three R';

each R' is independently selected from F, Cl, Br, I, OH and $NH_2$;

each of the 5-6 membered heteroaryl, 5-10 membered heteroaryl and 5-9 membered heterocycloalkyl independently contains one, two, three or four heteroatoms or heteroatomic groups independently selected from —NH—, —C(=O)—, —O—, —S—and N.

2. The compound, the tautomer or stereoisomer thereof, or the pharmaceutically acceptable salt thereof as defined in claim 1, wherein R is selected

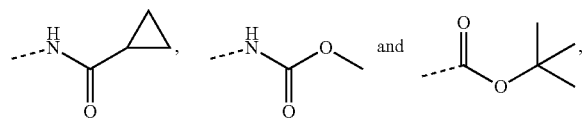

from F, Cl, Br, I, OH, NH$_2$, Me, Et, wherein each

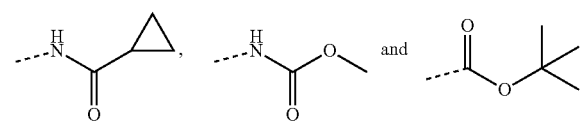

of the Me, Et, is optionally substituted by one, two or three R';
and/or, each R$_a$ is independently selected from H, F, Cl, Br, I, OH, NH$_2$ and Me;
and/or, each of R$_2$ and R$_3$ is independently selected from H, F, Cl, Br, I, OH, NH$_2$ and Me;
and/or, R$_4$ is selected from H and Me.

3. The compound, the tautomer or stereoisomer thereof, or the pharmaceutically acceptable salt thereof as defined in claim 2, wherein R is selected
from F, Cl, Br, I, OH, NH$_2$, Me,

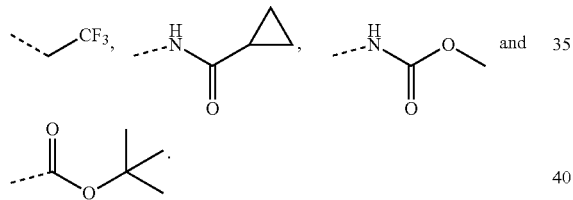

4. The compound, the tautomer or stereoisomer thereof, or the pharmaceutically acceptable salt thereof as defined in claim 1, wherein R$_1$ is selected from methyl, ethyl, propyl, isopropyl, butyl, tert-butyl, NH$_2$—(C=O)—CH$_2$—, isoindoline-1,3-dione—(CH$_2$)$_2$—, cyclopropyl, cyclobutyl, cyclopentyl, cyclohexyl, piperidinyl, tetrahydropyranyl, tetrahydrofuranyl, 1,4-diazepanyl, —C$_{1-4}$ alkyl—phenyl, 2-azaspiro[3.3]heptyl and 7-azaspiro[3.5]nonanyl, wherein each of the methyl, ethyl, propyl, isopropyl, butyl, tert-butyl, NH$_2$—(C=O)—CH$_2$—, isoindoline-1,3-dione—(CH$_2$)$_2$—, cyclopropyl, cyclobutyl, cyclopentyl, cyclohexyl, piperidinyl, tetrahydropyranyl, tetrahydrofuranyl, 1,4-diazepanyl, —C$_{1-4}$ alkyl—phenyl, 2-azaspiro[3.3]heptanyl and 7-azaspiro[3.5]nonanyl is optionally substituted by one, two or three R.

5. The compound, the tautomer or stereoisomers thereof, or the pharmaceutically acceptable salt thereof as defined in claim 4, wherein R$_1$ is selected

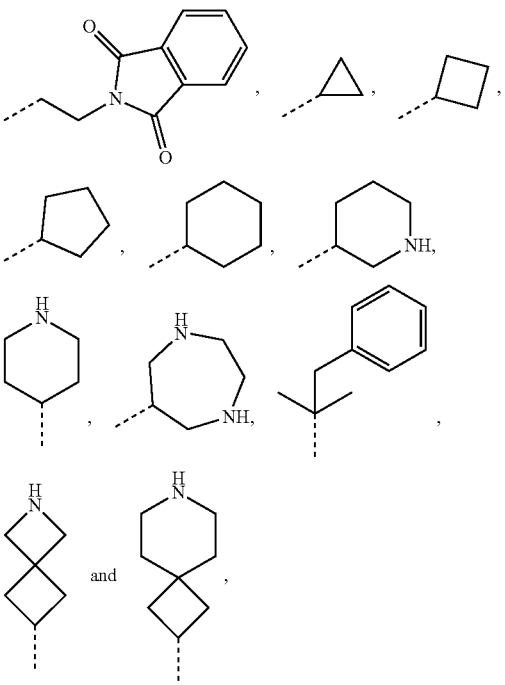

from Me, Et,
wherein each of the

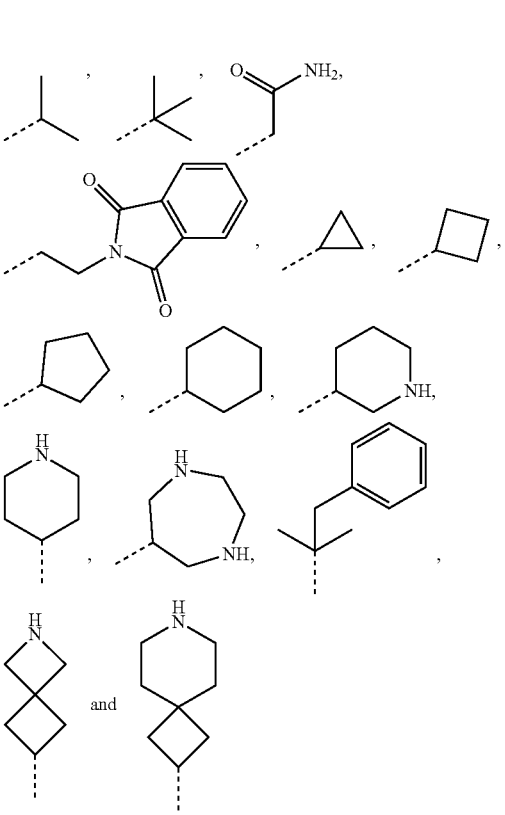

Me, Et,
is optionally substituted by one, two or three R.

6. The compound, the tautomer or stereoisomer thereof, or the pharmaceutically acceptable salt thereof as defined in claim 5, wherein $R_1$ is selected from Me,

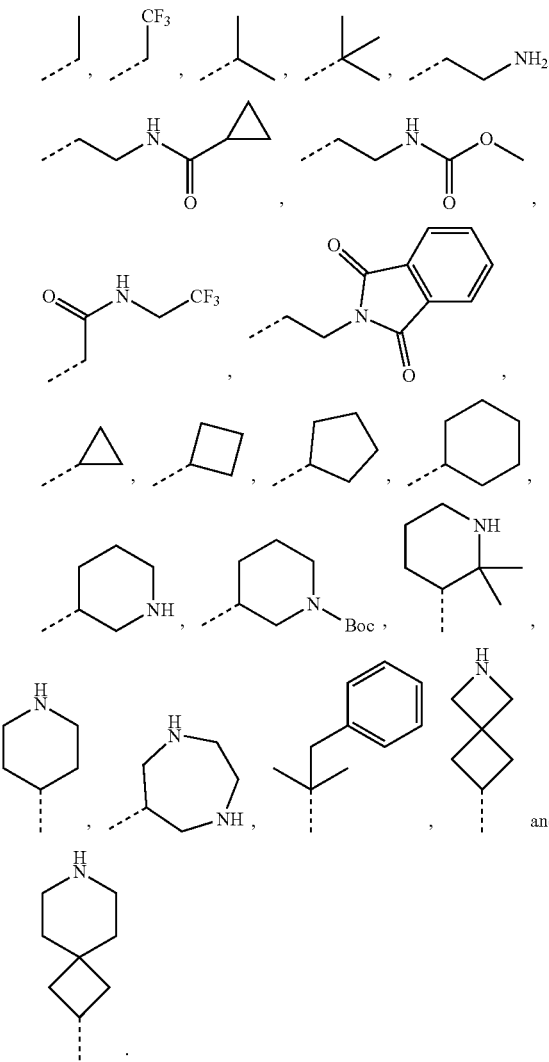

7. The compound, the tautomer or stereoisomer thereof, or the pharmaceutically acceptable salt thereof as defined in claim 1, wherein ring A is selected from furanyl, oxazolyl, isoxazolyl, thienyl, thiazolyl, isothiazolyl, pyridyl and phenyl, wherein each of the furanyl, oxazolyl, isoxazolyl, thienyl, thiazolyl, isothiazolyl, pyridyl and phenyl is optionally substituted by one, two or three $R_a$.

8. The compound, the tautomer or stereoisomer thereof, or the pharmaceutically acceptable salt thereof as defined in claim 1,

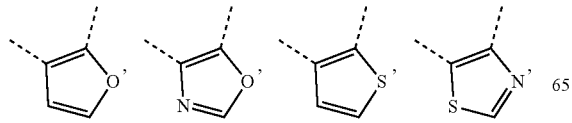

-continued

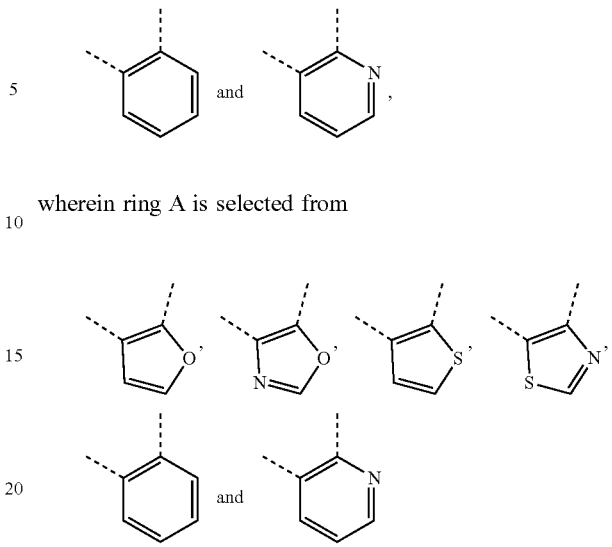

wherein each of the
is optionally substituted by one, two or three $R_a$.

9. The compound, the tautomer or stereoisomer thereof, or the pharmaceutically acceptable salt thereof as defined in claim 1,
wherein ring A is selected from

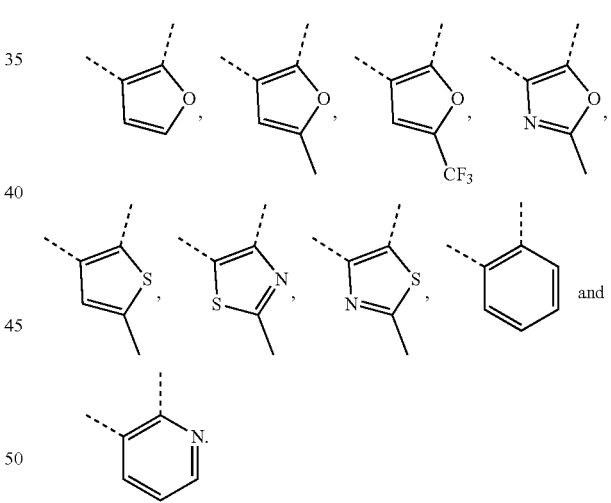

10. The compound, the tautomer or stereoisomer thereof, or the pharmaceutically acceptable salt thereof as defined in claim 1,
wherein the moiety

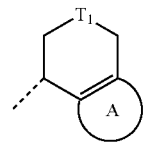

is selected from

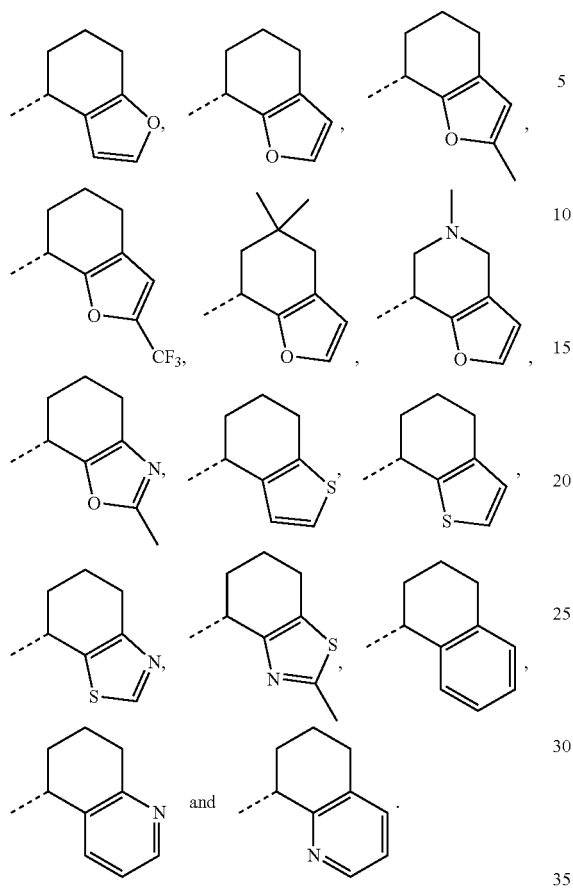

11. The compound, the tautomer or stereoisomer thereof, or the pharmaceutically acceptable salt thereof as defined in claim 1, wherein the compound is selected from:

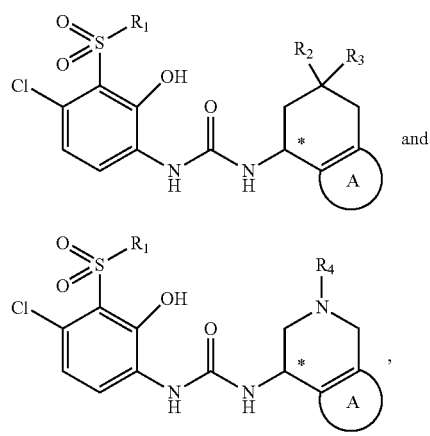

wherein,
$R_1$ is as defined in claim 1;
$R_2$ and $R_3$ are as defined in claim 1;
$R_4$ is as defined in claim 1;
ring A is as defined in claim 1;
the carbon atom marked with "*" is a chiral carbon atom presented in the form of single (R) or (S) enantiomer or enriching in one enantiomer.

12. The compound, the tautomer or stereoisomer thereof, or the pharmaceutically acceptable salt thereof as defined in claim 1, wherein the compound is selected from:

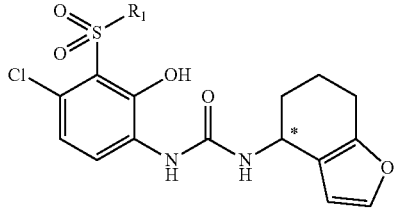

(I-1)

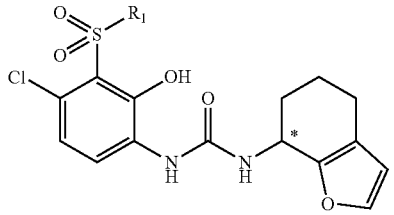

(I-2)

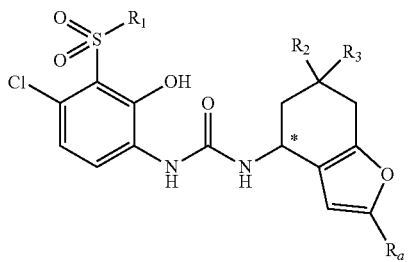

(II-1)

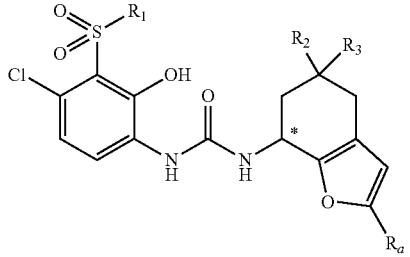

(II-2)

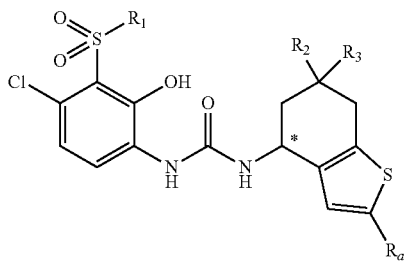

(II-3)

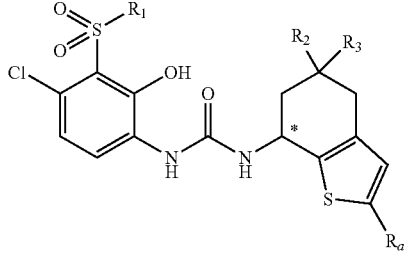

(II-4)

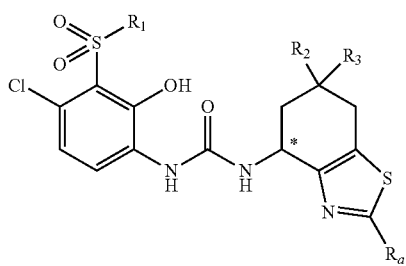 (II-5)

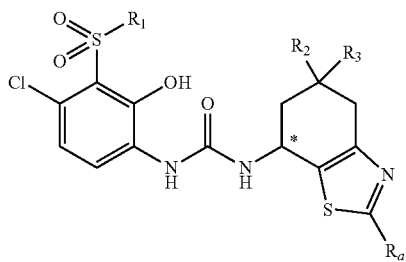 (II-6)

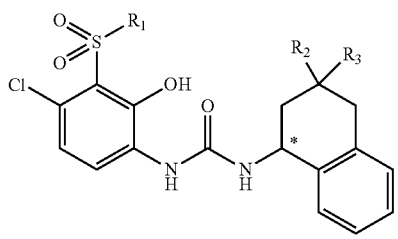 (II-7)

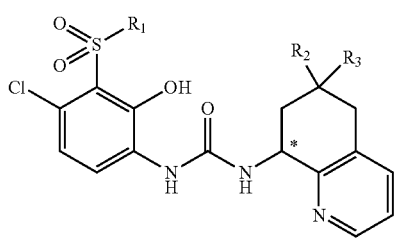 (II-8)

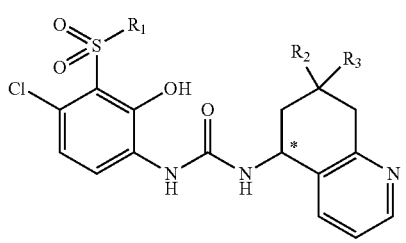 (II-9) and

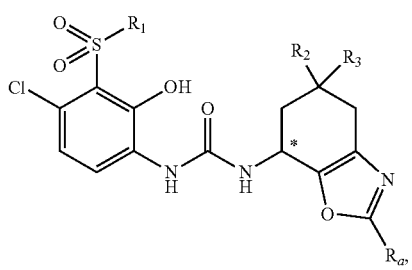 (II-10)

wherein,

R₁ is as defined in claim 1;

R₂ and R₃ are as defined in claim 1;

R₄ is as defined in claim 1;

the carbon atom marked with "*" is a chiral carbon atom presented in the form of single (R) or (S) enantiomer or enriching in one enantiomer.

13. The compound, the tautomer or stereoisomer thereof, or the pharmaceutically acceptable salt thereof as defined in claim 1, wherein the compound is selected from:

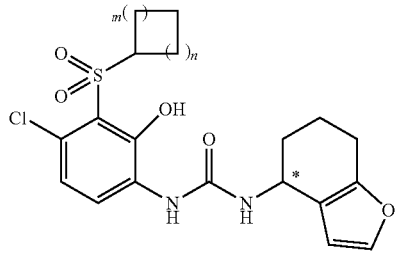 (I-3)

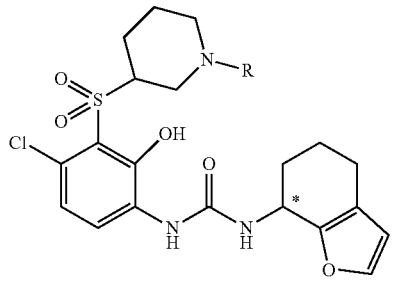 (I-4)

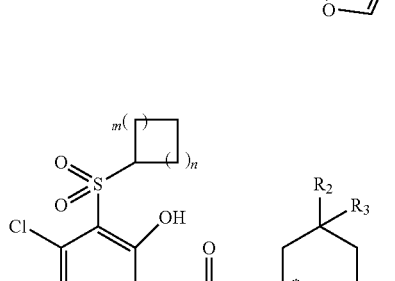 (II-11)

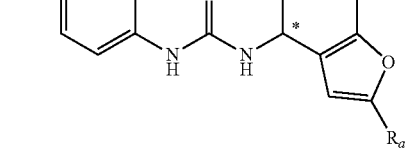

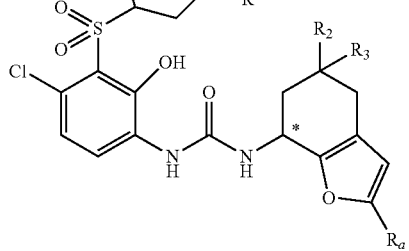 (II-12)

-continued

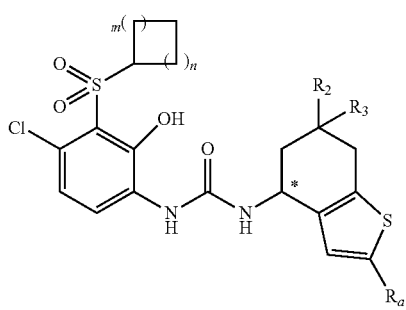
(II-13)

and

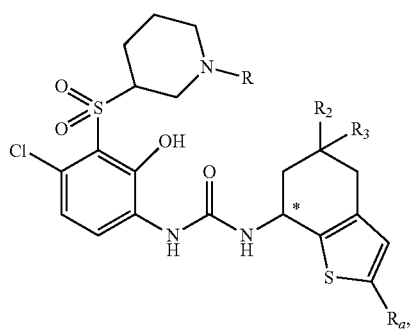
(II-14)

wherein, m is 0, 1 or 2;

n is 1 or 2;

R is as defined in claim 1;

R₂ and R₃ are as defined in claim 1;

R₄ is as defined in claim 1;

Rₐ is as defined in claim 1;

the carbon atom marked with "*" is a chiral carbon atom presented in the form of single (R) or (S) enantiomer or enriching in one enantiomer of (R) or (S).

14. A compound, a tautomer or stereoisomer thereof, or a pharmaceutically acceptable salt thereof, wherein the compound is selected from

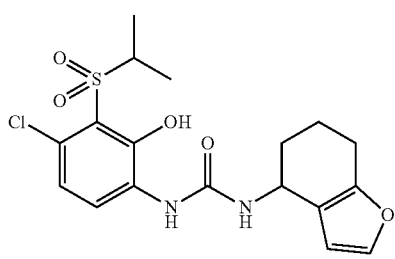

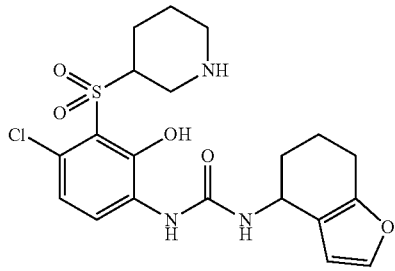

-continued

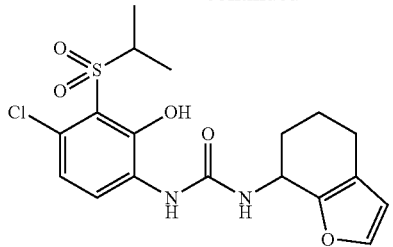

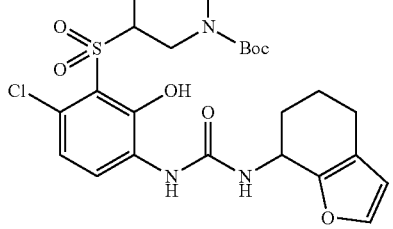

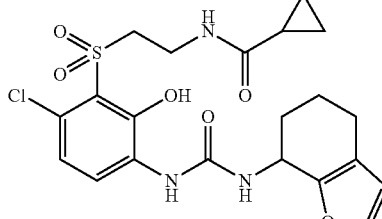

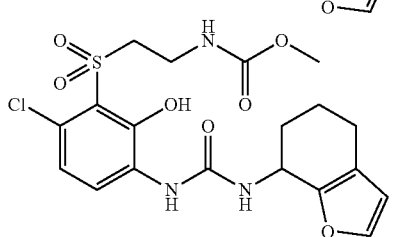

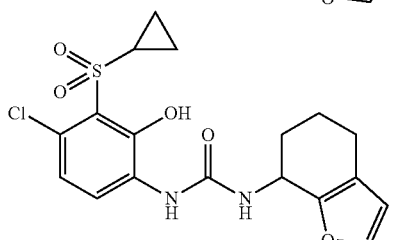

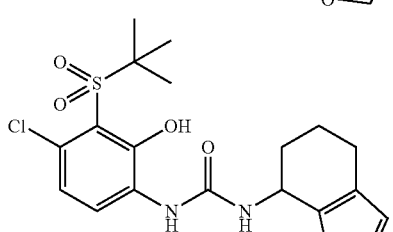

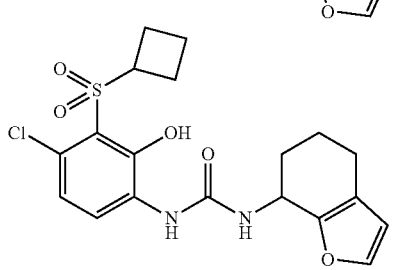

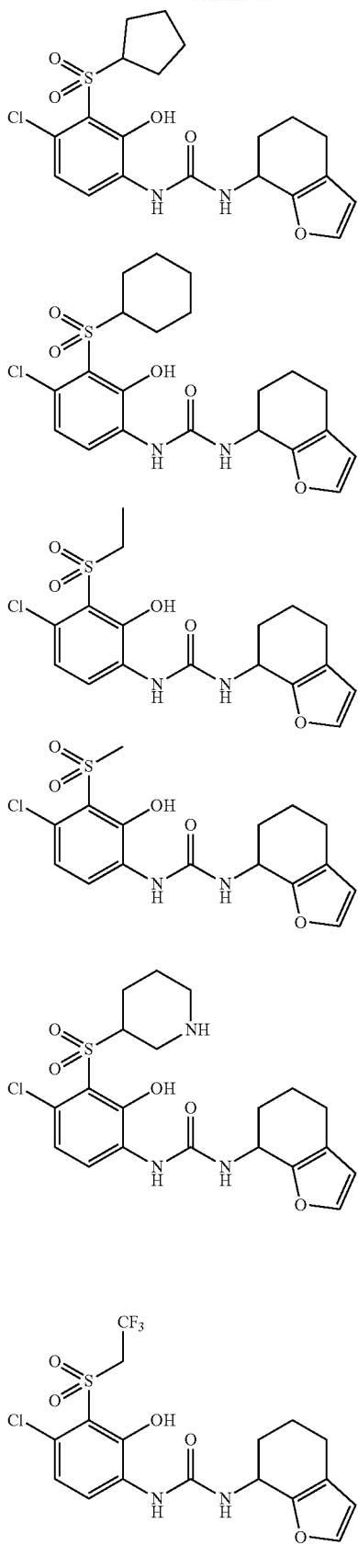
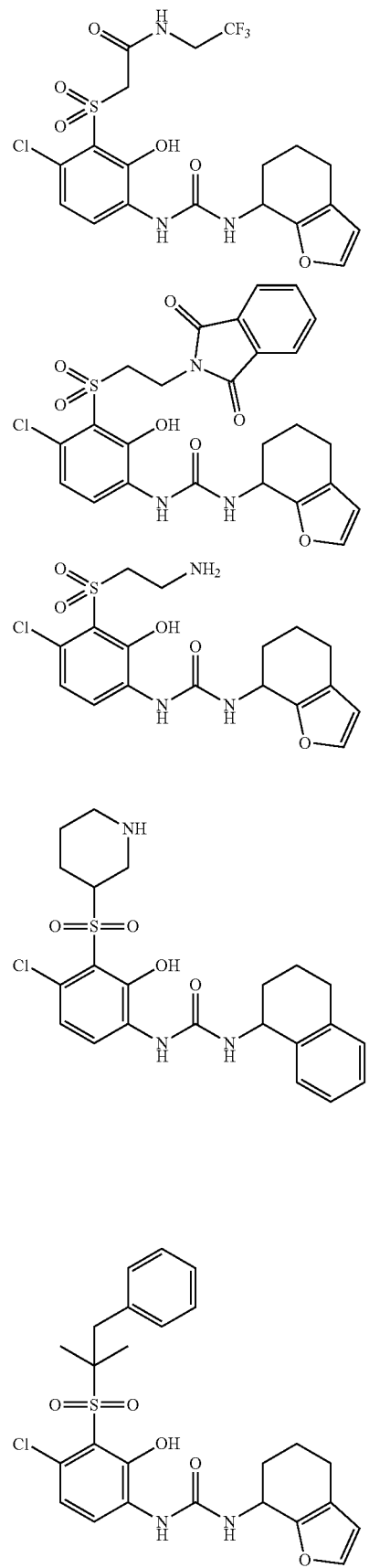

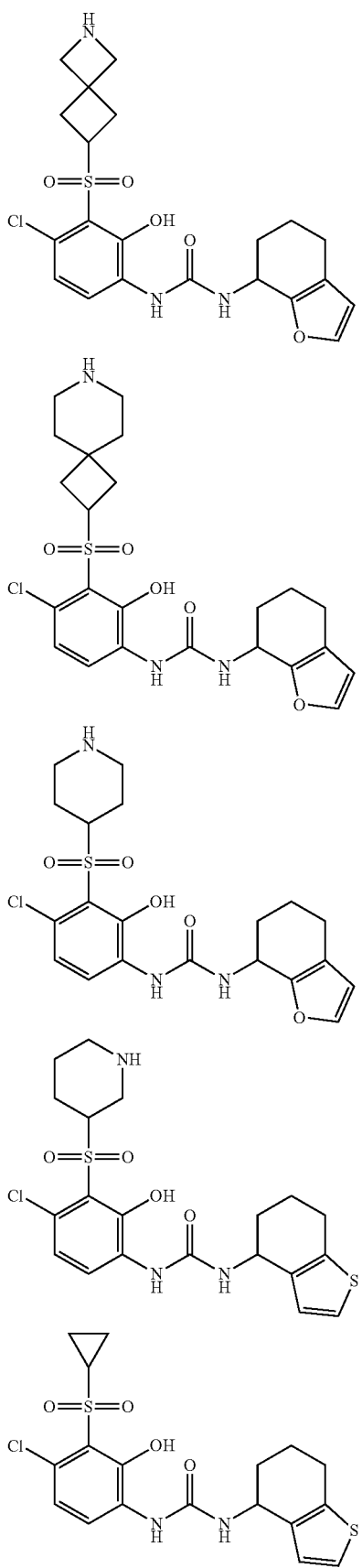
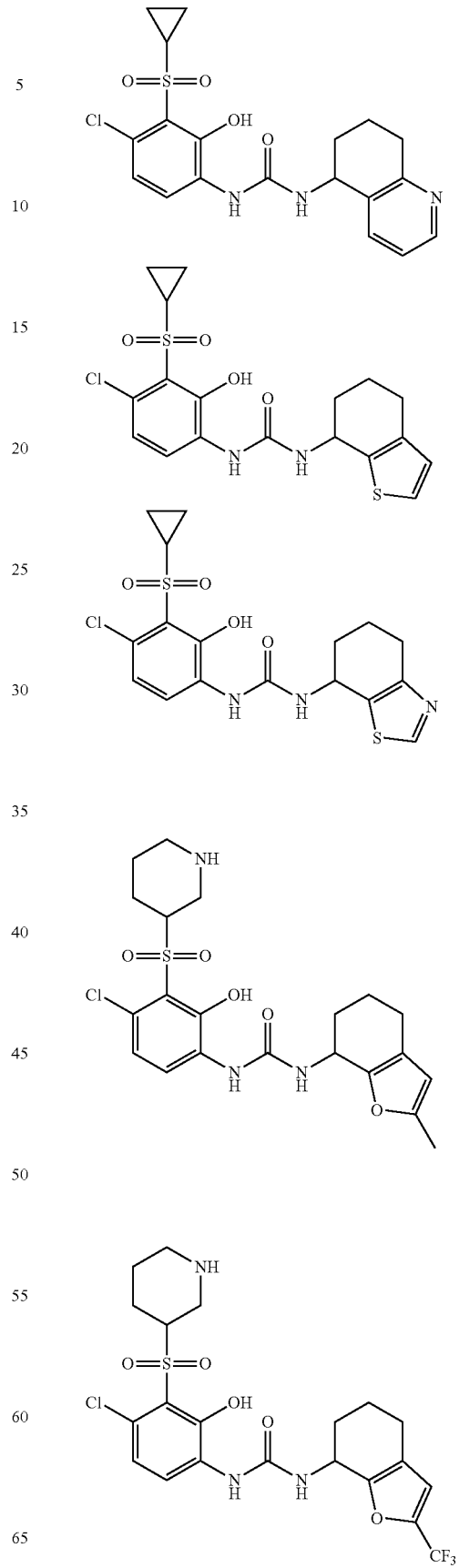

165
-continued
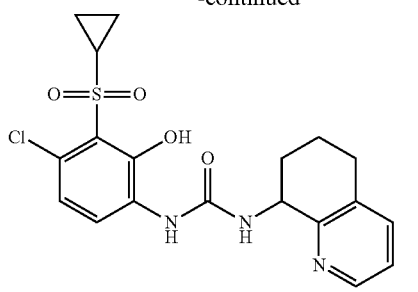
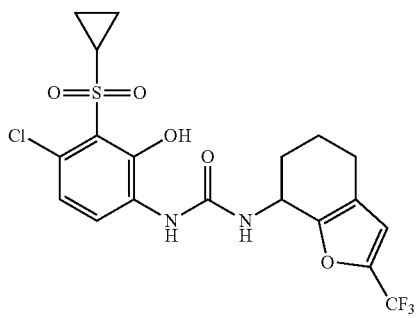
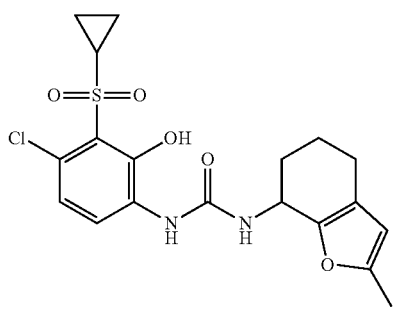
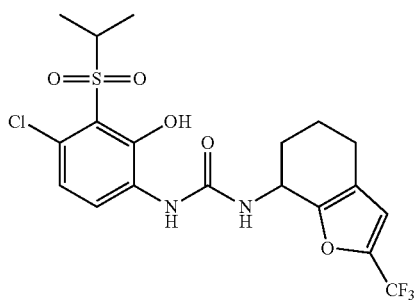
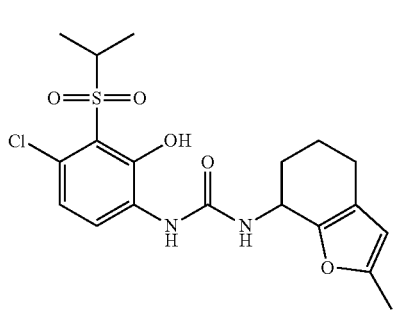
166
-continued
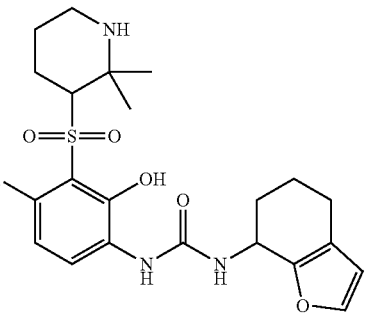
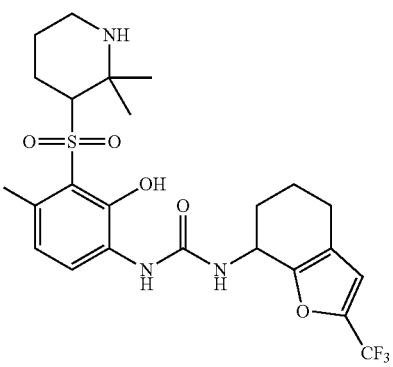
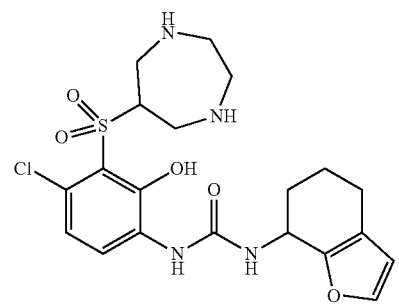
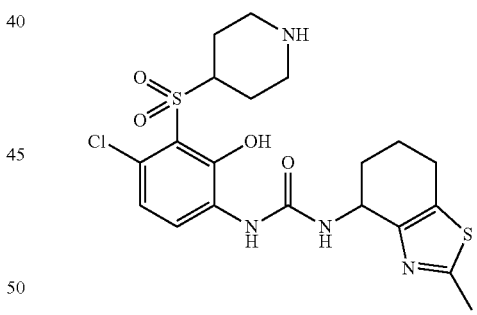
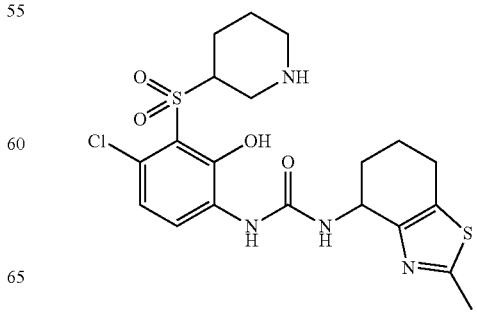

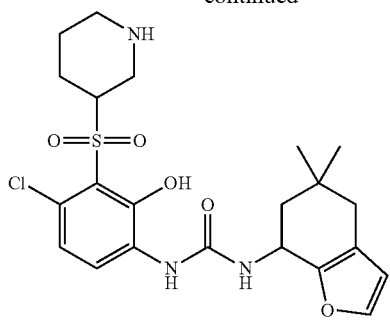
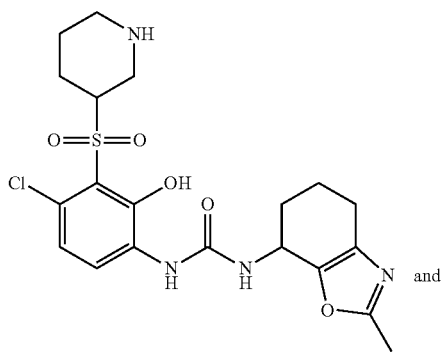
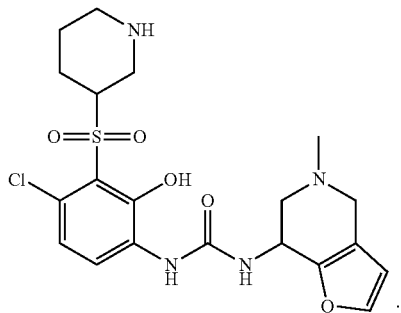
15. The compound, the tautomer or stereoisomer thereof, or the pharmaceutically acceptable salt thereof as defined in claim 14, wherein the compound is selected from
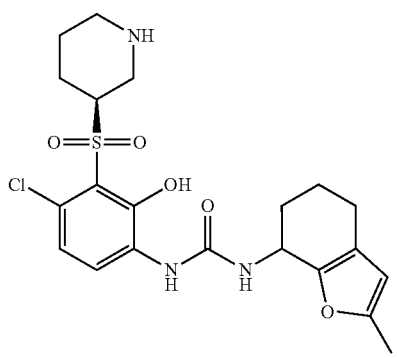
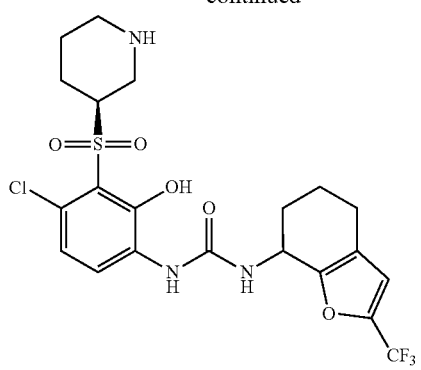
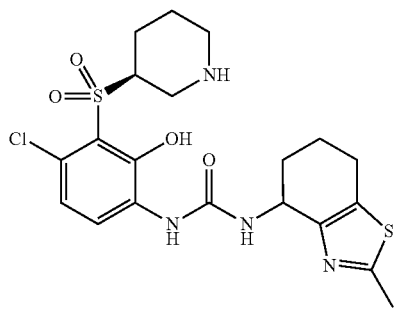
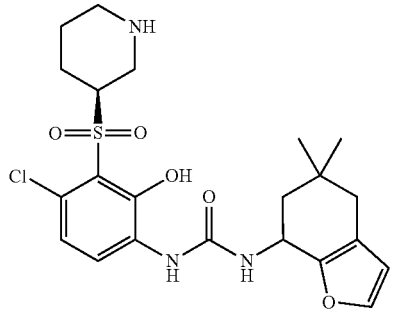
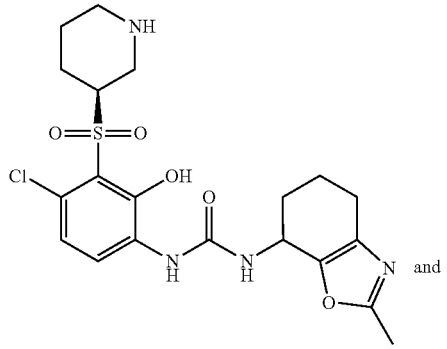
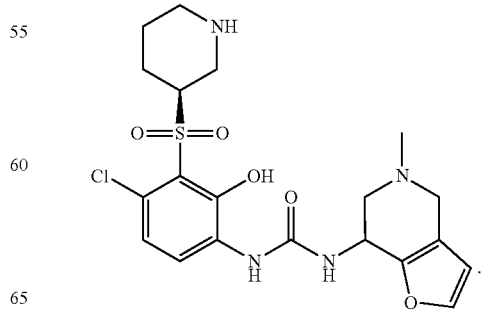

16. The compound, the tautomer or stereoisomer thereof, or the pharmaceutically acceptable salt thereof as defined in claim 14, wherein the compound is selected from
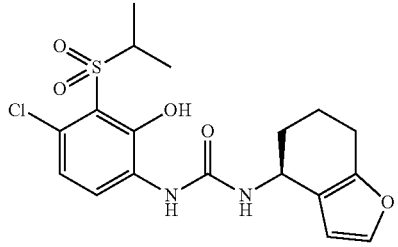
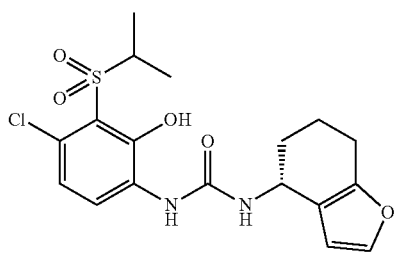
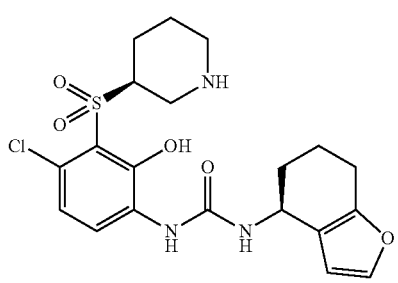
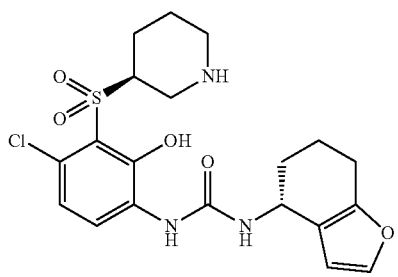
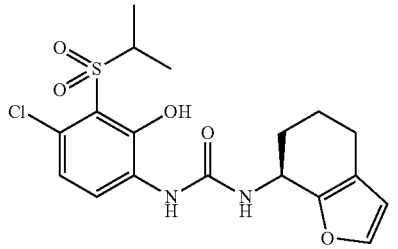
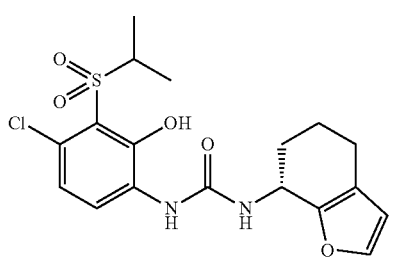
-continued
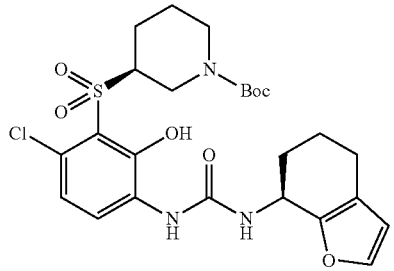
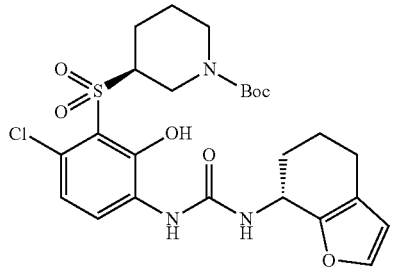
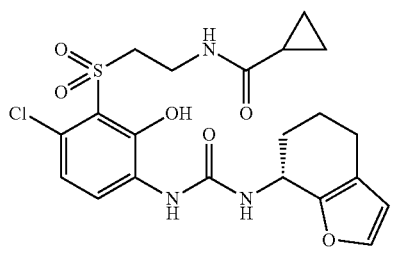
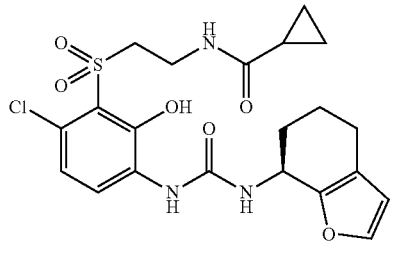
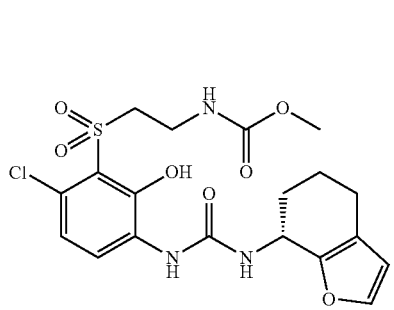
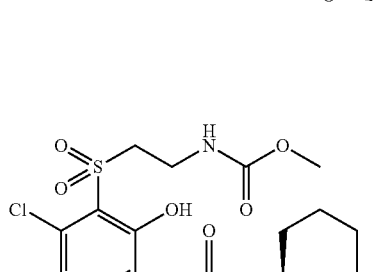

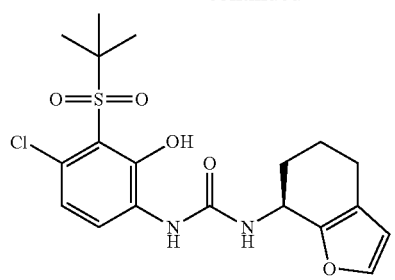
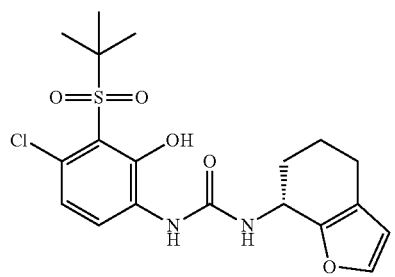
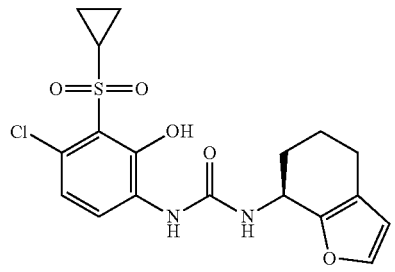
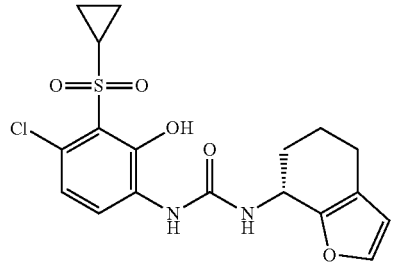
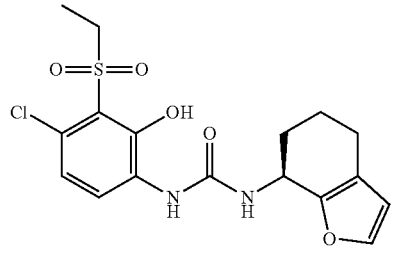
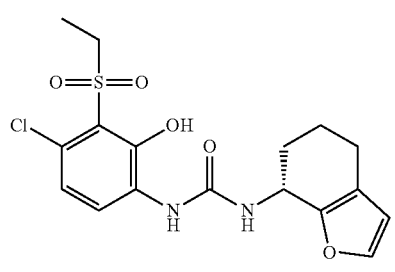
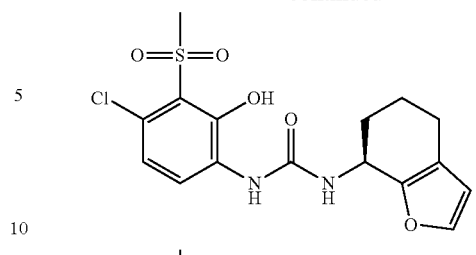
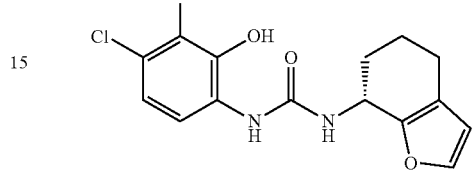
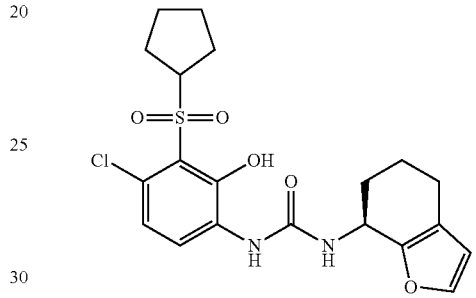
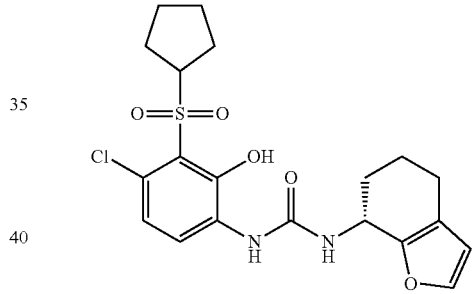
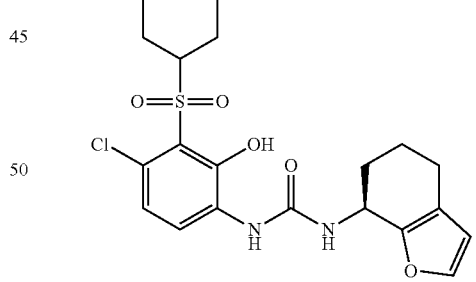
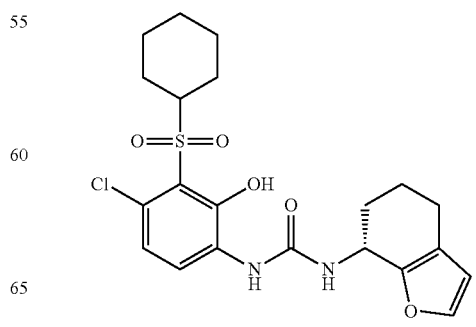

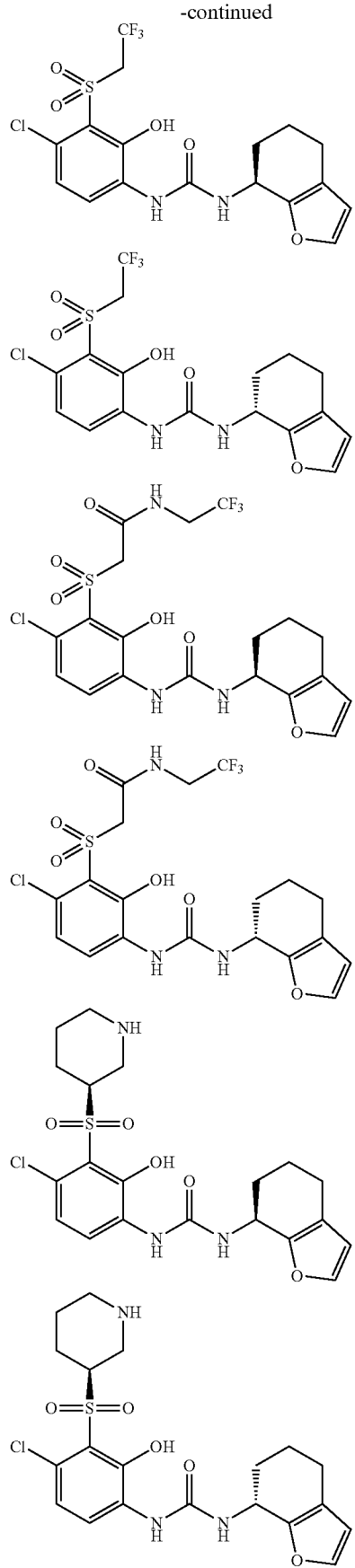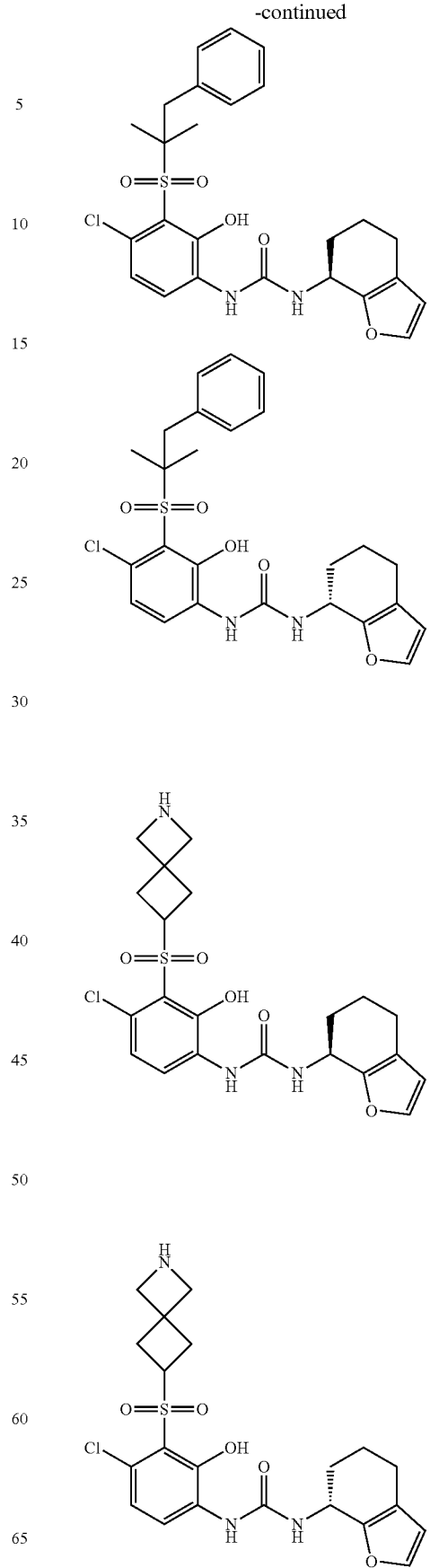

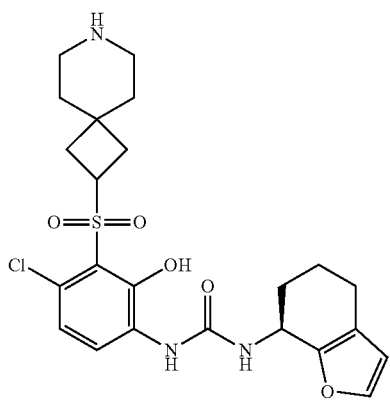
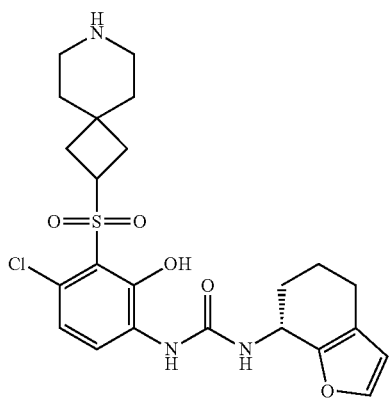
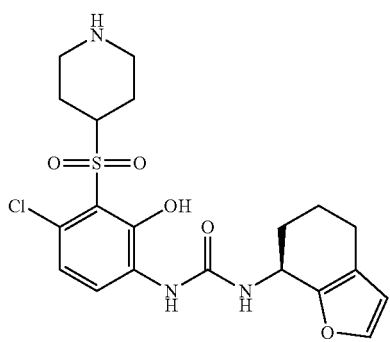
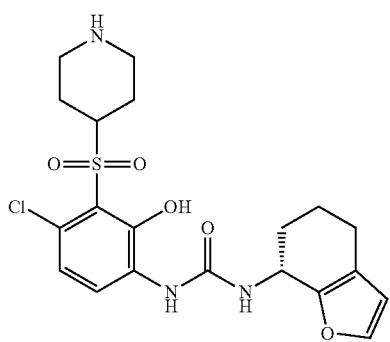
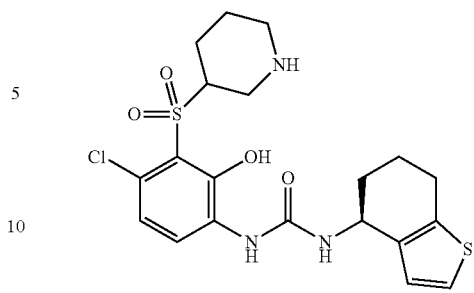
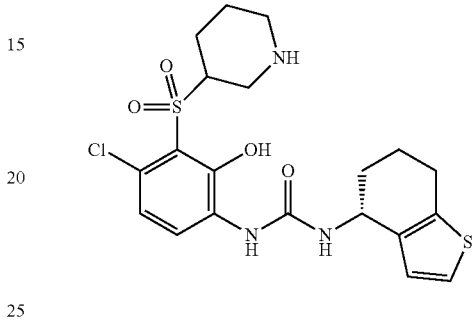
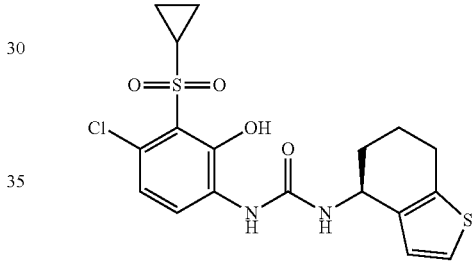
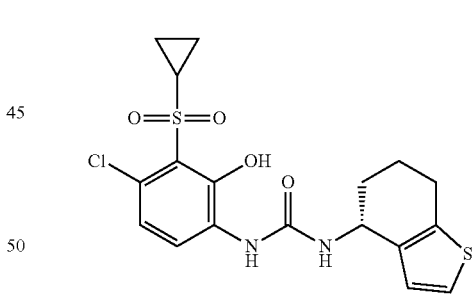
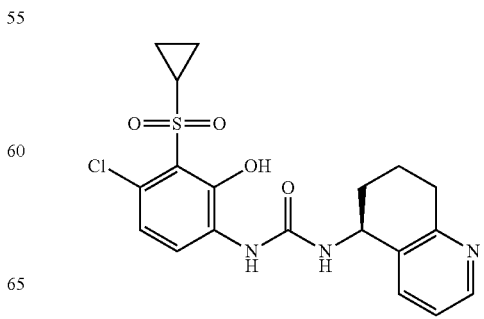

177
-continued

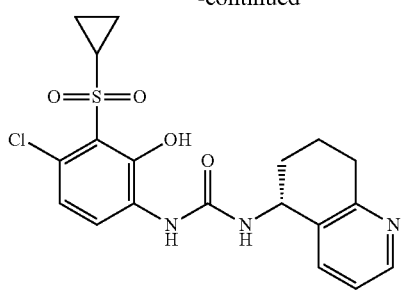

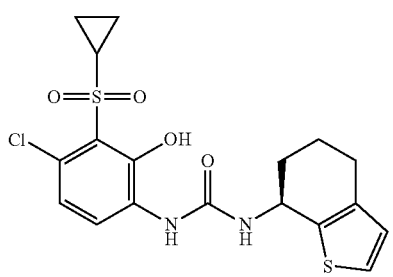

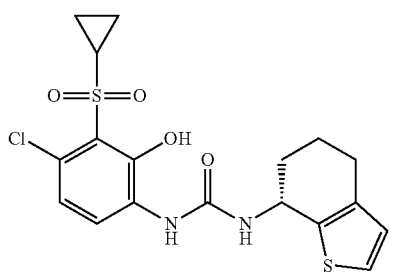

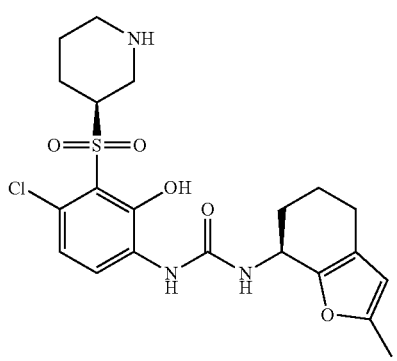

178
-continued

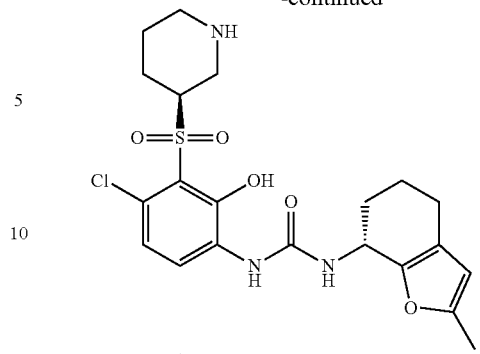

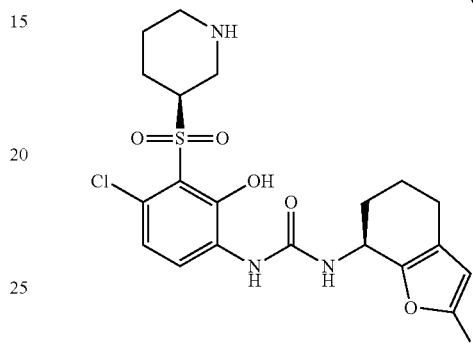

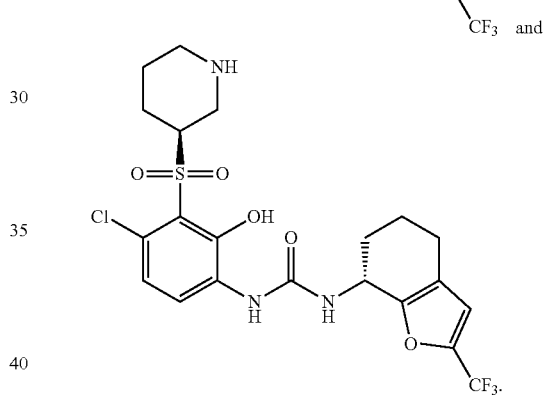

and

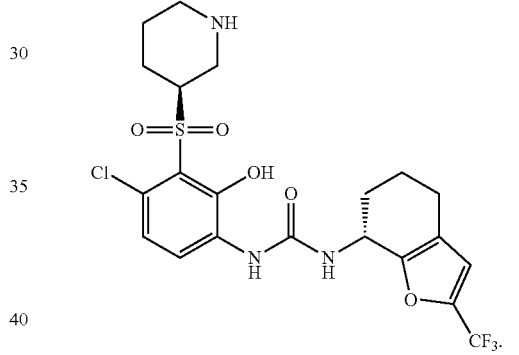

17. A pharmaceutical composition comprising a therapeutically effective amount of the compound, the tautomer or stereoisomer thereof or the pharmaceutically acceptable salt thereof as defined in claim 1 as an active ingredient, and a pharmaceutically acceptable carrier.

18. A method for treating COPD in a subject in need thereof, comprising administering a therapeutically effective amount of the compound, the tautomer or stereoisomer or the pharmaceutically acceptable salt thereof as defined in claim 1 to the subject.

* * * * *